(12) United States Patent
Deng et al.

(10) Patent No.: US 8,389,508 B2
(45) Date of Patent: Mar. 5, 2013

(54) HETEROCYCLIC COMPOUNDS

(75) Inventors: Guanghui Deng, Shanghai (CN); Xichen Lin, Shanghai (CN); Feng Ren, Shanghai (CN); Baowei Zhao, Shanghai (CN)

(73) Assignee: Glaxo Group Limited, Greenfield, Middlesex (GB)

( * ) Notice: Subject to any disclaimer, the term of this patent is extended or adjusted under 35 U.S.C. 154(b) by 46 days.

(21) Appl. No.: 13/096,641

(22) Filed: Apr. 28, 2011

(65) Prior Publication Data

US 2011/0269738 A1   Nov. 3, 2011

(30) Foreign Application Priority Data

Apr. 30, 2010   (WO) ................ PCT/CN2010/072351
Apr. 27, 2011   (WO) ................ PCT/CN2011/000741

(51) Int. Cl.
*A61K 31/433*   (2006.01)
*A61K 31/454*   (2006.01)
*C07D 417/04*   (2006.01)
*C07D 413/04*   (2006.01)

(52) U.S. Cl. ................... 514/210.18; 514/326; 514/361; 514/363; 546/209; 548/136; 548/128; 548/204

(58) Field of Classification Search ........................ None
See application file for complete search history.

(56) References Cited

U.S. PATENT DOCUMENTS 7,572,811 B2 *   8/2009   Pan et al. ...................... 514/315

\* cited by examiner

*Primary Examiner* — Yong Chu
(74) *Attorney, Agent, or Firm* — Barbara J. Carter

(57) ABSTRACT

The present invention relates to novel compounds having pharmacological activity, processes for their preparation, pharmaceutical compositions containing them and their use in the treatment of various disorders.

9 Claims, No Drawings

HETEROCYCLIC COMPOUNDS

The present invention relates to novel compounds having pharmacological activity, processes for their preparation, pharmaceutical compositions containing them and their use in the treatment of various disorders.

Sphingosine 1-phosphate (S1P) is a bioactive lipid mediator formed by the phosphorylation of sphingosine by sphingosine kinases and is found in high levels in the blood. It is produced and secreted by a number of cell types, including those of hematopoietic origin such as platelets and mast cells (Okamoto et al 1998 J Biol Chem 273(42):27104; Sanchez and Hla 2004, J Cell Biochem 92:913). It has a wide range of biological actions, including regulation of cell proliferation, differentiation, motility, vascularisation, and activation of inflammatory cells and platelets (Pyne and Pyne 2000, Biochem J. 349: 385). Five subtypes of S1P responsive receptor have been described, S1P1 (Edg-1), S1P2 (Edg-5), S1P3 (Edg-3), S1P4 (Edg-6), and S1P5 (Edg-8), forming part of the G-protein coupled endothelial differentiation gene family of receptors (Chun et al 2002 Pharmacological Reviews 54:265, Sanchez and Hla 2004 J Cellular Biochemistry, 92:913). These 5 receptors show differential mRNA expression, with S1P1-3 being widely expressed, S1P4 expressed on lymphoid and hematopoietic tissues and S1P5 primarily in brain and to a lower degree in spleen. They signal via different subsets of G proteins to promote a variety of biological responses (Kluk and Hla 2002 Biochem et Biophysica Acta 1582:72, Sanchez and Hla 2004, J Cellular Biochem 92:913).

Proposed roles for the S1P1 receptor include lymphocyte trafficking, cytokine induction/suppression and effects on endothelial cells (Rosen and Goetzl 2005 Nat Rev Immunol. 5:560). Agonists of the S1P1 receptor have been used in a number of autoimmune and transplantation animal models, including Experimental Autoimmune Encephalomelitis (EAE) models of MS, to reduce the severity of the induced disease (Brinkman et al 2003 JBC 277:21453; Fujino et al 2003 J Pharmacol Exp Ther 305:70; Webb et al 2004 J Neuroimmunol 153:108; Rausch et al 2004 J Magn Reson Imaging 20:16). This activity is reported to be mediated by the effect of S1P1 agonists on lymphocyte circulation through the lymph system. Treatment with S1P1 agonists results in the sequestration of lymphocytes within secondary lymphoid organs such as the lymph nodes, inducing a reversible peripheral lymphopoenia in animal models (Chiba et al 1998, J Immunology 160:5037, Forrest et al 2004 J Pharmacol Exp Ther 309:758; Sanna et al 2004 JBC 279:13839). Published data on agonists suggests that compound treatment induces loss of the S1P1 receptor from the cell surface via internalisation (Graler and Goetzl 2004 FASEB J 18:551; Matloubian et al 2004 Nature 427:355; Jo et al 2005 Chem Biol 12:703) and it is this reduction of S1P1 receptor on immune cells which contributes to the reduction of movement of T cells from the lymph nodes back into the blood stream.

S1P1 gene deletion causes embryonic lethality. Experiments to examine the role of the S1P1 receptor in lymphocyte migration and trafficking have included the adoptive transfer of labelled S1P1 deficient T cells into irradiated wild type mice. These cells showed a reduced egress from secondary lymphoid organs (Matloubian et al 2004 Nature 427:355).

S1P1 has also been ascribed a role in endothelial cell junction modulation (Allende et al 2003 102:3665, Blood Singelton et al 2005 FASEB J 19:1646). With respect to this endothelial action, S1P1 agonists have been reported to have an effect on isolated lymph nodes which may be contributing to a role in modulating immune disorders. S1P1 agonists caused a closing of the endothelial stromal 'gates' of lymphatic sinuses which drain the lymph nodes and prevent lymphocyte egress (Wei wt al 2005, Nat. Immunology 6:1228).

The immunosuppressive compound FTY720 (JP11080026-A) has been shown to reduce circulating lymphocytes in animals and man, have disease modulating activity in animal models of immune disorders and reduce remission rates in relapsing remitting Multiple Sclerosis (Brinkman et al 2002 JBC 277:21453, Mandala et al 2002 Science 296:346, Fujino et al 2003 J Pharmacology and Experimental Therapeutics 305:45658, Brinkman et al 2004 American J Transplantation 4:1019, Webb et al 2004 J Neuroimmunology 153:108, Morris et al 2005 EurJ Immunol 35:3570, Chiba 2005 Pharmacology and Therapeutics 108:308, Kahan et al 2003, Transplantation 76:1079, Kappos et al 2006 New Eng J Medicine 335:1124). This compound is a prodrug that is phosphorylated in vivo by sphingosine kinases to give a molecule that has agonist activity at the S1P1, S1P3, S1P4 and S1P5 receptors. Clinical studies have demonstrated that treatment with FTY720 results in bradycardia in the first 24 hours of treatment (Kappos et al 2006 New Eng J Medicine 335:1124). The bradycardia is thought to be due to agonism at the S1P3 receptor, based on a number of cell based and animal experiments. These include the use of S1P3 knock-out animals which, unlike wild type mice, do not demonstrate bradycardia following FTY720 administration and the use of S1P1 selective compounds. (Hale et al 2004 Bioorganic & Medicinal Chemistry Letters 14:3501, Sanna et al 2004 JBC 279: 13839, Koyrakh et al 2005 American J Transplantation 5:529)

Hence, there is a need for S1P1 receptor agonist compounds with selectivity over S1P3 which might be expected to show a reduced tendency to induce bradycardia.

The following patent applications describe oxadiazole derivatives as S1P1 agonists: WO03/105771, WO05/058848, WO06/047195, WO06/100633, WO06/115188, WO06/131336, WO07/024,922, WO07/116,866, WO2009043889, and WO2009043890.

The following patent application describes indole-oxadiazole derivatives as antipicornaviral agents: WO96/009822. The following patent applications describe indole-carboxylic acid derivatives as leukotriene receptor antagonists, pesticides and agrochemical fungicides respectively: WO06/090817, EP 0 439 785 and DE 39 39 238.

International patent applications WO08/074,821 and WO08/76356 describe oxadiazole-indole derivatives as S1P1 agonists.

GB patent applications 0911126.1 (WO10/148,649) and 0911130.3 (WO10/148,650) describe further S1P1 agonists.

A structurally novel class of compounds has now been found which provides agonists of the S1P1 receptor.

The present invention therefore provides compounds of formula (I) or a salt thereof:

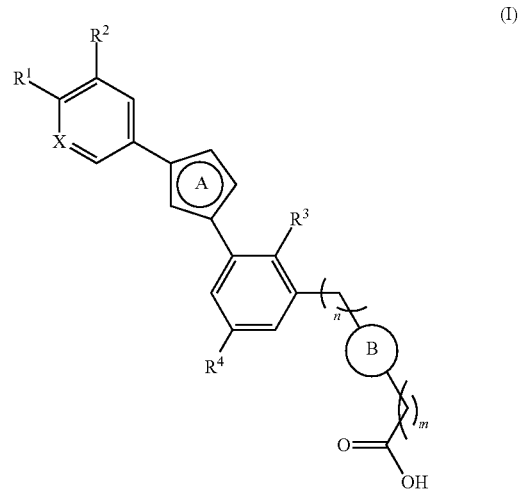

wherein
X is CH or N;
R$^1$ is C$_{1-6}$alkoxy or C$_{1-6}$alkyl;
R$^2$ is cyano, CF$_3$, halogen C$_{1-4}$alkoxy or CH$_2$OCH$_3$;
R$^3$ is halogen, C$_{1-6}$alkoxy or C$_{1-6}$alkyl;
R$^4$ is hydrogen, halogen, C$_{1-3}$alkyl, or C$_{1-3}$alkoxyl;
n=0, 1, 2 or 3;
m=0, 1, 2 or 3;
A is a 5-membered heteroaryl ring in any orientation selected from:

(a)
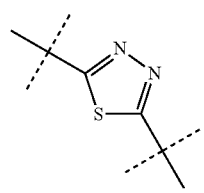

(b)
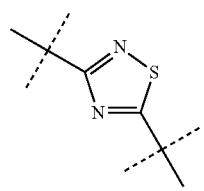

(c)
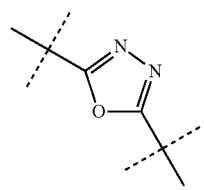

(d)
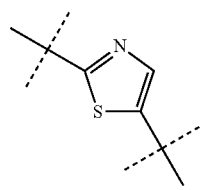

(e)
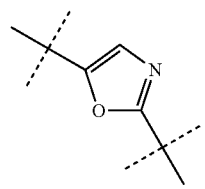

(f)
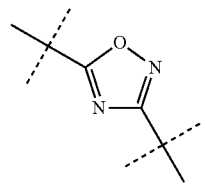

B is a 4 to 7-membered heterocyclic ring, in any orientation selected from:

(g)
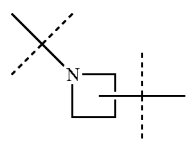

(h)
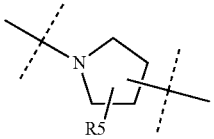

(i)
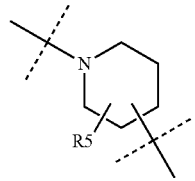

(j)
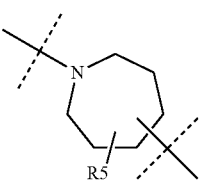

and
R$^5$ is one or two substituents independently selected from hydrogen, halogen, C$_{1-3}$alkyl, C$_{1-3}$alkoxyl and hydroxyl.

In one embodiment X is CH. In another embodiment X is N.

In one embodiment R$^1$ is C$_{1-6}$alkoxy or C$_{1-6}$alkyl. In another embodiment R$^1$ is isopropoxy or isobutyl. In a further embodiment R$^1$ is isopropoxy.

In one embodiment R$^2$ is cyano, CF$_3$ or halogen. In another embodiment R$^2$ is cyano, CF$_3$ or chloro. In a further embodiment R$^2$ is cyano or chloro. In another embodiment R$^2$ is chloro.

In one embodiment A is a 5-membered heteroaryl ring selected from (a), (b) and (d). In another embodiment A is (a) or (b). In a further embodiment A is (a). In a further embodiment, when A is (b) it is orientated with its sulphur atom closest to the ring containing X.

In one embodiment B is a 4- to 7-membered heteroaryl ring selected from (g), (h) and (i). In another embodiment B is a 4- to 7-membered heteroaryl ring selected from (g) and (i). In a further embodiment B is (g). In a further embodiment B is orientated with the (CH$_2$)$_m$COOH group attached to a carbon atom. In another embodiment, when B is (g) or (i) it is orientated with the (CH$_2$)$_m$COOH group attached to a carbon atom para to the nitrogen atom.

In one embodiment R$^3$ is C$_{1-6}$alkoxy or C$_{1-6}$alkyl. In another embodiment R$^3$ is methoxy, methyl or ethyl. In a further embodiment R$^3$ is methoxy or ethyl. In another embodiment R$^3$ is ethyl.

In one embodiment R$^4$ is hydrogen or halogen. In another embodiment R$^4$ is hydrogen or fluoro. In a further embodiment R$^4$ is hydrogen.

In one embodiment n is 1, 2 or 3. In another embodiment n is 1 or 2. In a further embodiment n is 1.

In one embodiment m is 0, 1 or 2. In a further embodiment m is 0 or 1. In another embodiment m is 0.

In one embodiment $R^5$ is hydrogen.
In one embodiment
X is CH;
$R^1$ is $C_{1-6}$alkoxy or $C_{1-6}$alkyl;
$R^2$ is cyano, $CF_3$ or halogen;
$R^3$ is $C_{1-6}$alkoxy or $C_{1-6}$alkyl;
$R^4$ is hydrogen or halogen;
n=1 or 2;
m=0 or 1;
A is a 5-membered heteroaryl ring selected from (a), (b) and (d);
B is a 4 to 7-membered heterocyclic ring selected from (g), (h) and (i); and
$R^5$ is hydrogen.
In one embodiment
X is CH;
$R^1$ is isopropoxy or isobutyl;
$R^2$ is cyano, $CF_3$ or chloro;
$R^3$ is ethyl or methoxy;
$R^4$ is hydrogen or fluoro;
n=1 or 2;
m=0;
A is a 5-membered heteroaryl ring selected from (a), b) and (d);
B is a 4 to 7-membered heterocyclic ring selected from (g), (h) and (i); and
$R^5$ is hydrogen.
In one embodiment X is CH;
$R^1$ is $C_{1-6}$alkoxy or $C_{1-6}$alkyl;
$R^2$ is cyano, $CF_3$ or halogen;
$R^3$ is $C_{1-6}$alkoxy or $C_{1-6}$alkyl;
$R^4$ is hydrogen;
n=1 or 2;
m=0 or 1;
A is a 5-membered heteroaryl ring selected from (a), (b) and (d);
B is a 4 to 7-membered heterocyclic ring selected from (g), (h) and (i); and
$R^5$ is hydrogen.
In one embodiment
X is CH;
$R^1$ is isopropoxy or isobutyl;
$R^2$ is cyano, $CF_3$ or chloro;
$R^3$ is ethyl or methoxy;
$R^4$ is hydrogen;
n=1 or 2;
m=0;
A is a 5-membered heteroaryl ring selected from (a), (b) and (d);
B is a 4 to 7-membered heterocyclic ring selected from (g), (h) and (i); and
$R^5$ is hydrogen.
In a further aspect, this invention provides processes for preparation of a compound of formula (I), $R_1$, $R_2$, $R_3$ and $R_4$, in schemes I-VI are as defined for formula (I), A is (a), (b) or (d) and X is CH and n is 1 or 2.

Scheme I

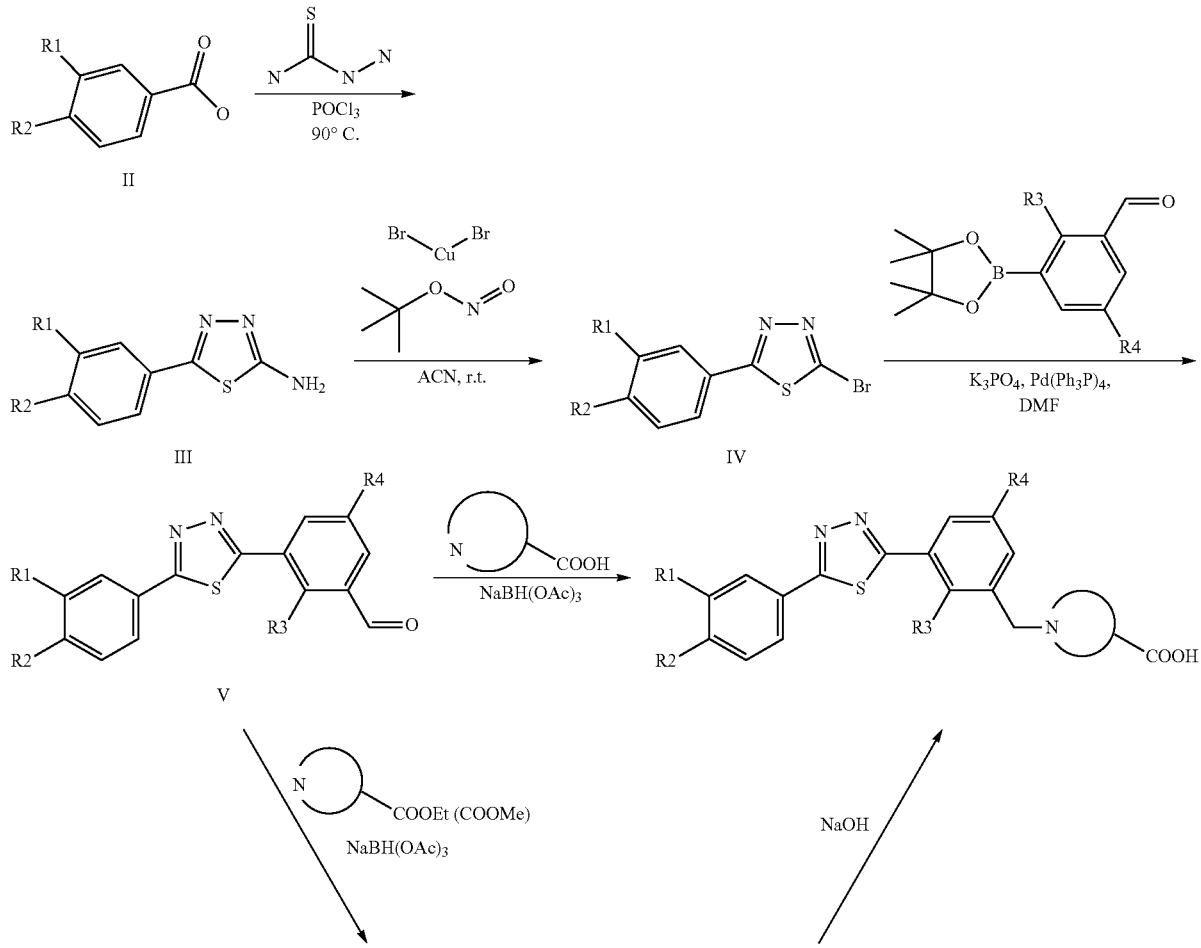

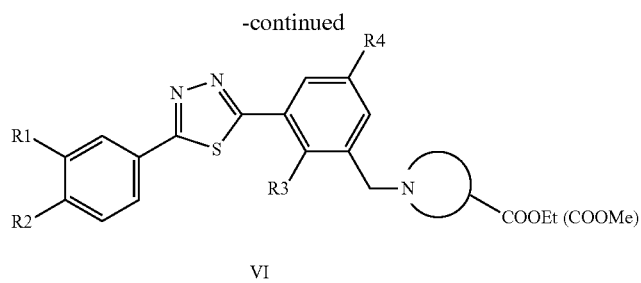

VI

The first step of the process (II to III) is carried out in POCl₃ at elevated temperatures In the second step of the process (III to IV) suitable reagents include CuBr2 and 1,1-dimethylethyl nitrite. In the third step of Suzuki coupling process (IV to V) suitable reagents include Pd(PPh₃)₄ and K₃PO₄ in a solvent such as DMF or DME under microwave condition. In the last step, formula (V) can be converted to (I) by treatment with suitable reagents cyclic amino acid or ester and NaBH(OAc)₃ in a suitable solvent such as methanol or CH₂Cl₂ at room temperature, then the ester (VI) is hydrolysed by treatment with basic (such as sodium hydroxide in a suitable solvent such as isopropanol) conditions.

In another aspect, other compounds of formula (I) can be prepared by the processes in Schemes II, III, IV, V or Scheme VI.

Scheme II

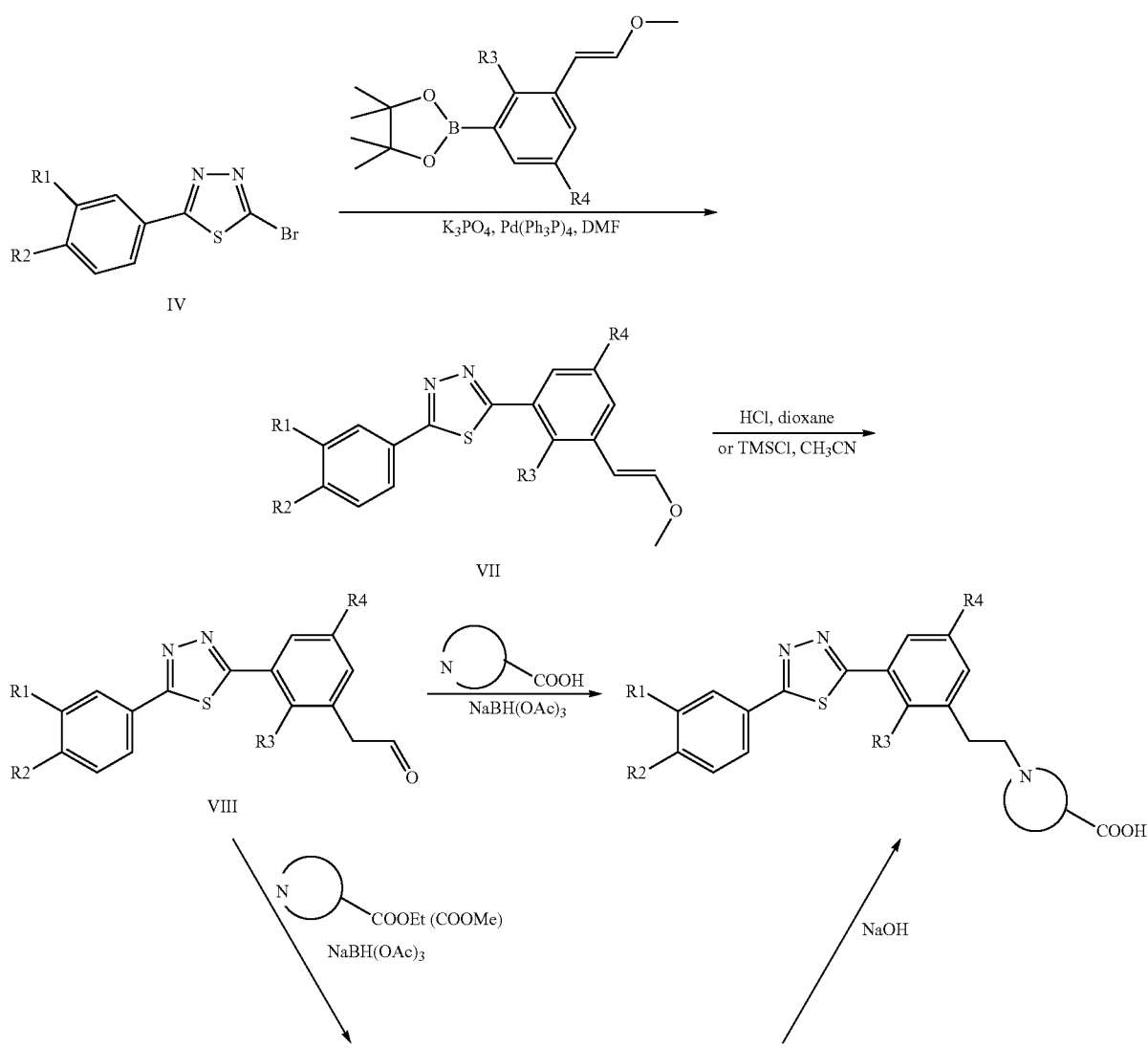

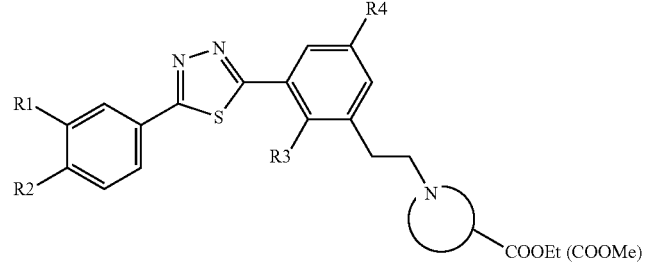

VIV

In the first step of Suzuki coupling process (IV to VII) suitable reagents include Pd(PPh$_3$)$_4$ and K$_3$PO$_4$ in a solvent such as DMF or DME under microwave condition. In the second step of the process (VII to VIII) suitable reagents in suitable solvents (HCl in dioxane or TMSCl in acetonitrile) are used at room temperature. The last step (VIII to I) is similar to process (V to I) in scheme I.

Scheme III

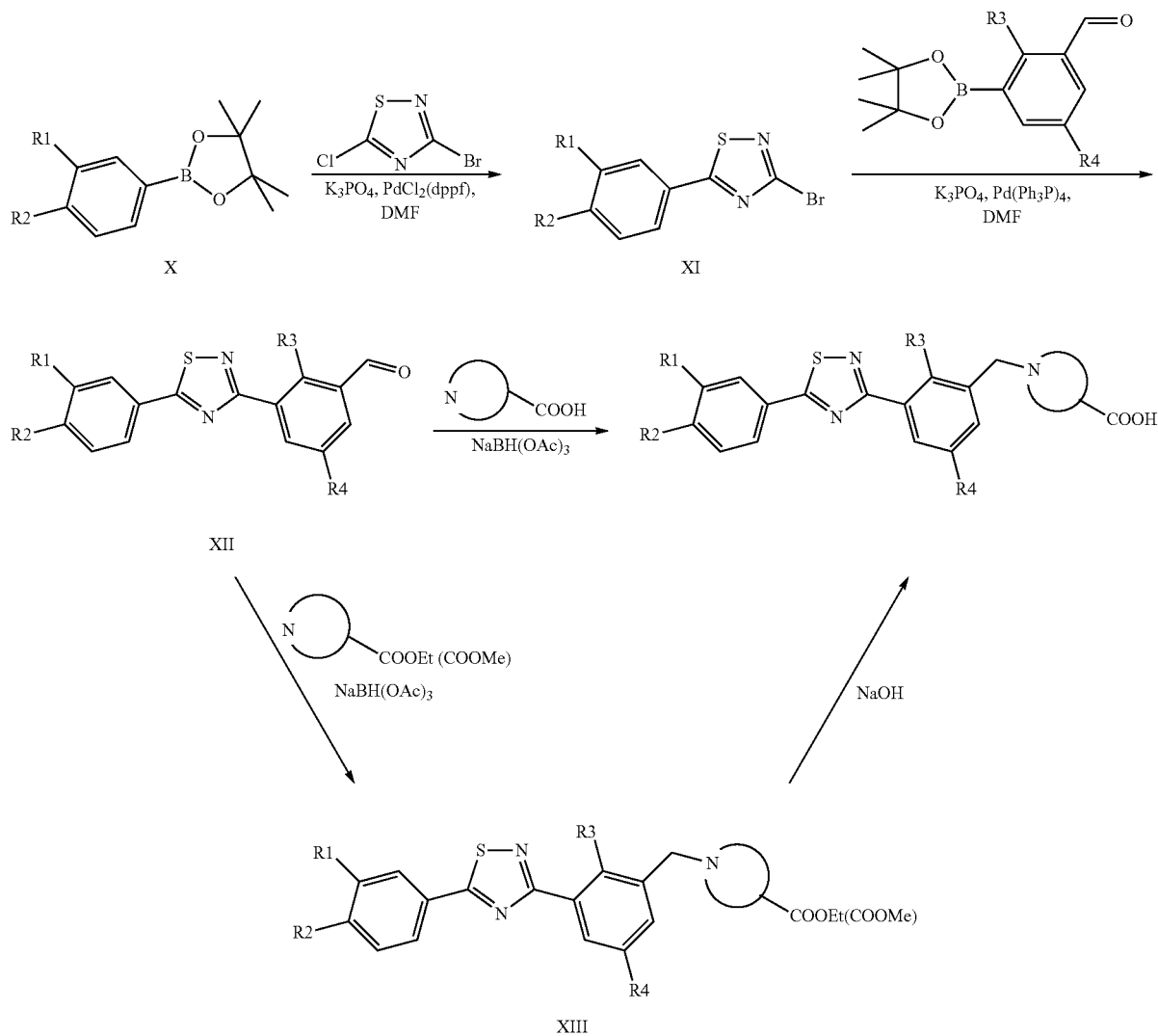

In the first two steps of Suzuki coupling process (X to XII) suitable reagents include PdCl$_2$(dppf) or Pd(PPh$_3$)$_4$ and K$_3$PO$_4$ in a solvent such as DMF or DME under microwave condition. The last step (XII to I) is similar with process (V to I) in scheme I.

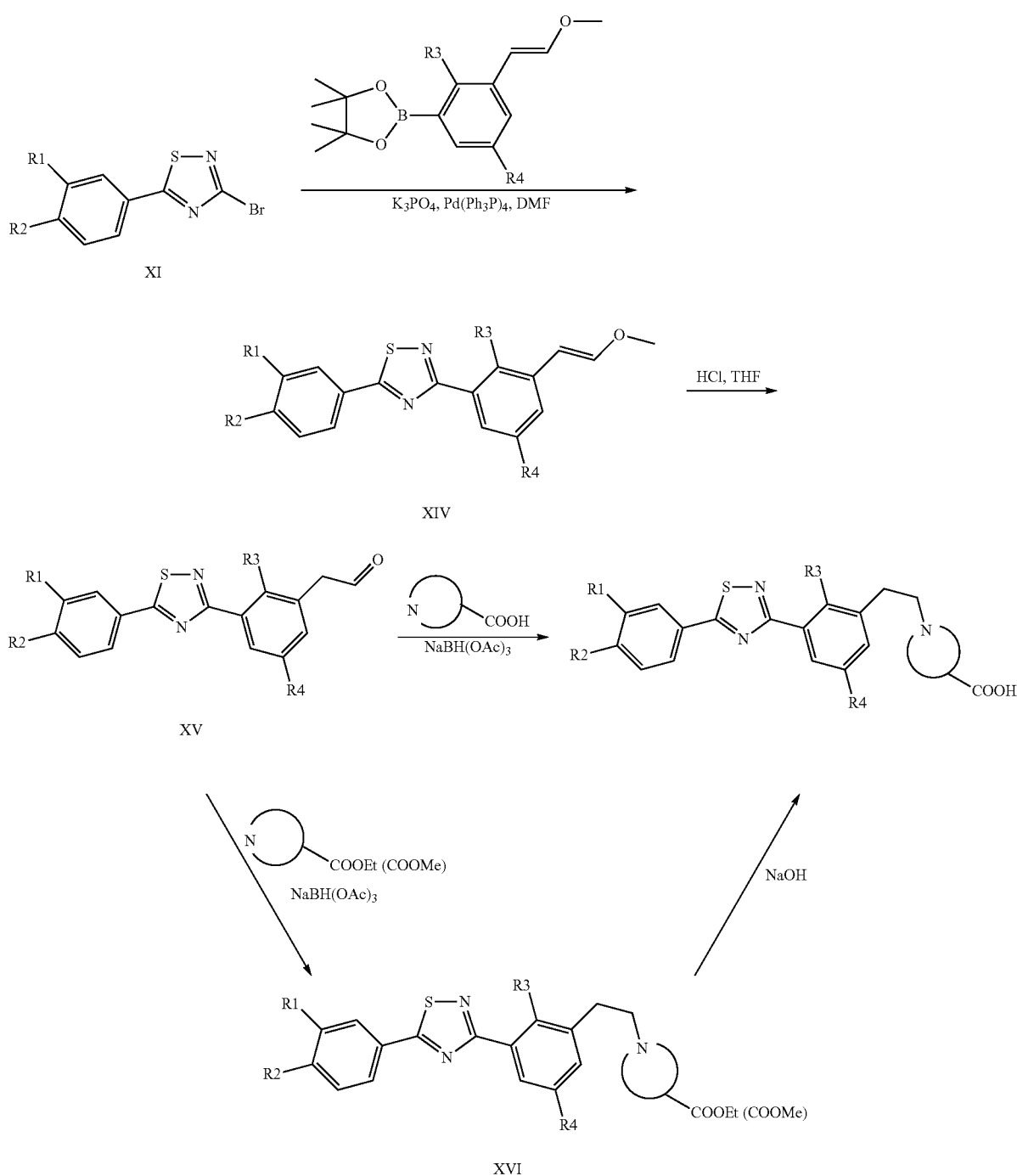

Scheme IV

In the first step of Suzuki coupling process (XI to XIV) suitable reagents include Pd(PPh$_3$)$_4$ and K$_3$PO$_4$ in a solvent such as DMF or DME under microwave condition. The last two steps (XIV to I) are similar to process (VIII to I) in scheme II.

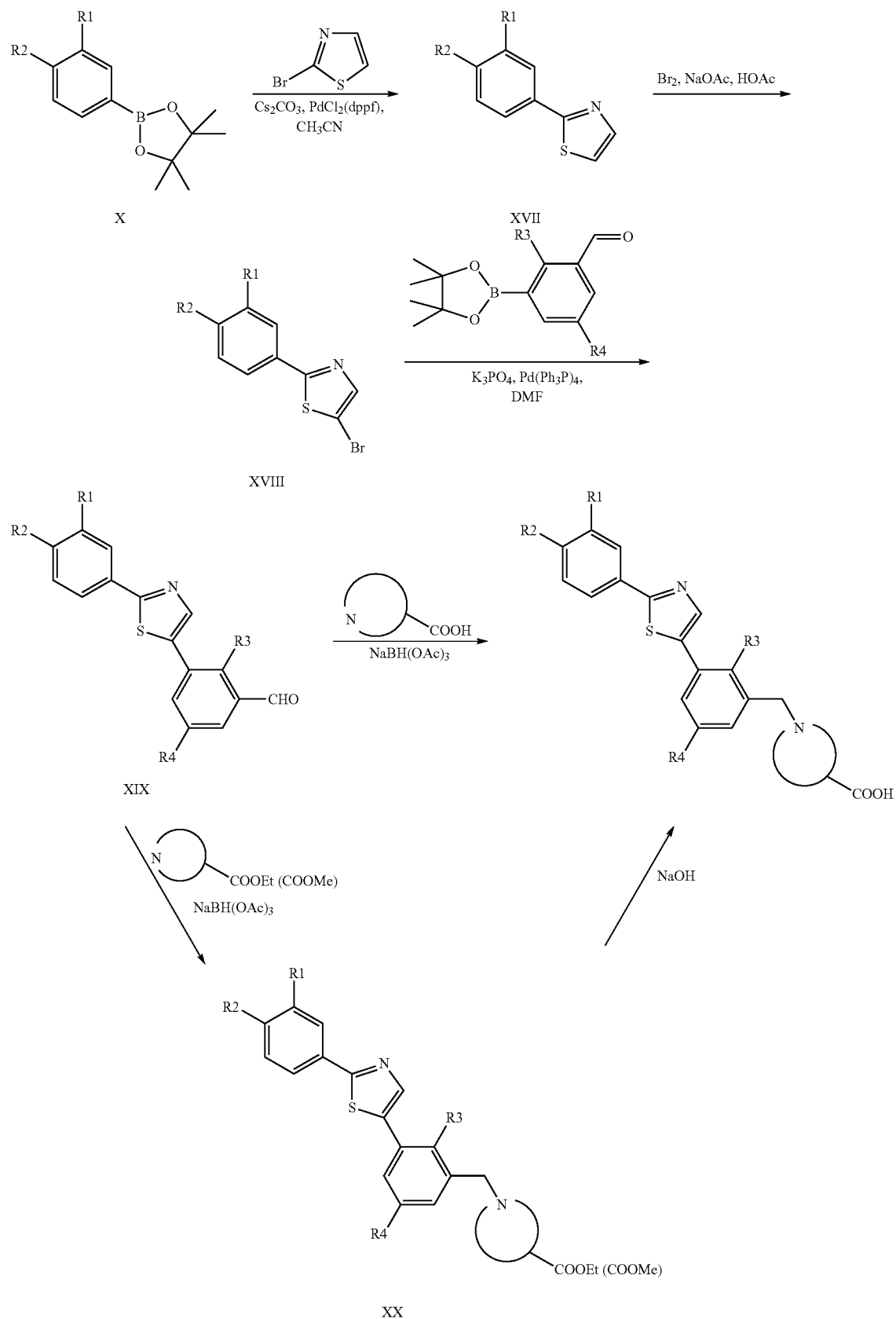

In the first step of Suzuki coupling process (X to XVII) suitable reagents include PdCl$_2$(dppf) and Cs$_2$CO$_3$ in a solvent such as CH$_3$CN or DME under microwave condition. The second step of the process (XVII to XVIII) is carried out by treatment with Br$_2$ in a suitable solvent such as HOAc at room temperature. The last two steps (XVIII to I) are similar to process (XI to I) in scheme III.

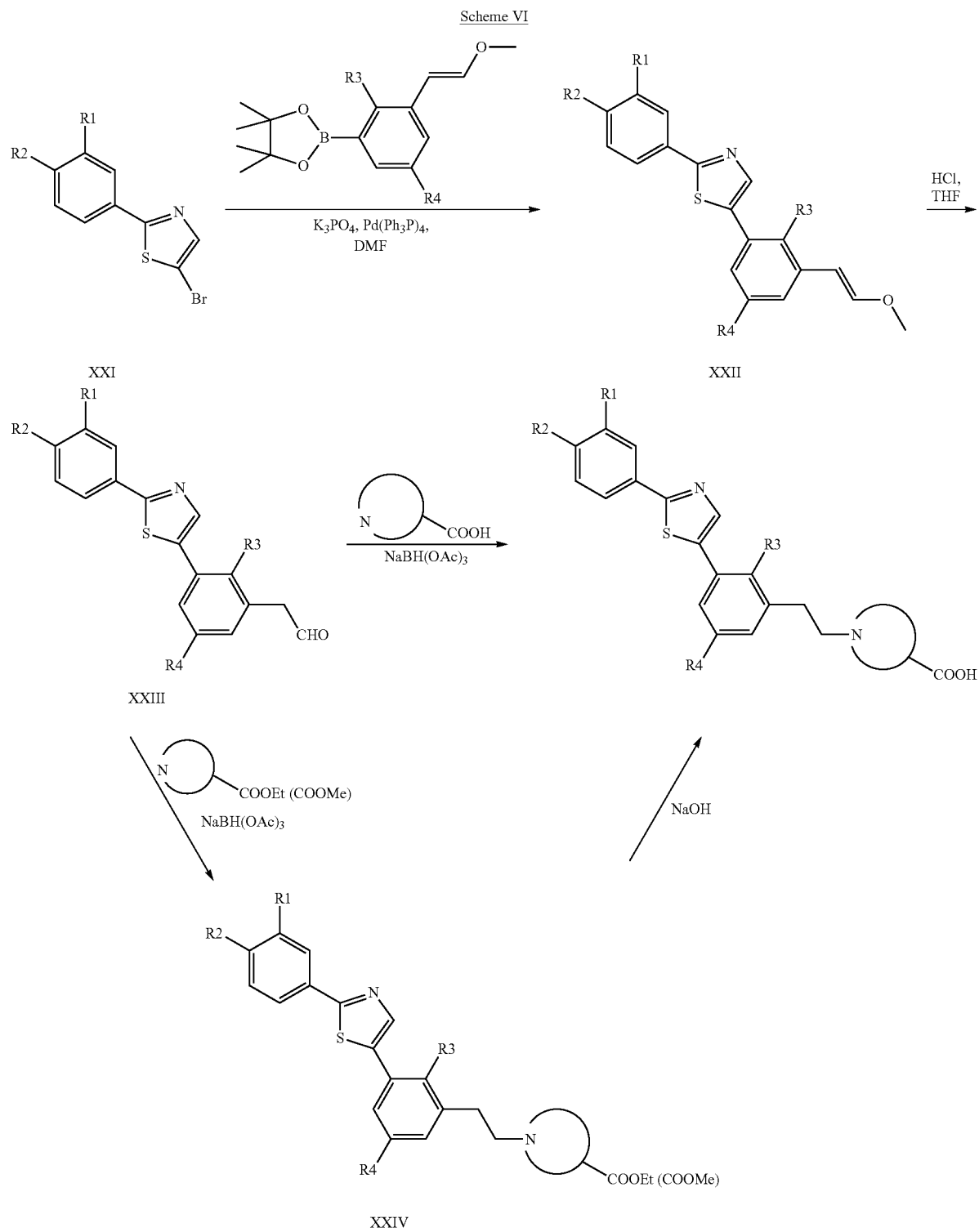

Scheme VI

The four steps of process (XXI to I) are similar with process (XI to I) in scheme IV.

Other compounds of formula (I) may be prepared analogously to the processes described in Schemes I-VI or the Examples described hereafter from commercially available starting materials.

Certain of the compounds herein can exist in various tautomeric forms and it is to be understood that the invention encompasses all such tautomeric forms.

Suitable compounds of formula (I) are:

1-[(2-ethyl-3-{5-[4-[(1-methylethyl)oxy]-3-(trifluoromethyl)phenyl]-1,3,4-thiadiazol-2-yl}phenyl)methyl]-4-piperidinecarboxylic acid;

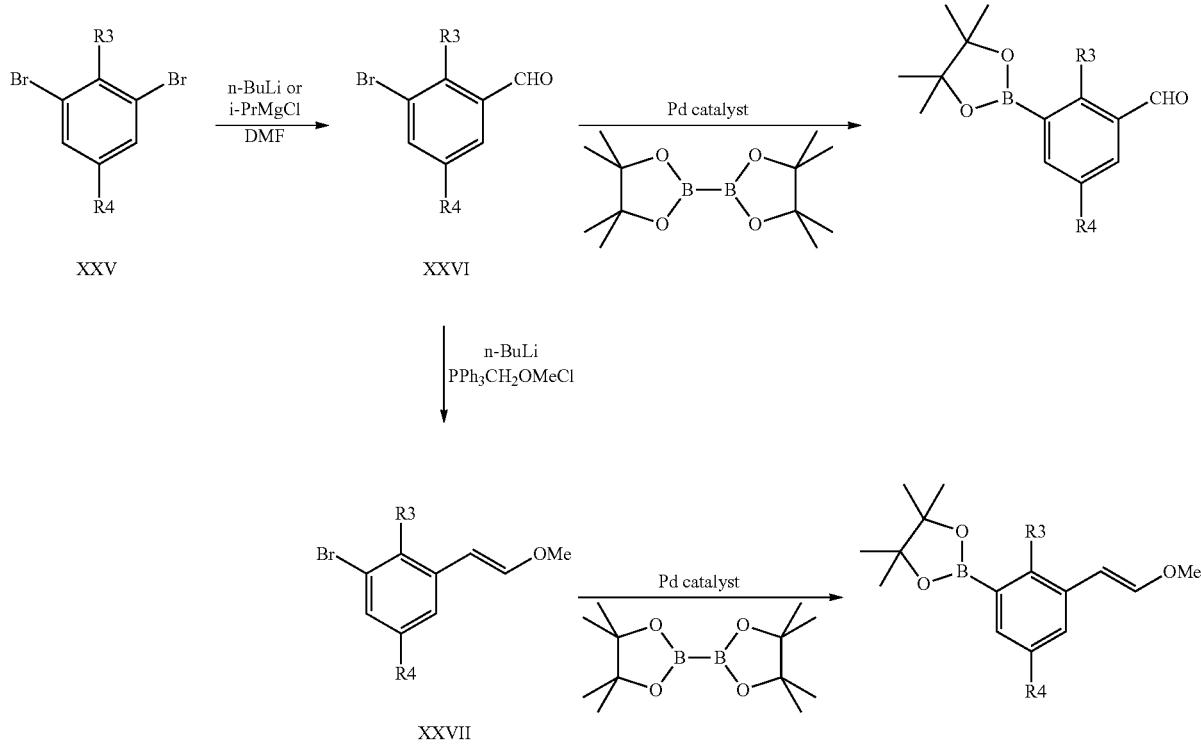

Scheme VII

General procedures for the boronic esters used in scheme I-VI for Suzuki couplings are described in scheme VII. Starting materials (XXV) either are commercially available, or were reported in literature, or are one step of transformation (bromination of the phenyl ring) from literature compounds. The first step (XXV-XXVI) may be carried out in DMF, with a suitable organometalic reagent such as n-butyllithium or isopropyl magnesium chloride. Conversion of the aldehyde (XXVI) to the vinyl ether (XXVII) could be achieved by Wittig reaction condition with a suitable base (n-BuLi) and the phosphine reagent (PPh$_3$CH$_2$OMeCl). Both compounds XXVI and XXVII could be transformed to the corresponding boronic esters using Miyaura borylation reaction with a suitable palladium catalyst and bis(pinacolato)diboron in a suitable solvent.

In certain of the compounds of formula (I), dependent upon the nature of the substituent there are chiral carbon atoms and therefore compounds of formula (I) may exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

1-[(2-ethyl-3-{5-[4-[(1-methylethyl)oxy]-3-(trifluoromethyl)phenyl]-1,3,4-thiadiazol-2-yl}phenyl)methyl]-3-azetidinecarboxylic acid;

1-{[3-(5-{3-chloro-4-[(1-methylethyl)oxy]phenyl}-1,3,4-thiadiazol-2-yl)-2-ethylphenyl]methyl}-4-piperidinecarboxylic acid;

1-{[3-(5-{3-chloro-4-[(1-methylethyl)oxy]phenyl}-1,3,4-thiadiazol-2-yl)-2-ethylphenyl]methyl}-3-azetidinecarboxylic acid;

1-{2-[3-(5-{3-chloro-4-[(1-methylethyl)oxy]phenyl}-1,3,4-thiadiazol-2-yl)-2-ethylphenyl]ethyl}-4-piperidinecarboxylic acid;

1-{2-[3-(5-{3-chloro-4-[(1-methylethyl)oxy]phenyl}-1,3,4-thiadiazol-2-yl)-2-ethylphenyl]ethyl}-3-azetidinecarboxylic acid;

1-[2-(2-ethyl-3-{5-[4-[(1-methylethyl)oxy]-3-(trifluoromethyl)phenyl]-1,3,4-thiadiazol-2-yl}phenyl)ethyl]-3-azetidinecarboxylic acid;

1-[(3-{5-[3-cyano-4-(2-methylpropyl)phenyl]-1,3,4-thiadiazol-2-yl}-2-ethylphenyl)methyl]-4-piperidinecarboxylic acid;

1-[(3-{5-[3-cyano-4-(2-methylpropyl)phenyl]-1,3,4-thiadiazol-2-yl}-2-ethylphenyl)methyl]-3-azetidinecarboxylic acid;

1-[2-(3-{5-[3-cyano-4-(2-methylpropyl)phenyl]-1,3,4-thiadiazol-2-yl}-2-ethylphenyl)ethyl]-3-azetidinecarboxylic acid;

1-[2-(3-{5-[3-cyano-4-(2-methylpropyl)phenyl]-1,3,4-thiadiazol-2-yl}-2-ethylphenyl)ethyl]-4-piperidinecarboxylic acid;

1-{2-[3-(5-{3-chloro-4-[(1-methylethyl)oxy]phenyl}-1,3,4-thiadiazol-2-yl)-2-ethylphenyl]ethyl}-3-pyrrolidinecarboxylic acid;

1-{2-[5-fluoro-3-{5-[4-[(1-methylethyl)oxy]-3-(trifluoromethyl)phenyl]-1,3,4-thiadiazol-2-yl}-2-(methyloxy)phenyl]ethyl}-4-piperidinecarboxylic acid;

1-{2-[5-fluoro-3-{5-[4-[(1-methylethyl)oxy]-3-(trifluoromethyl)phenyl]-1,3,4-thiadiazol-2-yl}-2-(methyloxy)phenyl]ethyl}-3-azetidinecarboxylic acid;

1-{2-[3-{5-[3-cyano-4-(2-methylpropyl)phenyl]-1,3,4-thiadiazol-2-yl}-5-fluoro-2-(methyloxy)phenyl]ethyl}-3-azetidinecarboxylic acid;

1-{[3-(5-{3-cyano-4-[(1-methylethyl)oxy]phenyl}-1,2,4-thiadiazol-3-yl)-2-ethylphenyl]methyl}-4-piperidinecarboxylic acid;

1-{[3-(5-{3-cyano-4-[(1-methylethyl)oxy]phenyl}-1,2,4-thiadiazol-3-yl)-2-ethylphenyl]methyl}-3-azetidinecarboxylic acid;

1-[(2-ethyl-3-{5-[4-[(1-methylethyl)oxy]-3-(trifluoromethyl)phenyl]-1,2,4-thiadiazol-3-yl}phenyl)methyl]-4-piperidinecarboxylic acid;

1-[(2-ethyl-3-{5-[4-[(1-methylethyl)oxy]-3-(trifluoromethyl)phenyl]-1,2,4-thiadiazol-3-yl}phenyl)methyl]-3-azetidinecarboxylic acid;

{1-[(2-ethyl-3-{5-[4-[(1-methylethyl)oxy]-3-(trifluoromethyl)phenyl]-1,2,4-thiadiazol-3-yl}phenyl)methyl]-4-piperidinyl}acetic acid;

1-[2-(2-ethyl-3-{5-[4-[(1-methylethyl)oxy]-3-(trifluoromethyl)phenyl]-1,2,4-thiadiazol-3-yl}phenyl)ethyl]-4-piperidinecarboxylic acid;

1-[2-(2-ethyl-3-{5-[4-[(1-methylethyl)oxy]-3-(trifluoromethyl)phenyl]-1,2,4-thiadiazol-3-yl}phenyl)ethyl]-3-azetidinecarboxylic acid;

1-{2-[3-(5-{3-chloro-4-[(1-methylethyl)oxy]phenyl}-1,2,4-thiadiazol-3-yl)-2-ethylphenyl]ethyl}-3-azetidinecarboxylic acid;

1-{2-[3-(5-{3-chloro-4-[(1-methylethyl)oxy]phenyl}-1,2,4-thiadiazol-3-yl)-2-ethylphenyl]ethyl}-4-piperidinecarboxylic acid;

1-{[3-(5-{3-chloro-4-[(1-methylethyl)oxy]phenyl}-1,2,4-thiadiazol-3-yl)-2-ethylphenyl]methyl}-3-azetidinecarboxylic acid;

1-{2-[3-(5-{3-cyano-4-[(1-methylethyl)oxy]phenyl}-1,2,4-thiadiazol-3-yl)-2-ethylphenyl]ethyl}-3-azetidinecarboxylic acid;

1-[(3-{5-[3-cyano-4-(2-methylpropyl)phenyl]-1,2,4-thiadiazol-3-yl}-2-ethylphenyl)methyl]-3-azetidinecarboxylic acid;

1-[(3-{5-[3-cyano-4-(2-methylpropyl)phenyl]-1,2,4-thiadiazol-3-yl}-2-ethylphenyl)methyl]-4-piperidinecarboxylic acid;

1-[2-(3-{5-[3-cyano-4-(2-methylpropyl)phenyl]-1,2,4-thiadiazol-3-yl}-2-ethylphenyl)ethyl]-4-piperidinecarboxylic acid;

1-[2-(3-{5-[3-cyano-4-(2-methylpropyl)phenyl]-1,2,4-thiadiazol-3-yl}-2-ethylphenyl)ethyl]-3-azetidinecarboxylic acid;

1-[(2-ethyl-3-{2-[4-[(1-methylethyl)oxy]-3-(trifluoromethyl)phenyl]-1,3-thiazol-5-yl}phenyl)methyl]-3-azetidinecarboxylic acid;

1-[(2-ethyl-3-{2-[4-[(1-methylethyl)oxy]-3-(trifluoromethyl)phenyl]-1,3-thiazol-5-yl}phenyl)methyl]-4-piperidinecarboxylic acid;

1-{2-[3-(2-{3-chloro-4-[(1-methylethyl)oxy]phenyl}-1,3-thiazol-5-yl)-5-fluoro-2-(methyloxy)phenyl]ethyl}-3-azetidinecarboxylic acid;

1-{2-[3-(2-{3-cyano-4-[(1-methylethyl)oxy]phenyl}-1,3-thiazol-5-yl)-2-ethylphenyl]ethyl}-3-azetidinecarboxylic acid;

1-{[3-(2-{3-cyano-4-[(1-methylethyl)oxy]phenyl}-1,3-thiazol-5-yl)-2-ethylphenyl]methyl}-4-piperidinecarboxylic acid;

1-{[3-(2-{3-chloro-4-[(1-methylethyl)oxy]phenyl}-1,3-thiazol-5-yl)-2-ethylphenyl]methyl}-4-piperidinecarboxylic acid;

1-{2-[3-(2-{3-cyano-4-[(1-methylethyl)oxy]phenyl}-1,3-thiazol-5-yl)-2-ethylphenyl]ethyl}-4-piperidinecarboxylic acid;

1-{[3-(2-{3-cyano-4-[(1-methylethyl)oxy]phenyl}-1,3-thiazol-5-yl)-2-ethylphenyl]methyl}-3-azetidinecarboxylic acid;

1-{[3-(2-{3-chloro-4-[(1-methylethyl)oxy]phenyl}-1,3-thiazol-5-yl)-2-ethylphenyl]methyl}-3-azetidinecarboxylic acid;

1-{2-[3-(2-{3-chloro-4-[(1-methylethyl)oxy]phenyl}-1,3-thiazol-5-yl)-2-ethylphenyl]ethyl}-4-piperidinecarboxylic acid;

1-{2-[3-(2-{3-chloro-4-[(1-methylethyl)oxy]phenyl}-1,3-thiazol-5-yl)-2-ethylphenyl]ethyl}-3-azetidinecarboxylic acid;

1-[(3-{2-[3-cyano-4-(2-methylpropyl)phenyl]-1,3-thiazol-5-yl}-2-ethylphenyl)methyl]-4-piperidinecarboxylic acid;

1-[(3-{2-[3-cyano-4-(2-methylpropyl)phenyl]-1,3-thiazol-5-yl}-2-ethylphenyl)methyl]-3-azetidinecarboxylic acid;

1-{[3-(5-{3-chloro-4-[(1-methylethyl)oxy]phenyl}-1,3,4-thiadiazol-2-yl)-2-ethylphenyl]methyl}-3-pyrrolidinecarboxylic acid;

(3S)-1-{[3-(5-{3-chloro-4-[(1-methylethyl)oxy]phenyl}-1,3,4-thiadiazol-2-yl)-2-ethylphenyl]methyl}-3-pyrrolidinecarboxylic acid;

1-{[3-(5-{3-chloro-4-[(1-methylethyl)oxy]phenyl}-1,3,4-thiadiazol-2-yl)-2-ethylphenyl]methyl}-3-piperidinecarboxylic acid;

(3S)-1-{[3-(5-{3-chloro-4-[(1-methylethyl)oxy]phenyl}-1,3,4-thiadiazol-2-yl)-2-ethylphenyl]methyl}-3-piperidinecarboxylic acid;

1-[(3-{5-[3-cyano-4-(2-methylpropyl)phenyl]-1,3,4-thiadiazol-2-yl}-2-ethylphenyl)methyl]-3-pyrrolidinecarboxylic acid;

(3S)-1-[(3-{5-[3-cyano-4-(2-methylpropyl)phenyl]-1,3,4-thiadiazol-2-yl}-2-ethylphenyl)methyl]-3-pyrrolidinecarboxylic acid;

1-[(3-{5-[3-cyano-4-(2-methylpropyl)phenyl]-1,3,4-thiadiazol-2-yl}-2-ethylphenyl)methyl]-3-piperidinecarboxylic acid;

(3S)-1-[(3-{5-[3-cyano-4-(2-methylpropyl)phenyl]-1,3,4-thiadiazol-2-yl}-2-ethylphenyl)methyl]-3-piperidinecarboxylic acid;

1-{2-[3-(5-{3-chloro-4-[(1-methylethyl)oxy]phenyl}-1,3,4-thiadiazol-2-yl)-2-ethylphenyl]ethyl}-L-proline;

1-{2-[3-(5-{3-chloro-4-[(1-methylethyl)oxy]phenyl}-1,3,4-thiadiazol-2-yl)-2-ethylphenyl]ethyl}-D-proline;

(3S)-1-{2-[3-(5-{3-chloro-4-[(1-methylethyl)oxy]phenyl}-1,3,4-thiadiazol-2-yl)-2-ethylphenyl]ethyl}-3-pyrrolidinecarboxylic acid;

(4R)-1-{2-[3-(5-{3-chloro-4-[(1-methylethyl)oxy]phenyl}-1,3,4-thiadiazol-2-yl)-2-ethylphenyl]ethyl}-4-hydroxy-L-proline;

1-{2-[3-(5-{3-chloro-4-[(1-methylethyl)oxy]phenyl}-1,3,4-thiadiazol-2-yl)-2-ethylphenyl]ethyl}-3-piperidinecarboxylic acid;

(3S)-1-{2-[3-(5-{3-chloro-4-[(1-methylethyl)oxy]phenyl}-1,3,4-thiadiazol-2-yl)-2-ethylphenyl]ethyl}-3-piperidinecarboxylic acid;

1-{2-[3-(5-{3-chloro-4-[(1-methylethyl)oxy]phenyl}-1,3,4-thiadiazol-2-yl)-2-methylphenyl]ethyl}-4-piperidinecarboxylic acid;

1-[2-(3-{5-[3-cyano-4-(2-methylpropyl)phenyl]-1,3,4-thiadiazol-2-yl}-2-ethylphenyl)ethyl]-L-proline;

1-[2-(3-{5-[3-cyano-4-(2-methylpropyl)phenyl]-1,3,4-thiadiazol-2-yl}-2-ethylphenyl)ethyl]-D-proline;

1-[2-(3-{5-[3-cyano-4-(2-methylpropyl)phenyl]-1,3,4-thiadiazol-2-yl}-2-ethylphenyl)ethyl]-3-pyrrolidinecarboxylic acid;

(3S)-1-[2-(3-{5-[3-cyano-4-(2-methylpropyl)phenyl]-1,3,4-thiadiazol-2-yl}-2-ethylphenyl)ethyl]-3-pyrrolidinecarboxylic acid;

1-[2-(3-{5-[3-cyano-4-(2-methylpropyl)phenyl]-1,3,4-thiadiazol-2-yl}-2-ethylphenyl)ethyl]-3-piperidinecarboxylic acid;

(3S)-1-[2-(3-{5-[3-cyano-4-(2-methylpropyl)phenyl]-1,3,4-thiadiazol-2-yl}-2-ethylphenyl)ethyl]-3-piperidinecarboxylic acid;

1-{2-[3-(5-{3-chloro-4-[(1-methylethyl)oxy]phenyl}-1,2,4-thiadiazol-3-yl)-2-ethylphenyl]ethyl}-L-proline;

1-{2-[3-(5-{3-chloro-4-[(1-methylethyl)oxy]phenyl}-1,2,4-thiadiazol-3-yl)-2-ethylphenyl]ethyl}-D-proline;

1-{2-[3-(5-{3-chloro-4-[(1-methylethyl)oxy]phenyl}-1,2,4-thiadiazol-3-yl)-2-ethylphenyl]ethyl}-3-pyrrolidinecarboxylic acid;

(3S)-1-{2-[3-(5-{3-chloro-4-[(1-methylethyl)oxy]phenyl}-1,2,4-thiadiazol-3-yl)-2-ethylphenyl]ethyl}-3-pyrrolidinecarboxylic acid;

(4R)-1-{2-[3-(5-{3-chloro-4-[(1-methylethyl)oxy]phenyl}-1,2,4-thiadiazol-3-yl)-2-ethylphenyl]ethyl}-4-hydroxy-L-proline;

1-{2-[3-(5-{3-chloro-4-[(1-methylethyl)oxy]phenyl}-1,2,4-thiadiazol-3-yl)-2-ethylphenyl]ethyl}-3-piperidinecarboxylic acid;

(3S)-1-{2-[3-(5-{3-chloro-4-[(1-methylethyl)oxy]phenyl}-1,2,4-thiadiazol-3-yl)-2-ethylphenyl]ethyl}-3-piperidinecarboxylic acid;

(1-{2-[3-(5-{3-chloro-4-[(1-methylethyl)oxy]phenyl}-1,2,4-thiadiazol-3-yl)-2-ethylphenyl]ethyl}-4-piperidinyl)acetic acid;

1-{2-[3-(5-{3-chloro-4-[(1-methylethyl)oxy]phenyl}-1,2,4-thiadiazol-3-yl)-2-(methyloxy)phenyl]ethyl}-4-piperidinecarboxylic acid trifluoroacetate;

1-{2-[3-(5-{3-chloro-4-[(1-methylethyl)oxy]phenyl}-1,2,4-thiadiazol-3-yl)-2-methylphenyl]ethyl}-4-piperidinecarboxylic acid;

1-{2-[3-(5-{5-chloro-6-[(1-methylethyl)oxy]-3-pyridinyl}-1,2,4-thiadiazol-3-yl)-2-ethylphenyl]ethyl}-4-piperidinecarboxylic acid;

1-[2-(3-{5-[3-cyano-4-(2-methylpropyl)phenyl]-1,2,4-thiadiazol-3-yl}-2-ethylphenyl)ethyl]-L-proline;

1-[2-(3-{5-[3-cyano-4-(2-methylpropyl)phenyl]-1,2,4-thiadiazol-3-yl}-2-ethylphenyl)ethyl]-D-proline;

1-[2-(3-{5-[3-cyano-4-(2-methylpropyl)phenyl]-1,2,4-thiadiazol-3-yl}-2-ethylphenyl)ethyl]-3-pyrrolidinecarboxylic acid;

(3S)-1-[2-(3-{5-[3-cyano-4-(2-methylpropyl)phenyl]-1,2,4-thiadiazol-3-yl}-2-ethylphenyl)ethyl]-3-pyrrolidinecarboxylic acid;

(3S)-1-[2-(3-{5-[3-cyano-4-(2-methylpropyl)phenyl]-1,2,4-thiadiazol-3-yl}-2-ethylphenyl)ethyl]-3-piperidinecarboxylic acid;

1-{[3-(2-{3-cyano-4-[(1-methylethyl)oxy]phenyl}-1,3-thiazol-5-yl)-2-ethylphenyl]methyl}-L-proline;

1-{[3-(2-{3-cyano-4-[(1-methylethyl)oxy]phenyl}-1,3-thiazol-5-yl)-2-ethylphenyl]methyl}-D-proline;

1-{[3-(2-{3-cyano-4-[(1-methylethyl)oxy]phenyl}-1,3-thiazol-5-yl)-2-ethylphenyl]methyl}-3-pyrrolidinecarboxylic acid;

(3S)-1-{[3-(2-{3-cyano-4-[(1-methylethyl)oxy]phenyl}-1,3-thiazol-5-yl)-2-ethylphenyl]methyl}-3-pyrrolidinecarboxylic acid;

(4R)-1-{[3-(2-{3-cyano-4-[(1-methylethyl)oxy]phenyl}-1,3-thiazol-5-yl)-2-ethylphenyl]methyl}-4-hydroxy-L-proline;

1-{[3-(2-{3-cyano-4-[(1-methylethyl)oxy]phenyl}-1,3-thiazol-5-yl)-2-ethylphenyl]methyl}-3-piperidinecarboxylic acid;

(1-{[3-(2-{3-cyano-4-[(1-methylethyl)oxy]phenyl}-1,3-thiazol-5-yl)-2-ethylphenyl]methyl}-4-piperidinyl)acetic acid;

1-{2-[3-(2-{3-cyano-4-[(1-methylethyl)oxy]phenyl}-1,3-thiazol-5-yl)-2-ethylphenyl]ethyl}-L-proline;

1-{2-[3-(2-{3-cyano-4-[(1-methylethyl)oxy]phenyl}-1,3-thiazol-5-yl)-2-ethylphenyl]ethyl}-D-proline;

1-{2-[3-(2-{3-cyano-4-[(1-methylethyl)oxy]phenyl}-1,3-thiazol-5-yl)-2-ethylphenyl]ethyl}-3-pyrrolidinecarboxylic acid;

(4R)-1-{2-[3-(2-{3-cyano-4-[(1-methylethyl)oxy]phenyl}-1,3-thiazol-5-yl)-2-ethylphenyl]ethyl}-4-hydroxy-L-proline;

1-{2-[3-(2-{3-cyano-4-[(1-methylethyl)oxy]phenyl}-1,3-thiazol-5-yl)-2-ethylphenyl]ethyl}-3-piperidinecarboxylic acid;

1-{3-[3-(2-{3-cyano-4-[(1-methylethyl)oxy]phenyl}-1,3-thiazol-5-yl)-2-ethylphenyl]propyl}-3-azetidinecarboxylic acid;

1-{3-[3-(2-{3-cyano-4-[(1-methylethyl)oxy]phenyl}-1,3-thiazol-5-yl)-2-ethylphenyl]propyl}-3-pyrrolidinecarboxylic acid;

3-{4-[3-(5-{3-chloro-4-[(1-methylethyl)oxy]phenyl}-1,3,4-thiadiazol-2-yl)-2-ethylphenyl]-1-piperidinyl}propanoic acid;

3-[4-(3-{5-[3-cyano-4-(2-methylpropyl)phenyl]-1,3,4-thiadiazol-2-yl}-2-ethylphenyl)-1-piperidinyl]propanoic acid;

4-{4-[3-(5-{3-chloro-4-[(1-methylethyl)oxy]phenyl}-1,3,4-thiadiazol-2-yl)-2-ethylphenyl]-1-piperidinyl}butanoic acid;

4-[4-(3-{5-[3-cyano-4-(2-methylpropyl)phenyl]-1,3,4-thiadiazol-2-yl}-2-ethylphenyl)-1-piperidinyl]butanoic acid;

{4-[3-(5-{3-chloro-4-[(1-methylethyl)oxy]phenyl}-1,2,4-thiadiazol-3-yl)-2-ethylphenyl]-1-piperidinyl}acetic acid;

3-{4-[3-(5-{3-chloro-4-[(1-methylethyl)oxy]phenyl}-1,2,4-thiadiazol-3-yl)-2-ethylphenyl]-1-piperidinyl}propanoic acid;

3-[4-(3-{5-[3-cyano-4-(2-methylpropyl)phenyl]-1,2,4-thiadiazol-3-yl}-2-ethylphenyl)-1-piperidinyl]propanoic acid;

4-{4-[3-(5-{3-chloro-4-[(1-methylethyl)oxy]phenyl}-1,2,4-thiadiazol-3-yl)-2-ethylphenyl]-1-piperidinyl}butanoic acid;

4-[4-(3-{5-[3-cyano-4-(2-methylpropyl)phenyl]-1,2,4-thiadiazol-3-yl}-2-ethylphenyl)-1-piperidinyl]butanoic acid;

4-[3-(3-{5-[3-cyano-4-(2-methylpropyl)phenyl]-1,2,4-thiadiazol-3-yl}-2-ethylphenyl)-1-azetidinyl]butanoic acid;

(4-{[3-(5-{3-chloro-4-[(1-methylethyl)oxy]phenyl}-1,2,4-thiadiazol-3-yl)-2-ethylphenyl]methyl}-1-piperidinyl)acetic acid;

3-(4-{[3-(5-{3-chloro-4-[(1-methylethyl)oxy]phenyl}-1,2,4-thiadiazol-3-yl)-2-ethylphenyl]methyl}-1-piperidinyl)propanoic acid; or salts thereof.

One suitable compound of formula (I) is 1-{[3-(5-{3-chloro-4-[(1-methylethyl)oxy]phenyl}-1,3,4-thiadiazol-2-yl)-2-ethylphenyl]methyl}-3-azetidinecarboxylic acid or salts thereof.

One embodiment of the invention is 1-{[3-(5-{3-chloro-4-[(1-methylethyl)oxy]phenyl}-1,3,4-thiadiazol-2-yl)-2-ethylphenyl]methyl}-3-azetidinecarboxylic acid hydrochloride.

Pharmaceutically acceptable derivatives of compounds of formula (I) include any pharmaceutically acceptable salt, ester or salt of such ester of a compound of formula (I) which, upon administration to the recipient is capable of providing (directly or indirectly) a compound of formula (I) or an active metabolic or residue thereof.

The compounds of formula (I) can form salts. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic, trifluoroacetic or naphthalenesulfonic acid. Certain of the compounds of formula (I) may form acid addition salts with one or more equivalents of the acid. The present invention includes within its scope all possible stoichiometric and non-stoichiometric forms. Salts may also be prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropylamine, tris(hydroxymethyl)aminomethane (TRIS, trometamol) and the like. Salts may also be formed from basic ion exchange resins, for example polyamine resins. When the compound of the present invention is basic, salts may be prepared from pharmaceutically acceptable acids, including inorganic and organic acids. Such acids include acetic, benzenesulfonic, benzoic, camphorsulfonic, citric, ethanesulfonic, ethanedisulfonic, fumaric, gluconic, glutamic, hydrobromic, hydrochloric, isethionic, lactic, maleic, malic, mandelic, methanesulfonic, mucic, pamoic, pantothenic, phosphoric, propionic, succinic, sulfuric, tartaric, p-toluenesulfonic acid, and the like.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

Included within the scope of the invention are all salts, solvates, hydrates, complexes, polymorphs, prodrugs, radiolabelled derivatives, stereoisomers and optical isomers of the compounds of formula (I).

Pharmaceutically acceptable salts may be prepared conventionally by reaction with the appropriate acid, base, acid derivative or base derivative.

The potencies and efficacies of the compounds of this invention for the S1P1 receptor can be determined by S1P1 assay performed on the human cloned receptor as described herein. Compounds of formula (I) have demonstrated agonist activity at the S1P1 receptor, using functional assays described herein.

Compounds of formula (I) and their pharmaceutically acceptable salts are therefore of use in the treatment of conditions or disorders which are mediated via the S1P1 receptor. In particular the compounds of formula (I) and their pharmaceutically acceptable salts are of use in the treatment of multiple sclerosis, autoimmune diseases, chronic inflammatory disorders, asthma, inflammatory neuropathies, Gillian-Barré syndrome, neuromyelitis optica (Devic's disease) and myasthenia gravis arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes.

Compounds of formula (I) and their pharmaceutically acceptable salts are therefore of use in the treatment of multiple sclerosis.

Compounds of formula (I) and their pharmaceutically acceptable salts may also be of use in the treatment of Parkinson's Disease, Alzheimer's disease, Huntington's chorea, amyotrophic lateral sclerosis, spinal muscular atrophy, polyglutamine expansion disorders, vascular dementia, Down's syndrome, HIV dementia, dementia, ocular diseases including glaucoma, aged related macular degeneration, cataracts, traumatic eye injury, diabetic retinopathy, traumatic brain injury, stroke, tauopathies and hearing loss.

It is to be understood that "treatment" as used herein includes prophylaxis as well as alleviation of established symptoms.

Thus the invention also provides a compound of formula (I) or a pharmaceutically acceptable salt thereof, for use as a therapeutic substance, in particular in the treatment of the conditions or disorders mediated via the S1P1 receptor. In particular the invention provides a compound of formula (I) or a pharmaceutically acceptable salt thereof for use as a therapeutic substance in the treatment of multiple sclerosis, autoimmune diseases, chronic inflammatory disorders, asthma, inflammatory neuropathies, Gillian-Barré syndrome, neuromyelitis optica (Devic's disease) and myasthenia gravis, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes. The invention further provides a method of treatment of conditions or disorders in mammals including humans which can be mediated via the S1P1 receptor, which comprises administering to the sufferer a therapeutically safe and effective amount of a compound of formula (I) or a pharmaceutically acceptable salt thereof.

Compounds of formula (I) and their pharmaceutically acceptable salts are of use as therapeutic substances in the treatment of multiple sclerosis.

In another aspect, the invention provides for the use of a compound of formula (I) or a pharmaceutically acceptable salt thereof in the manufacture of a medicament for use in the treatment of the conditions or disorders mediated via the S1P1 receptor The invention provides a method of treatment of multiple sclerosis, which comprises administering to the sufferer a therapeutically safe and effective amount of a compound of formula (I) or a pharmaceutically acceptable salt thereof.

In order to use the compounds of formula (I) and pharmaceutically acceptable salts thereof in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salts thereof and a sterile vehicle. Formulations for injection may be presented in unit dosage form e.g. in ampoules or in multi-dose, utilising a compound of the invention or pharmaceutically acceptable derivatives thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) or pharmaceutically acceptable salts thereof may also be formulated in rectal compositions such as suppositories or retention enemas, e.g. containing conventional suppository bases such as cocoa butter or other glycerides.

The compounds of formula (I) or pharmaceutically acceptable salts thereof may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of formula (I) or pharmaceutically acceptable salts thereof, may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose).

The compounds of formula (I) or pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, 1.0 to 500 mg or 1.0 to 200 mg and such unit doses may be administered more than once a day, for example two or three times a day.

Compounds of formula (I) or pharmaceutically acceptable salts thereof may be used in combination preparations. For example, the compounds of the invention may be used in combination with cyclosporin A, methotrexate, steroids, rapamycin, proinflammatory cytokine inhibitors, immuno-modulators including biologicals or other therapeutically active compounds.

The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^{3}H$, $^{11}C$, $^{14}C$, $^{18}F$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{8}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula (I) and following of this invention can generally be prepared by carrying out the procedures disclosed in the Schemes and/or in the Examples below, by substituting a readily available isotopically labelled reagent for a non-isotopically labeled reagent.

In a further aspect, this invention provides processes for preparation of a compound of formula (I).

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

Abbreviations

| | |
|---|---|
| g - | grams |
| mg - | milligrams |
| mL - | milliliters |
| min - | minute |
| h - | hour |
| ul - | microliters |
| MeCN - | acetonitrile |
| EtOAc/EA - | ethyl acetate |
| DCM - | dichloromethane |
| DME - | 1,2-bis(methyloxy)ethane |
| DMF - | N,N-dimethylformamide |
| DMSO - | dimethylsulphoxide |
| PE - | petroleum ether |
| i-PrOH - | isopropylalcohol |
| THF - | tetrahydrofuran |

-continued

| | |
|---|---|
| NaH - | sodium hydride |
| NaOH - | sodium hydroxide |
| NaHCO$_3$- | sodium bicarbonate |
| Na$_2$S$_2$O$_3$- | sodium thiosulfate |
| Na$_2$SO$_4$- | sodium sulfate |
| LiOH- | lithium hydroxide |
| Cs$_2$CO$_3$- | cesium carbonate |
| K$_2$CO$_3$- | potassium carbonate |
| LDA - | lithium diisopropylamide |
| i-PrMgBr - | isopropylmagnesium bromideMgSO$_4$- magnesium sulfate |
| Zn(CN)$_2$- | zinc(II) cyanide |
| DIPEA - | diisopropyl ethylamine |
| TMSCl - | chloro trimethylsilane |
| n-BuLi- | n-butyllithium |
| CBr$_4$ - | carbon tetrabromide |
| Br$_2$ - | bromine |
| POCl$_3$ - | phosphorus oxochloride |
| Pd(PPh$_3$)$_4$ | tetrakis(triphenylphosphine)palladium(0) |
| PdCl$_2$(dPPf)-CH$_2$Cl$_2$ - | [1,1'-bis(diphenylphosphino)ferrocene] palladium(0) dichloride dichloromethane complex (1:1) |
| X-phos - | 2-dicyclohexylphosphino-2',4',6'-triisopropylbiphenyl |
| brine - | saturated aqueous sodium chloride solution |
| AcOH - | acetic acid |
| HCl - | hydrochloride |
| HBr - | hydrobromide |
| NH$_4$Cl - | ammonium chloride |
| pH/PH - | potential for hydrogen ion concentration |
| ° C. - | degrees Celsius |
| M - | Molar |
| N - | Normal |
| H - | proton |
| s - | singlet |
| d - | doublet |
| dd - | doublet doublet |
| t - | triplet |
| q - | quartet |
| m - | multiplet |
| br - | broad |
| MHz - | megahertz |
| CDCl$_3$ - | deuterated chloroform |
| MeOD - | deuterated methanol |
| DMSO-d$_6$ - | deuterated dimethylsulphoxide |
| LCMS - | Liquid Chromatography Mass Spectrometry |
| LC/MS - | Liquid Chromatography Mass Spectrometry |
| MS - | mass spectrometry |
| ES - | Electrospray |
| M + H$^+$ - | mass ion + H$^+$ |
| MDAP - | mass directed automated preparative liquid chromatography. |
| sat. - | saturated |

General Chemistry Section

The intermediates for the preparation of the examples may not necessarily have been prepared from the specific batch of precursor described.

As will be understood by the skilled chemist, references to preparations carried out in a similar manner to, or by the general method of, other preparations, may encompass variations in routine parameters such as time, temperature, work up conditions, misor changes in reagent amounts etc.

Reactions involving metal hydrides including lithium hydride, lithium aluminium hydride, di-isobutylaluminium hydride, sodium hydride, sodium borohydride and sodium triacetoxyborohydride are carried out under argon or other inert gas.

Chromatography

Unless stated otherwise, all chromatography was carried out using silica columns.

LCMS

1) Acidic Condition:
   Mobile phase: water containing 0.05% TFA/acetonitrile
   Column: XBridge™ C18 30×100 mm—5 microns
   Detection: MS and photodiode array detector (PDA)
2) Basic Condition:
   Mobile phase: water containing 0.08% NH$_4$HCO$_3$/acetonitrile
   Column: XBridge™ C18 30×100 mm—5 microns;
   Detection: MS and photodiode array detector (PDA)

MDAP

1) Acidic Condition 1:
   Instrument: Waters instrument
   Column: Sunfire Prep C18 column (5 um, 19×50 mm)
   Mobile phase: water containing 0.05% TFA/acetonitrile.
2) Acidic Condition 2:
   Instrument: Gilson GX-281
   Column: Sunfire prep C18 OBD; 5 um, 100 mm*30 mm;
   Mobile phase: A: 0.05% TFA/H$_2$O; B: MeCN;
3) Basic Condition 1:
   Instrument: Waters instrument
   Column: Xbridge Prep C18 column (5 um, 19×50 mm)
   Mobile phase: water containing 0.04% ammonia/acetonitrile.
4) Basic Condition 2:
   Instrument: Gilson 281(PHG-005);
   Column: Shimadzu PRC-ODS 20×250 mm, 15 um two connected in series;
   Mobile phase: A: 10 mM NH$_4$HCO$_3$ B:MeCN;
5) Basic Condition 3:
   Instrument: Gilson GX-281;
   Column: Agela Durashell RP 21.5*250 mm 10 μm;
   Mobile phase: A: 0.04% NH$_3$H$_2$O/water; B: CH$_3$CN;

Description for D1

4-[(1-methylethyl)oxy]-3-(trifluoromethyl)benzonitrile (D1)

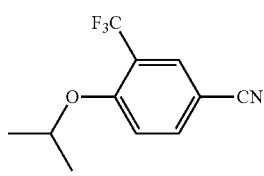 [SMILES: CC(C)Oc1ccc(C#N)cc1C(F)(F)F]

To a solution of 4-fluoro-3-(trifluoromethyl)benzonitrile (10 g), i-PrOH (8.15 mL) in tetrahydrofuran (THF) (90 mL) stirred under nitrogen at −10° C. was added solid NaH (3.46 g) portionwise during 30 min. The reaction mixture was stirred at −10° C. for 6 h. The reaction mixture was quenched with water, partitioned between ether (100 mL) and water (50 mL). The organic phase was dried over magnesium sulphate and evaporated in vacuo to give the crude product 4-[(1-methylethyl)oxy]-3-(trifluoromethyl)benzonitrile (D10) (15 g).

Description for D2

4-[(1-methylethyl)oxy]-3-(trifluoromethyl)benzoic acid (D2)

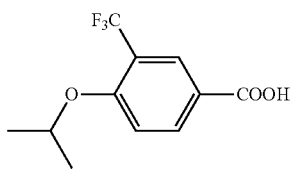 [SMILES: CC(C)Oc1ccc(C(=O)O)cc1C(F)(F)F]

To a solution of 4-[(1-methylethyl)oxy]-3-(trifluoromethyl)benzonitrile (D1) (15 g) in ethanol (150 mL) was added 5M NaOH aqueous solution (41.9 mL) under nitrogen. The reaction mixture was heated to 90° C. for 8 h. After cooling the reaction, the mixture was concentrated, treated with 2N HCl, extracted with EtOAc (200 mL), dried and concentrated to afford 4-[(1-methylethyl)oxy]-3-(trifluoromethyl)benzoic acid (D2) (13.4 g). δH (CDCl$_3$, 400 MHz): 1.41 (6H, d), 4.76 (1H, m), 7.05 (1H, d), 8.22 (1H, m), 8.33 (1H, d). MS (ES): C$_{11}$H$_{11}$F$_3$O$_3$ requires 248. found 249.1 (M+H$^+$).

Description for D3

5-[4-[(1-methylethyl)oxy]-3-(trifluoromethyl)phenyl]-1,3,4-thiadiazol-2-amine (D3)

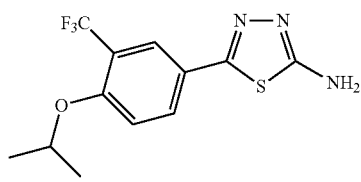 [SMILES: CC(C)Oc1ccc(-c2nnc(N)s2)cc1C(F)(F)F]

To a suspension 4-[(1-methylethyl)oxy]-3-(trifluoromethyl)benzoic acid (D2) (3 g) in POCl$_3$ (11.27 mL) was added hydrazinecarbothioamide (1.652 g). The reaction mixture was heated at 90° C. for 3 h. The reaction was quenched with ice water, the pH value was adjusted to about 9 with NaOH solid. The mixture was extracted with EA/THF for 3 times. The combined organic layers were washed with brine, dried over anhydrous magnesium sulfate and concentrated to afford 5-[4-[(1-methylethyl)oxy]-3-(trifluoromethyl)phenyl]-1,3,4-thiadiazol-2-amine (D3) (4.41 g). MS (ES): C$_{12}$H$_{12}$F$_3$N$_3$OS requires 303. found 304.1 (M+H$^+$).

Description for D4

2-bromo-5-[4-[(1-methylethyl)oxy]-3-(trifluoromethyl)phenyl]-1,3,4-thiadiazole (D4)

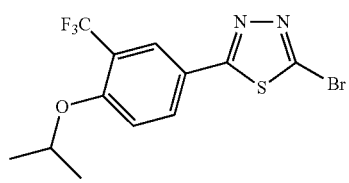 [SMILES: CC(C)Oc1ccc(-c2nnc(Br)s2)cc1C(F)(F)F]

To a suspension of copper(II) bromide (1.473 g) in acetonitrile (10 mL) was added 1,1-dimethylethyl nitrite (0.791 mL). Then a solution of 5-[4-[(1-methylethyl)oxy]-3-(trifluoromethyl)phenyl]-1,3,4-thiadiazol-2-amine (D3) (1 g) in acetonitrile (10 ml) was added dropwise at 0° C. The reaction mixture was stirred at 0° C. for 1 h. Sat. aq. NH$_4$Cl was added to quench the reaction. The mixture was extracted with EA for 3 times, the combined organic layers were washed with brine, dried over anhydrous sodium sulfate and concentrated, the residue was purified by column chromatography to give 2-bromo-5-[4-[(1-methylethyl)oxy]-3-(trifluoromethyl)phenyl]-1,3,4-thiadiazole (D4) (634 mg) as a yellow solid. MS (ES): $C_{12}H_{10}BrF_3N_2OS$ requires 366. found 367.0 (M+H$^+$).

Description for D5

2-ethyl-3-(4,4,5,5-tetramethyl-1,3,2-dioxaborolan-2-yl)benzaldehyde (D5)

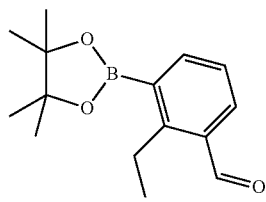 [SMILES: CCc1c(C=O)cccc1B1OC(C)(C)C(C)(C)O1]

To a solution of 3-bromo-2-ethylbenzaldehyde (2 g) in N,N-dimethylformamide (DMF) (20 mL) was added 4,4,4',4',5,5,5',5'-octamethyl-2,2'-bi-1,3,2-dioxaborolane (3.10 g), potassium acetate (2.76 g) and PdCl$_2$(dppf)-CH$_2$Cl$_2$ adduct (1.150 g). The reaction mixture was heated to 80° C. overnight. The solvent was removed in vacuo and the residue was purified by column chromatography to afford 2-ethyl-3-(4,4,5,5-tetramethyl-1,3,2-dioxaborolan-2-yl)benzaldehyde (D5) (1.27 g). MS (ES): $C_{15}H_{21}BO_3$ requires 260. found 261.2 (M+H$^+$).

Description for D6

2-ethyl-3-{5-[4-[(1-methylethyl)oxy]-3-(trifluoromethyl)phenyl]-1,3,4-thiadiazol-2-yl}benzaldehyde (D6)

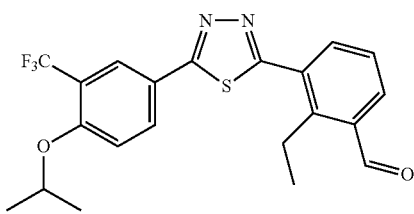 [SMILES: CCc1c(C=O)cccc1-c1nnc(-c2ccc(OC(C)C)c(C(F)(F)F)c2)s1]

To a solution of 2-bromo-5-[4-[(1-methylethyl)oxy]-3-(trifluoromethyl)phenyl]-1,3,4-thiadiazole (D4) (100 mg), 2-ethyl-3-(4,4,5,5-tetramethyl-1,3,2-dioxaborolan-2-yl)benzaldehyde (D5) (85 mg) and tripotassium phosphate (145 mg) in N,N-dimethylformamide (DMF) (6 mL) and water (1.5 mL) stirred under nitrogen at room temperature was added Pd(Ph$_3$P)$_4$ (31.5 mg). The reaction vessel was sealed and heated under microwave at 130° C. for 8 min. After cooling the reaction, water was added to quench the reaction. After filtered through the celite, the filtrate was partitioned between the organic and aqueous layers. The aqueous layer was extracted with EA for 3 times. The combined organic layers were washed with brine, dried over anhydrous sodium sulfate. The dried solution was concentrated, and purified by column chromatography to afford 2-ethyl-3-{5-[4-[(1-methylethyl)oxy]-3-(trifluoromethyl)phenyl]-1,3,4-thiadiazol-2-yl}benzaldehyde (D6) (60.4 mg). MS (ES): $C_{21}H_{19}F_3N_2O_2S$ requires 420. found 421.1 (M+H$^+$).

Description for D7 ethyl 1-[(2-ethyl-3-{5-[4-[(1-methylethyl)oxy]-3-(trifluoromethyl)phenyl]-1,3,4-thiadiazol-2-yl}phenyl)methyl]-4-piperidinecarboxylate (D7)

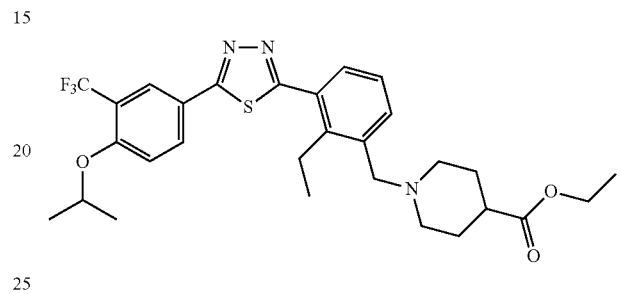

To a solution of 2-ethyl-3-{5-[4-[(1-methylethyl)oxy]-3-(trifluoromethyl)phenyl]-1,3,4-thiadiazol-2-yl}benzaldehyde (D6) (54 mg) and ethyl 4-piperidinecarboxylate (101 mg) in ethanol (10 mL) stirred at room temperature was added AcOH (0.037 mL). The reaction mixture was stirred at room temperature for 10 min. Then the solvent was removed by evaporation. To the residue was added dichloromethane (DCM) (10 mL) and sodium triacetoxyborohydride (82 mg). Stirring continued for 2 h. Water was added to quench the reaction, and DCM was removed by evaporation. The mixture was extracted by EA for 3 times. The combined organic phases were washed by brine, dried over anhydrous Na$_2$SO$_4$. The dried solution was filtered and concentrated to afford the crude product ethyl 1-[(2-ethyl-3-{5-[4-[(1-methylethyl)oxy]-3-(trifluoromethyl)phenyl]-1,3,4-thiadiazol-2-yl}phenyl)methyl]-4-piperidinecarboxylate (D7) (72.1 mg). MS (ES): $C_{29}H_{34}F_3N_3O_3S$ requires 561. found 562.1 (M+H$^+$).

Description for D8 methyl 1-[(2-ethyl-3-{5-[4-[(1-methylethyl)oxy]-3-(trifluoromethyl)phenyl]-1,3,4-thiadiazol-2-yl}phenyl)methyl]-3-azetidinecarboxylate (D8)

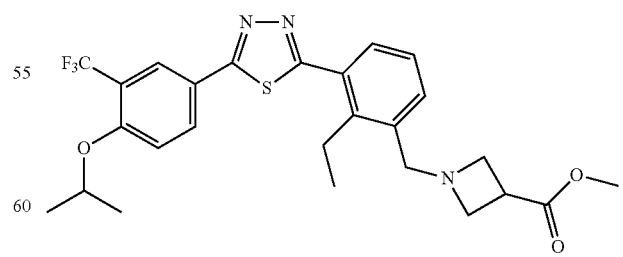

To a solution of 2-ethyl-3-{5-[4-[(1-methylethyl)oxy]-3-(trifluoromethyl)phenyl]-1,3,4-thiadiazol-2-yl}benzaldehyde (D6) (52 mg) and methyl 3-azetidinylacetate (109 mg) in methanol (10.00 mL) stirred at room temperature was added sodium acetate (55 mg) and AcOH (0.035 mL). The reaction mixture was stirred at room temperature for 10 min. After that, the solvent was removed by evaporation. The residue was dissolved in dichloromethane (DCM) (10 mL), sodium triacetoxyborohydride (79 mg) was added. Stirring continued for 2 h. Water was added to quench the reaction, and DCM was removed by evaporation. The mixture was extracted by EA for 3 times. The combined organic solution was washed by brine, dried over anhydrous $Na_2SO_4$. The dried solution was filtered and concentrated to afford methyl 1-[(2-ethyl-3-{5-[4-[(1-methylethyl)oxy]-3-(trifluoromethyl)phenyl]-1,3,4-thiadiazol-2-yl}phenyl)methyl]-3-azetidinecarboxylate (D8) (64.3 mg), which was used for the next without further purification. MS (ES): $C_{26}H_{28}F_3N_3O_3S$ requires 519. found 520.2 (M+H+).

Description for D9

5-{3-chloro-4-[(1-methylethyl)oxy]phenyl}-1,3,4-thiadiazol-2-amine (D9)

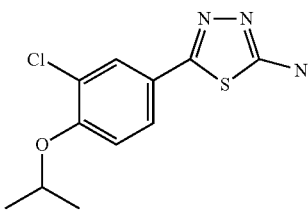 [SMILES: CC(C)Oc1ccc(-c2nnc(N)s2)cc1Cl]

The mixture of 3-chloro-4-[(1-methylethyl)oxy]benzoic acid (5 g), hydrazinecarbothioamide (2.229 g) in phosphoric trichloride (21.43 g) was stirred at 75° C. for 3 h. Concentrated the mixture in vacuum to remove $POCl_3$, the residue was poured into crush ice. Basified the mixture with aqueous NaOH. Extracted it with EA twice. The EA layer was concentrated in vacuum to give crude product 5-{3-chloro-4-[(1-methylethyl)oxy]phenyl}-1,3,4-thiadiazol-2-amine (D9) (7.5 g), which was used in the next step without further purification. MS (ES): $C_{11}H_{12}ClN_3OS$ requires 269. found 270.1 (M+H+).

Description for D10

2-bromo-5-{3-chloro-4-[(1-methylethyl)oxy]phenyl}-1,3,4-thiadiazole (D10)

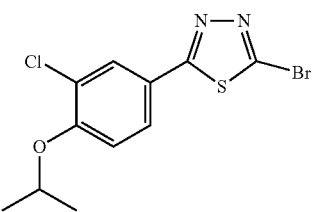 [SMILES: CC(C)Oc1ccc(-c2nnc(Br)s2)cc1Cl]

The mixture of crude 5-{3-chloro-4-[(1-methylethyl)oxy]phenyl}-1,3,4-thiadiazol-2-amine (D9) (6.25 g), copper(II) bromide (10.35 g) in acetonitrile (60 mL) was stirred at room temperature, then 1,1-dimethylethyl nitrite (5.51 mL) was added. The mixture was stirred at room temperature for 3 h. It was treated with EA and aqueous HCl, the EA layer was combined and purified by column chromatography (PE/EA, 9/1) to give 2-bromo-5-{3-chloro-4-[(1-methylethyl)oxy]phenyl}-1,3,4-thiadiazole (D10) (4.76 g). MS (ES): $C_{11}H_{10}BrClN_2OS$ requires 333. found 334.0 (M+H+).

Description for D11

3-(5-{3-chloro-4-[(1-methylethyl)oxy]phenyl}-1,3,4-thiadiazol-2-yl)-2-ethylbenzaldehyde (D11)

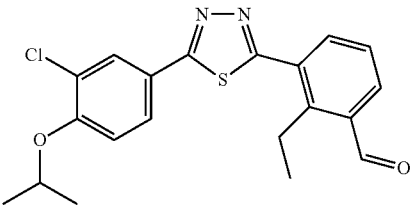 [SMILES: CCc1c(C=O)cccc1-c1nnc(-c2ccc(OC(C)C)c(Cl)c2)s1]

To a suspension of 2-bromo-5-{3-chloro-4-[(1-methylethyl)oxy]phenyl}-1,3,4-thiadiazole (D10) (0.5 g), 2-ethyl-3-(4,4,5,5-tetramethyl-1,3,2-dioxaborolan-2-yl)benzaldehyde (D5) (0.468 g) and tripotassium phosphate (0.795 g) in N,N-dimethylformamide (DMF) (10 mL) and $Pd(Ph_3P)_4$ (0.173 g). The reaction mixture was degassed and then the reaction vial was sealed and heated under microwave at 130° C. for 10 min. Water was then added to the reaction mixture. The mixture was extracted with EA. The combined organic solution was dried over anhydrous sodium sulphate. After filtration and concentration, the residue was purified by column chromatography to give 3-(5-{3-chloro-4-[(1-methylethyl)oxy]phenyl}-1,3,4-thiadiazol-2-yl)-2-ethylbenzaldehyde (D11) (164 mg). MS (ES): $C_{20}H_{19}ClN_2O_2S$ requires 386. found 387.1 (M+H+).

Description for D12 ethyl 1-{[3-(5-{3-chloro-4-[(1-methylethyl)oxy]phenyl}-1,3,4-thiadiazol-2-yl)-2-ethylphenyl]methyl}-4-piperidinecarboxylate (D12)

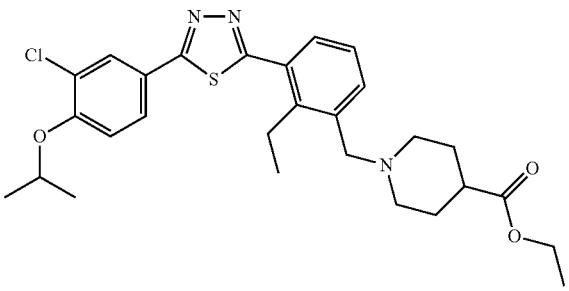 [SMILES: CCOC(=O)C1CCN(Cc2cccc(-c3nnc(-c4ccc(OC(C)C)c(Cl)c4)s3)c2CC)CC1]

To a solution of 3-(5-{3-chloro-4-[(1-methylethyl)oxy]phenyl}-1,3,4-thiadiazol-2-yl)-2-ethylbenzaldehyde (D11) (44 mg) and ethyl 4-piperidinecarboxylate (89 mg) in methanol (10.00 mL) stirred at room temperature was added sodium acetate (55 mg) and AcOH (0.033 mL). The reaction mixture was stirred at room temperature for 10 min. And the solvent was removed by evaporation. The residue was dissolved in dichloromethane (DCM) (10 mL), and sodium triacetoxyborohydride (72.3 mg) was added. Stirring continued for 2 h. Water was added to quench the reaction, and DCM was removed by evaporation. The mixture was extracted by EA for 3 times. The combined organic solution was washed by brine, dried over anhydrous $Na_2SO_4$. The dried solution was filtered and concentrated to afford ethyl 1-{[3-(5-{3-chloro-4-[(1-methylethyl)oxy]phenyl}-1,3,4-thiadiazol-2-yl)-2-ethylphenyl]methyl}-4-piperidinecarboxylate (D12) (60.1 mg). MS (ES): $C_{28}H_{34}ClN_3O_3S$ requires 527. found 528.2 (M+H+).

Description for D13 methyl 1-{[3-(5-{3-chloro-4-[(1-methylethyl)oxy]phenyl}-1,3,4-thiadiazol-2-yl)-2-ethylphenyl]methyl}-3-azetidinecarboxylate (D13)

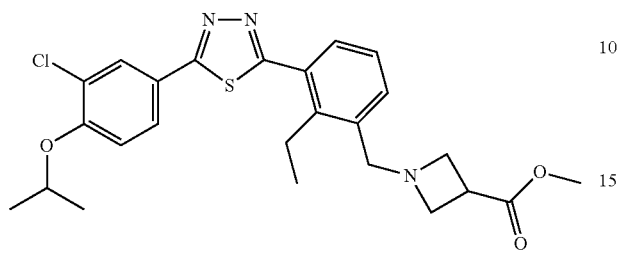

To a solution of 3-(5-{3-chloro-4-[(1-methylethyl)oxy]phenyl}-1,3,4-thiadiazol-2-yl)-2-ethylbenzaldehyde (D11) (43 mg) and methyl 3-azetidinylacetate (92 mg) in methanol (10.00 mL) stirred at room temperature was added sodium acetate (45.6 mg) and AcOH (0.032 mL). The reaction mixture was stirred at room temperature for 10 min. Then the solvent was removed by evaporation. The residue was dissolved in dichloromethane (DCM) (10 mL), and sodium triacetoxyborohydride (70.7 mg) was added. Stirring continued for 2 h. Water was added to quench the reaction, and DCM was removed by evaporation. The mixture was extracted by EA 3 times. The combined organic solution was washed by brine, dried over anhydrous $Na_2SO_4$. The dried solution was filtered and concentrated to give crude methyl 1-{[3-(5-{3-chloro-4-[(1-methylethyl)oxy]phenyl}-1,3,4-thiadiazol-2-yl)-2-ethylphenyl]methyl}-3-azetidinecarboxylate (D13) (54 mg). MS (ES): $C_{25}H_{28}ClN_3O_3S$ requires 485. found 486.0 (M+H$^+$).

Description for D14

2-{3-chloro-4-[(1-methylethyl)oxy]phenyl}-5-{2-ethyl-3-[(E)-2-(methyloxy)ethenyl]phenyl}-1,3,4-thiadiazole (D14)

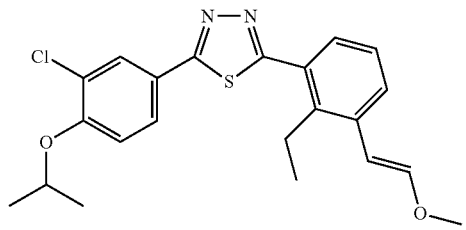 [SMILES: CCc1c(/C=C/OC)cccc1-c1nnc(-c2ccc(OC(C)C)c(Cl)c2)s1]

To a suspension of 2-bromo-5-{3-chloro-4-[(1-methylethyl)oxy]phenyl}-1,3,4-thiadiazole (D10) (300 mg), 2-{2-ethyl-3-[(E)-2-(methyloxy)ethenyl]phenyl}-4,4,5,5-tetramethyl-1,3,2-dioxaborolane (259 mg) and tripotassium phosphate (477 mg) in N,N-dimethylformamide (DMF) (8 mL) and water (2 mL) under nitrogen was added Pd(Ph$_3$P)$_4$ (104 mg). The reaction vessel was sealed and heated under microwave at 120° C. for 10 min. The reaction mixture was extracted with EA for 3 times, the combined organic layers were washed with brine, dried over anhydrous sodium sulfate, the dried solution was concentrated, and purified by column chromatography to afford 2-{3-chloro-4-[(1-methylethyl)oxy]phenyl}-5-{2-ethyl-3-[(E)-2-(methyloxy)ethenyl]phenyl}-1,3,4-thiadiazole (D14) (290 mg) as a yellow oil. MS (ES): $C_{22}H_{23}ClN_2O_2S$ requires 414. found 415.2 (M+H$^+$).

Description for D15

[3-(5-{3-chloro-4-[(1-methylethyl)oxy]phenyl}-1,3,4-thiadiazol-2-yl)-2-ethylphenyl]acetaldehyde (D15)

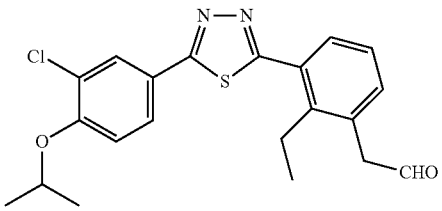 [SMILES: CCc1c(CC=O)cccc1-c1nnc(-c2ccc(OC(C)C)c(Cl)c2)s1]

To a solution of 2-{3-chloro-4-[(1-methylethyl)oxy]phenyl}-5-{2-ethyl-3-[(E)-2-(methyloxy)ethenyl]phenyl}-1,3,4-thiadiazole (D14) (100 mg) in tetrahydrofuran (THF) (15 mL) stirred under nitrogen at room temperature was added 2M HCl/water (0.3 mL). The reaction mixture was stirred at 70° C. for 4 h. The reaction mixture was concentrated to afford the crude product [3-(5-{3-chloro-4-[(1-methylethyl)oxy]phenyl}-1,3,4-thiadiazol-2-yl)-2-ethylphenyl]acetaldehyde (D15) (97 mg). MS (ES): $C_{21}H_{21}ClN_2O_2S$ requires 400. found 401.1 (M+H$^+$).

Description for D16 ethyl 1-{2-[3-(5-{3-chloro-4-[(1-methylethyl)oxy]phenyl}-1,3,4-thiadiazol-2-yl)-2-ethylphenyl]ethyl}-4-piperidinecarboxylate (D16)

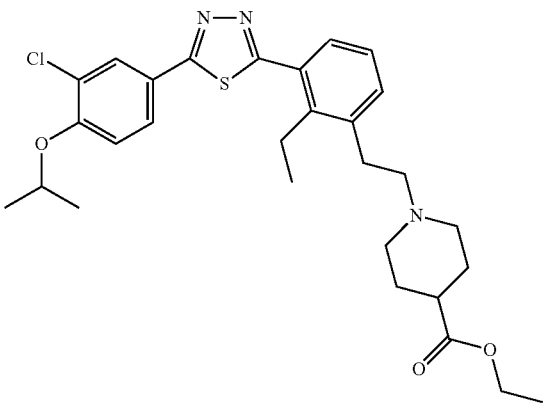 [SMILES: CCOC(=O)C1CCN(CCc2cccc(-c3nnc(-c4ccc(OC(C)C)c(Cl)c4)s3)c2CC)CC1]

To a solution of [3-(5-{3-chloro-4-[(1-methylethyl)oxy]phenyl}-1,3,4-thiadiazol-2-yl)-2-ethylphenyl]acetaldehyde (D15) (97 mg) and ethyl 4-piperidinecarboxylate (234 mg) in ethanol (10.00 mL) stirred at room temperature was added sodium acetate (99 mg) and AcOH (0.069 mL). The reaction mixture was stirred at room temperature for 10 min. The residue was dissolved in dichloromethane (DCM) (10 mL), and sodium triacetoxyborohydride (154 mg) was added. Stirring continued for overnight. Water was added to quench the reaction, and DCM was removed by evaporation. The mixture was extracted by EA for 3 times. The combined organic solution was washed by brine, dried over anhydrous $Na_2SO_4$. The dried solution was filtered and concentrated to give ethyl 1-{2-[3-(5-{3-chloro-4-[(1-methylethyl)oxy]phenyl}-1,3,4- thiadiazol-2-yl)-2-ethylphenyl]ethyl}-4-piperidinecarboxylate (D16) (92 mg), which was used for the next without further purification. MS (ES): $C_{29}H_{35}ClN_3O_3S$ requires 541. found 542.3 (M+H$^+$).

Description for D17 methyl 1-{2-[3-(5-{3-chloro-4-[(1-methylethyl)oxy]phenyl}-1,3,4-thiadiazol-2-yl)-2-ethylphenyl]ethyl}-3-azetidinecarboxylate (D17)

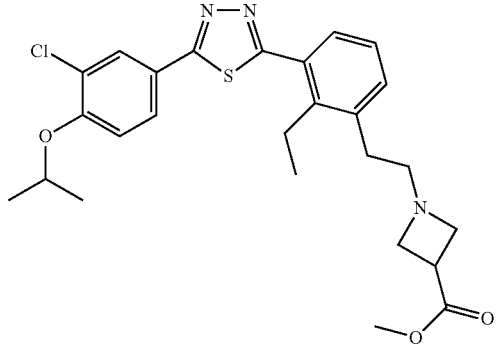 [SMILES: CCc1c(CCN2CC(C(=O)OC)C2)cccc1-c1nnc(-c2ccc(OC(C)C)c(Cl)c2)s1]

To a solution of [3-(5-{3-chloro-4-[(1-methylethyl)oxy]phenyl}-1,3,4-thiadiazol-2-yl)-2-ethylphenyl]acetaldehyde (D15) (73 mg) and methyl 3-azetidinecarboxylate (138 mg) in methanol (10.00 mL) stirred at room temperature was added sodium acetate (74.7 mg) and AcOH (0.15 mL). The reaction mixture was stirred at room temperature for 10 min. The residue was dissolved in dichloromethane (DCM) (10 mL), and sodium triacetoxyborohydride (116 mg) was added. Stirring continued for overnight. Water was added to quench the reaction, and DCM was removed by evaporation. The mixture was extracted by EA for 3 times. The combined organic solution was washed by brine, dried over anhydrous Na$_2$SO$_4$. The dried solution was filtered and concentrated to give methyl 1-{2-[3-(5-{3-chloro-4-[(1-methylethyl)oxy]phenyl}-1,3,4-thiadiazol-2-yl)-2-ethylphenyl]ethyl}-3-azetidinecarboxylate (D17) (18.21 mg). MS (ES): $C_{26}H_{30}ClN_3O_3S$ requires 499. found 500.2 (M+H$^+$).

Description for D18

2-{2-ethyl-3-[(E)-2-(methyloxy)ethenyl]phenyl}-5-[4-[(1-methylethyl)oxy]-3-(trifluoromethyl)phenyl]-1,3,4-thiadiazole (D18)

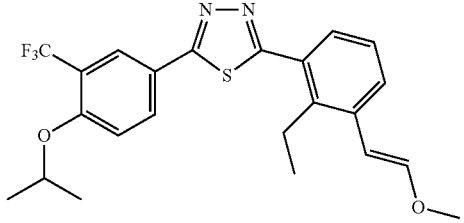 [SMILES: CCc1c(/C=C/OC)cccc1-c1nnc(-c2ccc(OC(C)C)c(C(F)(F)F)c2)s1]

To a suspension of 2-bromo-5-[4-[(1-methylethyl)oxy]-3-(trifluoromethyl)phenyl]-1,3,4-thiadiazole (D4) (55 mg), 2-{2-ethyl-3-[(E)-2-(methyloxy)ethenyl]phenyl}-4,4,5,5-tetramethyl-1,3,2-dioxaborolane (64.8 mg) and tripotassium phosphate (79 mg) in N,N-dimethylformamide (DMF) (4 mL) and water (1 mL) under nitrogen was added Pd(Ph$_3$P)$_4$ (17.31 mg). The reaction vessel was sealed and heated under microwave at 120° C. for 10 min. After cooling the reaction, water was added. The reaction mixture was extracted with EA for 3 times, the combined organic layers were washed with brine, dried over anhydrous sodium sulfate, the dried solution was concentrated, the residue was purified by column chromatography to afford 2-{2-ethyl-3-[(E)-2-(methyloxy)ethenyl]phenyl}-5-[4-[(1-methylethyl)oxy]-3-(trifluoromethyl)phenyl]-1,3,4-thiadiazole (D18) (43 mg) as a yellow oil. MS (ES): $C_{23}H_{23}F_3N_2O_2S$ requires 448. found 449.1 (M+H$^+$).

Description for D19

(2-ethyl-3-{5-[4-[(1-methylethyl)oxy]-3-(trifluoromethyl)phenyl]-1,3,4-thiadiazol-2-yl}phenyl)acetaldehyde (D19)

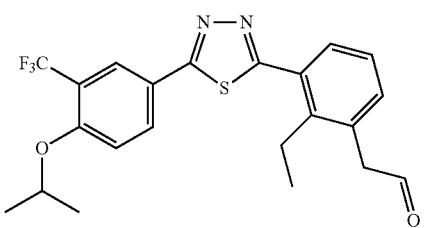 [SMILES: CCc1c(CC=O)cccc1-c1nnc(-c2ccc(OC(C)C)c(C(F)(F)F)c2)s1]

To a solution of 2-{2-ethyl-3-[(E)-2-(methyloxy)ethenyl]phenyl}-5-[4-[(1-methylethyl)oxy]-3-(trifluoromethyl)phenyl]-1,3,4-thiadiazole (D18) (42 mg) in 1,4-dioxane (15 mL) stirred under nitrogen at room temperature was added 6 M HCl/water (15 mL). The reaction mixture was stirred at 20° C. for 5 h. Water was added. EA was used to extracted the aqueous layer for 3 times. The combined organic phases were washed with brine, dried over sodium sulphate and evaporated in vacuo to give the crude product (2-ethyl-3-{5-[4-[(1-methylethyl)oxy]-3-(trifluoromethyl)phenyl]-1,3,4-thiadiazol-2-yl}phenyl)acetaldehyde (D19) (40 mg), which was used directly for the next step. MS (ES): $C_{22}H_{21}F_3N_2O_2S$ requires 434. found 435.0 (M+H$^+$).

Description for D20 methyl 1-[2-(2-ethyl-3-{5-[4-[(1-methylethyl)oxy]-3-(trifluoromethyl)phenyl]-1,3,4-thiadiazol-2-yl}phenyl)ethyl]-3-azetidinecarboxylate (D20)

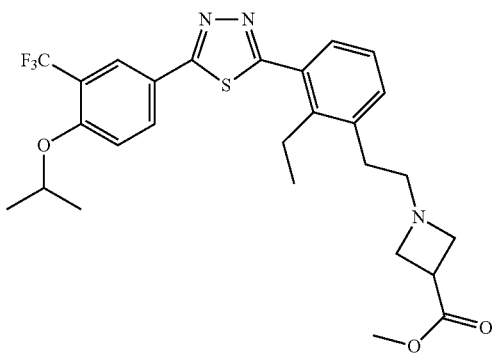 [SMILES: CCc1c(CCN2CC(C(=O)OC)C2)cccc1-c1nnc(-c2ccc(OC(C)C)c(C(F)(F)F)c2)s1]

To a solution of (2-ethyl-3-{5-[4-[(1-methylethyl)oxy]-3-(trifluoromethyl)phenyl]-1,3,4-thiadiazol-2-yl}phenyl)acetaldehyde (D19) (40 mg) and methyl 3-azetidinecarboxylate (53.0 mg) in methanol (10 mL) stirred at room temperature was added sodium acetate (37.8 mg) and AcOH (0.026 mL). The reaction mixture was stirred at room temperature for 10 min. The residue was dissolved in dichloromethane (DCM) (10 mL), and sodium triacetoxyborohydride (58.5 mg) was added. Stirring continued for overnight. Water was added to quench the reaction, and DCM was removed by evaporation. The mixture was extracted by EA for 3 times. The combined organic solution was washed by brine, dried over anhydrous $Na_2SO_4$. The dried solution was filtered and concentrated to afford methyl 1-[2-(2-ethyl-3-{5-[4-[(1-methylethyl)oxy]-3-(trifluoromethyl)phenyl]-1,3,4-thiadiazol-2-yl}phenyl)ethyl]-3-azetidinecarboxylate (D20) (25 mg), which was used for the next without further purification. MS (ES): $C_{27}H_{30}F_3N_3O_3S$ requires 533. found 534.2 (M+H$^+$).

Description for D21 methyl 3-cyano-4-hydroxybenzoate (D21)

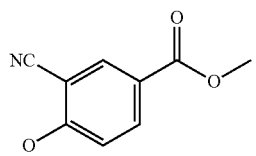

To a solution of methyl 4-hydroxy-3-iodobenzoate (2.78 g) and $Zn(CN)_2$ (1.409 g) in N,N-dimethylformamide (DMF) (30 mL) stirred under nitrogen at room temperature was added $Pd(Ph_3P)_4$ (1.155 g). The reaction mixture was stirred at 140° C. for 12 h. After cooling the reaction, EA (100 mL) and water (40 mL) were added to the solution. After filtration, the filtrate was washed with water and brine, dried over anhydrous $Na_2SO_4$. The solvent was removed under reduced pressure and the crude product was purified by column chromatography to afford methyl 3-cyano-4-hydroxybenzoate (D21) (1.3 g) as a white solid. MS (ES): $C_9H_7NO_3$ requires 177. found 178.0 (M+H$^+$).

Description for D22 methyl 3-cyano-4-{[(trifluoromethyl)sulfonyl]oxy}benzoate (D22)

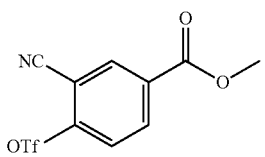 [SMILES: COC(=O)c1ccc(OS(=O)(=O)C(F)(F)F)c(C#N)c1]

To a solution of methyl 3-cyano-4-hydroxybenzoate (D21) (1.3 g) and 1,1,1-trifluoro-N-phenyl-N-[(trifluoromethyl)sulfonyl]methanesulfonamide (3.28 g) in acetonitrile (50 mL) at room temperature was added DIPEA (1.602 mL). Then the reaction mixture was stirred at 25° C. for 12 h. The solvent was removed under reduced pressure and the crude product was purified by column chromatography to afford methyl 3-cyano-4-{[(trifluoromethyl)sulfonyl]oxy}benzoate (D22) (1.9 g) as a colorless oil. MS (ES): $C_{10}H_6F_3NO_5S$ requires 309. found 309.9 (M+H$^+$).

Description for D23 methyl 3-cyano-4-(2-methylpropyl)benzoate (D23)

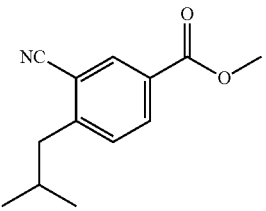 [SMILES: COC(=O)c1ccc(CC(C)C)c(C#N)c1]

To a solution of (2-methylpropyl)boronic acid (0.508 g), methyl 3-cyano-4-{[(trifluoromethyl)sulfonyl]oxy}benzoate (D22) (1.4 g) and $Cs_2CO_3$ (4.43 g) in toluene (10 mL) and water (1 mL) stirred under nitrogen at room temperature was added $PdCl_2(dppf)$-$CH_2Cl_2$ adduct (0.370 g). The reaction mixture was stirred at 100° C. for 12 h. The solvent was removed under reduced pressure. The residue was dissolved in EA (80 mL) and washed with water and brine, dried over anhydrous $Na_2SO_4$. The solution was concentrated and the crude product was purified by column chromatography to afford methyl 3-cyano-4-(2-methylpropyl)benzoate (D23) (800 mg) as a colorless oil. MS (ES): $C_{13}H_{15}NO_2$ requires 217. found 218.1 (M+H$^+$).

Description for D24

3-cyano-4-(2-methylpropyl)benzoic acid (D24)

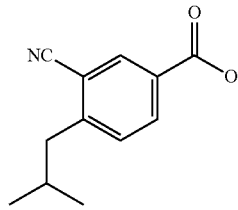

To a solution of methyl 3-cyano-4-(2-methylpropyl)benzoate (D23) (800 mg) in methanol (30 mL) and water (5 mL) at room temperature was added LiOH (441 mg). Then the reaction mixture was stirred at 25° C. for 4 h. Methanol was removed under reduced pressure and water (30 mL) was added. 2N HCl was added to the solution until pH=5. After filtration, the solid was dried to give 3-cyano-4-(2-methylpropyl)benzoic acid (D24) (735 mg) as a white solid. MS (ES): $C_{12}H_{13}NO_2$ requires 203. found 204.1 (M+H$^+$).

Description for D25

5-(5-amino-1,3,4-thiadiazol-2-yl)-2-(2-methylpropyl)benzonitrile (D25)

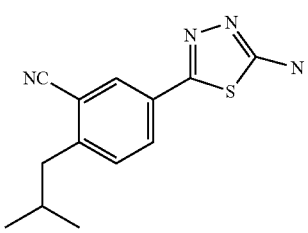 [SMILES: CC(C)Cc1ccc(-c2nnc(N)s2)cc1C#N]

To a suspension 3-cyano-4-(2-methylpropyl)benzoic acid (D24) (305 mg) in POCl₃ (2 mL) was added hydrazinecarbothioamide (211 mg). The reaction mixture was heated at 90° C. for 3 h. The reaction was quenched with ice water. NaOH solid was added until Ph=8-9. The mixture was extracted with EA/THF for 3 times. The combined organic layers were washed with brine, dried over anhydrous sodium sulfate. The dried solution was concentrated to afford the 5-(5-amino-1,3,4-thiadiazol-2-yl)-2-(2-methylpropyl)benzonitrile (D25) (438 mg), which was used for the next step without further purification. MS (ES): $C_{13}H_{14}N_4S$ requires 258. found 259.1 (M+H⁺).

Description for D26

5-(5-bromo-1,3,4-thiadiazol-2-yl)-2-(2-methylpropyl)benzonitrile (D26)

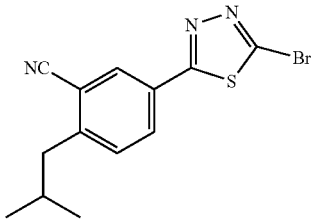 [SMILES: CC(C)Cc1ccc(-c2nnc(Br)s2)cc1C#N]

To a solution of 5-(5-amino-1,3,4-thiadiazol-2-yl)-2-(2-methylpropyl)benzonitrile (D25) (438 mg) in acetonitrile (20 mL) stirred at room temperature was added 1,1-dimethylethyl nitrite (350 mg) and copper(II) bromide (757 mg). The reaction mixture was stirred at room temperature for 3 h. Sat. aq. NH₄Cl was added to quench the reaction. After filtered through the celite, the filtrate was extracted with EA for 3 times. The combined organic layers were washed with brine, dried over anhydrous sodium sulfate. The dried solution was concentrated, and purified by column chromatography to afford 5-(5-bromo-1,3,4-thiadiazol-2-yl)-2-(2-methylpropyl)benzonitrile (D26) (362 mg) as a yellow oil. MS (ES): $C_{13}H_{12}BrN_3S$ requires 321. found 322.0 (M+H⁺).

Description for D27

5-[5-(2-ethyl-3-formylphenyl)-1,3,4-thiadiazol-2-yl]-2-(2-methylpropyl)benzonitrile (D27)

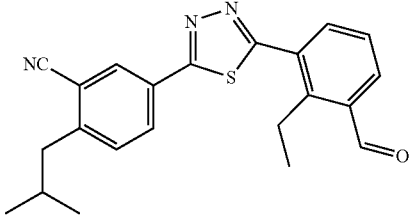 [SMILES: CCc1c(C=O)cccc1-c1nnc(-c2ccc(CC(C)C)c(C#N)c2)s1]

To a suspension of 5-(5-bromo-1,3,4-thiadiazol-2-yl)-2-(2-methylpropyl)benzonitrile (D26) (100 mg), 2-ethyl-3-(4,4,5,5-tetramethyl-1,3,2-dioxaborolan-2-yl)benzaldehyde (D5) (121 mg) and tripotassium phosphate (165 mg) in N,N-dimethylformamide (DMF) (4 mL) and water (1 mL) under nitrogen was added Pd(Ph₃P)₄ (35.9 mg). The reaction vessel was sealed and heated under microwave at 120° C. for 10 min. Water was added. The reaction mixture was extracted with EA for 3 times, the combined organic layers were washed with brine, dried over anhydrous sodium sulfate, the dried solution was concentrated, and purified by column chromatography to afford 5-[5-(2-ethyl-3-formylphenyl)-1,3,4-thiadiazol-2-yl]-2-(2-methylpropyl)benzonitrile (D27) (63 mg) as a yellow solid. MS (ES): $C_{22}H_{21}N_3OS$ requires 375. found 376.2 (M+H⁺).

Description for D28 ethyl 1-[(3-{5-[3-cyano-4-(2-methylpropyl)phenyl]-1,3,4-thiadiazol-2-yl}-2-ethylphenyl)methyl]-4-piperidinecarboxylate (D28)

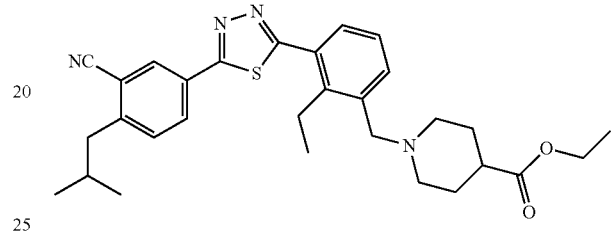

To a solution of 5-[5-(2-ethyl-3-formylphenyl)-1,3,4-thiadiazol-2-yl]-2-(2-methylpropyl)benzonitrile (D27) (31 mg) and ethyl 4-piperidinecarboxylate (64.9 mg) in ethanol (10 mL) stirred at room temperature was added AcOH (0.15 mL). The reaction mixture was stirred at room temperature for 10 min. The residue was dissolved in dichloromethane (DCM) (10 mL), and sodium triacetoxyborohydride (52.5 mg) was added. Stirring continued for overnight. Water was added to quench the reaction, and DCM was removed by evaporation. The mixture was extracted by EA for 3 times. The combined organic solution was washed by brine, dried over anhydrous Na₂SO₄. The dried solution was filtered and concentrated to give ethyl 1-[(3-{5-[3-cyano-4-(2-methylpropyl)phenyl]-1,3,4-thiadiazol-2-yl}-2-ethylphenyl)methyl]-4-piperidinecarboxylate (D28) (38.4 mg). MS (ES): $C_{30}H_{36}N_4O_2S$ requires 516. found 517.3 (M+H⁺).

Description for D29 methyl 1-[(3-{5-[3-cyano-4-(2-methylpropyl)phenyl]-1,3,4-thiadiazol-2-yl}-2-ethylphenyl)methyl]-3-azetidinecarboxylate (D29)

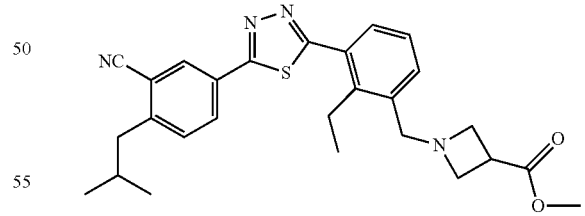

To a solution of 5-[5-(2-ethyl-3-formylphenyl)-1,3,4-thiadiazol-2-yl]-2-(2-methylpropyl)benzonitrile (D27) (31 mg) and methyl 3-azetidinecarboxylate (62.6 mg) in ethanol (10 mL) stirred at room temperature was added sodium acetate (33.9 mg) and AcOH (0.15 mL). The reaction mixture was stirred at room temperature for 10 min. The residue was dissolved in dichloromethane (DCM) (10 mL), sodium triacetoxyborohydride (52.5 mg) was added. Stirring continued for overnight. Water was added to quench the reaction, and DCM was removed by evaporation. The mixture was extracted by EA for 3 times. The combined organic solution was washed by brine, dried over anhydrous Na$_2$SO$_4$. The dried solution was filtered and concentrated to afford methyl 1-[(3-{5-[3-cyano-4-(2-methylpropyl)phenyl]-1,3,4-thiadiazol-2-yl}-2-ethylphenyl)methyl]-3-azetidinecarboxylate (D29) (39 mg). MS (ES): C$_{27}$H$_{30}$N$_4$O$_2$S requires 474. found 475.2 (M+H$^+$).

Description for D30

5-(5-{2-ethyl-3-[(E)-2-(methyloxy)ethenyl]phenyl}-1,3,4-thiadiazol-2-yl)-2-(2-methylpropyl)benzonitrile (D30)

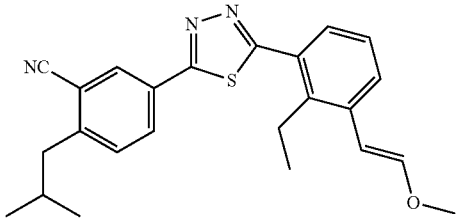 [SMILES: CCc1c(/C=C/OC)cccc1-c1nnc(-c2ccc(CC(C)C)c(C#N)c2)s1]

To a suspension of 5-(5-bromo-1,3,4-thiadiazol-2-yl)-2-(2-methylpropyl)benzonitrile (D26) (151 mg), 2-{2-ethyl-3-[(E)-2-(methyloxy)ethenyl]phenyl}-4,4,5,5-tetramethyl-1,3,2-dioxaborolane (203 mg) and tripotassium phosphate (249 mg) in N,N-dimethylformamide (DMF) (6 mL) and water (1.5 mL) under nitrogen was added Pd(Ph$_3$P)$_4$ (54.2 mg). The reaction vessel was sealed and heated under microwave at 120° C. for 10 min. Water was added. The reaction mixture was extracted with EA for 3 times, the combined organic layers were washed with brine, dried over anhydrous sodium sulfate, the dried solution was concentrated, and purified by column chromatography to afford 5-(5-{2-ethyl-3-[(E)-2-(methyloxy)ethenyl]phenyl}-1,3,4-thiadiazol-2-yl)-2-(2-methylpropyl)benzonitrile (D30) (185 mg) as a yellow oil. MS (ES): C$_{24}$H$_{25}$N$_3$OS requires 403. found 404.2 (M+H$^+$).

Description for D31

5-{5-[2-ethyl-3-(2-oxoethyl)phenyl]-1,3,4-thiadiazol-2-yl}-2-(2-methylpropyl)benzonitrile (D31)

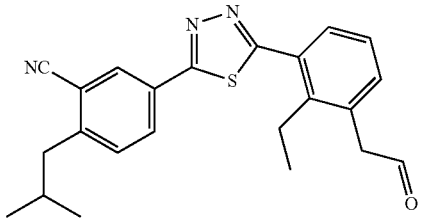 [SMILES: CCc1c(CC=O)cccc1-c1nnc(-c2ccc(CC(C)C)c(C#N)c2)s1]

To a solution of 5-(5-{2-ethyl-3-[(E)-2-(methyloxy)ethenyl]phenyl}-1,3,4-thiadiazol-2-yl)-2-(2-methylpropyl)benzonitrile (D30) (120 mg) and sodium iodide (89 mg) in acetonitrile (20 mL) stirred under nitrogen at room temperature was added TMSCl (0.076 mL) dropwise. The reaction mixture was stirred at room temperature for 10 min. Water was added. The aqueous solution was extracted with EA for 3 times. The organic phase was washed with saturated Na$_2$S$_2$O$_3$ solution and saturated brine, dried over sodium sulphate and evaporated in vacuo to afford the crude product 5-{5-[2-ethyl-3-(2-oxoethyl)phenyl]-1,3,4-thiadiazol-2-yl}-2-(2-methylpropyl)benzonitrile (D31) (104 mg) as a yellow oil. MS (ES): C$_{23}$H$_{23}$N$_3$OS requires 389. found 390.1 (M+H$^+$).

Description for D32 methyl 1-[2-(3-{5-[3-cyano-4-(2-methylpropyl)phenyl]-1,3,4-thiadiazol-2-yl}-2-ethylphenyl)ethyl]-3-azetidinecarboxylate (D32)

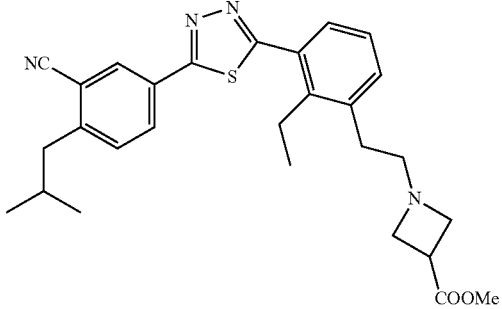 [SMILES: CCc1c(CCN2CC(C(=O)OC)C2)cccc1-c1nnc(-c2ccc(CC(C)C)c(C#N)c2)s1]

To a solution of 5-{5-[2-ethyl-3-(2-oxoethyl)phenyl]-1,3,4-thiadiazol-2-yl}-2-(2-methylpropyl)benzonitrile (D31) (52 mg) and methyl 3-azetidinecarboxylate (60.7 mg) in ethanol (10 mL) stirred at room temperature was added sodium acetate (32.9 mg) and AcOH (0.15 mL). The reaction mixture was stirred at room temperature for 10 min. The residue was dissolved in dichloromethane (DCM) (10 mL), sodium triacetoxyborohydride (85 mg) was added. Stirring continued for overnight. Water was added to quench the reaction, and DCM was removed by evaporation. The mixture was extracted by EA for 3 times. The combined organic solution was washed by brine, dried over anhydrous Na$_2$SO$_4$. The dried solution was filtered and concentrated to afford methyl 1-[2-(3-{5-[3-cyano-4-(2-methylpropyl)phenyl]-1,3,4-thiadiazol-2-yl}-2-ethylphenyl)ethyl]-3-azetidinecarboxylate (D32) (58.7 mg). MS (ES): C$_{28}$H$_{32}$N$_4$O$_2$S requires 488. found 489.2 (M+H$^+$).

Description for D33 ethyl 1-[2-(3-{5-[3-cyano-4-(2-methylpropyl)phenyl]-1,3,4-thiadiazol-2-yl}-2-ethylphenyl)ethyl]-4-piperidinecarboxylate (D33)

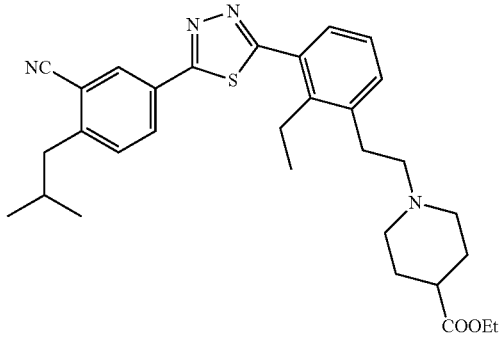 [SMILES: CCOC(=O)C1CCN(CCc2cccc(-c3nnc(-c4ccc(CC(C)C)c(C#N)c4)s3)c2CC)CC1]

To a solution of 5-{5-[2-ethyl-3-(2-oxoethyl)phenyl]-1,3,4-thiadiazol-2-yl}-2-(2-methylpropyl)benzonitrile (D31) (52 mg) and ethyl 4-piperidinecarboxylate (105 mg) in ethanol (10 mL) stirred at room temperature was added sodium acetate (32.9 mg) and AcOH (0.15 mL). The reaction mixture was stirred at room temperature for 10 min. The residue was dissolved in dichloromethane (DCM) (10 mL), sodium triacetoxyborohydride (85 mg) was added. Stirring continued for overnight. Water was added to quench the reaction, and DCM was removed by evaporation. The mixture was extracted by EA for 3 times. The combined organic solution was washed by brine, dried over anhydrous Na$_2$SO$_4$. The dried solution was filtered and concentrated to afford ethyl 1-[2-(3-{5-[3-cyano-4-(2-methylpropyl)phenyl]-1,3,4-thiadiazol-2-yl}-2-ethylphenyl)ethyl]-4-piperidinecarboxylate (D33) (63.8 mg). MS (ES): C$_{31}$H$_{38}$N$_4$O$_2$S requires 530. found 531.3 (M+H$^+$).

Description for D34

2-{5-fluoro-2-(methyloxy)-3-[(E)-2-(methyloxy)ethenyl]phenyl}-5-[4-[(1-methylethyl)oxy]-3-(trifluoromethyl)phenyl]-1,3,4-thiadiazole (D34)

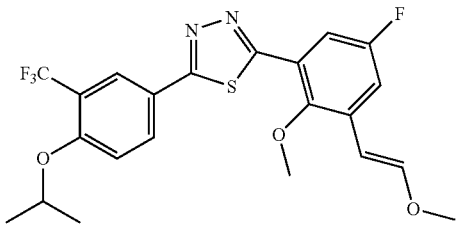 [SMILES: CO/C=C/c1cc(F)cc(-c2nnc(-c3ccc(OC(C)C)c(C(F)(F)F)c3)s2)c1OC]

To a suspension of 2-bromo-5-[4-[(1-methylethyl)oxy]-3-(trifluoromethyl)phenyl]-1,3,4-thiadiazole (D4) (393 mg), 2-{5-fluoro-2-(methyloxy)-3-[(E)-2-(methyloxy)ethenyl]phenyl}-4,4,5,5-tetramethyl-1,3,2-dioxaborolane (495 mg) and tripotassium phosphate (568 mg) in N,N-dimethylformamide (DMF) (8 mL) and water (2 mL) under nitrogen was added Pd(Ph$_3$P)$_4$ (61.8 mg). The reaction vessel was sealed and heated under microwave at 120° C. for 10 min. Water was added. The reaction mixture was extracted with EA for 3 times, the combined organic layers were washed with brine, dried over anhydrous sodium sulfate, the dried solution was concentrated, and purified by column chromatography to afford 2-{5-fluoro-2-(methyloxy)-3-[(E)-2-(methyloxy)ethenyl]phenyl}-5-[4-[(1-methylethyl)oxy]-3-(trifluoromethyl)phenyl]-1,3,4-thiadiazole (D34) (170 mg) as a yellow solid. MS (ES): C$_{22}$H$_{20}$F$_4$N$_2$O$_3$S requires 468. found 469.1 (M+H$^+$).

Description for D35

[5-fluoro-3-{5-[4-[(1-methylethyl)oxy]-3-(trifluoromethyl)phenyl]-1,3,4-thiadiazol-2-yl}-2-(methyloxy)phenyl]acetaldehyde (D35)

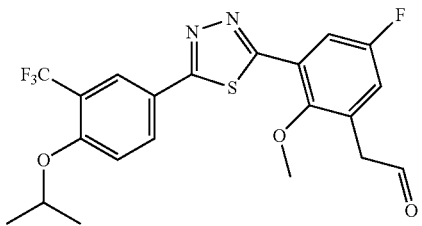 [SMILES: COc1c(CC=O)cc(F)cc1-c1nnc(-c2ccc(OC(C)C)c(C(F)(F)F)c2)s1]

To a solution of 2-{5-fluoro-2-(methyloxy)-3-[(E)-2-(methyloxy)ethenyl]phenyl}-5-[4-[(1-methylethyl)oxy]-3-(trifluoromethyl)phenyl]-1,3,4-thiadiazole (D34) (170 mg) and sodium iodide (109 mg) in acetonitrile (20 mL) stirred under nitrogen at room temperature was added TMSCl (0.093 mL) dropwise. The reaction mixture was stirred at room temperature for 10 min. Water was added. The aqueous solution was extracted with EA for 3 times. The organic phase was washed with saturated Na$_2$S$_2$O$_3$ solution and saturated brine, dried over sodium sulphate and evaporated in vacuo to afford the crude product [5-fluoro-3-{5-[4-[(1-methylethyl)oxy]-3-(trifluoromethyl)phenyl]-1,3,4-thiadiazol-2-yl}-2-(methyloxy)phenyl]acetaldehyde (D35) (170 mg) as a yellow oil. MS (ES): C$_{21}$H$_{18}$F$_4$N$_2$O$_3$S requires 454. found 455.1 (M+H$^+$).

Description for D36

5-(5-{5-fluoro-2-(methyloxy)-3-[(E)-2-(methyloxy)ethenyl]phenyl}-1,3,4-thiadiazol-2-yl)-2-(2-methylpropyl)benzonitrile (D36)

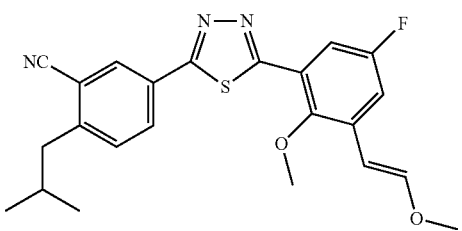 [SMILES: CO/C=C/c1cc(F)cc(-c2nnc(-c3ccc(CC(C)C)c(C#N)c3)s2)c1OC]

To a suspension of 2-bromo-5-[4-[(1-methylethyl)oxy]-3-(trifluoromethyl)phenyl]-1,3,4-thiadiazole (D26) (400 mg), 2-{5-fluoro-2-(methyloxy)-3-[(E)-2-(methyloxy)ethenyl]phenyl}-4,4,5,5-tetramethyl-1,3,2-dioxaborolane (459 mg) and tripotassium phosphate (659 mg) in N,N-dimethylformamide (DMF) (8 mL) and water (2 mL) under nitrogen was added Pd(Ph$_3$P)$_4$ (71.7 mg). The reaction vessel was sealed and heated under microwave at 120° C. for 10 min. Water was added. The reaction mixture was extracted with EA for 3 times, the combined organic layers were washed with brine, dried over anhydrous sodium sulfate, the dried solution was concentrated, and purified by column chromatography to afford 5-(5-{5-fluoro-2-(methyloxy)-3-[(E)-2-(methyloxy)ethenyl]phenyl}-1,3,4-thiadiazol-2-yl)-2-(2-methylpropyl)benzonitrile (D36) (140 mg) as a yellow solid. MS (ES): C$_{23}$H$_{22}$FN$_3$O$_2$S requires 423. found 424.1 (M+H$^+$).

Description for D37

5-{5-[5-fluoro-2-(methyloxy)-3-(2-oxoethyl)phenyl]-1,3,4-thiadiazol-2-yl}-2-(2-methylpropyl)benzonitrile (D37)

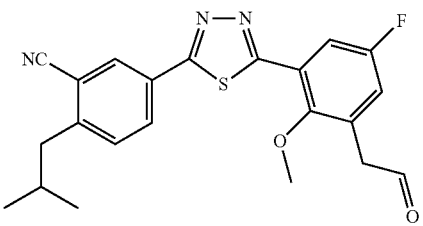 [SMILES: COc1c(CC=O)cc(F)cc1-c1nnc(-c2ccc(CC(C)C)c(C#N)c2)s1]

To a solution of 5-(5-{5-fluoro-2-(methyloxy)-3-[(E)-2-(methyloxy)ethenyl]phenyl}-1,3,4-thiadiazol-2-yl)-2-(2-methylpropyl)benzonitrile (D36) (130 mg) and sodium iodide (92 mg) in acetonitrile (20 mL) stirred under nitrogen at room temperature was added TMSCl (0.078 mL) dropwise.

The reaction mixture was stirred at room temperature for 10 min. Water was added. The aqueous solution was extracted with EA for 3 times. The organic phase was washed with saturated Na$_2$S$_2$O$_3$ solution and saturated brine, dried over sodium sulphate and evaporated in vacuo to afford the crude product 5-{5-[5-fluoro-2-(methyloxy)-3-(2-oxoethyl)phenyl]-1,3,4-thiadiazol-2-yl}-2-(2-methylpropyl)benzonitrile (D37) (75 mg) as a yellow oil. MS (ES): C$_{22}$H$_{20}$FN$_3$O$_2$S requires 409. found 410.2 (M+H$^+$).

Description for D38

5-bromo-2-[(1-methylethyl)oxy]benzonitrile (D38)

To a solution of 5-bromo-2-hydroxybenzonitrile (25 g) in acetonitrile (150 mL) was added 2-iodopropane (15.14 mL) and potassium carbonate (34.9 g). The reaction mixture was stirred at room temperature for two days. The solvent was removed in vacuo, the residue was dissolved in ethyl acetate (150 mL), washed with water (2*30 mL), the organic phase was dried over sodium sulphate and concentrated to afford 5-bromo-2-[(1-methylethyl)oxy]benzonitrile (D38) (29.8 g) as a white solid without further purification. δH (CDCl$_3$, 400 MHz): 1.39 (6H, d), 4.61 (1H, m), 6.85 (1H, d), 7.58 (1H, dd), 7.64 (1H, d). MS (ES): C$_{10}$H$_{10}$BrNO requires 239. found 240.0 (M+H$^+$).

Description for D39

2-[(1-methylethyl)oxy]-5-(4,4,5,5-tetramethyl-1,3,2-dioxaborolan-2-yl)benzonitrile (D39)

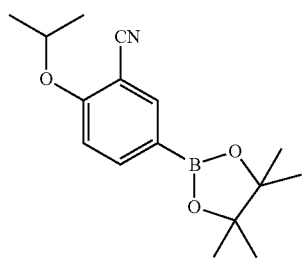 [SMILES: CC(C)Oc1ccc(B2OC(C)(C)C(C)(C)O2)cc1C#N]

To a suspension of 5-bromo-2-[(1-methylethyl)oxy]benzonitrile (D38) (123 mg), 4,4,4',4',5,5,5',5'-octamethyl-2,2'-bi-1,3,2-dioxaborolane (156 mg) and potassium acetate (101 mg) in N,N-dimethylformamide (DMF) (150 mL) stirred under nitrogen at room temperature was added PdCl$_2$(dppf)-CH$_2$Cl$_2$ adduct (25.1 mg). The reaction vessel was sealed and heated under microwave at 120° C. for 1 h. After cooling the reaction, the reaction mixture was concentrated in vacuo and the residue was purified by column chromatography to give 2-[(1-methylethyl)oxy]-5-(4,4,5,5-tetramethyl-1,3,2-dioxaborolan-2-yl)benzonitrile (D39) (54 mg). MS (ES): C$_{16}$H$_{22}$BNO$_3$ requires 287. found 288.2 (M+H$^+$).

Description for D40

4-bromo-1-fluoro-2-(trifluoromethyl)benzene (D40)

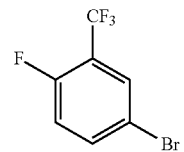

To a suspension of copper(II) bromide (7.48 g) in acetonitrile (50 mL) was added 1,1-dimethylethyl nitrite (5.02 mL) dropwise under ice-cooling, the mixture was stirred under nitrogen for 5 min. A solution of 4-fluoro-3-(trifluoromethyl)aniline (5 g) in acetonitrile was added to the reaction mixture under ice-cooling, the mixture was stirred at room temperature under nitrogen for 2 h. To the resulting suspension was added 1N HCl and the reaction mixture was concentrated in vacuo. The residue was diluted with water and extracted with ethyl acetate, the combined organic phases were dried over sodium sulphate and concentrated, the residue was purified by column chromatography to give 4-bromo-1-fluoro-2-(trifluoromethyl)benzene (D40) (2 g). δH (CDCl$_3$, 400 MHz): 7.11 (1H, t), 7.66 (1H, m), 7.74 (1H, dd). δF (CDCl$_3$, 376 MHz): −116.2, −61.7.

Description for D41

4-bromo-1-[(1-methylethyl)oxy]-2-(trifluoromethyl)benzene (D41)

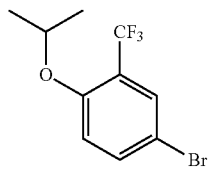

To a solution of 2-propanol (1.997 mL) in dry tetrahydrofuran (THF) (50 mL) under nitrogen was added potassium tert-butoxide (3.49 g). The reaction mixture was heated to 50° C. for 10 min, then 4-bromo-1-fluoro-2-(trifluoromethyl)benzene (D40) (6.3 g) was added. The resulting mixture was stirred at 50° C. overnight. After cooling the reaction, the solvent was removed in vacuo, the residue was diluted with ethyl acetate (100 mL), washed with water, the organic phase was dried over sodium sulphate, concentrated and the residue was purified by column chromatography to give 4-bromo-1-[(1-methylethyl)oxy]-2-(trifluoromethyl)benzene (D41) (5.21 g) as a clear oil. δH (CDCl$_3$, 600 MHz): 1.36 (6H, d), 4.60 (1H, m), 6.88 (1H, d), 7.55 (1H, dd), 7.66 (1H, d).

Description for D42

4,4,5,5-tetramethyl-2-[4-[(1-methylethyl)oxy]-3-(trifluoromethyl)phenyl]-1,3,2-dioxaborolane (D42)

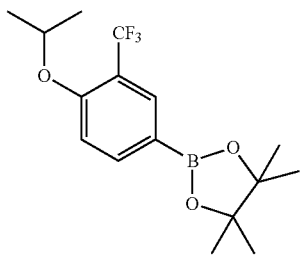

To a solution of 4-bromo-1-[(1-methylethyl)oxy]-2-(trifluoromethyl)benzene (D41) (5.21 g) in dry tetrahydrofuran (THF) (50 mL) was added n-BuLi (12.65 mL) dropwise at −78° C. (maintaining the temperature <−60° C.). The resulting solution was stirred at −78° C. for 30 min before triisopropyl borate (5.13 mL) was added dropwise (<−60° C.). The reaction mixture was allowed to warm to room temperature, then pinacol (0.70 g) and AcOH (2.107 mL) was added and the reaction mixture stirred at room temperature overnight. The reaction was quenched with saturated aqueous $NH_4Cl$, the mixture was diluted with ethyl acetate and washed with saturated aqueous $NaHCO_3$ and brine, the organic phase was dried over sodium sulphate and concentrated. The residue was purified by column chromatography to give 4,4,5,5-tetramethyl-2-[4-[(1-methylethyl)oxy]-3-(trifluoromethyl)phenyl]-1,3,2-dioxaborolane (D42) (5.3 g) as a clear oil. δH ($CDCl_3$, 600 MHz): 1.33 (12H, s), 1.36 (6H, d), 4.69 (1H, m), 6.97 (1H, d), 7.88 (1H, d), 7.99 (1H, s). MS (ES): $C_{15}H_{22}BF_3O_3$ requires 330. found 331.2 (M+H$^+$).

Description for D43

3-bromo-5-{3-chloro-4-[(1-methylethyl)oxy]phenyl}-1,2,4-thiadiazole (D43)

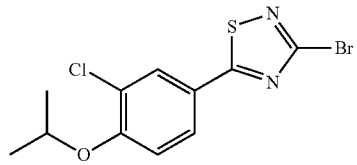 [SMILES: CC(C)Oc1ccc(-c2nc(Br)ns2)cc1Cl]

To a solution of 3-bromo-5-chloro-1,2,4-thiadiazole (558 mg), {3-chloro-4-[(1-methylethyl)oxy]phenyl}boronic acid (300 mg) and tripotassium phosphate (148 mg) in N,N-dimethylformamide (DMF) (3 mL) and water (0.600 mL) under nitrogen was added $PdCl_2(dppf)\text{-}CH_2Cl_2$ adduct (3.427 g). The reaction vessel was sealed and heated under microwave at 80° C. for 1 h. After cooling the reaction, the mixture was filtered and the filtrate was diluted with ethyl acetate (50 mL), washed with brine (2*10 mL), dried over sodium sulphate, concentrated and purified by column chromatography to afford 3-bromo-5-{3-chloro-4-[(1-methylethyl)oxy]phenyl}-1,2,4-thiadiazole (D43) (450 mg) as a clear oil. MS (ES): $C_{11}H_{10}BrClN_2OS$ requires 332. found 333.0 (M+H$^+$).

Description for D44

5-(3-bromo-1,2,4-thiadiazol-5-yl)-2-[(1-methylethyl)oxy]benzonitrile (D44)

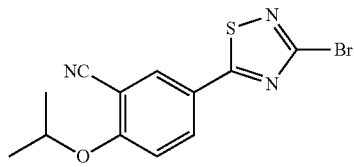

To a solution of 2-[(1-methylethyl)oxy]-5-(4,4,5,5-tetramethyl-1,3,2-dioxaborolan-2-yl)benzonitrile (D39) (280 mg), 3-bromo-5-chloro-1,2,4-thiadiazole (194 mg) and tripotassium phosphate (517 mg) in 1,2-dimethoxyethane (DME) (4 mL) and water (1 mL) under nitrogen was added $Pd(Ph_3P)_4$ (113 mg). The reaction vessel was sealed and heated under microwave at 120° C. for 10 min. Water was added, the reaction mixture was filtered through the celite. The aqueous layer was extracted with EA for 3 times. the combined organic layers were washed with brine, dried over anhydrous sodium sulfate. The dried solution was concentrated and purified by column chromatography to give 5-(3-bromo-1,2,4-thiadiazol-5-yl)-2-[(1-methylethyl)oxy]benzonitrile (D44) (152 mg) as a white solid. MS (ES): $C_{12}H_{10}BrN_3OS$ requires 323. found 324.0 (M+H$^+$).

Description for D45

3-bromo-5-[4-[(1-methylethyl)oxy]-3-(trifluoromethyl)phenyl]-1,2,4-thiadiazole (D45)

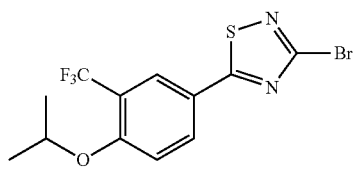 [SMILES: CC(C)Oc1ccc(-c2nc(Br)ns2)cc1C(F)(F)F]

To a solution of 3-bromo-5-chloro-1,2,4-thiadiazole (604 mg), 4,4,5,5-tetramethyl-2-[4-[(1-methylethyl)oxy]-3-(trifluoromethyl)phenyl]-1,3,2-dioxaborolane (D42) (500 mg) and tripotassium phosphate (964 mg) in N,N-dimethylformamide (DMF) (3 mL) and water (0.600 mL) stirred under nitrogen at room temperature was added $PdCl_2(dppf)\text{-}CH_2Cl_2$ adduct (618 mg). The reaction mixture was sealed and heated under microwave at 80° C. for 1 h. The reaction mixture was concentrated and the residue was purified by column chromatography to give 3-bromo-5-[4-[(1-methylethyl)oxy]-3-(trifluoromethyl)phenyl]-1,2,4-thiadiazole (D45) (294 mg) as a white solid. MS (ES): $C_{12}H_{10}BrF_3N_2OS$ requires 366. found 367.2 (M+H$^+$).

Description for D46

5-[3-(2-ethyl-3-formylphenyl)-1,2,4-thiadiazol-5-yl]-2-[(1-methylethyl)oxy]benzonitrile (D46)

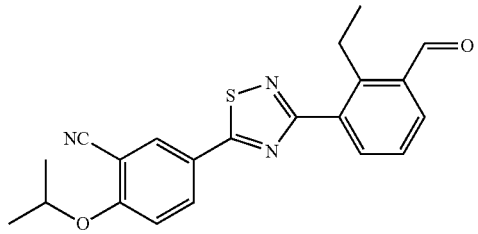 [SMILES: CCc1c(C=O)cccc1-c1nsc(-c2ccc(OC(C)C)c(C#N)c2)n1]

To a solution of 5-(3-bromo-1,2,4-thiadiazol-5-yl)-2-[(1-methylethyl)oxy]benzonitrile (D44) (550 mg), 2-ethyl-3-(4,4,5,5-tetramethyl-1,3,2-dioxaborolan-2-yl)benzaldehyde (463 mg) and tripotassium phosphate (1080 mg) in N,N-dimethylformamide (DMF) (4 mL) and water (1.000 mL) stirred under nitrogen was added Pd(Ph$_3$P)$_4$ (196 mg). The reaction was sealed and heated under microwave at 120° C. for 15 min. After cooling, the reaction mixture was diluted with ethyl acetate (20 mL), washed with water (2*8 mL), dried over sodium sulphate, concentrated and purified by column chromatography to afford 5-[3-(2-ethyl-3-formylphenyl)-1,2,4-thiadiazol-5-yl]-2-[(1-methylethyl)oxy]benzonitrile (D46) (420 mg) as a solid. MS (ES): C$_{21}$H$_{19}$N$_3$O$_2$S requires 377. found 378.0 (M+H$^+$).

Description for D47

2-ethyl-3-{5-[4-[(1-methylethyl)oxy]-3-(trifluoromethyl)phenyl]-1,2,4-thiadiazol-3-yl}benzaldehyde (D47)

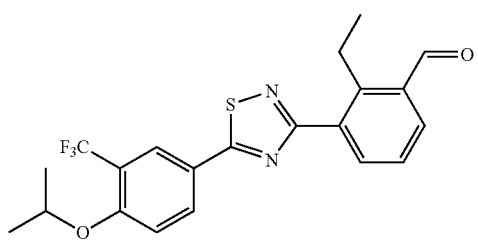 [SMILES: CCc1c(C=O)cccc1-c1nsc(-c2ccc(OC(C)C)c(C(F)(F)F)c2)n1]

To a solution of 3-bromo-5-[4-[(1-methylethyl)oxy]-3-(trifluoromethyl)phenyl]-1,2,4-thiadiazole (D45) (0.93 g), 2-ethyl-3-(4,4,5,5-tetramethyl-1,3,2-dioxaborolan-2-yl)benzaldehyde (D5) (0.659 g) and tripotassium phosphate (1.344 g, 6.33 mmol)) in N,N-dimethylformamide (DMF) (6 mL) and water (1.500 mL) stirred under nitrogen was added Pd(Ph$_3$P)$_4$ (0.585 g). The reaction was sealed and heated under microwave at 120° C. for 15 min. After cooling, the reaction mixture was diluted with ethyl acetate (20 mL), washed with water (2*8 mL), dried over sodium sulphate, concentrated and purified by column chromatography to afford 2-ethyl-3-{5-[4-[(1-methylethyl)oxy]-3-(trifluoromethyl)phenyl]-1,2,4-thiadiazol-3-yl}benzaldehyde (D47) (1 g) as a brown oil. MS (ES): C$_{21}$H$_{19}$F$_3$N$_2$O$_2$S requires 420. found 421.1 (M+H$^+$).

Description for D48

3-[3-(bromomethyl)-2-ethylphenyl]-5-[4-[(1-methylethyl)oxy]-3-(trifluoromethyl)phenyl]-1,2,4-thiadiazole (D48)

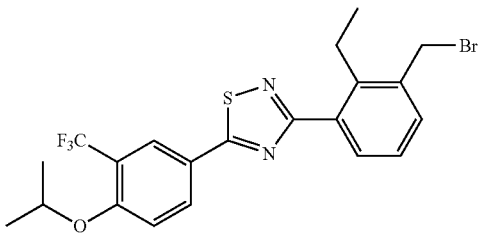 [SMILES: CCc1c(CBr)cccc1-c1nsc(-c2ccc(OC(C)C)c(C(F)(F)F)c2)n1]

To a solution of 2-ethyl-3-{5-[4-[(1-methylethyl)oxy]-3-(trifluoromethyl)phenyl]-1,2,4-thiadiazol-3-yl}benzaldehyde (D47) (650 mg) in methanol (10 mL) was added sodium borohydride (117 mg) at 0° C. The reaction mixture was stirred at room temperature for overnight. The solvent was removed in vacuo and the residue was dissolved in ethyl acetate (50 mL), washed with water, the organic phase was dried over sodium sulphate, concentrated to afford the alcohol. To the solution of the alcohol in dichloromethane (DCM) (10.00 mL) was added CBr$_4$ (615 mg), followed by triphenylphosphine (608 mg) in dichloromethane (DCM) (10.00 mL) at 0° C. After the addition, the reaction solution was stirred at room temperature for 1 h. The solvent was removed in vacuo and the residue was purified by column chromatography to afford 3-[3-(bromomethyl)-2-ethylphenyl]-5-[4-[(1-methylethyl)oxy]-3-(trifluoromethyl)phenyl]-1,2,4-thiadiazole (D48) (400 mg). MS (ES): C$_{21}$H$_{20}$BrF$_3$N$_2$OS requires 484. found 485.0 (M+H$^+$).

Description for D49

3-{2-ethyl-3-[(E)-2-(methyloxy)ethenyl]phenyl}-5-[4-[(1-methylethyl)oxy]-3-(trifluoromethyl)phenyl]-1,2,4-thiadiazole (D49)

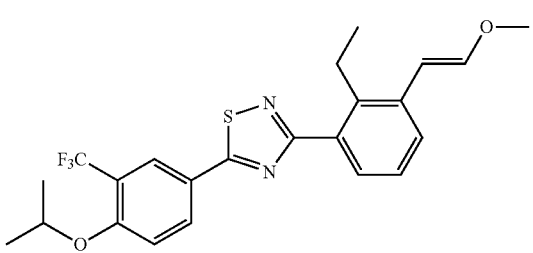

To a solution of 3-bromo-5-[4-[(1-methylethyl)oxy]-3-(trifluoromethyl)phenyl]-1,2,4-thiadiazole (D45) (487 mg), 2-{2-ethyl-3-[(E)-2-(methyloxy)ethenyl]phenyl}-4,4,5,5-tetramethyl-1,3,2-dioxaborolane (573 mg) and tripotassium phosphate (845 mg) in N,N-dimethylformamide (DMF) (4 mL) and water (0.800 mL) stirred under nitrogen at room temp was added Pd(Ph$_3$P)$_4$ (153 mg). The reaction mixture was sealed and heated under microwave at 120° C. for 10 min. After cooling the reaction, the mixture was concentrated and purified by column chromatography to give 3-{2-ethyl-3-[(E)-2-(methyloxy)ethenyl]phenyl}-5-[4-[(1-methylethyl)oxy]-3-(trifluoromethyl)phenyl]-1,2,4-thiadiazole (D49) (580 mg) as a colorless oil. MS (ES): $C_{23}H_{23}F_3N_2O_2S$ requires 448. found 449.1 (M+H$^+$).

Description for D50

(2-ethyl-3-{5-[4-[(1-methylethyl)oxy]-3-(trifluoromethyl)phenyl]-1,2,4-thiadiazol-3-yl}phenyl)acetaldehyde (D50)

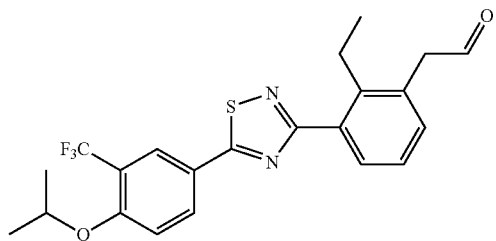 [SMILES: CCc1c(CC=O)cccc1-c1nsc(-c2ccc(OC(C)C)c(C(F)(F)F)c2)n1]

To a solution of 3-{2-ethyl-3-[(E)-2-(methyloxy)ethenyl]phenyl}-5-[4-[(1-methylethyl)oxy]-3-(trifluoromethyl)phenyl]-1,2,4-thiadiazole (D49) (140 mg) in tetrahydrofuran (THF) (10 mL) stirred under nitrogen at room temperature was added hydrochloric acid (0.2 mL). The reaction mixture was stirred at 70° C. for 5 h. After cooling the reaction, the solution was condensed under reduced pressure to give (2-ethyl-3-{5-[4-[(1-methylethyl)oxy]-3-(trifluoromethyl)phenyl]-1,2,4-thiadiazol-3-yl}phenyl)acetaldehyde (D50) (108 mg) as a colorless oil, which was used directly in the next step without further purification. MS (ES): $C_{22}H_{21}F_3N_2O_2S$ requires 434. found 435.2 (M+H$^+$).

Description for D51

5-{3-chloro-4-[(1-methylethyl)oxy]phenyl}-3-{2-ethyl-3-[(E)-2-(methyloxy)ethenyl]phenyl}-1,2,4-thiadiazole (D51)

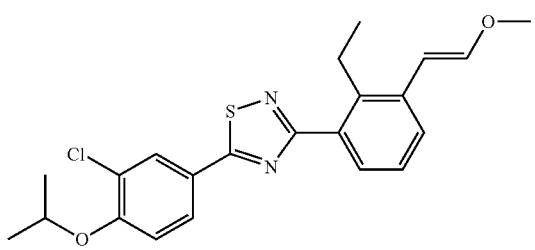 [SMILES: CCc1c(/C=C/OC)cccc1-c1nsc(-c2ccc(OC(C)C)c(Cl)c2)n1]

To a solution of 3-bromo-5-{3-chloro-4-[(1-methylethyl)oxy]phenyl}-1,2,4-thiadiazole (D43) (388 mg), 2-{2-ethyl-3-[(E)-2-(methyloxy)ethenyl]phenyl}-4,4,5,5-tetramethyl-1,3,2-dioxaborolane (335 mg) and tripotassium phosphate (741 mg) in N,N-dimethylformamide (DMF) (10 mL) and water (1.000 mL) stirred under nitrogen was added Pd(Ph$_3$P)$_4$ (134 mg). The mixture was sealed and heated under microwave at 120° C. for 10 min. After cooling the reaction, the mixture was concentrated and purified by column chromatography to give 5-{3-chloro-4-[(1-methylethyl)oxy]phenyl}-3-{2-ethyl-3-[(E)-2-(methyloxy)ethenyl]phenyl}-1,2,4-thiadiazole (D51) (313 mg) as a colorless oil. MS (ES): $C_{22}H_{23}ClN_2O_2S$ requires 414. found 415.1 (M+H$^+$).

Description for D52

[3-(5-{3-chloro-4-[(1-methylethyl)oxy]phenyl}-1,2,4-thiadiazol-3-yl)-2-ethylphenyl]acetaldehyde (D52)

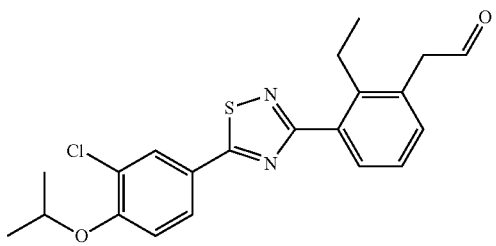 [SMILES: CCc1c(CC=O)cccc1-c1nsc(-c2ccc(OC(C)C)c(Cl)c2)n1]

To a solution of 5-{3-chloro-4-[(1-methylethyl)oxy]phenyl}-3-{2-ethyl-3-[(E)-2-(methyloxy)ethenyl]phenyl}-1,2,4-thiadiazole (D51) (313 mg) in tetrahydrofuran (THF) (20 mL) stirred under nitrogen at room temperature was added 14 drops 2M hydrochloric acid. The reaction mixture was stirred at 70° C. for 4 h. After cooling the reaction, the solution was condensed under reduced pressure to give [3-(5-{3-chloro-4-[(1-methylethyl)oxy]phenyl}-1,2,4-thiadiazol-3-yl)-2-ethylphenyl]acetaldehyde (D52) (300 mg), which was used directly in the next step without further purification. MS (ES): $C_{21}H_{21}ClN_2O_2S$ requires 400. found 401.1 (M+H$^+$).

Description for D53

3-(5-{3-chloro-4-[(1-methylethyl)oxy]phenyl}-1,2,4-thiadiazol-3-yl)-2-ethylbenzaldehyde (D53)

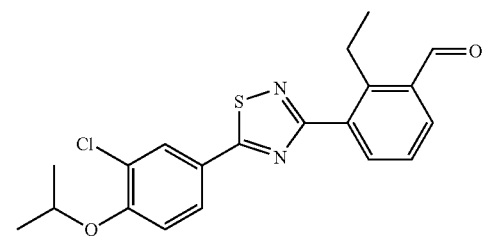 [SMILES: CCc1c(C=O)cccc1-c1nsc(-c2ccc(OC(C)C)c(Cl)c2)n1]

To a solution of 3-bromo-5-{3-chloro-4-[(1-methylethyl)oxy]phenyl}-1,2,4-thiadiazole (D43) (500 mg), 2-ethyl-3-(4,4,5,5-tetramethyl-1,3,2-dioxaborolan-2-yl)benzaldehyde (D5) (390 mg) and tripotassium phosphate (954 mg) in N,N-dimethylformamide (DMF) (3 mL) and water (0.75 mL) stirred under nitrogen was added Pd(Ph$_3$P)$_4$ (173 mg). The mixture was sealed and heated under microwave at 120° C. for 15 min. After cooling the reaction, the mixture was diluted with ethyl acetate (50 mL), the organic phase was washed with water, dried over sodium sulphate and concentrated, the residue was purified by column chromatography to give 3-(5-{3-chloro-4-[(1-methylethyl)oxy]phenyl}-1,2,4-thiadiazol- 3-yl)-2-ethylbenzaldehyde (D53) (450 mg) as an oil. MS (ES): $C_{20}H_{19}ClN_2O_2S$ requires 386. found 387.1 (M+H⁺).

Description for D54

5-(3-{2-ethyl-3-[(E)-2-(methyloxy)ethenyl]phenyl}-1,2,4-thiadiazol-5-yl)-2-[(1-methylethyl)oxy]benzonitrile (D54)

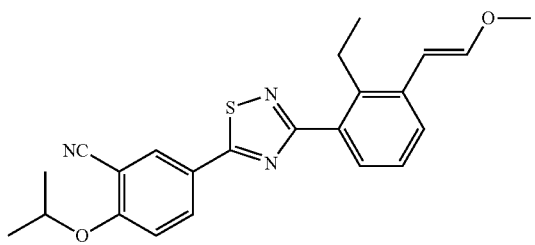 [SMILES: CCc1c(/C=C/OC)cccc1-c1nsc(-c2ccc(OC(C)C)c(C#N)c2)n1]

To a solution of 5-(3-bromo-1,2,4-thiadiazol-5-yl)-2-[(1-methylethyl)oxy]benzonitrile (D44) (630 mg), 2-{2-ethyl-3-[(E)-2-(methyloxy)ethenyl]phenyl}-4,4,5,5-tetramethyl-1,3,2-dioxaborolane (560 mg) and tripotassium phosphate (1237 mg) in N,N-dimethylformamide (DMF) (5 mL) and water (1.25 mL) stirred under nitrogen was added Pd(Ph₃P)₄ (225 mg). The mixture was sealed and heated under microwave at 120° C. for 15 min. After cooling the reaction, the mixture was concentrated and purified by column chromatography to give 5-(3-{2-ethyl-3-[(E)-2-(methyloxy)ethenyl]phenyl}-1,2,4-thiadiazol-5-yl)-2-[(1-methylethyl)oxy]benzonitrile (D54) (670 mg) as a colorless oil. MS (ES): $C_{23}H_{23}N_3O_2S$ requires 405. found 406.2 (M+H⁺).

Description for D55

5-{3-[2-ethyl-3-(2-oxoethyl)phenyl]-1,2,4-thiadiazol-5-yl}-2-[(1-methylethyl)oxy]benzonitrile (D55)

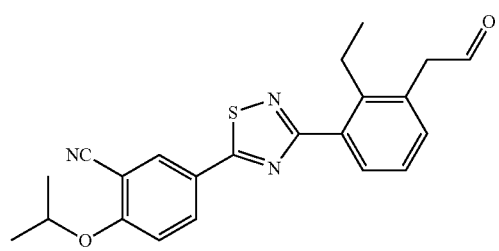 [SMILES: CCc1c(CC=O)cccc1-c1nsc(-c2ccc(OC(C)C)c(C#N)c2)n1]

To a solution of 5-(3-{2-ethyl-3-[(E)-2-(methyloxy)ethenyl]phenyl}-1,2,4-thiadiazol-5-yl)-2-[(1-methylethyl)oxy]benzonitrile (D54) (670 mg) in tetrahydrofuran (THF) (20 mL) stirred under nitrogen at room temperature was added 2M hydrochloric acid (0.826 mL). The reaction mixture was stirred at 65° C. for 3 h. After cooling the reaction, the solution was condensed under reduced pressure to give 5-{3-[2-ethyl-3-(2-oxoethyl)phenyl]-1,2,4-thiadiazol-5-yl}-2-[(1-methylethyl)oxy]benzonitrile (D55) (647 mg), which was used directly in the next step without further purification. MS (ES): $C_{22}H_{21}N_3O_2S$ requires 391. found 392.2 (M+H⁺).

Description for D56

2-(2-methylpropyl)-5-nitrobenzonitrile (D56)

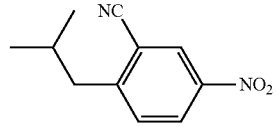

To a solution of isobutylboronic acid (5.89 g), 2-bromo-5-nitrobenzo nitrile (12.5 g) and $Cs_2CO_3$ (35.9 g) in toluene (150 mL) and water (5 mL) stirred under nitrogen at room temperature was added solid $PdCl_2(dppf)$-$CH_2Cl_2$ adduct (2.248 g) in one charge. The reaction mixture was stirred at 100° C. for 16 h. After cooling the reaction, the solvent was removed in vacuo. The residue was purified by column chromatography to give 2-(2-methylpropyl)-5-nitrobenzonitrile (D56) (11 g) as a light yellow oil. δH (CDCl₃, 400 MHz): 1.00 (6H, d), 2.06 (1H, m), 2.86 (2H, d), 7.52 (1H, d), 8.37 (1H, dd), 8.51 (1H, d).

Description for D57

5-amino-2-(2-methylpropyl)benzonitrile (D57)

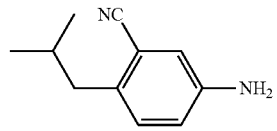

To a solution of 2-isobutyl-5-nitrobenzonitrile (D56) (7.5 g) in methanol (80 mL) and water (80 mL) was added ammonium formate (51.9 g) and zinc (26.9 g). The reaction mixture was stirred at 80° C. for 4 h. After cooling the reaction, the solid was filtered, the filtrate was concentrated under reduced pressure, the residue was extracted with EtOAc (300 mL*2), the combined organic layers were washed with water (30 mL*2), dried and concentrated to give 5-amino-2-(2-methylpropyl)benzonitrile (D57) (17.5 g) as a colorless solid. MS (ES): $C_{11}H_{14}N_2$ requires 174. found 175.1 (M+H⁺).

Description for D58

5-bromo-2-(2-methylpropyl)benzonitrile (D58)

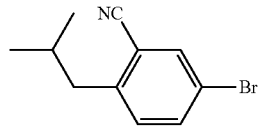

To a solution of 5-amino-2-isobutylbenzonitrile (D57) (34 g) in acetonitrile (500 mL) was added HBr (24.37 mL) at 0° C. Then a solution of sodium nitrite (16.16 g) in water (50 mL) was added to the reaction mixture. After stirring for 30 min, copper(II) bromide (87 g) and copper(I) bromide (5.60 g)

were added to the reaction mixture. The mixture was stirred at room temperature for 16 h. Saturated aqueous sodium bicarbonate solution was added to quench the reaction. The mixture was extracted with EA. The combined organic solution was dried over anhydrous sodium sulphate. After filtration and concentration, the residue was purified by column chromatography to give 5-bromo-2-(2-methylpropyl)benzonitrile (D58) (36 g) as a colorless oil. δH (CDCl$_3$, 400 MHz): 0.96 (6H, d), 1.98 (1H, m), 2.69 (2H, d), 7.18 (1H, d), 7.64 (1H, dd), 7.55 (1H, d).

Description for D59

2-(2-methylpropyl)-5-(4,4,5,5-tetramethyl-1,3,2-dioxaborolan-2-yl)benzonitrile (D59)

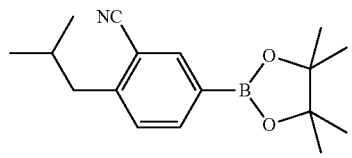 [SMILES: CC(C)Cc1ccc(B2OC(C)(C)C(C)(C)O2)cc1C#N]

To a solution of 5-bromo-2-isobutylbenzonitrile (D58) (10 g, 42.0 mmol), 4,4,4',4',5,5,5',5'-octamethyl-2,2'-bi(1,3,2-dioxaborolane) (11.20 g) and potassium acetate (12.36 g) in 1,4-dioxane (150 mL) stirred at room temperature under nitrogen was added PdCl$_2$(dppf)-CH$_2$Cl$_2$ adduct (1.715 g). The reaction mixture was heated and stirred at 80° C. for 12 h. The solvent was removed under reduced pressure. The residue was dissolved in EA (300 mL) and the organic phase was washed with water and brine, dried over anhydrous Na$_2$SO$_4$. The dried solution was concentrated and the residue was purified by column chromatography to give 2-(2-methylpropyl)-5-(4,4,5,5-tetramethyl-1,3,2-dioxaborolan-2-yl)benzonitrile (D59) (10.1 g) as a white solid. δH (CDCl$_3$, 400 MHz): 0.96 (6H, d), 1.37 (12H, s), 2.01 (1H, m), 2.74 (2H, d), 7.29 (1H, d), 7.90 (1H, d), 8.07 (1H, s).

Description for D60

5-(3-bromo-1,2,4-thiadiazol-5-yl)-2-(2-methylpropyl)benzonitrile (D60)

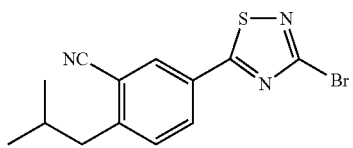 [SMILES: CC(C)Cc1ccc(-c2nc(Br)ns2)cc1C#N]

To a solution of 2-(2-methylpropyl)-5-(4,4,5,5-tetramethyl-1,3,2-dioxaborolan-2-yl)benzonitrile (D59) (500 mg), 3-bromo-5-chloro-1,2,4-thiadiazole (699 mg) and tripotassium phosphate (1116 mg) in N,N-dimethylformamide (DMF) (6 mL) and water (1.500 mL) stirred under nitrogen was added PdCl$_2$(dppf) (154 mg). The reaction mixture was sealed and heated under microwave at 80° C. for 1 h. After cooling the reaction, the mixture was diluted with ethyl acetate, the organic phase was washed with water, dried and concentrated, the residue was purified by column chromatography to afford 5-(3-bromo-1,2,4-thiadiazol-5-yl)-2-(2-methylpropyl)benzonitrile (D60) (500 mg). δH (CDCl$_3$, 400 MHz): 0.99 (6H, d), 2.04 (1H, m), 2.80 (2H, d), 7.46 (1H, d), 8.05 (1H, dd), 8.22 (1H, d). MS (ES): C$_{13}$H$_{12}$BrN$_3$S requires 321. found 322.0 (M+H$^+$).

Description for D61

5-(3-{2-ethyl-3-[(E)-2-(methyloxy)ethenyl]phenyl}-1,2,4-thiadiazol-5-yl)-2-(2-methylpropyl)benzonitrile (D61)

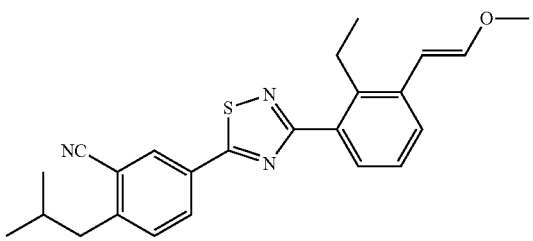 [SMILES: CCc1c(/C=C/OC)cccc1-c1nsc(-c2ccc(CC(C)C)c(C#N)c2)n1]

To a solution of 5-(3-bromo-1,2,4-thiadiazol-5-yl)-2-(2-methylpropyl)benzonitrile (D60) (500 mg), 2-{2-ethyl-3-[(E)-2-(methyloxy)ethenyl]phenyl}-4,4,5,5-tetramethyl-1,3,2-dioxaborolane (470 mg) and tripotassium phosphate (988 mg) in N,N-dimethylformamide (DMF) (6 mL) and water (1.5 mL) stirred under nitrogen was added Pd(Ph$_3$P)$_4$ (179 mg). The mixture was sealed and heated under microwave at 120° C. for 15 min. After cooling the reaction, the mixture was diluted with ethyl acetate, washed with water, dried over sodium sulphate, concentrated and purified by column chromatography to give 5-(3-{2-ethyl-3-[(E)-2-(methyloxy)ethenyl]phenyl}-1,2,4-thiadiazol-5-yl)-2-(2-methylpropyl)benzonitrile (D61) (500 mg). MS (ES): C$_{24}$H$_{25}$N$_3$OS requires 403. found 404.2 (M+H$^+$).

Description for D62

5-{3-[2-ethyl-3-(2-oxoethyl)phenyl]-1,2,4-thiadiazol-5-yl}-2-(2-methylpropyl)benzonitrile (D62)

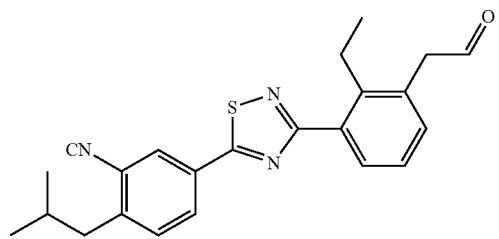

To a solution of 5-(3-{2-ethyl-3-[(E)-2-(methyloxy)ethenyl]phenyl}-1,2,4-thiadiazol-5-yl)-2-(2-methylpropyl)benzonitrile (D61) (500 mg) in tetrahydrofuran (THF) (20 mL) stirred under nitrogen at room temperature was added 2M hydrochloric acid (1.239 mL). The reaction mixture was stirred at 70° C. for 2 h. After cooling the reaction, the solution was condensed under reduced pressure to give 5-{3-[2-ethyl-3-(2-oxoethyl)phenyl]-1,2,4-thiadiazol-5-yl}-2-(2-methylpropyl)benzonitrile (D62) (483 mg), which was used directly

Description for D63

5-[3-(2-ethyl-3-formylphenyl)-1,2,4-thiadiazol-5-yl]-2-(2-methylpropyl)benzonitrile (D63)

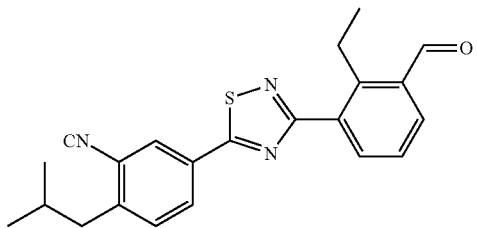

To a solution of 5-(3-bromo-1,2,4-thiadiazol-5-yl)-2-(2-methylpropyl)benzonitrile (D60) (500 mg), 2-ethyl-3-(4,4,5,5-tetramethyl-1,3,2-dioxaborolan-2-yl)benzaldehyde (D5) (424 mg) and tripotassium phosphate (988 mg) in N,N-dimethylformamide (DMF) (4 mL) and water (1 mL) stirred under nitrogen was added Pd(Ph$_3$P)$_4$ (179 mg). The mixture was sealed and heated under microwave at 120° C. for 15 min. After cooling the reaction, the mixture was diluted with ethyl acetate, washed with water, dried over sodium sulphate, concentrated and purified by column chromatography to give 5-[3-(2-ethyl-3-formylphenyl)-1,2,4-thiadiazol-5-yl]-2-(2-methylpropyl)benzonitrile (D63) (520 mg). δH (CDCl$_3$, 400 MHz): 1.00 (6H, d), 1.37 (3H, t), 2.81 (2H, d), 3.38 (2H, q), 4.11 (1H, m), 7.48 (2H, m), 8.02 (1H, d), 8.14 (2H, m), 8.30 (1H, d), 10.48 (1H, s). MS (ES): C$_{22}$H$_{21}$N$_3$OS requires 375. found 376.1 (M+H$^+$).

Description for D64

2-[(1-methylethyl)oxy]-5-(1,3-thiazol-2-yl)benzonitrile (D64)

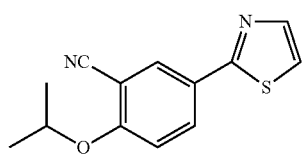 [SMILES: CC(C)Oc1ccc(-c2nccs2)cc1C#N]

To a suspension of 2-[(1-methylethyl)oxy]-5-(4,4,5,5-tetramethyl-1,3,2-dioxaborolan-2-yl)benzonitrile (D39) (109 mg), 2-bromo-1,3-thiazole (93 mg) and cesium carbonate (148 mg) in acetonitrile (3 mL)/water (0.750 mL) stirred under nitrogen was added PdCl$_2$(dppf)-CH$_2$Cl$_2$ adduct (31.0 mg). The reaction vessel was sealed and heated under microwave at 120° C. for 1 h. After cooling the reaction, the reaction mixture was diluted with ethyl acetate, filtered through celite. The filtrate was partitioned between ethyl acetate and water. The organic phase was dried over sodium sulphate and evaporated in vacuo to give the crude product, which was purified by column chromatography to afford 2-[(1-methylethyl)oxy]-5-(1,3-thiazol-2-yl)benzonitrile (D64) (50 mg). MS (ES): C$_{13}$H$_{12}$N$_2$OS requires 244. found 245.1 (M+H$^+$).

Description for D65

5-(5-bromo-1,3-thiazol-2-yl)-2-[(1-methylethyl)oxy]benzonitrile (D65)

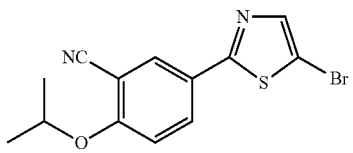 [SMILES: CC(C)Oc1ccc(-c2ncc(Br)s2)cc1C#N]

To a solution of 2-[(1-methylethyl)oxy]-5-(1,3-thiazol-2-yl)benzonitrile (D64) (215 mg) and sodium acetate (144 mg) in acetic acid (8 mL) stirred at room temperature was added a solution of Br$_2$ (0.045 mL) in acetic acid (1 mL) dropwise. The reaction mixture was stirred at 20° C. until start material was consumed completely. The reaction mixture was basified with 2M NaOH, then diluted with ethyl acetate. The mixture was washed with water and brine. The organic phase was dried over anhydrous sodium sulphate. After concentration, the crude product 5-(5-bromo-1,3-thiazol-2-yl)-2-[(1-methylethyl)oxy]benzonitrile (D65) (320 mg) was used for next step without further purification. δH (CDCl$_3$, 600 MHz): 1.36 (6H, d), 4.65 (1H, m), 6.95 (1H, d), 7.64 (1H, s), 7.92 (1H, d), 7.97 (1H, dd).

Description for D66

2-[4-[(1-methylethyl)oxy]-3-(trifluoromethyl)phenyl]-1,3-thiazole (D66)

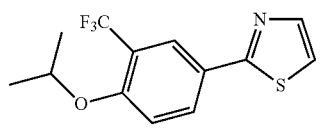 [SMILES: CC(C)Oc1ccc(-c2nccs2)cc1C(F)(F)F]

To a solution of 4,4,5,5-tetramethyl-2-[4-[(1-methylethyl)oxy]-3-(trifluoromethyl)phenyl]-1,3,2-dioxaborolane (D42) (160 mg), 2-bromo-1,3-thiazole (119 mg) and cesium carbonate (237 mg) in acetonitrile (15 mL) and water (3.75 mL) stirred under nitrogen at room temperature was added PdCl$_2$(dppf)-CH$_2$Cl$_2$ adduct (39.6 mg) in one charge. The reaction vessel was sealed and heated under microwave at 120° C. for 1 h. After cooling the reaction, the reaction mixture was filtered and the filtrate was partitioned between ethyl acetate (150 mL) and saturated brine (50 mL). The organic phase was dried over sodium sulphate and evaporated in vacuo. The crude product was purified by column chromatography to give 2-[4-[(1-methylethyl)oxy]-3-(trifluoromethyl)phenyl]-1,3-thiazole (D66) (73 mg). MS (ES): C$_{13}$H$_{12}$F$_3$NOS requires 287. found 288.1 (M+H$^+$).

Description for D67

5-bromo-2-[4-[(1-methylethyl)oxy]-3-(trifluoromethyl)phenyl]-1,3-thiazole (D67)

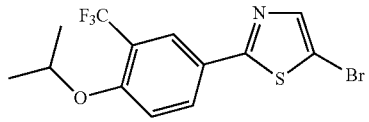 [SMILES: CC(C)Oc1ccc(-c2ncc(Br)s2)cc1C(F)(F)F]

To a solution of 2-[4-[(1-methylethyl)oxy]-3-(trifluoromethyl)phenyl]-1,3-thiazole (D66) (143 mg) and sodium acetate (82 mg) in acetic acid (5 mL) stirred at 5° C. was added a solution of $Br_2$ (0.026 mL) in acetic acid (1 mL) dropwise. The reaction mixture was stirred at 20° C. until start material was consumed completely. The reaction mixture was basified with 2M NaOH. The resulting solution was diluted with ethyl acetate. The mixture was washed with brine. The organic phase was dried over anhydrous sodium sulphate and evaporated in vacuo. The crude product was purified by column chromatography to give 5-bromo-2-[4-[(1-methylethyl)oxy]-3-(trifluoromethyl)phenyl]-1,3-thiazole (D67) (120 mg). δH (CDCl₃, 600 MHz): 1.31 (6H, d), 4.63 (1H, m), 7.05 (1H, d), 7.70 (1H, s), 7.94 (1H, dd), 8.06 (1H, d).

Description for D68

4-bromo-2-chloro-1-[(1-methylethyl)oxy]benzene (D68)

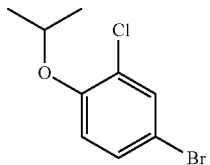

To a solution of 4-bromo-2-chlorophenol (50 g) in N,N-dimethylformamide (DMF) (250 mL) stirred under nitrogen at room temperature was added $K_2CO_3$ (100 g) and 2-bromopropane (136 mL) in one charge. The reaction mixture was stirred at 85° C. for 16 h. After cooling the reaction, the reaction mixture was filtered, the solvent of the filtrate was removed in vacuo. The residue was dissolved in diethyl ether (300 mL), washed with water (6*100 mL), the organic phase was dried over $MgSO_4$ and concentrated to give 4-bromo-2-chlorophenyl 1-methylethyl ether (D68) (56 g) as a yellow oil. δH (CDCl₃, 400 MHz): 1.37 (6H, d), 4.52 (1H, m), 6.82 (1H, d), 7.29 (1H, m), 7.50 (1H, d).

Description for D69

2-{3-chloro-4-[(1-methylethyl)oxy]phenyl}-4,4,5,5-tetramethyl-1,3,2-dioxaborolane (D69)

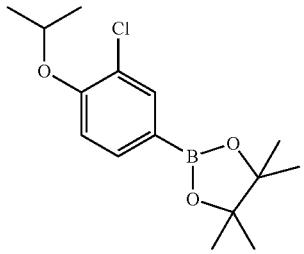 [SMILES: CC(C)Oc1ccc(B2OC(C)(C)C(C)(C)O2)cc1Cl]

To a suspension of 4-bromo-2-chloro-1-[(1-methylethyl)oxy]benzene (D68) (10 g), 4,4,4',4',5,5,5',5'-octamethyl-2,2'-bi-1,3,2-dioxaborolane (15.26 g) and potassium acetate (15.73 g) in N,N-dimethylformamide (DMF) (150 mL) stirred under nitrogen at room temperature was added $PdCl_2$(dppf)-$CH_2Cl_2$ adduct (1.964 g). The reaction mixture was stirred at 80° C. overnight. After cooling the reaction, the reaction mixture was concentrated in vacuo, the residue was diluted with ethyl acetate and filtered through celite, the filtrate was washed with water and brine, the organic phase was dried over anhydrous $Na_2SO_4$. After removing the solvent, the residue was purified by column chromatography to give 2-{3-chloro-4-[(1-methylethyl)oxy]phenyl}-4,4,5,5-tetramethyl-1,3,2-dioxaborolane (D69) (11.8 g). MS (ES): $C_{15}H_{22}BClO_3$ requires 296. found 297.1 (M+H⁺).

Description for D70

2-{3-chloro-4-[(1-methylethyl)oxy]phenyl}-1,3-thiazole (D70)

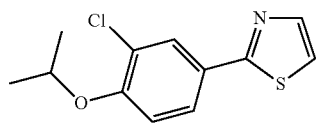 [SMILES: CC(C)Oc1ccc(-c2nccs2)cc1Cl]

To a suspension of 2-{3-chloro-4-[(1-methylethyl)oxy]phenyl}-4,4,5,5-tetramethyl-1,3,2-dioxaborolane (D69) (3 g), 2-bromo-1,3-thiazole (1.659 g) and $Cs_2CO_3$ (3.95 g) in 1,2-dimethoxyethane (DME) (40 mL)/water (10 mL) stirred under nitrogen at room temperature was added $PdCl_2$(dppf)-$CH_2Cl_2$ adduct (661 mg) in one charge. The reaction vessel was sealed and heated under microwave at 120° C. for 2 h. After cooling the reaction, the reaction mixture was filtered and the filtrate was partitioned between ethyl acetate (150 mL) and saturated brine (50 mL). The organic phase was dried over sodium sulphate and evaporated in vacuo. The crude product was purified by column chromatography to give 2-{3-chloro-4-[(1-methylethyl)oxy]phenyl}-1,3-thiazole (D70) (1.5 g). MS (ES): $C_{12}H_{12}ClNOS$ requires 253. found 254.1 (M+H⁺).

Description for D71

5-bromo-2-{3-chloro-4-[(1-methylethyl)oxy]phenyl}-1,3-thiazole (D71)

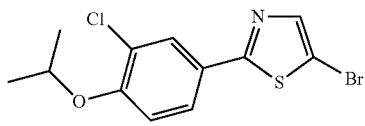 [SMILES: CC(C)Oc1ccc(-c2ncc(Br)s2)cc1Cl]

To a solution of 2-{3-chloro-4-[(1-methylethyl)oxy]phenyl}-1,3-thiazole (D70) (1.5 g) and sodium acetate (0.970 g) in acetic acid (10 mL) stirred at room temperature was added a solution of $Br_2$ (0.31 ml) in acetic acid (1 mL) dropwise during 30 min. The reaction mixture was stirred at 20° C. until start material was consumed completely. The reaction mixture was basified with 2M NaOH. The resulting solution was diluted with ethyl acetate. The mixture was washed with brine. The organic phase was dried over anhydrous sodium sulphate and evaporated in vacuo. The crude product was purified by column chromatography to give 5-bromo-2-{3- chloro-4-[(1-methylethyl)oxy]phenyl}-1,3-thiazole (D71) (1.2 g). MS (ES): $C_{12}H_{11}BrClNOS$ requires 332. found 333.0 (M+H$^+$).

Description for D72

2-ethyl-3-{2-[4-[(1-methylethyl)oxy]-3-(trifluoromethyl)phenyl]-1,3-thiazol-5-yl}benzaldehyde (D72)

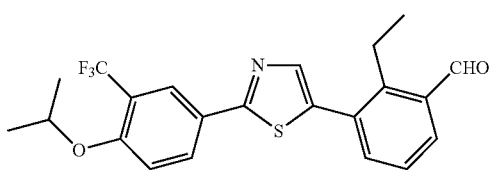 [SMILES: CCc1c(C=O)cccc1-c1cnc(-c2ccc(OC(C)C)c(C(F)(F)F)c2)s1]

To a solution of 5-bromo-2-[4-[(1-methylethyl)oxy]-3-(trifluoromethyl)phenyl]-1,3-thiazole (D67) (120 mg), 2-ethyl-3-(4,4,5,5-tetramethyl-1,3,2-dioxaborolan-2-yl)benzaldehyde (D5) (77 mg) and tripotassium phosphate (157 mg) in 1,2-dimethoxyethane (DME) (3 mL) and water (0.750 mL) stirred under nitrogen at room temperature was added Pd(Ph$_3$P)$_4$ (34.1 mg) in one charge. The reaction vessel was sealed and heated under microwave at 130° C. for 15 min. After cooling the reaction, the reaction mixture was filtered and the filtrate was partitioned between ethyl acetate (250 mL) and saturated brine (50 mL). The organic phase was dried over sodium sulphate and evaporated in vacuo. The crude product was purified by column chromatography to give 2-ethyl-3-{2-[4-[(1-methylethyl)oxy]-3-(trifluoromethyl)phenyl]-1,3-thiazol-5-yl}benzaldehyde (D72) (60 mg). MS (ES): $C_{22}H_{20}F_3NO_2S$ requires 419. found 420.0 (M+H$^+$).

Description for D73

5-[5-(2-ethyl-3-formylphenyl)-1,3-thiazol-2-yl]-2-[(1-methylethyl)oxy]benzonitrile (D73)

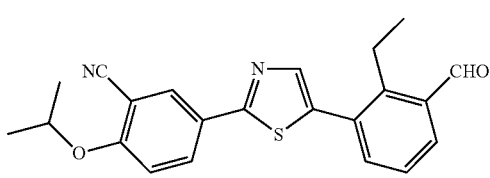 [SMILES: CCc1c(C=O)cccc1-c1cnc(-c2ccc(OC(C)C)c(C#N)c2)s1]

To a solution of 5-(5-bromo-1,3-thiazol-2-yl)-2-[(1-methylethyl)oxy]benzonitrile (D65) (500 mg), 2-ethyl-3-(4,4,5,5-tetramethyl-1,3,2-dioxaborolan-2-yl)benzaldehyde (443 mg) and tripotassium phosphate (657 mg) in N,N-dimethylformamide (DMF) (12 mL) and water (2 mL) stirred under nitrogen at room temperature was added Pd(Ph$_3$P)$_4$ (179 mg) in one charge. The reaction vessel was sealed and heated under microwave at 120° C. for 15 min. After cooling the reaction, the reaction mixture was filtered and the filtrate was partitioned between ethyl acetate (250 mL) and saturated brine (50 mL). The organic phase was dried over sodium sulphate and evaporated in vacuo. The crude product was purified by column chromatography to give 5-[5-(2-ethyl-3-formylphenyl)-1,3-thiazol-2-yl]-2-[(1-methylethyl)oxy]benzonitrile (D73) (500 mg) as a brown oil. MS (ES): $C_{22}H_{20}N_2O_2S$ requires 376. found 377.1 (M+H$^+$).

Description for D74

3-(2-{3-chloro-4-[(1-methylethyl)oxy]phenyl}-1,3-thiazol-5-yl)-2-ethylbenzaldehyde (D74)

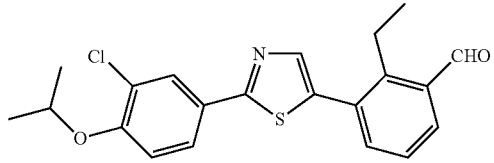 [SMILES: CCc1c(C=O)cccc1-c1cnc(-c2ccc(OC(C)C)c(Cl)c2)s1]

To a solution of 5-bromo-2-{3-chloro-4-[(1-methylethyl)oxy]phenyl}-1,3-thiazole (D71) (500 mg), 2-ethyl-3-(4,4,5,5-tetramethyl-1,3,2-dioxaborolan-2-yl)benzaldehyde (430 mg) and tripotassium phosphate (638 mg) in N,N-dimethylformamide (DMF) (12 mL) and water (2 mL) stirred under nitrogen at room temperature was added Pd(Ph$_3$P)$_4$ (174 mg) in one charge. The reaction vessel was sealed and heated under microwave at 120° C. for 15 min. After cooling the reaction, the reaction mixture was filtered and the filtrate was partitioned between ethyl acetate (250 mL) and saturated brine (50 mL). The organic phase was dried over sodium sulphate and evaporated in vacuo. The crude product was purified by column chromatography to give 3-(2-{3-chloro-4-[(1-methylethyl)oxy]phenyl}-1,3-thiazol-5-yl)-2-ethylbenzaldehyde (D74) (500 mg) as a brown oil. MS (ES): $C_{21}H_{20}ClNO_2S$ requires 385. found 386.0 (M+H$^+$).

Description for D75

5-(5-{2-ethyl-3-[(E)-2-(methyloxy)ethenyl]phenyl}-1,3-thiazol-2-yl)-2-[(1-methylethyl)oxy]benzonitrile (D75)

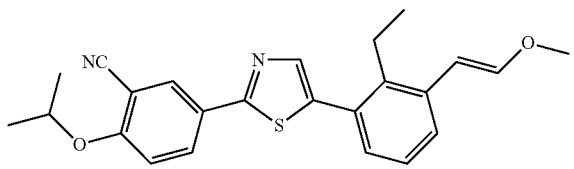 [SMILES: CCc1c(/C=C/OC)cccc1-c1cnc(-c2ccc(OC(C)C)c(C#N)c2)s1]

To a solution of 5-(5-bromo-1,3-thiazol-2-yl)-2-[(1-methylethyl)oxy]benzonitrile (D65) (500 mg), 2-{2-ethyl-3-[(E)-2-(methyloxy)ethenyl]phenyl}-4,4,5,5-tetramethyl-1,3,2-dioxaborolane (401 mg) and tripotassium phosphate (591 mg) in N,N-dimethylformamide (DMF) (12 mL) and water (2 mL) stirred under nitrogen at room temperature was added Pd(Ph$_3$P)$_4$ (161 mg) in one charge. The reaction vessel was sealed and heated under microwave at 120° C. for 15 min. After cooling the reaction, the reaction mixture was filtered and the filtrate was partitioned between ethyl acetate (250 mL) and saturated brine (50 mL). The organic phase was dried over sodium sulphate and evaporated in vacuo. The crude product was purified by column chromatography to give 5-(5-{2-ethyl-3-[(E)-2-(methyloxy)ethenyl]phenyl}-1,3-thiazol-2-yl)-2-[(1-methylethyl)oxy]benzonitrile (D75) (548 mg) as a brown oil. MS (ES): $C_{24}H_{24}N_2O_2S$ requires 404. found 405.2 (M+H$^+$).

Description for D76

5-{5-[2-ethyl-3-(2-oxoethyl)phenyl]-1,3-thiazol-2-yl}-2-[(1-methylethyl)oxy]benzonitrile (D76)

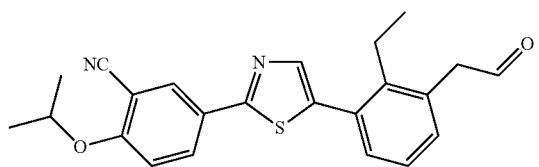 [SMILES: CCc1c(CC=O)cccc1-c1cnc(-c2ccc(OC(C)C)c(C#N)c2)s1]

To a mixture of 5-(5-{2-ethyl-3-[(E)-2-(methyloxy)ethenyl]phenyl}-1,3-thiazol-2-yl)-2-[(1-methylethyl)oxy]benzonitrile (D75) (550 mg) in tetrahydrofuran (THF) (20 mL) under nitrogen was added HCl (1.360 mL). The reaction was heated to 75° C. for 6 h. The mixture was concentrated to give the crude product 5-{5-[2-ethyl-3-(2-oxoethyl)phenyl]-1,3-thiazol-2-yl}-2-[(1-methylethyl)oxy]benzonitrile (D76) (531 mg) as a brown oil. MS (ES): $C_{23}H_{22}N_2O_2S$ requires 390. found 391.0 (M+H$^+$).

Description for D77

2-{3-chloro-4-[(1-methylethyl)oxy]phenyl}-5-{2-ethyl-3-[(E)-2-(methyloxy)ethenyl]phenyl}-1,3-thiazole (D77)

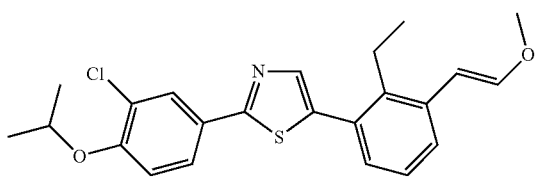 [SMILES: CCc1c(/C=C/OC)cccc1-c1cnc(-c2ccc(OC(C)C)c(Cl)c2)s1]

To a solution of 5-bromo-2-{3-chloro-4-[(1-methylethyl)oxy]phenyl}-1,3-thiazole (D71) (500 mg), 2-{2-ethyl-3-[(E)-2-(methyloxy)ethenyl]phenyl}-4,4,5,5-tetramethyl-1,3,2-dioxaborolane (530 mg) and tripotassium phosphate (651 mg) in N,N-dimethylformamide (DMF) (12 mL) and water (2 mL) stirred under nitrogen at room temperature was added Pd(Ph$_3$P)$_4$ (177 mg) in one charge. The reaction vessel was sealed and heated under microwave at 120° C. for 15 min. After cooling the reaction, the reaction mixture was filtered and the filtrate was partitioned between ethyl acetate (250 mL) and saturated brine (50 mL). The organic phase was dried over sodium sulphate and evaporated in vacuo. The crude product was purified by column chromatography to give 2-{3-chloro-4-[(1-methylethyl)oxy]phenyl}-5-{2-ethyl-3-[(E)-2-(methyloxy)ethenyl]phenyl}-1,3-thiazole (D77) (500 mg) as a brown oil. MS (ES): $C_{23}H_{24}ClNO_2S$ requires 413. found 414.2 (M+H$^+$).

Description for D78

[3-(2-{3-chloro-4-[(1-methylethyl)oxy]phenyl}-1,3-thiazol-5-yl)-2-ethylphenyl]acetaldehyde (D78)

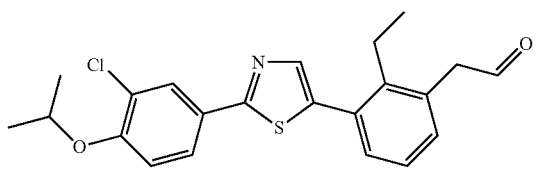 [SMILES: CCc1c(CC=O)cccc1-c1cnc(-c2ccc(OC(C)C)c(Cl)c2)s1]

To a mixture of 2-{3-chloro-4-[(1-methylethyl)oxy]phenyl}-5-{2-ethyl-3-[(E)-2-(methyloxy)ethenyl]phenyl}-1,3-thiazole (D77) (500 mg) in tetrahydrofuran (THF) (100 mL) under nitrogen was added HCl (0.805 mL). The reaction was heated to 75° C. for 3 h. The mixture was concentrated to give the crude product [3-(2-{3-chloro-4-[(1-methylethyl)oxy]phenyl}-1,3-thiazol-5-yl)-2-ethylphenyl]acetaldehyde (D78) (483 mg) as a brown oil. MS (ES): $C_{22}H_{22}ClNO_2S$ requires 399. found 400.1 (M+H$^+$).

Description for D79

2-{3-chloro-4-[(1-methylethyl)oxy]phenyl}-5-{5-fluoro-2-(methyloxy)-3-[(E)-2-(methyloxy)ethenyl]phenyl}-1,3-thiazole (D79)

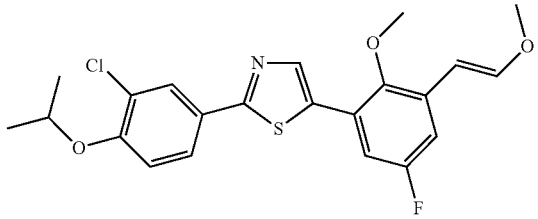 [SMILES: CO/C=C/c1cc(F)cc(-c2cnc(-c3ccc(OC(C)C)c(Cl)c3)s2)c1OC]

To a solution of 5-bromo-2-{3-chloro-4-[(1-methylethyl)oxy]phenyl}-1,3-thiazole (D71) (500 mg), 2-{5-fluoro-2-(methyloxy)-3-[(E)-2-(methyloxy)ethenyl]phenyl}-4,4,5,5-tetramethyl-1,3,2-dioxaborolane (510 mg) and tripotassium phosphate (702 mg) in N,N-dimethylformamide (DMF) (12 mL) and water (2 mL) stirred under nitrogen at room temperature was added Pd(Ph$_3$P)$_4$ (191 mg) in one charge. The reaction vessel was sealed and heated under microwave at 120° C. for 15 min. After cooling the reaction, the reaction mixture was filtered and the filtrate was partitioned between ethyl acetate (250 mL) and saturated brine (50 mL). The organic phase was dried over sodium sulphate and evaporated in vacuo. The crude product was purified by column chromatography to give 2-{3-chloro-4-[(1-methylethyl)oxy]phenyl}-5-{5-fluoro-2-(methyloxy)-3-[(E)-2-(methyloxy)ethenyl]phenyl}-1,3-thiazole (D79) (311 mg) as a brown oil. MS (ES): $C_{22}H_{21}ClFNO_3S$ requires 433. found 434.1 (M+H$^+$).

Description for D80

[3-(2-{3-chloro-4-[(1-methylethyl)oxy]phenyl}-1,3-thiazol-5-yl)-5-fluoro-2-(methyloxy)phenyl]acetaldehyde (D80)

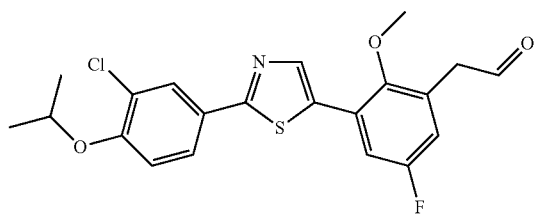 [SMILES: COc1c(CC=O)cc(F)cc1-c1cnc(-c2ccc(OC(C)C)c(Cl)c2)s1]

To a mixture of 2-{3-chloro-4-[(1-methylethyl)oxy]phenyl}-5-{5-fluoro-2-(methyloxy)-3-[(E)-2-(methyloxy)ethenyl]phenyl}-1,3-thiazole (D79) (100 mg) in tetrahydrofuran (THF) (20 mL) under nitrogen was added HCl (0.5 mL). The reaction was heated to 70° C. for 2 h. The mixture was filtered and the filtrate was concentrated to give the crude product [3-(2-{3-chloro-4-[(1-methylethyl)oxy]phenyl}-1,3-thiazol-5-yl)-5-fluoro-2-(methyloxy)phenyl]acetaldehyde (D80) (90 mg) as a brown oil. MS (ES): $C_{21}H_{19}ClFNO_3S$ requires 419. found 420.1 (M+H$^+$).

Description for D81 ethyl 1-[(2-ethyl-3-{2-[4-[(1-methylethyl)oxy]-3-(trifluoromethyl)phenyl]-1,3-thiazol-5-yl}phenyl)methyl]-4-piperidinecarboxylate (D81)

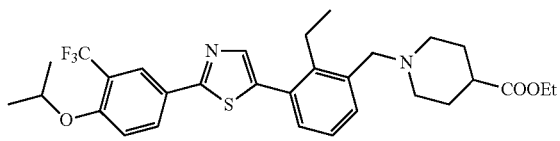 [SMILES: CCOC(=O)C1CCN(Cc2cccc(-c3cnc(-c4ccc(OC(C)C)c(C(F)(F)F)c4)s3)c2CC)CC1]

To a solution of 2-ethyl-3-{2-[4-[(1-methylethyl)oxy]-3-(trifluoromethyl)phenyl]-1,3-thiazol-5-yl}benzaldehyde (D72) (64 mg), acetic acid (0.044 mL) and sodium acetate (62.6 mg) in methanol (10.00 mL) stirred under nitrogen at room temperature was added ethyl 4-piperidinecarboxylate (120 mg) in one charge. The reaction mixture was stirred at room temperature for 1 h, then the solvent was evaporated in vacuo. The residue was dissolved in dichloromethane (DCM) (10 mL), sodium triacetoxyborohydride (97 mg) was added to the mixture. The reaction mixture was stirred at room temperature overnight. The reaction mixture was partitioned between ethyl acetate (100 mL) and saturated brine (30 mL). The organic phase was dried over sodium sulphate and evaporated in vacuo to give the crude product ethyl 1-[(2-ethyl-3-{2-[4-[(1-methylethyl)oxy]-3-(trifluoromethyl)phenyl]-1,3-thiazol-5-yl}phenyl)methyl]-4-piperidinecarboxylate (D81) (160 mg). The crude product was used for next step without further purification. MS (ES): $C_{30}H_{35}F_3N_2O_3S$ requires 560. found 561.3 (M+H$^+$).

Description for D82 methyl 1-{2-[3-(2-{3-chloro-4-[(1-methylethyl)oxy]phenyl}-1,3-thiazol-5-yl)-5-fluoro-2-(methyloxy)phenyl]ethyl}-3-azetidinecarboxylate (D82)

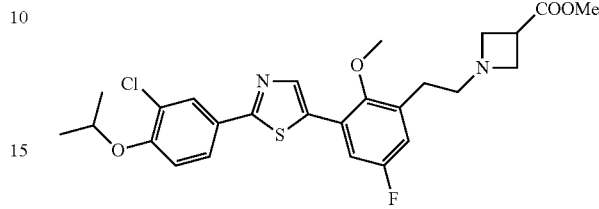

To a solution of [3-(2-{3-chloro-4-[(1-methylethyl)oxy]phenyl}-1,3-thiazol-5-yl)-5-fluoro-2-(methyloxy)phenyl]acetaldehyde (D80) (95 mg), acetic acid (0.044 mL) and sodium acetate (113 mg) in ethanol (20.00 mL) stirred under nitrogen at room temperature was added methyl 3-azetidinecarboxylate (106 mg) in one charge. The reaction mixture was stirred at room temperature for 1 h, then the solvent was evaporated in vacuo. The residue was dissolved in dichloromethane (DCM) (20 mL), sodium triacetoxyborohydride (195 mg) was added to the mixture. The reaction mixture was stirred at room temperature overnight. The reaction mixture was partitioned between ethyl acetate (100 mL) and saturated brine (30 mL). The organic phase was dried over sodium sulphate and evaporated in vacuo to give the crude product methyl 1-{2-[3-(2-{3-chloro-4-[(1-methylethyl)oxy]phenyl}-1,3-thiazol-5-yl)-5-fluoro-2-(methyloxy)phenyl]ethyl}-3-azetidinecarboxylate (D82) (100 mg). The crude product was used for next step without further purification. MS (ES): $C_{26}H_{28}ClFN_2O_4S$ requires 518. found 519.2 (M+H$^+$).

Description for D83 methyl 1-{2-[3-(2-{3-cyano-4-[(1-methylethyl)oxy]phenyl}-1,3-thiazol-5-yl)-2-ethylphenyl]ethyl}-3-azetidinecarboxylate (D83)

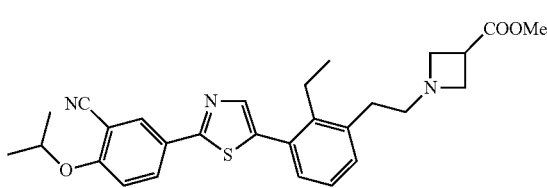 [SMILES: CCc1c(CCN2CC(C(=O)OC)C2)cccc1-c1cnc(-c2ccc(OC(C)C)c(C#N)c2)s1]

To a solution of 5-{5-[2-ethyl-3-(2-oxoethyl)phenyl]-1,3-thiazol-2-yl}-2-[(1-methylethyl)oxy]benzonitrile (D76) (150 mg), acetic acid (0.044 mL) and sodium acetate (63 mg) in ethanol (20.00 mL) stirred under nitrogen at room temperature was added methyl 3-azetidinecarboxylate (175 mg) in one charge. The reaction mixture was stirred at room temperature for 30 min, then the solvent was evaporated in vacuo. The residue was dissolved in dichloromethane (DCM) (20 mL), sodium triacetoxyborohydride (204 mg) was added to the mixture. The reaction mixture was stirred at room temperature overnight. The reaction mixture was partitioned between ethyl acetate (100 mL) and saturated brine (30 mL). The organic phase was dried over sodium sulphate and evaporated in vacuo to give the crude product methyl 1-{2-[3-(2-{3-cyano-4-[(1-methylethyl)oxy]phenyl}-1,3-thiazol-5-yl)-2-ethylphenyl]ethyl}-3-azetidinecarboxylate (D83) (188 mg). The crude product was used for next step without further purification. MS (ES): $C_{28}H_{31}N_3O_3S$ requires 489. found 490.2 (M+H$^+$).

Description for D84 ethyl 1-{[3-(2-{3-cyano-4-[(1-methylethyl)oxy]phenyl}-1,3-thiazol-5-yl)-2-ethylphenyl]methyl}-4-piperidinecarboxylate (D84)

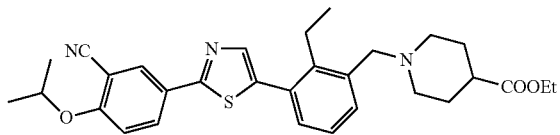 [SMILES: CCOC(=O)C1CCN(Cc2cccc(-c3cnc(-c4ccc(OC(C)C)c(C#N)c4)s3)c2CC)CC1]

To a solution of 5-[5-(2-ethyl-3-formylphenyl)-1,3-thiazol-2-yl]-2-[(1-methylethyl)oxy]benzonitrile (D73) (120 mg), acetic acid (0.036 mL) and sodium acetate (52.3 mg) in ethanol (20.00 mL) stirred under nitrogen at room temperature was added ethyl 4-piperidinecarboxylate (200 mg) in one charge. The reaction mixture was stirred at room temperature for 30 min, then the solvent was evaporated in vacuo. The residue was dissolved in dichloromethane (DCM) (20 mL), sodium triacetoxyborohydride (169 mg) was added to the mixture. The reaction mixture was stirred at room temperature overnight. The reaction mixture was partitioned between ethyl acetate (100 mL) and saturated brine (30 mL). The organic phase was dried over sodium sulphate and evaporated in vacuo to give the crude product ethyl 1-{[3-(2-{3-cyano-4-[(1-methylethyl)oxy]phenyl}-1,3-thiazol-5-yl)-2-ethylphenyl]methyl}-4-piperidinecarboxylate (D84) (165 mg). The crude product was used for next step without further purification. MS (ES): $C_{30}H_{35}N_3O_3S$ requires 517. found 518.3 (M+H$^+$).

Description for D85 ethyl 1-{[3-(2-{3-chloro-4-[(1-methylethyl)oxy]phenyl}-1,3-thiazol-5-yl)-2-ethylphenyl]methyl}-4-piperidinecarboxylate (D85)

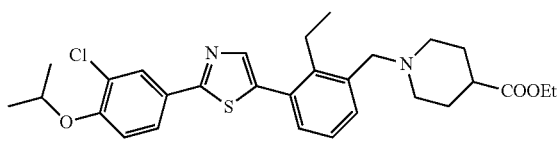 [SMILES: CCOC(=O)C1CCN(Cc2cccc(-c3cnc(-c4ccc(OC(C)C)c(Cl)c4)s3)c2CC)CC1]

To a solution of 3-(2-{3-chloro-4-[(1-methylethyl)oxy]phenyl}-1,3-thiazol-5-yl)-2-ethylbenzaldehyde (D74) (120 mg), acetic acid (0.036 mL) and sodium acetate (51.0 mg) in ethanol (20.00 mL) stirred under nitrogen at room temperature was added ethyl 4-piperidinecarboxylate (196 mg) in one charge. The reaction mixture was stirred at room temperature for 30 min, then the solvent was evaporated in vacuo. The residue was dissolved in dichloromethane (DCM) (20 mL), sodium triacetoxyborohydride (165 mg) was added to the mixture. The reaction mixture was stirred at room tempera-ture overnight. The reaction mixture was partitioned between ethyl acetate (100 mL) and saturated brine (30 mL). The organic phase was dried over sodium sulphate and evaporated in vacuo to give the crude product ethyl 1-{[3-(2-{3-chloro-4-[(1-methylethyl)oxy]phenyl}-1,3-thiazol-5-yl)-2-ethylphenyl]methyl}-4-piperidinecarboxylate (D85) (164 mg). The crude product was used for next step without further purification. MS (ES): $C_{29}H_{35}ClN_2O_3S$ requires 526. found 527.2 (M+H$^+$).

Description for D86 ethyl 1-{2-[3-(2-{3-cyano-4-[(1-methylethyl)oxy]phenyl}-1,3-thiazol-5-yl)-2-ethylphenyl]ethyl}-4-piperidinecarboxylate (D86)

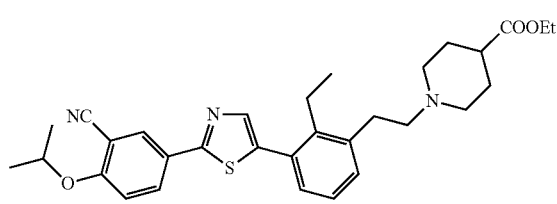 [SMILES: CCOC(=O)C1CCN(CCc2cccc(-c3cnc(-c4ccc(OC(C)C)c(C#N)c4)s3)c2CC)CC1]

To a solution of 5-{5-[2-ethyl-3-(2-oxoethyl)phenyl]-1,3-thiazol-2-yl}-2-[(1-methylethyl)oxy]benzonitrile (D76) (150 mg), acetic acid (0.044 mL) and sodium acetate (63.0 mg) in ethanol (20.00 mL) stirred under nitrogen at room temperature was added ethyl 4-piperidinecarboxylate (181 mg) in one charge. The reaction mixture was stirred at room temperature for 30 min, then the solvent was evaporated in vacuo. The residue was dissolved in dichloromethane (DCM) (20 mL), sodium triacetoxyborohydride (204 mg) was added to the mixture. The reaction mixture was stirred at room temperature overnight. The reaction mixture was partitioned between ethyl acetate (100 mL) and saturated brine (30 mL). The organic phase was dried over sodium sulphate and evaporated in vacuo to give the crude product ethyl 1-{2-[3-(2-{3-cyano-4-[(1-methylethyl)oxy]phenyl}-1,3-thiazol-5-yl)-2-ethylphenyl]ethyl}-4-piperidinecarboxylate (D86) (204 mg) as a brown oil. The crude product was used for next step without further purification. MS (ES): $C_{31}H_{37}N_3O_3S$ requires 531. found 532.3 (M+H$^+$).

Description for D87 methyl 1-{[3-(2-{3-cyano-4-[(1-methylethyl)oxy]phenyl}-1,3-thiazol-5-yl)-2-ethylphenyl]methyl}-3-azetidinecarboxylate (D87)

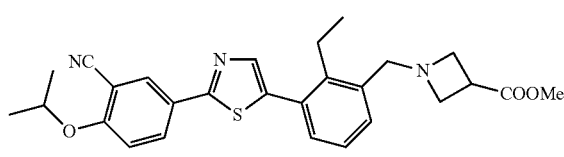 [SMILES: CCc1c(CN2CC(C(=O)OC)C2)cccc1-c1cnc(-c2ccc(OC(C)C)c(C#N)c2)s1]

To a solution of 5-[5-(2-ethyl-3-formylphenyl)-1,3-thiazol-2-yl]-2-[(1-methylethyl)oxy]benzonitrile (D73) (120 mg), acetic acid (0.023 mL) and sodium acetate (32.7 mg) in ethanol (20.00 mL) stirred under nitrogen at room temperature was added methyl 3-azetidinecarboxylate (92 mg) in one charge. The reaction mixture was stirred at room temperature for 30 min, then the solvent was evaporated in vacuo. The residue was dissolved in dichloromethane (DCM) (20 mL), sodium triacetoxyborohydride (169 mg) was added to the mixture. The reaction mixture was stirred at room temperature overnight. The reaction mixture was partitioned between ethyl acetate (100 mL) and saturated brine (30 mL). The organic phase was dried over sodium sulphate and evaporated in vacuo to give the crude product methyl 1-{[3-(2-{3-cyano-4-[(1-methylethyl)oxy]phenyl}-1,3-thiazol-5-yl)-2-ethylphenyl]methyl}-3-azetidinecarboxylate (D87) (126 mg). The crude product was used for next step without further purification. MS (ES): $C_{27}H_{29}N_3O_3S$ requires 475. found 476.2 (M+H$^+$).

Description for D88 methyl 1-{[3-(2-{3-chloro-4-[(1-methylethyl)oxy] phenyl}-1,3-thiazol-5-yl)-2-ethylphenyl]methyl}-3-azetidinecarboxylate (D88)

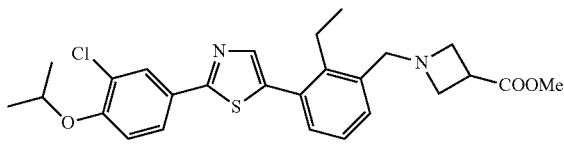 [SMILES: CCc1c(CN2CC(C(=O)OC)C2)cccc1-c1cnc(-c2ccc(OC(C)C)c(Cl)c2)s1]

To a solution of 3-(2-{3-chloro-4-[(1-methylethyl)oxy] phenyl}-1,3-thiazol-5-yl)-2-ethylbenzaldehyde (D74) (120 mg), acetic acid (0.022 mL) and sodium acetate (31.9 mg) in ethanol (20.00 mL) stirred under nitrogen at room temperature was added methyl 3-azetidinecarboxylate (90 mg) in one charge. The reaction mixture was stirred at room temperature for 30 min, then the solvent was evaporated in vacuo. The residue was dissolved in dichloromethane (DCM) (20 mL), sodium triacetoxyborohydride (137 mg) was added to the mixture. The reaction mixture was stirred at room temperature overnight. The reaction mixture was partitioned between ethyl acetate (100 mL) and saturated brine (30 mL). The organic phase was dried over sodium sulphate and evaporated in vacuo to give the crude product methyl 1-{[3-(2-{3-chloro-4-[(1-methylethyl)oxy]phenyl}-1,3-thiazol-5-yl)-2-ethylphenyl]methyl}-3-azetidinecarboxylate (D88) (226 mg) as a brown oil. The crude product was used for next step without further purification. MS (ES): $C_{26}H_{29}ClN_2O_3S$ requires 484. found 485.2 (M+H$^+$).

Description for D89 ethyl 1-{2-[3-(2-{3-chloro-4-[(1-methylethyl)oxy] phenyl}-1,3-thiazol-5-yl)-2-ethylphenyl]ethyl}-4-piperidinecarboxylate (D89)

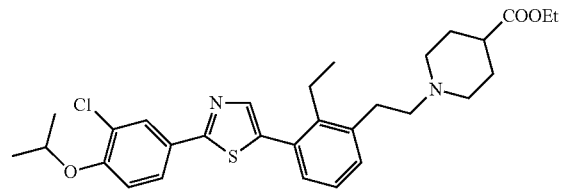 [SMILES: CCOC(=O)C1CCN(CCc2cccc(-c3cnc(-c4ccc(OC(C)C)c(Cl)c4)s3)c2CC)CC1]

To a solution of [3-(2-{3-chloro-4-[(1-methylethyl)oxy] phenyl}-1,3-thiazol-5-yl)-2-ethylphenyl]acetaldehyde (D78) (160 mg), acetic acid (0.036 mL) and sodium acetate (51.0 mg) in ethanol (20.00 mL) stirred under nitrogen at room temperature was added ethyl 4-piperidinecarboxylate (189 mg) in one charge. The reaction mixture was stirred at room temperature for 30 min, then the solvent was evaporated in vacuo. The residue was dissolved in dichloromethane (DCM) (20 mL), sodium triacetoxyborohydride (165 mg) was added to the mixture. The reaction mixture was stirred at room temperature overnight. The reaction mixture was partitioned between ethyl acetate (100 mL) and saturated brine (30 mL). The organic phase was dried over sodium sulphate and evaporated in vacuo to give the crude product ethyl 1-{2-[3-(2-{3-chloro-4-[(1-methylethyl)oxy]phenyl}-1,3-thiazol-5-yl)-2-ethylphenyl]ethyl}-4-piperidinecarboxylate (D89) (216 mg) as a brown oil. The crude product was used for next step without further purification. MS (ES): $C_{30}H_{37}ClN_2O_3S$ requires 540. found 541.2 (M+H$^+$).

Description for D90 methyl 1-{2-[3-(2-{3-chloro-4-[(1-methylethyl)oxy] phenyl}-1,3-thiazol-5-yl)-2-ethylphenyl]ethyl}-3-azetidinecarboxylate (D90)

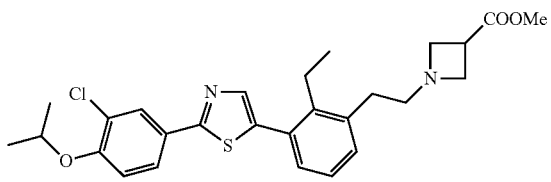 [SMILES: CCc1c(CCN2CC(C(=O)OC)C2)cccc1-c1cnc(-c2ccc(OC(C)C)c(Cl)c2)s1]

To a solution of [3-(2-{3-chloro-4-[(1-methylethyl)oxy] phenyl}-1,3-thiazol-5-yl)-2-ethylphenyl]acetaldehyde (D78) (160 mg), acetic acid (0.036 mL) and sodium acetate (51.0 mg) in ethanol (20.00 mL) stirred under nitrogen at room temperature was added methyl 3-azetidinecarboxylate hydrochloride (182 mg) in one charge. The reaction mixture was stirred at room temperature for 30 min, then the solvent was evaporated in vacuo. The residue was dissolved in dichloromethane (DCM) (20 mL), sodium triacetoxyborohydride (165 mg) was added to the mixture. The reaction mixture was stirred at room temperature overnight. The reaction mixture was partitioned between ethyl acetate (100 mL) and saturated brine (30 mL). The organic phase was dried over sodium sulphate and evaporated in vacuo to give the crude product methyl 1-{2-[3-(2-{3-chloro-4-[(1-methylethyl)oxy]phenyl}-1,3-thiazol-5-yl)-2-ethylphenyl]ethyl}-3-azetidinecarboxylate (D90) (200 mg) as a brown oil. The crude product was used for next step without further purification. MS (ES): $C_{27}H_{31}ClN_2O_3S$ requires 498. found 499.2 (M+H$^+$).

Description for D91

5-(5-bromo-1,3-thiazol-2-yl)-2-(2-methylpropyl) benzonitrile (D91)

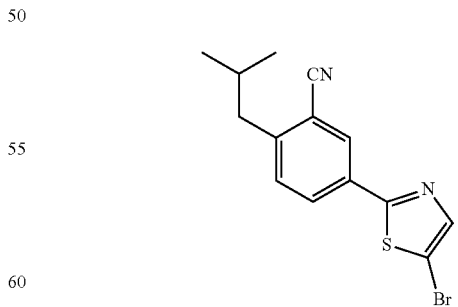

To a suspension of 2-(2-methylpropyl)-5-(4,4,5,5-tetramethyl-1,3,2-dioxaborolan-2-yl)benzonitrile (D59) (600 mg), 2,5-dibromo-1,3-thiazole (767 mg), and $Cs_2CO_3$ (1028 mg) in 1,2-dimethoxyethane (DME) (10 mL)/water (2 mL) stirred under nitrogen at room temperature was added PdCl$_2$(dppf)-

CH$_2$Cl$_2$ adduct (344 mg). The reaction mixture was sealed and heated under microwave at 120° C. for 4 h. After cooling the reaction, the mixture was diluted with ethyl acetate and filtered through silical gel. The filtrate was washed with aqueous saturated ammonium chloride and saturated brine. The organic phase was collected and dried over anhydrous sodium sulphate. The solvent was removed in vacuo to give the crude product, which was purified by column chromatography to afford 5-(5-bromo-1,3-thiazol-2-yl)-2-(2-methylpropyl)benzonitrile (D91) (400 mg). MS (ES): C$_{14}$H$_{13}$BrN$_2$S requires 320. found 321.0 (M+H$^+$).

Description for D92

5-[5-(2-ethyl-3-formylphenyl)-1,3-thiazol-2-yl]-2-(2-methylpropyl)benzonitrile (D92)

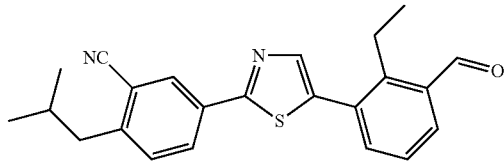 [SMILES: CCc1c(C=O)cccc1-c1cnc(-c2ccc(CC(C)C)c(C#N)c2)s1]

To a solution of 5-(5-bromo-1,3-thiazol-2-yl)-2-(2-methylpropyl)benzonitrile (D91) (1.1 g), 2-ethyl-3-(4,4,5,5-tetramethyl-1,3,2-dioxaborolan-2-yl)benzaldehyde (D5) (443 mg) and Cs$_2$CO$_3$ (1.12 g) in 1,2-dimethoxyethane (DME) (15 mL) and water (3 mL) stirred under nitrogen at room temperature was added PdCl$_2$(dppf)-CH$_2$Cl$_2$ adduct (2.80 g) in one charge. The reaction vessel was sealed and heated under microwave at 120° C. for 1.5 h. After cooling the reaction, the reaction mixture was filtered through silica gel and the filtrate was washed with aqueous saturated ammonium chloride and saturated brine. The organic phase was collected and dried over anhydrous sodium sulphate. After concentration, the crude product was purified by column chromatography to give 5-[5-(2-ethyl-3-formylphenyl)-1,3-thiazol-2-yl]-2-(2-methylpropyl)benzonitrile (D92) (1.2 g). MS (ES): C$_{23}$H$_{22}$N$_2$OS requires 374. found 375.1 (M+H$^+$).

Description for D93

3-bromo-2-methylbenzaldehyde (D93)

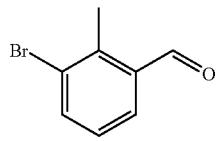

To a solution of 1,3-dibromo-2-methylbenzene (3 g, 12.00 mmol) in Tetrahydrofuran (THF) (100 mL) stirred under nitrogen at −78° C. was added BuLi (9.00 mL, 14.40 mmol) dropwise. The reaction mixture was stirred at −78° C. for 20 min. DMF (1.115 mL, 14.40 mmol) was added dropwise. The reaction mixture was continuously stirred for 2 hours. The reaction was quenched with sat. aq. ammonia chloride solution. The aqueous layers were separated and extracted by EA for 3 times. The combined organic layers were washed by brine, dried over anhydrous sodium sulfate. The dried solution was concentrated in vacuo to afford 3-bromo-2-methylbenzaldehyde (D93) (2.4 g), which was used for the next step without further purification. MS (ES): C$_8$H$_7$BrO requires 197.9. found 199 (M+H$^+$)

Description for D94

(E)-2-(3-bromo-2-methylphenyl)ethenyl methyl ether (D94)

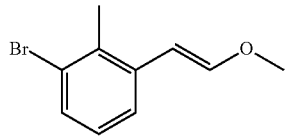

To a solution of [(methyloxy)methyl](triphenyl)phosphonium chloride (2.1 g, 6.13 mmol) in Tetrahydrofuran (THF) (40 mL) stirred under nitrogen at 0° C. was added BuLi (4.08 mL, 6.53 mmol) dropwise. The reaction mixture was stirred at −78° C. for 30 min. Then a solution of 3-bromo-2-methylbenzaldehyde (D93) (1 g, 5.02 mmol) in Tetrahydrofuran (THF) (40 mL) was added dropwise. The reaction mixture was continuously stirred overnight. The reaction was quenched with sat. aq. NH4Cl. The aqueous layers were separated and extracted with EA for 3 times. The combined organic layers were washed with brine, dried over anhydrous sodium sulfate. The dried solution was concentrated, and purified by ISCO column chromatography (PE: EA=8:2) to afford (E)-2-(3-bromo-2-methylphenyl)ethenyl methyl ether (D94) (938 mg) as a yellow oil. MS (ES): C$_{10}$H$_{11}$BrO requires 255.9. found 227 (M+H$^+$)

Description for D95

4,4,5,5-tetramethyl-2-{2-methyl-3-[(E)-2-(methyloxy)ethenyl]phenyl}-1,3,2-dioxaborolane (D95)

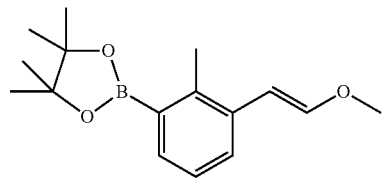

To a solution of 2-(3-bromo-2-methylphenyl)ethenyl methyl ether (D94) (800 mg, 3.52 mmol) in N,N-Dimethylformamide (DMF) (15 mL) stirred under nitrogen at room temperature was added 4,4,4',4',5,5,5',5'-octamethyl-2,2'-bi-1,3,2-dioxaborolane (1342 mg, 5.28 mmol), potassium acetate (1037 mg, 10.57 mmol), and PdCl$_2$(dppf)-CH$_2$Cl$_2$ adduct (288 mg, 0.352 mmol). The reaction mixture was stirred at 90° C. for 1.5 hours. Water was added. The mixture was filtered through the celite. The filtrate was separated, and the aqueous layers was extracted with EA for 3 times. The organic layers were washed by brine, dried over anhydrous sodium sulfate. The dried solution was concentrated and purified by ISCO column chromatography to afford 4,4,5,5-tetramethyl-2-{2-methyl-3-[(E)-2-(methyloxy)ethenyl]phenyl}-1,3,2-dioxaborolane (D95) (614 mg) as a yellow oil. MS (ES): $C_{16}H_{23}BO_3$ requires 274.1. found 275.1 (M+H$^+$).

Description for D96

2-{3-chloro-4-[(1-methylethyl)oxy]phenyl}-5-{2-methyl-3-[(E)-2-(methyloxy)ethenyl]phenyl}-1,3,4-thiadiazole (D96)

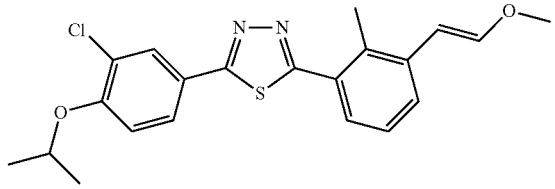 [SMILES: CO/C=C/c1cccc(-c2nnc(-c3ccc(OC(C)C)c(Cl)c3)s2)c1C]

To a solution of 2-bromo-5-{3-chloro-4-[(1-methylethyl)oxy]phenyl}-1,3,4-thiadiazole(D10) (680 mg, 2.038 mmol) in N,N-Dimethylformamide (DMF) (6 mL) and Water (1.5 mL) was added 4,4,5,5-tetramethyl-2-{2-methyl-3-[(E)-2-(methyloxy)ethenyl]phenyl}-1,3,2-dioxaborolane (D95) (719 mg, 2.62 mmol), Pd(Ph$_3$P)$_4$ (118 mg, 0.102 mmol) and tripotassium phosphate (1082 mg, 5.10 mmol). The reaction vessel was sealed and heated in Biotage Initiator using initial high to 120° C. for 10 min. Water was added. The reaction mixture were combined and extracted with EA for 3 times. The combined organic layers were washed with brine, dried over anhydrous sodium sulfate. The dried solution was concentrated, and purified by ISCO column chromatography (PE:EA=8:2) to afford 2-{3-chloro-4-[(1-methylethyl)oxy]phenyl}-5-{2-methyl-3-[(E)-2-(methyloxy)ethenyl]phenyl}-1,3,4-thiadiazole (D96) (690 mg) as a yellow gel. MS (ES): $C_{21}H_{21}ClN_2O_2S$ requires 400.1. found 401.1 (M+H$^+$).

Description for D97

[3-(5-{3-chloro-4-[(1-methylethyl)oxy]phenyl}-1,3,4-thiadiazol-2-yl)-2-methylphenyl]acetaldehyde (D97)

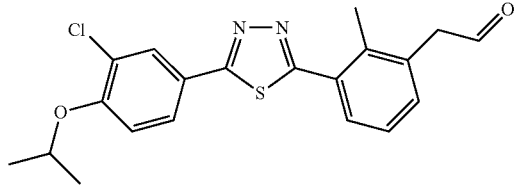 [SMILES: Cc1c(CC=O)cccc1-c1nnc(-c2ccc(OC(C)C)c(Cl)c2)s1]

To a solution of 2-{3-chloro-4-[(1-methylethyl)oxy]phenyl}-5-{2-methyl-3-[(E)-2-(methyloxy)ethenyl]phenyl}-1,3,4-thiadiazole (D96) (690 mg, 1.721 mmol) and sodium iodide (516 mg, 3.44 mmol) in Acetonitrile (20 mL) stirred under nitrogen at room temperature was added TMSCl (0.440 mL, 3.44 mmol) dropwise. The reaction mixture was stirred at room temperature for 10 min. Water was added. The aqueous solution was extracted with EA for 3 times. The organic phase was washed with saturated Na$_2$S$_2$O$_3$ solution and saturated brine, dried over sodium sulphate and evaporated in vacuo to afford the crude [3-(5-{3-chloro-4-[(1-methylethyl)oxy]phenyl}-1,3,4-thiadiazol-2-yl)-2-methylphenyl]acetaldehyde (D97) (666 mg) as a yellow oil, which was used for the next step without further purification. MS (ES): $C_{20}H_{19}ClN_2O_2S$ requires 386.0. found 387.0 (M+H$^+$).

Description for D98

3-bromo-2-hydroxybenzaldehyde (D98)

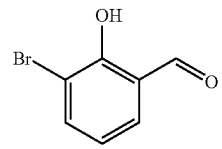

To a 500 mL 3-neck round flask, paraformaldehyde (5.96 g, 199 mmol), and 12.60 g of anhydrous MgCl$_2$ (12.60 g, 132 mmol) was added in acetonitrile (300 mL). Then 13.40 g of triethylamine was introduced slowly at room temperature. The mixture was stirred at room temperature for 20 min. 2-bromophenol (11.45 g, 66.2 mmol) was added to the above mixture. Then the reaction mixture was refluxed overnight. Then the mixture was cooled to room temperature, HCl (3N, 150 mL) were added to dilute the mixture. The resulted mixture was filtered through celite, and washed with tertbutyl methyl ether (200 mL). The organic solution was washed with 1N HCl (100 mL×2). The combined acid phase was extracted with EtOAc (100 mL×2). The combined organic layers were washed with brine (100 mL×2), water (100 mL×2), dried over sodium sulphate and concentrated to give 3-bromo-2-hydroxybenzaldehyde (D98) (2.1 g) as yellow oil, which was directly used in next step. MS (ES): $C_7H_5BrO_2$ requires 199.9. found 201.0 (M+H$^+$).

Description for D99

3-bromo-2-(methyloxy)benzaldehyde (D99)

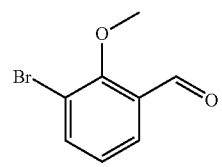

To a 500 mL two-neck round flask charged with 3-bromo-2-hydroxybenzaldehyde (D98) (13 g, 64.7 mmol) was added DMF (300 mL). Then K$_2$CO$_3$ (17.88 g, 129 mmol) was added, followed with methyl iodide (18.36 g, 129 mmol) at room temperature. The resulted mixture was stirred at room temperature. The mixture was stirred at room temperature overnight. The mixture was filtered through celite and washed with EtOAc. The resulted filtration was concentrated under reduced pressure. The residue was dissolved in EtOAc (250 mL), and washed with water (100 mL), 1N HCl (100 mL×2) and brine (100 mL×2). The organic layers was dried with sodium sulphate and concentrated. The residue was purified with ISCO column chromatography to afford 3-bromo-2-(methyloxy)benzaldehyde (D99) (4.05 g) as pale yellow oil. MS (ES): $C_8H_7BrO_2$ requires 213.9. found 215.0 (M+H$^+$).

Description for D100

1-bromo-2-(methyloxy)-3-[(E)-2-(methyloxy)ethenyl]benzene (D100)

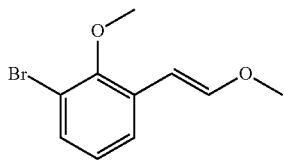

In a dried three-necked flask, to a solution of [(methyloxy)methyl](triphenyl) phosphonium chloride (3.59 g, 10.46 mmol) in THF (20 mL) was added BuLi (3.91 mL, 9.77 mmol) dropwise at −78° C. After addition, the reaction mixture was stirred at room temperature for 20 min. Then the reaction mixture was cooled to −78° C. A solution of 3-bromo-2-(methyloxy)benzaldehyde (D99) (1.5 g, 6.98 mmol) in THF (5 mL) to the reaction mixture dropwise. After addition, the reaction mixture was stirred at −78° C. for 2 hour and then warmed to room temperature. The mixture was stirred at room temperature overnight. Then the reaction was quenched with water. The organic phase was separated. The aqueous phase was extracted with EA (10 mL). The combined organic solution was dried over anhydrous sodium sulphate. After filtration, and concentration, the residue was purified by column chromatography (EA/Hexane: 0 to 30%) to give 1-bromo-2-(methyloxy)-3-[(E)-2-(methyloxy)ethenyl]benzene (D100) (1.43 g). MS (ES): $C_{10}H_{11}BrO_2$ requires 241.9. found 243.0 (M+H$^+$).

Description for D101

{2-(methyloxy)-3-[(E)-2-(methyloxy)ethenyl]phenyl}boronic acid (D101)

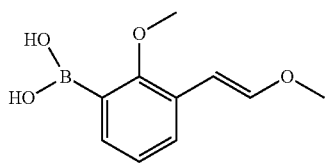

To a solution of 1-bromo-2-(methyloxy)-3-[(E)-2-(methyloxy)ethenyl]benzene (D100) (930 mg, 3.83 mmol) in Tetrahydrofuran (THF) (10 mL) was added BuLi (1.989 mL, 4.97 mmol) dropwise at −78° C. under nitrogen. The reaction mixture was stirred at −78° C. for 2 hours. Tris(1-methylethyl) borate (1.319 mL, 5.74 mmol) was added to the reaction mixture by syringe at −78° C. Then the reaction was stirred at −78° C. for 30 min, and then warmed to room temperature slowly. Then the reaction was quenched with water. The mixture was extracted with EA (15 mL×3). The combined organic layers was dried over anhydrous sodium sulphate. After filtration and concentration, the crude {2-(methyloxy)-3-[(E)-2-(methyloxy)ethenyl]phenyl}boronic acid (D101) (741 mg) was used directly in the next step. MS (ES): $C_{10}H_{13}BO_4$ requires 208.1. found 209.0 (M+H$^+$)

Description for D102

5-{3-chloro-4-[(1-methylethyl)oxy]phenyl}-3-{2-(methyloxy)-3-[(E)-2-(methyloxy)ethenyl]phenyl}-1,2,4-thiadiazole (D102)

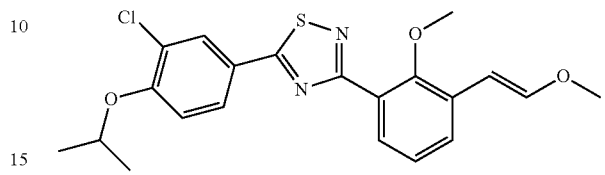

A mixture of 3-bromo-5-{3-chloro-4-[(1-methylethyl)oxy]phenyl}-1,2,4-thiadiazole (D43) (200 mg, 0.599 mmol), {2-(methyloxy)-3-[(E)-2-(methyloxy)ethenyl]phenyl}boronic acid (D101) (187 mg, 0.899 mmol), tripotassium phosphate (318 mg, 1.499 mmol) and Pd(Ph3P)$_4$ (69.3 mg, 0.060 mmol) in N,N-Dimethylformamide (DMF) (5 mL) and Water (2 mL) was stirred at 120° C. (Microwave) for 10 min. The reaction mixture was poured to water. Then the mixture was extracted with EA. The combined organic layers were washed with water and then dried over anhydrous sodium sulphate. After filtration and concentration, the residue was purified by column chromatography to give 5-{3-chloro-4-[(1-methylethyl)oxy]phenyl}-3-{2-(methyloxy)-3-[(E)-2-(methyloxy)ethenyl]phenyl}-1,2,4-thiadiazole (D102) (152 mg). MS (ES): $C_{21}H_{21}ClN_2O_3S$ requires 416.1. found 417.1 (M+H$^+$).

Description for D103

[3-(5-{3-chloro-4-[(1-methylethyl)oxy]phenyl}-1,2,4-thiadiazol-3-yl)-2-(methyloxy)phenyl]acetaldehyde (D103)

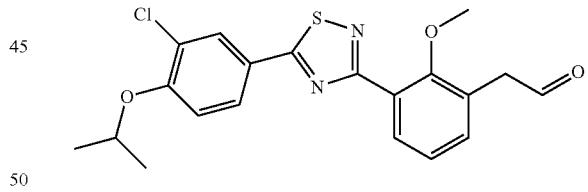

To a solution of 5-{3-chloro-4-[(1-methylethyl)oxy]phenyl}-3-{2-(methyloxy)-3-[(E)-2-(methyloxy)ethenyl]phenyl}-1,2,4-thiadiazole (D102) (152 mg, 0.365 mmol) and sodium iodide (109 mg, 0.729 mmol) in Acetonitrile (10 mL) was added TMSCl (0.093 mL, 0.729 mmol) dropwise. The reaction mixture was stirred at room temperature overnight (16 h). The reaction was quenched with water (10 mL). Then EA (10 mL) was added to the reaction mixture. The organic phase was separated. The aqueous phase was extracted with EA (10 mL×2). The combined organic layers was dried over anhydrous sodium sulphate. After filtration and concentration, the residue was purified by column chromatography (EA/Hexane: 0 to 50%) to afford [3-(5-{3-chloro-4-[(1-methylethyl)oxy]phenyl}-1,2,4-thiadiazol-3-yl)-2-(methyloxy)phenyl]acetaldehyde (D103) (87.6 mg). MS (ES): $C_{20}H_{19}ClN_2O_3S$ requires 402.1. found 403.1 (M+H$^+$).

Description for D104 ethyl 1-{2-[3-(5-{3-chloro-4-[(1-methylethyl)oxy]phenyl}-1,2,4-thiadiazol-3-yl)-2-(methyloxy)phenyl]ethyl}-4-piperidinecarboxylate (D104)

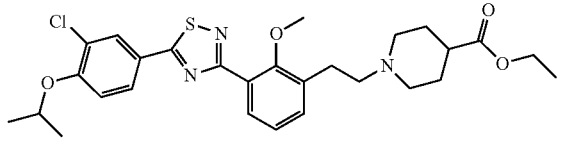 [SMILES: CCOC(=O)C1CCN(CCc2cccc(-c3nsc(-c4ccc(OC(C)C)c(Cl)c4)n3)c2OC)CC1]

To a mixture of [3-(5-{3-chloro-4-[(1-methylethyl)oxy]phenyl}-1,2,4-thiadiazol-3-yl)-2-(methyloxy)phenyl]acetaldehyde (D103) (87.6 mg, 0.217 mmol) and ethyl 4-piperidinecarboxylate (137 mg, 0.870 mmol) in Dichloromethane (DCM) (5 mL) was added 3 drops of HOAc. The mixture was stirred at room temperature for 20 min. Then sodium triacetoxyborohydride (92 mg, 0.435 mmol) was added to the reaction mixture. The reaction mixture was stirred at room temperature overnight (16 h). The reaction was quenched with water. DCM was removed. The residue was extracted with EA (10 mL×3). The combined organic layers were dried over anhydrous sodium sulphate. After filtration and concentration, the residue was purified by column chromatography to afford ethyl 1-{2-[3-(5-{3-chloro-4-[(1-methylethyl)oxy]phenyl}-1,2,4-thiadiazol-3-yl)-2-(methyloxy)phenyl]ethyl}-4-piperidinecarboxylate (D104) (38.7 mg). MS (ES): $C_{28}H_{34}ClN_3O_4S$ requires 513.2. found 514.2 (M+H$^+$).

Description for D105

5-{3-chloro-4-[(1-methylethyl)oxy]phenyl}-3-{2-methyl-3-[(E)-2-(methyloxy)ethenyl]phenyl}-1,2,4-thiadiazole (D105)

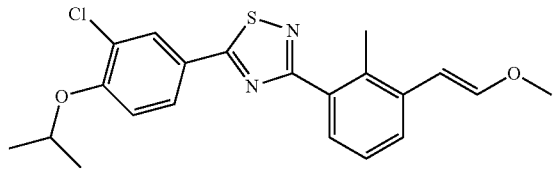 [SMILES: CO/C=C/c1cccc(-c2nsc(-c3ccc(OC(C)C)c(Cl)c3)n2)c1C]

To a tube was added 3-bromo-5-{3-chloro-4-[(1-methylethyl)oxy]phenyl}-1,2,4-thiadiazole (D95) (150 mg, 0.450 mmol), 4,4,5,5-tetramethyl-2-{2-methyl-3-[(E)-2-(methyloxy)ethenyl]phenyl}-1,3,2-dioxaborolane (D43) (150 mg, 0.547 mmol), Pd(Ph$_3$P)$_4$ (26.0 mg, 0.022 mmol), tripotassium phosphate (239 mg, 1.124 mmol), N,N-Dimethylformamide (DMF) (6 mL) and Water (1.5 mL). The reaction vessel was sealed and heated in Biotage Initiator using initial high to 120° C. for 10 min. Water was added. The reaction mixture were combined and extracted with EA for 3 times, The combined organic layers were washed with brine, dried over anhydrous sodium sulfate, concentrated, and purified by ISCO column chromatography (PE:EA=8:2) to afford 5-{3-chloro-4-[(1-methylethyl)oxy]phenyl}-3-{2-methyl-3-[(E)-2-(methyloxy)ethenyl]phenyl}-1,2,4-thiadiazole (D105) (130 mg) as a yellow gel.

Description for D106

[3-(5-{3-chloro-4-[(1-methylethyl)oxy]phenyl}-1,2,4-thiadiazol-3-yl)-2-methylphenyl]acetaldehyde (D106)

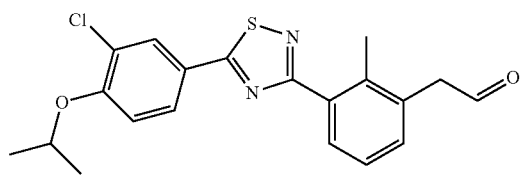 [SMILES: Cc1c(CC=O)cccc1-c1nsc(-c2ccc(OC(C)C)c(Cl)c2)n1]

To a solution of 5-{3-chloro-4-[(1-methylethyl)oxy]phenyl}-3-{2-methyl-3-[(E)-2-(methyloxy)ethenyl]phenyl}-1,2,4-thiadiazole (D105) (130 mg, 0.324 mmol) and sodium iodide (97 mg, 0.649 mmol) in Acetonitrile (8 mL) stirred under nitrogen at room temperature was added TMSCl (0.083 mL, 0.649 mmol) dropwise. The reaction mixture was stirred at room temperature for 1 hr. Water was added. The aqeuous solution was extracted with EA for 3 times. The organic phase was washed with saturated Na$_2$S$_2$O$_3$ solution and saturated brine, dried over sodium sulphate and evaporated in vacuo to afford the crude product [3-(5-{3-chloro-4-[(1-methylethyl)oxy]phenyl}-1,2,4-thiadiazol-3-yl)-2-methylphenyl]acetaldehyde (D106) (120 mg) as a yellow oil, which was used for the next step without further purification. MS (ES): $C_{20}H_{19}ClN_2O_2S$ requires 386.1. found 387.2 (M+H$^+$).

Description for D107

5-bromo-3-chloro-2-[(1-methylethyl)oxy]pyridine (D107)

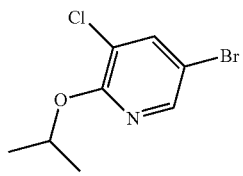

Potassium tert-butoxide (25.7 g, 229 mmol) was added to 2-propanol (100 mL, 57.3 mmol) and the solution was stirred at 95° C. for 3 h, then 5-bromo-2,3-dichloropyridine (13 g, 57.3 mmol) was added. This reaction was refluxed overnight. The reaction mixture was cooled to room temperature and partitioned between ethyl acetate and water. The organic phase was washed with water and saturated brine, dried over sodium sulphate and evaporated in vacuo to afford the crude product 5-bromo-3-chloro-2-[(1-methylethyl)oxy]pyridine (D107) (14.5 g), which was used directly without further purification.

Description for D108

3-chloro-2-[(1-methylethyl)oxy]-5-(4,4,5,5-tetramethyl-1,3,2-dioxaborolan-2-yl)pyridine (D108)

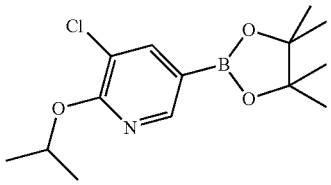 [SMILES: CC(C)Oc1ncc(B2OC(C)(C)C(C)(C)O2)cc1Cl]

A suspension of 5-bromo-3-chloro-2-[(1-methylethyl)oxy]pyridine (D107) (6 g, 23.95 mmol), 4,4,4',4',5,5,5',5'-octamethyl-2,2'-bi-1,3,2-dioxaborolane (7.30 g, 28.7 mmol), PdCl$_2$(dppf)-CH2Cl2 adduct (1.565 g, 1.916 mmol) and potassium acetate (9.40 g, 96 mmol) in 1,2-Dimethoxyethane (100 mL) was degassed and charged with nitrogen, stirred at 90° C. for 3 h. The reaction mixture was cooled to room temperature and filtered through celite. The filtrate was concentrated to give the crude product, which was purified by ISCO column chromatography to afford 3-chloro-2-[(1-methylethyl)oxy]-5-(4,4,5,5-tetramethyl-1,3,2-dioxaborolan-2-yl)pyridine (D108) (6 g). MS (ES): $C_{14}H_{21}BClNO_3$ requires 297.1. found 298.1 (M+H$^+$).

Description for D109

5-(3-bromo-1,2,4-thiadiazol-5-yl)-3-chloro-2-[(1-methylethyl)oxy]pyridine (D109)

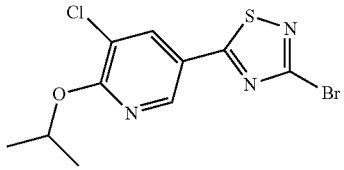 [SMILES: CC(C)Oc1ncc(-c2nc(Br)ns2)cc1Cl]

3-chloro-2-[(1-methylethyl)oxy]-5-(4,4,5,5-tetramethyl-1,3,2-dioxaborolan-2-yl)pyridine (D108) (1.2 g, 4.03 mmol), 3-bromo-5-chloro-1,2,4-thiadiazole (1.609 g, 8.06 mmol), tripotassium phosphate (2.57 g, 12.10 mmol) and PdCl$_2$(dppf)-CH$_2$Cl$_2$ adduct (0.329 g, 0.403 mmol) were heated by Biotage Initiator to 80° C. for 1 hr. The reaction mixture was concentrated and the slurry was diluted with ethyl acetate. The resulted solution was washed with water, dried and purified by ISCO column chromatography to afford 5-(3-bromo-1,2,4-thiadiazol-5-yl)-3-chloro-2-[(1-methylethyl)oxy]pyridine (D109) (1.3 g). δH (CDCl$_3$, 400 MHz): 1.43 (6H, d), 5.45 (1H, m), 8.21 (1H, d), 8.59 (1H, d). MS (ES): $C_{10}H_9BrClN_3OS$ requires 332.9. found 334.0 (M+H$^+$).

Description for D110

3-chloro-5-(3-{2-ethyl-3-[(E)-2-(methyloxy)ethenyl]phenyl}-1,2,4-thiadiazol-5-yl)-2-[(1-methylethyl)oxy]pyridine (D110)

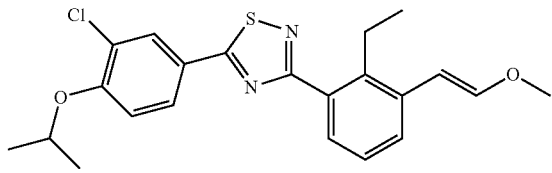 [SMILES: CCc1c(/C=C/OC)cccc1-c1nsc(-c2ccc(OC(C)C)c(Cl)c2)n1]

5-(3-bromo-1,2,4-thiadiazol-5-yl)-3-chloro-2-[(1-methylethyl)oxy]pyridine (D109) (1.3 g, 3.89 mmol), 2-{2-ethyl-3-[(E)-2-(methyloxy)ethenyl]phenyl}-4,4,5,5-tetramethyl-1,3,2-dioxaborolane (2.239 g, 7.77 mmol), tripotassium phosphate (2.474 g, 11.66 mmol) and Pd(Ph$_3$P)$_4$ (0.449 g, 0.389 mmol) in N,N-Dimethylformamide (DMF) (5 mL) and Water (5.00 mL) were heated by Biotage Initiator to 120° C. for 30 min. The reaction solution was concentrated and the slurry was diluted with ethyl acetate, washed with water, dried and purified by ISCO column chromatography to afford 3-chloro-5-(3-{2-ethyl-3-[(E)-2-(methyloxy)ethenyl]phenyl}-1,2,4-thiadiazol-5-yl)-2-[(1-methylethyl)oxy]pyridine (D110) (2 g). MS (ES): $C_{21}H_{22}ClN_3O_2S$ requires 415.1. found 416.1 (M+H$^+$).

Description for D111

[3-(5-{5-chloro-6-[(1-methylethyl)oxy]-3-pyridinyl}-1,2,4-thiadiazol-3-yl)-2-ethylphenyl]acetaldehyde (D111)

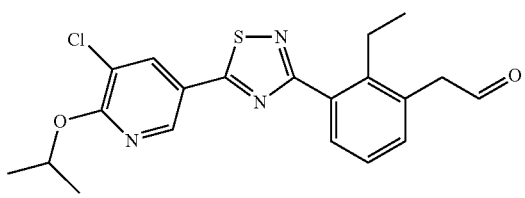 [SMILES: CCc1c(CC=O)cccc1-c1nsc(-c2cnc(OC(C)C)c(Cl)c2)n1]

To a solution of 3-chloro-5-(3-{2-ethyl-3-[(E)-2-(methyloxy)ethenyl]phenyl}-1,2,4-thiadiazol-5-yl)-2-[(1-methylethyl)oxy]pyridine (D110) (2 g, 4.81 mmol) in Tetrahydrofuran (50 mL) was added HCl (4.81 mL, 9.62 mmol). The resulted solution was heated to 70° C. for 2 h. THF was removed in vacuo to afford [3-(5-{5-chloro-6-[(1-methylethyl)oxy]-3-pyridinyl}-1,2,4-thiadiazol-3-yl)-2-ethylphenyl]acetaldehyde (D111) (2 g, 4.98 mmol, 103% yield) as a crude product, which was used directly without further purification. MS (ES): $C_{20}H_{20}ClN_3O_2S$ requires 401.0. found 402.0 (M+H$^+$).

Description for D112 ethyl 1-{2-[3-(5-{5-chloro-6-[(1-methylethyl)oxy]-3-pyridinyl}-1,2,4-thiadiazol-3-yl)-2-ethylphenyl]ethyl}-4-piperidinecarboxylate (D112)

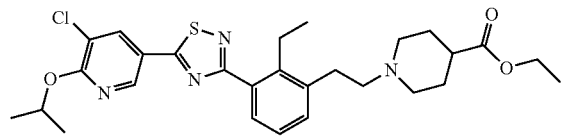 [SMILES: CCOC(=O)C1CCN(CCc2cccc(-c3nsc(-c4cnc(OC(C)C)c(Cl)c4)n3)c2CC)CC1]

To a solution of [3-(5-{5-chloro-6-[(1-methylethyl)oxy]-3-pyridinyl}-1,2,4-thiadiazol-3-yl)-2-ethylphenyl]acetaldehyde (D111) (2 g, 2.488 mmol) in Dichloromethane (DCM) (10 mL) was added ethyl 4-piperidinecarboxylate (0.430 g, 2.74 mmol). The reaction solution was stirred for 5 min before sodium triacetoxyborohydride (0.791 g, 3.73 mmol) was added. The reaction solution was stirred overnight. The reaction solution was washed with water, dried, concentrated and purified by ISCO column chromatography to afford the crude product ethyl 1-{2-[3-(5-{5-chloro-6-[(1-methylethyl)oxy]-3-pyridinyl}-1,2,4-thiadiazol-3-yl)-2-ethylphenyl]

83 ethyl}-4-piperidinecarboxylate (D112) (450 mg). MS (ES): $C_{28}H_{35}ClN_4O_3S$ requires 542.2. found 543.2 (M+H$^+$).

Description for D113 ethyl (2E)-3-[3-(2-{3-cyano-4-[(1-methylethyl)oxy]phenyl}-1,3-thiazol-5-yl)-2-ethylphenyl]-2-propenoate (D113)

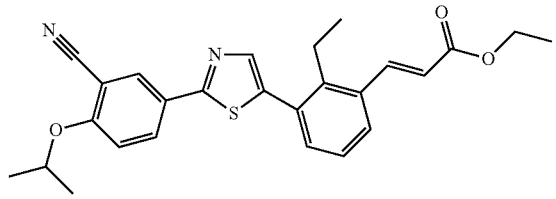 [SMILES: CCOC(=O)/C=C/c1cccc(-c2cnc(-c3ccc(OC(C)C)c(C#N)c3)s2)c1CC]

A solution of 5-[5-(2-ethyl-3-formylphenyl)-1,3-thiazol-2-yl]-2-[(1-methylethyl) oxy]benzonitrile (D73) (1 g, 2.66 mmol) and ethyl (triphenyl-lambda~5~-phosphanylidene)acetate (1.851 g, 5.31 mmol) was stirred at 80° C. for 2 h. The reaction mixture was cooled to room temperature. The mixture was partitioned between ethyl acetate and water. The organic phase was washed with water and saturated brine, dried over anhydrous sodium sulphate. The solvent was evaporated in vacuo and purified by ISCO column chromatography to afford ethyl (2E)-3-[3-(2-{3-cyano-4-[(1-methylethyl)oxy]phenyl}-1,3-thiazol-5-yl)-2-ethylphenyl]-2-propenoate (D113) (1.3 g). MS (ES): $C_{26}H_{26}N_2O_3S$ requires 446.2. found 447.2 (M+H$^+$)

Description for D114 ethyl 3-[3-(2-{3-cyano-4-[(1-methylethyl)oxy]phenyl}-1,3-thiazol-5-yl)-2-ethyl phenyl]propanoate (D114)

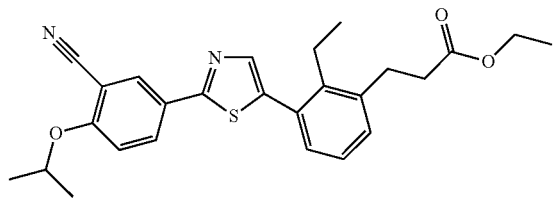 [SMILES: CCOC(=O)CCc1cccc(-c2cnc(-c3ccc(OC(C)C)c(C#N)c3)s2)c1CC]

To a solution of ethyl (2E)-3-[3-(2-{3-cyano-4-[(1-methylethyl)oxy]phenyl}-1,3-thiazol-5-yl)-2-ethylphenyl]-2-propenoate (D113) (1 g, 2.239 mmol) in Methanol (20 mL) was added Pd/C. The mixture was stirred at room temperature for 1 h. After filtration, the solvent was evaporated in vacuo to afford ethyl 3-[3-(2-{3-cyano-4-[(1-methylethyl)oxy]phenyl}-1,3-thiazol-5-yl)-2-ethylphenyl]propanoate (D114) (1 g). MS (ES): $C_{26}H_{28}N_2O_3S$ requires 448.2. found 449.2 (M+H$^+$).

84

Description for D115

5-{5-[2-ethyl-3-(3-oxopropyl)phenyl]-1,3-thiazol-2-yl}-2-[(1-methylethyl)oxy]benzonitrile (D115)

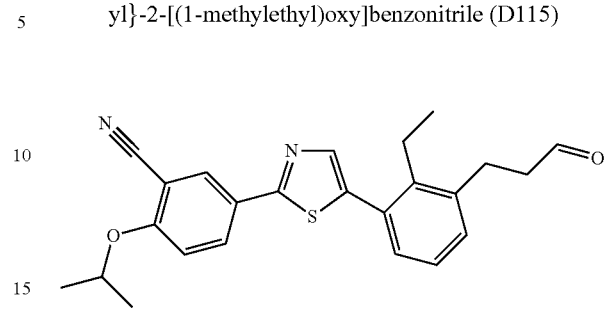

To a solution of ethyl 3-[3-(2-{3-cyano-4-[(1-methylethyl)oxy]phenyl}-1,3-thiazol-5-yl)-2-ethylphenyl]propanoate (D114) (900 mg, 2.006 mmol) in Dichloromethane (DCM) (20 mL) stirred under nitrogen at −70° C. was added a solution of DIBAL-H (4 ml, 4.00 mmol) dropwise during 30 min. The reaction mixture was stirred at −70° C. for 20 minutes. The reaction mixture was quenched with cooled aqueous HCl solution (10 mL, 10%). The organic layers were washed with water twice. Then the organic layers were separated and dried over anhydrous sodium sulphate. The organic solvent was evaporated in vacuo to afford 5-{5-[2-ethyl-3-(3-oxopropyl)phenyl]-1,3-thiazol-2-yl}-2-[(1-methylethyl)oxy]benzonitrile (D115) (1 g), which was used directly without further purification. MS (ES): $C_{24}H_{24}N_2O_2S$ requires 404.2. found 405.2 (M+H$^+$).

Description for D116

1-benzyl-4-(3-bromo-2-ethyl-phenyl)-piperidin-4-ol (D116)

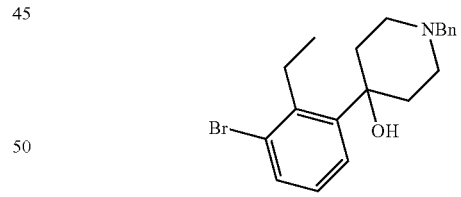

To a solution of 1,3-dibromo-2-ethyl-benzene (30 g, 113.65 mmol) in THF (150 mL) was added 45.5 mL of BuLi (2.5M in hexane, 113.65 mmol) under nitrogen. The mixture was stirred for 4 hr at −78° C. Then N-benzyl-4-piperidone (21.51 g, 113.65 mmol) was added to the above mixture and stirred overnight, The mixture was poured into sat. aqueous NH$_4$Cl solution and extracted with DCM. The organic layer was separated, dried over Na$_2$SO$_4$, and concentrated under reduced pressure give the crude 1-benzyl-4-(3-bromo-2-ethyl-phenyl)-piperidin-4-ol (D116) (30.4 g). MS (ES): $C_{20}H_{24}BrNO$ requires 373. found 374 (M+H$^+$).

Description for D117

1-benzyl-4-(3-bromo-2-ethyl-phenyl)-1,2,3,6-tetrahydro-pyridine (D117)

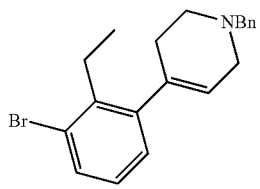 [SMILES: CCc1c(Br)cccc1C1=CCN(Cc2ccccc2)CC1]

To a solution of 1-benzyl-4-(3-bromo-2-ethyl-phenyl)-piperidin-4-ol (D116) (30 g, 80.15 mmol) in HOAc (300 mL) was added hydrochloric acid (45 mL, 37%). The reaction mixture was refluxed for 12 hr and concentrated in vacuo. The residue was purified by column chromatography to afford 1-benzyl-4-(3-bromo-2-ethyl-phenyl)-1,2,3,6-tetrahydro-pyridine (D117) (24 g). MS (ES): $C_{20}H_{22}BrN$ requires 355. found 356 (M+H$^+$).

Description for D118

1-Benzyl-4-[2-ethyl-3-(4,4,5,5-tetramethyl-[1,3,2]dioxaborolan-2-yl)-phenyl]-1,2,3,6-tetrahydro-pyridine (D118)

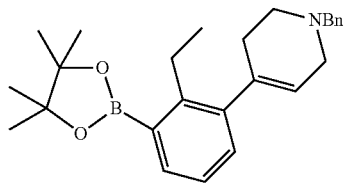 [SMILES: CCc1c(B2OC(C)(C)C(C)(C)O2)cccc1C1=CCN(Cc2ccccc2)CC1]

A mixture of 1-benzyl-4-(3-bromo-2-ethyl-phenyl)-1,2,3,6-tetrahydro-pyridine (D117) (20 g, 56.13 mmol), 4,4,4',4',5,5,5',5'-octamethyl-2,2'-bi-1,3,2-dioxaborolane (17.46 g, 68.76 mmol) and potassium acetate (16.52 g, 168.40 mmol), PdCl2(dppf)-CH2Cl2 adduct (4.58 g, 5.613 mmol) in dioxane (300 mL) was degassed with nitrogen, followed by bubbling nitrogen gas through the stirred reaction mixture for 5 minutes. The reaction mixture was heated to 90° C. overnight. The reaction mixture was allowed to cool to room temperature and dioxane removed in vacuo. The residue was partitioned between ethyl acetate and water. The mixture was filtered through celite, washed with ethyl acetate. The combined organic phases were concentrated and purified by column chromatography to afford 1-benzyl-4-[2-ethyl-3-(4,4,5,5-tetramethyl-[1,3,2]dioxaborolan-2-yl)-phenyl]1,2,3,6-tetrahydro-pyridine (D118) (15 g). MS (ES): $C_{26}H_{34}BNO_2$ requires 403. found 404 (M+H$^+$).

Description for D119

4-[2-ethyl-3-(4,4,5,5-tetramethyl-1,3,2-dioxaborolan-2-yl)phenyl]piperidine (D119)

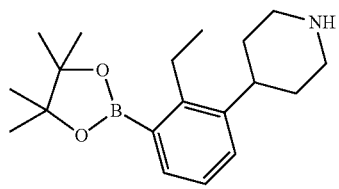 [SMILES: CCc1c(B2OC(C)(C)C(C)(C)O2)cccc1C1CCNCC1]

To a solution of 1-benzyl-4-[2-ethyl-3-(4,4,5,5-tetramethyl-[1,3,2]dioxaborolan-2-yl)-phenyl]-1,2,3,6-tetrahydro-pyridine (D118) (8 g, 19.83 mmol) in EtOAc (300 mL) was added dry Pd/C (8 g, 10%). The reaction mixture was hydrogenated under 55 psi at 50° C. for 12 hr, and then filtered. The filtrate was concentrated in vacuo. The residue was purified by Mass Directed AutoPrep to give 4-[2-Ethyl-3-(4,4,5,5-tetramethyl-[1,3,2]dioxaborolan-2-yl)-phenyl]-piperidine (D119) (2.5 g). MS (ES): $C_{19}H_{30}BNO_2$ requires 315.2. found 316.2 (M+H$^+$).

Description for D120

4-[3-(5-{3-chloro-4-[(1-methylethyl)oxy]phenyl}-1,3,4-thiadiazol-2-yl)-2-ethyl phenyl]piperidine (D120)

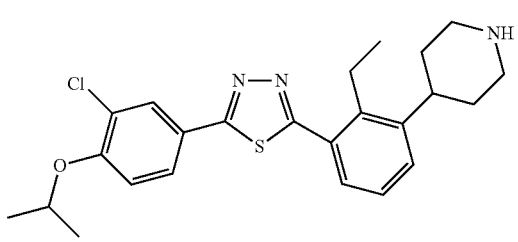 [SMILES: CCc1c(-c2nnc(-c3ccc(OC(C)C)c(Cl)c3)s2)cccc1C1CCNCC1]

To a solution of 2-bromo-5-{3-chloro-4-[(1-methylethyl)oxy]phenyl}-1,3,4-thiadiazole (D10) (635 mg, 1.903 mmol), 4-[2-ethyl-3-(4,4,5,5-tetramethyl-1,3,2-dioxaborolan-2-yl)phenyl]piperidine (D119) (600 mg, 1.903 mmol) and Pd(Ph$_3$P)$_4$ (220 mg, 0.190 mmol) in N,N-Dimethylformamide (DMF) (5 mL) and Water (1.000 mL) was added tripotassium phosphate (1616 mg, 7.61 mmol). The solution was charged with N2 and sealed, irritated in Microwave at 120° C. for 20 min. This solution was purified by reverse phase chromatography to afford 4-[3-(5-{3-chloro-4-[(1-methylethyl)oxy]phenyl}-1,3,4-thiadiazol-2-yl)-2-ethylphenyl]piperidine (D120) (100 mg). MS (ES): $C_{24}H_{28}ClN_3OS$ requires 441.1. found 442.1 (M+H$^+$).

Description for D121 ethyl 4-{-4-[2-ethyl-3-(4,4,5,5-tetramethyl-1,3,2-dioxaborolan-2-yl)phenyl]-1-piperidinyl}butanoate (D121)

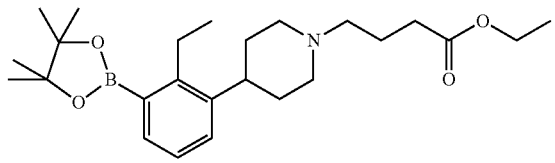 [SMILES: CCOC(=O)CCCN1CCC(c2cccc(B3OC(C)(C)C(C)(C)O3)c2CC)CC1]

To a solution of 4-[2-ethyl-3-(4,4,5,5-tetramethyl-1,3,2-dioxaborolan-2-yl)phenyl]piperidine (D119) (300 mg, 0.952 mmol) in N,N-Dimethylformamide (DMF) (10 mL) was added ethyl 4-bromobutanoate (0.272 mL, 1.903 mmol) and potassium carbonate (526 mg, 3.81 mmol). The reaction solution was heated to 60° C. overnight. Ethyl acetate was added and the resulting solution was washed with water, brine. The organic layer was dried over anhydrous $Na_2SO_4$ and concentrated to afford ethyl 4-{4-[2-ethyl-3-(4,4,5,5-tetramethyl-1,3,2-dioxaborolan-2-yl)phenyl]-1-piperidinyl}butanoate (D121) (200 mg). MS (ES): C25H40BNO4 requires 429.3. found 430.1 (M+H$^+$).

Description for D122

4-[3-(5-{3-chloro-4-[(1-methylethyl)oxy]phenyl}-1,2,4-thiadiazol-3-yl)-2-ethylphenyl]piperidine (D122)

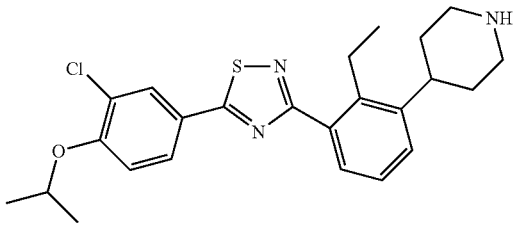 [SMILES: CCc1c(-c2nsc(-c3ccc(OC(C)C)c(Cl)c3)n2)cccc1C1CCNCC1]

To a solution of 3-bromo-5-{3-chloro-4-[(1-methylethyl)oxy]phenyl}-1,2,4-thiadiazole (D43) (548 mg, 1.643 mmol), 4-[2-ethyl-3-(4,4,5,5-tetramethyl-1,3,2-dioxaborolan-2-yl)phenyl]piperidine (D119) (544 mg, 1.725 mmol) and Pd(Ph$_3$P)$_4$ (190 mg, 0.164 mmol) in N,N-Dimethylformamide (DMF) (5 mL) and Water (1.000 mL) was added tripotassium phosphate (1395 mg, 6.57 mmol), The solution was sealed and irritated in Biotage MW at 120° C. for 20 min. The mixture was directly dried with silica gel and purified by column chromatography to afford 4-[3-(5-{3-chloro-4-[(1-methylethyl)oxy]phenyl}-1,2,4-thiadiazol-3-yl)-2-ethylphenyl]piperidine (D122) (169 mg). MS (ES): $C_{24}H_{28}ClN_3OS$ requires 441.2. found 442.2 (M+H$^+$).

Description for D123 ethyl 3-{4-[2-ethyl-3-(4,4,5-trimethyl-1,3,2-dioxaborolan-2-yl)phenyl]-1-piperidinyl}propanoate (D123)

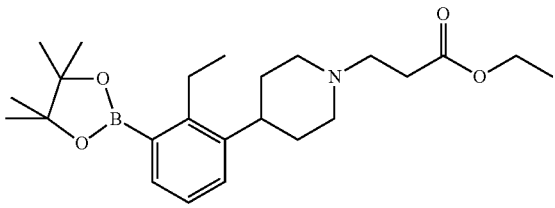 [SMILES: CCOC(=O)CCN1CCC(c2cccc(B3OC(C)(C)C(C)(C)O3)c2CC)CC1]

To a solution of 4-[2-ethyl-3-(4,4,5,5-tetramethyl-1,3,2-dioxaborolan-2-yl)phenyl]piperidine (D119) (80 mg, 0.186 mmol) and DBU (0.034 mL, 0.224 mmol) in Acetonitrile (8 mL) was added ethyl 2-propenoate (57 mg, 0.499 mmol). The solution was sealed and stirred at 80° C. for 2 h. The solution was evaporated in vacuo to afford ethyl 3-{4-[2-ethyl-3-(4,4,5-trimethyl-1,3,2-dioxaborolan-2-yl)phenyl]-1-piperidinyl}propanoate (D123) (46 mg). MS (ES): $C_{24}H_{38}BNO_4$ requires 415.3. found 416.3 (M+H$^+$).

Description for D124

1,1-dimethylethyl 4-(3-{5-[3-cyano-4-(2-methylpropyl)phenyl]-1,2,4-thiadiazol-3-yl}-2-ethylphenyl)-1-piperidinecarboxylate (D124)

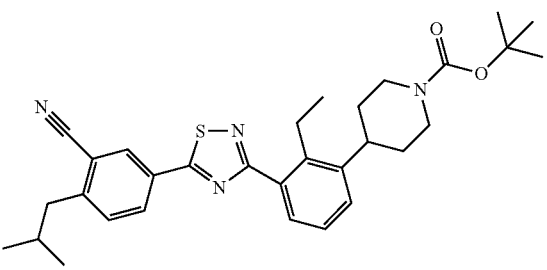 [SMILES: CCc1c(-c2nsc(-c3ccc(CC(C)C)c(C#N)c3)n2)cccc1C1CCN(C(=O)OC(C)(C)C)CC1]

To a solution of 1,1-dimethylethyl 4-[2-ethyl-3-(4,4,5,5-tetramethyl-1,3,2-dioxaborolan-2-yl)phenyl]-1-piperidinecarboxylate (70 mg, 0.169 mmol), 5-(3-bromo-1,2,4-thiadiazol-5-yl)-2-(2-methylpropyl)benzonitrile (D60) (81 mg, 0.253 mmol) and Pd(Ph$_3$P)$_4$ (19.47 mg, 0.017 mmol) in N,N-Dimethylformamide (DMF) (5 mL) and Water (1 mL) was added tripotassium phosphate (107 mg, 0.506 mmol). This solution was stirred in MW irradiation at 120° C. for 20 Min. The solution was dried directly with silica gel and purified on column chromatography to afford 1,1-dimethylethyl 4-(3-{5-[3-cyano-4-(2-methylpropyl)phenyl]-1,2,4-thiadiazol-3-yl}-2-ethylphenyl)-1-piperidinecarboxylate (D124) (89 mg). MS (ES): $C_{31}H_{38}N_4O_2S$ requires 530.3. found 531.3 (M+H$^+$).

Description for D125

5-{3-[2-ethyl-3-(4-piperidinyl)phenyl]-1,2,4-thiadiazol-5-yl}-2-(2-methylpropyl)benzonitrile (D125)

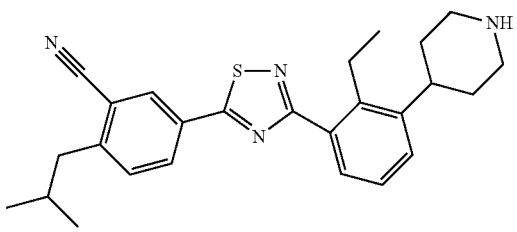 [SMILES: CCc1c(-c2nsc(-c3ccc(CC(C)C)c(C#N)c3)n2)cccc1C1CCNCC1]

To a solution of 1,1-dimethylethyl 4-(3-{5-[3-cyano-4-(2-methylpropyl)phenyl]-1,2,4-thiadiazol-3-yl}-2-ethylphenyl)-1-piperidinecarboxylate (D124) (0.089 g, 0.168 mmol) in Dichloromethane (DCM) (10 mL) at room temp was added TFA (0.388 mL, 5.04 mmol). This solution was stirred for 2 hr. This solution was condensed and dried in high vacuum to remove TFA to afford 5-{3-[2-ethyl-3-(4-piperidinyl)phenyl]-1,2,4-thiadiazol-5-yl}-2-(2-methylpropyl)benzonitrile (D125) (72 mg) as a brown oil residue, which was used directly in the next step. MS (ES): $C_{26}H_{30}N_4S$ requires 430.2. found 431.2 (M+H$^+$).

Description for D126

1-bromo-2-ethyl-3-iodo-benzene (D126)

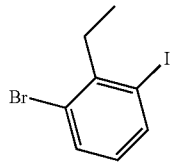

A three necked round-bottom flask was purged with argon and then filled with dry THF (250 mL), 1-bromo-3-iodo-benzene (50 g, 176.74 mmol) and ethyl iodide (50 g, 320.57 mmol). The mixture was cooled to −78° C. and LDA (made with 50 mL of iPr$_2$NH and 122.5 mL of BuLi (2.5 M in hexane) in 250 mL of THF) was added slowly at −50° C. The reaction was stirred for 4 hr and poured into sat. aq. NH$_4$Cl solution (1000 mL) and stirred vigorously for 20 min, extracted with DCM. The organic layers were separated, dried over Na$_2$SO$_4$ and evaporated to give the crude product, which was purified by column chromatography to afford 1-bromo-2-ethyl-3-iodo-benzene (D126) (50 g,). δH (CDCl$_3$-d$_6$, 400 MHz): 1.14 (3H, t), 3.06 (2H, q), 6.68 (1H, t), 7.52 (1H, d), 7.70 (1H, d)

Description for D127

2-(3-bromo-2-ethyl-phenyl)-malonic acid diethyl ester (D127)

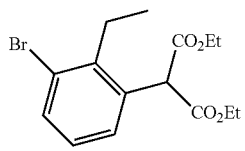 [SMILES: CCOC(=O)C(C(=O)OCC)c1cccc(Br)c1CC]

To a solution of malonic acid diethyl ester (24.72 g, 154.36 mmol) in dioxane (400 mL) was added sodium hydride (6.17 g, 60%, 154.36 mmol). The mixture was stirred for 15 minutes. Then 1-bromo-2-ethyl-3-iodo-benzene (D126) (40 g, 128.63 mmol) and cuprous bromide (22.13 g, 154.36 mmol) was added. The reaction mixture was refluxed for 10 hr, and then filtered. The filtrate was concentrated in vacuo to give the crude product, which purified by column chromatography to afford 2-(3-bromo-2-ethyl-phenyl)-malonic acid diethyl ester (D127) (20 g). δH (CDCl$_3$-d$_6$, 400 MHz): 1.13 (3H, t), 1.26 (6H, q), 2.88 (2H, m), 4.17 (1H, m), 4.93 (1H, s), 6.68 (1H, t), 7.41 (1H, d), 7.51 (1H, d).

Description for D128

2-(3-Bromo-2-ethyl-phenyl)-propane-1,3-diol (D128)

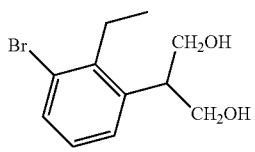

To a solution of 2-(3-bromo-2-ethyl-phenyl)-malonic acid diethyl ester (D127) (13 g, 37.88 mmol) in methanol (130 mL) was added sodium borohydride (14.33 g, 378.78 mmol), the reaction mixture was stirred for 12 hr at room temperature. Then water was added and extracted with CH$_2$Cl$_2$. The organic layers were separated, dried over Na$_2$SO$_4$, and concentrated in vacuo to afford 2-(3-bromo-2-ethyl-phenyl)-propane-1,3-diol (D128) (8 g). MS (ES): C$_{11}$H$_{15}$BrO$_2$ requires 258.0. found 223.0 (M+H$^+$-36).

Description for D129

1-benzhydryl-3-(3-bromo-2-ethyl-1-methylene-but-2-enyl)-azetidine (D129)

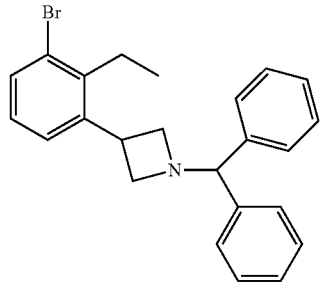 [SMILES: CCc1c(Br)cccc1C1CN(C(c2ccccc2)c2ccccc2)C1]

A mixture of 2-(3-bromo-2-ethyl-phenyl)-propane-1,3-diol (D128) (8 g, 30.87 mmol) in 150 mL of CH$_3$CN was added diphenylmethylamine (5.66 g, 30.87 mmol), trifluoromethanesulfonic anhydride, DIPEA at 0° C., and the reaction mixture was stirred for 12 hr at 70° C., then the reaction mixture was concentrated in vacuo. The residue was purified by column chromatography to afford 1-benzhydryl-3-(3-bromo-2-ethyl-1-methylene-but-2-enyl)-azetidine (D129) (3 g,).

Description for D130

1-benzhydryl-3-[2-ethyl-3-(4,4,5,5-tetramethyl-[1,3,2]dioxaborolan-2-yl)-phenyl]-azetidine (D130)

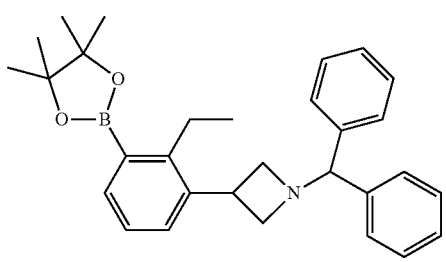 [SMILES: CCc1c(B2OC(C)(C)C(C)(C)O2)cccc1C1CN(C(c2ccccc2)c2ccccc2)C1]

A mixture of 1-benzhydryl-3-(3-bromo-2-ethyl-1-methylene-but-2-enyl)-azetidine (D129) (2 g, 4.92 mmol), bis(pinacolato)diboron (1.53 g, 6.03 mmol) and potassium acetate (1.453 g 14.765 mmol), dichloro[1,1-bis(diphenylphosphino)ferrocene]palladium (II) dichloromethane adduct (0.402 g, 0.492 mmol) in DMSO (30 mL) was degassed by nitrogen. The reaction mixture was stirred at 80° C. for 12 hr. The reaction mixture was added water and EtOAc. The organic layer was separated and dried over Na$_2$SO$_4$. The residue was purified by column chromatography to afford 1-benzhydryl-3-[2-ethyl-3-(4,4,5,5-tetramethyl-[1,3,2]dioxaborolan-2-yl)-phenyl]-azetidine (D130) (1.9 g). δH (CDCl$_3$-d$_6$, 400 MHz): 1.10 (3H, t), 2.66 (2H, m), 3.09 (2H, q), 3.66 (2H, m), 3.91 (1H, m), 7.17 (1H, m), 7.25 (2H, m), 7.33 (5H, m), 7.39 (5H, m).

Description for D131

3-[2-ethyl-3-(4,4,5,5-tetramethyl-[1,3,2]dioxaborolan-2-yl)-phenyl]-azetidine (D131)

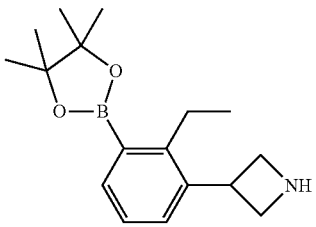 [SMILES: CCc1c(B2OC(C)(C)C(C)(C)O2)cccc1C1CNC1]

To a solution of 1-Benzhydryl-3-[2-ethyl-3-(4,4,5,5-tetramethyl-[1,3,2]dioxaborolan-2-yl)-phenyl]-azetidine (D130) (3.4 g, 7.489 mmol) in 80 mL of 1,2-dicholoroethane was added proton sponges (200 mg, 0.933 mmol) and 1-chloroethyl chloroformate. The reaction mixture was refluxed for 10 hr, and then filtered. The filtrate was concentrated under reduced pressure to give the crude product, which was purified by Mass Directed AutoPrep to afford 3-[2-ethyl-3-(4,4,5,5-tetramethyl-[1,3,2]dioxaborolan-2-yl)-phenyl]-azetidine (D131) (305 mg). δH (DMSO-$d_6$, 400 MHz): 0.98 (3H, t), 1.25 (12H, s), 2.72 (2H, q), 4.10 (2H, m), 4.24 (2H, m), 4.33 (1H, m), 7.23 (1H, m), 7.55 (2H, m), 9.0 (1H, br, s).

Description for D132 ethyl 4-{3-[2-ethyl-3-(4,4,5,5-tetramethyl-1,3,2-dioxaborolan-2-yl)phenyl]-1-azetidinyl}butanoate (D132)

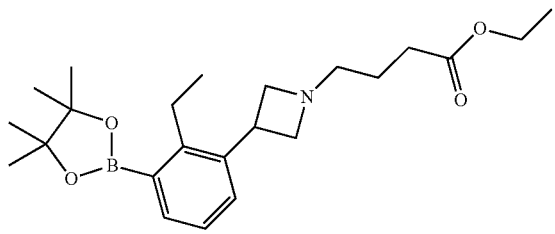 [SMILES: CCOC(=O)CCCN1CC(c2cccc(B3OC(C)(C)C(C)(C)O3)c2CC)C1]

To a solution of 3-[2-ethyl-3-(4,4,5,5-tetramethyl-[1,3,2]dioxaborolan-2-yl)-phenyl]-azetidine (D131) (295 mg, 0.735 mmol) in Acetonitrile (10 mL) was added potassium carbonate (305 mg, 2.206 mmol) and ethyl 4-bromobutanoate (0.158 mL, 1.103 mmol). The reaction solution was heated to 60° C. overnight. The solvent was removed in vacuo and the residue was diluted with ethyl acetate, washed with water, dried and concentrated to afford ethyl 4-{3-[2-ethyl-3-(4,4,5,5-tetramethyl-1,3,2-dioxaborolan-2-yl)phenyl]-1-azetidinyl}butanoate (D132) (295 mg) as an oil. MS (ES): $C_{23}H_{36}BNO_4$ requires 401.3. found 402.3 (M+H$^+$).

Description for D133

1-bromo-3-(bromomethyl)-2-ethylbenzene (D133)

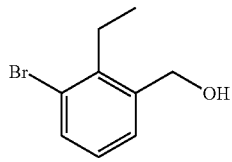

To a solution of 3-bromo-2-ethylbenzaldehyde (5 g, 23.47 mmol) in Methanol (50 mL) was added NaBH4 (1.776 g, 46.9 mmol) at 0° C. The reaction solution was stirred at room temperature for 2 hours. The solvent was removed in vacuo and the residue was dissolved in ethyl acetate, washed with water, dried over sodium sulphate, concentrated and purified by ISCO column chromatography to afford (3-bromo-2-ethylphenyl)methanol (D133) (3 g) as an oil. MS (ES): $C_9H_{11}BrO$ requires 213.99. found 197.0 (M+H$^+$-18).

Description for D134

1-bromo-3-(bromomethyl)-2-ethylbenzene (D134)

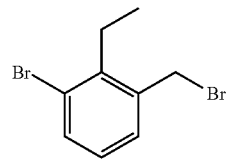

To a solution of (3-bromo-2-ethylphenyl)methanol (D133) (3 g, 13.95 mmol) in Dichloromethane (DCM) (50 mL) was added CBr$_4$ (5.55 g, 16.74 mmol). To the reaction solution was added triphenylphosphine (5.49 g, 20.92 mmol) portionwise at 0° C. The reaction solution was warmed to room temperature and stirred at the temp overnight. The solvent was removed in vacuo and the residue was purified by ISCO column chromatography to afford 1-bromo-3-(bromomethyl)-2-ethylbenzene (D134) (1.3 g) as an oil.

Description for D135 diethyl [(3-bromo-2-ethylphenyl)methyl]phosphonate (D135)

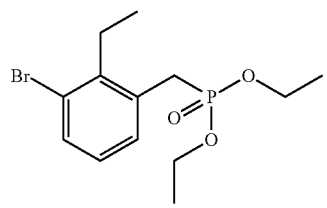 [SMILES: CCOP(=O)(Cc1cccc(Br)c1CC)OCC]

To a solution of 1-bromo-3-(bromomethyl)-2-ethylbenzene (D134) (1.3 g, 4.68 mmol) in Toluene (10 mL) was added triethyl phosphite (0.818 mL, 4.68 mmol). The reaction solution was heated in a sealed tube at 130° C. for 2 days. The solvent was removed in vacuo to afford diethyl [(3-bromo-2-ethylphenyl)methyl]phosphonate (D135) (1.567 g), which was used directly without further purification. MS (ES): $C_{13}H_{20}BrO_3P$ requires 334.0. found 335.0 (M+H$^+$).

Description for D136

1,1-dimethylethyl 4-[(3-bromo-2-ethylphenyl)methylidene]-1-piperidine carboxylate (D136)

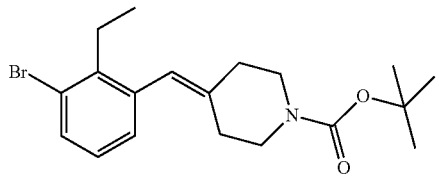 [SMILES: CCc1c(Br)cccc1C=C1CCN(C(=O)OC(C)(C)C)CC1]

To a suspension of NaH (0.155 g, 3.88 mmol) in Tetrahydrofuran (THF) (30 mL) was added diethyl [(3-bromo-2-ethylphenyl)methyl]phosphonate (D135) (1 g, 2.98 mmol) at 0° C. The reaction solution was warmed to room temperature and stirred for 1 hour. The reaction solution was cooled to 0° C. again and 1,1-dimethylethyl 4-oxo-1-piperidinecarboxylate (0.713 g, 3.58 mmol) was added. The reaction solution was warmed to room temperature and stirred overnight. Water was added and extracted with ethyl acetate, the organic phases were dried over sodium sulphate, concentrated and purified by ISCO column chromatography to afford 1,1-dimethylethyl 4-[(3-bromo-2-ethylphenyl)methylidene]-1-piperidinecarboxylate (D136) (0.73 g). MS (ES): $C_{19}H_{26}BrNO_2$ requires 379.1. found 324.1 (M+H$^+$-56).

Description for D137

4-[(3-bromo-2-ethylphenyl)methylidene]piperidine (D137)

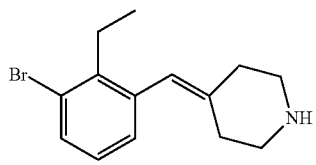

To a solution of 1,1-dimethylethyl 4-[(3-bromo-2-ethylphenyl)methylidene]-1-piperidinecarboxylate (D136) (3 g, 7.89 mmol) in Dichloromethane (DCM) (100 mL) was added TFA (6.08 mL, 79 mmol). The reaction solution was stirred at room temperature for 2 hours. The solvent was evaporated in vacuo to afford 4-[(3-bromo-2-ethylphenyl)methylidene]piperidine (D137) (1.9 g), which was used directly without further purification. MS (ES): $C_{14}H_{18}BrN$ requires 279.1. found 280.1 (M+H$^+$).

Description for D138 ethyl 3-{4-[(3-bromo-2-ethylphenyl)methylidene]-1-piperidinyl}propanoate (D138)

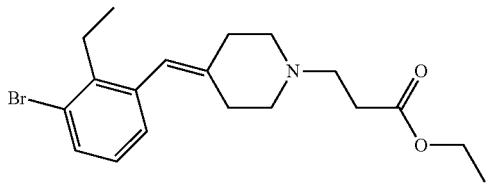 [SMILES: CCOC(=O)CCN1CCC(=Cc2cccc(Br)c2CC)CC1]

To a solution of 4-[(3-bromo-2-ethylphenyl)methylidene]piperidine (D137) (1 g, 3.57 mmol) in Acetonitrile (10 mL) was added DBU (0.807 mL, 5.35 mmol) and ethyl 2-propenoate (0.429 g, 4.28 mmol). The reaction solution was heated to 60° C. for overnight. The solvent was removed in vacuo and the residue was diluted with ethyl acetate, washed with water, dried and concentrated to afford ethyl 3-{4-[(3-bromo-2-ethylphenyl)methylidene]-1-piperidinyl}propanoate (D138) (1.35 g), which was used directly without further purification. MS (ES): $C_{19}H_{26}BrNO_2$ requires 379.1. found 380.1 (M+H$^+$).

Description for D139 ethyl 3-(4-{[2-ethyl-3-(4,4,5,5-tetramethyl-1,3,2-dioxaborolan-2-yl)phenyl]methylidene}-1-piperidinyl)propanoate (D139)

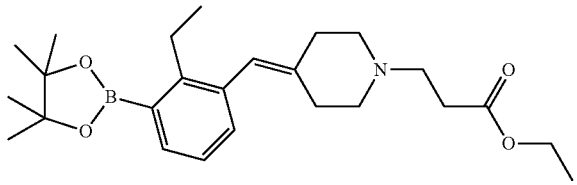 [SMILES: CCOC(=O)CCN1CCC(=Cc2cccc(B3OC(C)(C)C(C)(C)O3)c2CC)CC1]

To a solution of ethyl 3-(4-{[2-ethyl-3-(4,4,5,5-tetramethyl-1,3,2-dioxaborolan-2-yl)phenyl]methylidene}-1-piperidinyl)propanoate (D138) (1.35 g, 3.55 mmol) in N,N-Dimethylformamide (DMF) (10 mL) was added 4,4,4',4',5,5,5', 5'-octamethyl-2,2'-bi-1,3,2-dioxaborolane (1.803 g, 7.10 mmol), potassium acetate (1.045 g, 10.65 mmol) and PdCl2 (dppf)-CH2Cl2 adduct (0.290 g, 0.355 mmol). The reaction solution was heated to 80° C. overnight. The solvent was removed in vacuo and the residue was diluted with ethyl acetate, washed with water, brine, dried and concentrated, purified by ISCO column chromatography to afford ethyl 3-(4-{[2-ethyl-3-(4,4,5,5-tetramethyl-1,3,2-dioxaborolan-2-yl)phenyl]methylidene}-1-piperidinyl)propanoate (D139) (1.517 g). MS (ES): $C_{25}H_{38}BNO_4$ requires 427.3. found 428.3 (M+H$^+$).

Description for D140 ethyl 3-(4-{[2-ethyl-3-(4,4,5,5-tetramethyl-1,3,2-dioxaborolan-2-yl)phenyl]methyl}-1-piperidinyl)propanoate (D140)

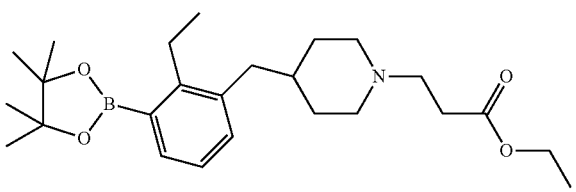 [SMILES: CCOC(=O)CCN1CCC(Cc2cccc(B3OC(C)(C)C(C)(C)O3)c2CC)CC1]

To a solution of ethyl 3-(4-{[2-ethyl-3-(4,4,5,5-tetramethyl-1,3,2-dioxaborolan-2-yl)phenyl]methylidene}-1-piperidinyl)propanoate (D139) (1.5 g, 3.51 mmol) in Ethanol (10 mL) was added Pd/C (0.037 g, 0.351 mmol). The reaction mixture was stirred under hydrogen atmosphere overnight. After filtration, the filtrate was concentrated to afford ethyl 3-(4-{[2-ethyl-3-(4,4,5,5-tetramethyl-1,3,2-dioxaborolan-2-yl)phenyl]methyl}-1-piperidinyl)propanoate (D140) (1.33 g), which was used directly without further purification. MS (ES): $C_{25}H_{40}BNO_4$ requires 429.3. found 430.2 (M+H$^+$).

Description for D141 ethyl 3-(4-{[3-(5-{3-chloro-4-[(1-methylethyl)oxy]phenyl}-1,2,4-thiadiazol-3-yl)-2-ethylphenyl]methyl}-1-piperidinyl)propanoate (D141)

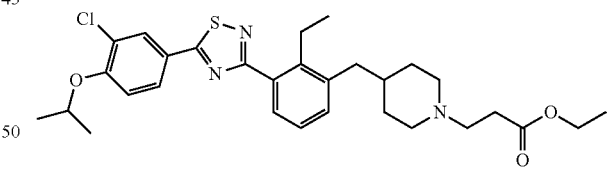

To a solution of ethyl 3-(4-{[2-ethyl-3-(4,4,5,5-tetramethyl-1,3,2-dioxaborolan-2-yl)phenyl]methyl}-1-piperidinyl)propanoate (D140) (1.3 g, 3.03 mmol) in N,N-Dimethylformamide (DMF) (6 mL) and Water (1.500 mL) was added 3-bromo-5-{3-chloro-4-[(1-methylethyl)oxy]phenyl}-1,2,4-thiadiazole (D43) (1.010 g, 3.03 mmol), tripotassium phosphate (1.928 g, 9.08 mmol) and Pd(Ph$_3$P)$_4$ (0.350 g, 0.303 mmol). The reaction mixture was heated by Biotage Initiator to 120° C. for 20 min. The reaction mixture was diluted with ethyl acetate, washed with water, dried and concentrated and purified by ISCO column chromatography to afford ethyl 3-(4-{[3-(5-{3-chloro-4-[(1-methylethyl)oxy]phenyl}-1,2,4-thiadiazol-3-yl)-2-ethylphenyl]methyl}-1-piperidinyl)propanoate (D141) (0.63 g). MS (ES): $C_{30}H_{38}ClN_3O_3S$ requires 555.2. found 556.2 (M+H$^+$).

Description for D142 ethyl {4-[(3-bromo-2-ethylphenyl)methylidene]-1-piperidinyl}acetate (D142)

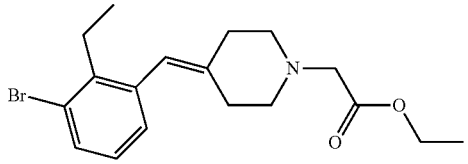 [SMILES: CCOC(=O)CN1CCC(=Cc2cccc(Br)c2CC)CC1]

To a solution of 4-[(3-bromo-2-ethylphenyl)methylidene]piperidine (D137) (0.53 g, 1.891 mmol) in N,N-Dimethylformamide (DMF) (10 mL) was added potassium carbonate (3.92 g, 28.4 mmol), followed by ethyl bromoacetate (0.190 mL, 1.702 mmol). The reaction solution was stirred at room temperature for 3 hours. The reaction solution was diluted with ethyl acetate, washed with water, dried over sodium sulphate, concentrated to afford ethyl {4-[(3-bromo-2-ethylphenyl)methylidene]-1-piperidinyl}acetate (D142) (0.693 g). MS (ES): $C_{18}H_{24}BrNO_2$ requires 365.1. found 366.1 (M+H$^+$).

Description for D143 ethyl (4-{[2-ethyl-3-(4,4,5,5-tetramethyl-1,3,2-dioxaborolan-2-yl)phenyl]methylidene}-1-piperidinyl)acetate (D143)

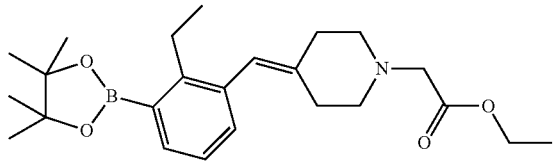 [SMILES: CCOC(=O)CN1CCC(=Cc2cccc(B3OC(C)(C)C(C)(C)O3)c2CC)CC1]

A reaction mixture of ethyl {4-[(3-bromo-2-ethylphenyl)methylidene]-1-piperidinyl}acetate (D142) (0.69 g, 1.884 mmol), 4,4,4',4',5,5,5',5'-octamethyl-2,2'-bi-1,3,2-dioxaborolane (0.718 g, 2.83 mmol), PdCl2(dppf)-CH2Cl2 adduct (0.154 g, 0.188 mmol) and potassium acetate (0.555 g, 5.65 mmol) was degassed and heated to 80° C. overnight. The solvent was removed in vacuo and the residue was purified by ISCO column chromatography to afford ethyl (4-{[2-ethyl-3-(4,4,5,5-tetramethyl-1,3,2-dioxaborolan-2-yl)phenyl]methylidene}-1-piperidinyl)acetate (D143) (0.37 g). MS (ES): $C_{24}H_{36}BNO_4$ requires 413.3. found 414.3 (M+H$^+$).

Description for D144 ethyl (4-{[2-ethyl-3-(4,4,5,5-tetramethyl-1,3,2-dioxaborolan-2-yl)phenyl]methyl}-1-piperidinyl)acetate (D144)

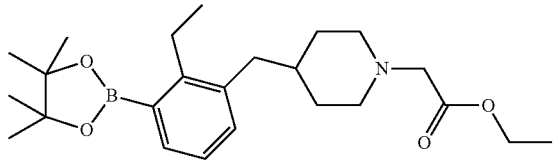 [SMILES: CCOC(=O)CN1CCC(Cc2cccc(B3OC(C)(C)C(C)(C)O3)c2CC)CC1]

To a solution of ethyl (4-{[2-ethyl-3-(4,4,5,5-tetramethyl-1,3,2-dioxaborolan-2-yl)phenyl]methylidene}-1-piperidinyl)acetate (D143) (0.37 g, 0.895 mmol) in Ethanol (10 mL) was added Pd/C (0.191 g, 0.179 mmol). The reaction solution was stirred under hydrogen atmosphere for 4 hours. After filtration, the filtrate was concentrated to afford ethyl (4-{[2-ethyl-3-(4,4,5,5-tetramethyl-1,3,2-dioxaborolan-2-yl)phenyl]methyl}-1-piperidinyl)acetate (D144) (300 mg). MS (ES): $C_{24}H_{38}BNO_4$ requires 415.3. found 416.3 (M+H$^+$).

Description for D145 ethyl (4-{[2-ethyl-3-(4,4,5,5-tetramethyl-1,3,2-dioxaborolan-2-yl)phenyl]methyl}-1-piperidinyl)acetate (D145)

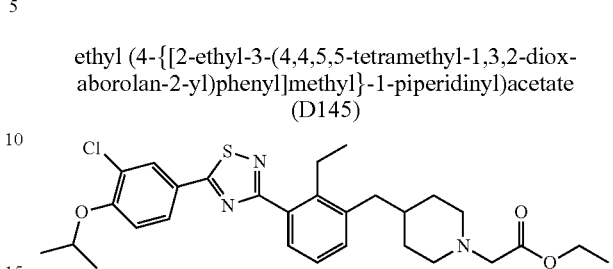

A solution of ethyl (4-{[2-ethyl-3-(4,4,5,5-tetramethyl-1,3,2-dioxaborolan-2-yl)phenyl]methyl}-1-piperidinyl)acetate (D144) (200 mg, 0.481 mmol), 3-bromo-5-{3-chloro-4-[(1-methylethyl)oxy]phenyl}-1,2,4-thiadiazole (D43) (161 mg, 0.481 mmol), tripotassium phosphate (307 mg, 1.444 mmol) and Pd(Ph$_3$P)$_4$ (55.6 mg, 0.048 mmol) in N,N-Dimethylformamide (DMF) (6 mL) and Water (1.500 mL) was heated by Biotage Initiator to 120° C. for 15 min. The reaction solution was diluted with ethyl acetate, washed with water, dried over sodium sulphate, concentrated and purified by ISCO column chromatography to afford ethyl (4-{[3-(5-{3-chloro-4-[(1-methylethyl)oxy]phenyl}-1,2,4-thiadiazol-3-yl)-2-ethylphenyl]methyl}-1-piperidinyl)acetate (D145) (80 mg). MS (ES): $C_{29}H_{36}ClN_3O_3S$ requires 541.2. found 542.2 (M+H$^+$).

EXAMPLE 1

1-[(2-ethyl-3-{5-[4-[(1-methylethyl)oxy]-3-(trifluoromethyl)phenyl]-1,3,4-thiadiazol-2-yl}phenyl)methyl]-4-piperidinecarboxylic acid (E1)

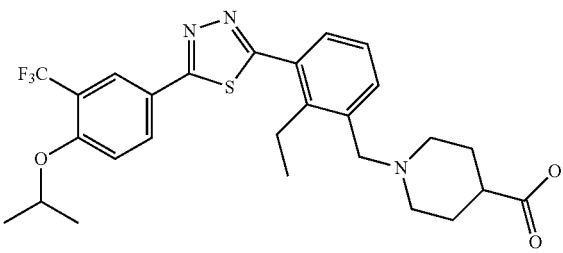 [SMILES: CCc1c(CN2CCC(C(=O)O)CC2)cccc1-c1nnc(-c2ccc(OC(C)C)c(C(F)(F)F)c2)s1]

To a solution of ethyl 1-[(2-ethyl-3-{5-[4-[(1-methylethyl)oxy]-3-(trifluoromethyl)phenyl]-1,3,4-thiadiazol-2-yl}phenyl)methyl]-4-piperidinecarboxylate (D7) (130 mg) in isopropanol (5 mL) and water (5 mL) was added sodium hydroxide (50 mg). The reaction mixture was stirred at room temperature for 1 h. The reaction mixture was neutralized with 2N HCl till pH ~6.0. The mixture was extracted with EA/THF for 3 times. The combined organic layers were washed with brine, dried over anhydrous sodium sulfate. The dried solution was concentrated and the residue was purified by Mass Directed AutoPrep to give 1-[(2-ethyl-3-{5-[4-[(1-methylethyl)oxy]-3-(trifluoromethyl)phenyl]-1,3,4-thiadiazol-2-yl}phenyl)methyl]-4-piperidinecarboxylic acid (E1) (50 mg) as an off-white solid. δH (DMSO-d$_6$, 400 MHz): 1.10 (3H, t), 1.33 (6H, d), 1.54 (2H, m), 1.77 (2H, m), 2.06 (2H, m), 2.22 (1H, m), 2.76 (2H, m), 2.91 (2H, m), 4.93 (1H, m), 7.34 (1H, m), 7.51 (3H, m), 8.23 (2H, m), 12.13 (1H, br s). δF (DMSO-d$_6$, 376 MHz): −61.3. MS (ES): C$_{27}$H$_{39}$F$_3$N$_3$O$_3$S requires 533. found 534.2 (M+H$^+$).

EXAMPLE 2

1-[(2-ethyl-3-{5-[4-[(1-methylethyl)oxy]-3-(trifluoromethyl)phenyl]-1,3,4-thiadiazol-2-yl}phenyl)methyl]-3-azetidinecarboxylic acid (E2)

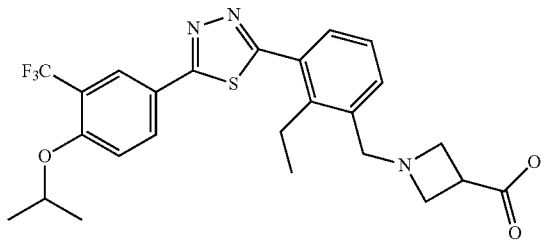 [SMILES: CCc1c(CN2CC(C(=O)O)C2)cccc1-c1nnc(-c2ccc(OC(C)C)c(C(F)(F)F)c2)s1]

To a solution of methyl 1-[(2-ethyl-3-{5-[4-[(1-methylethyl)oxy]-3-(trifluoromethyl)phenyl]-1,3,4-thiadiazol-2-yl}phenyl)methyl]-3-azetidinecarboxylate (D8) (64 mg) in isopropanol (3 mL) and water (3 mL) was added sodium hydroxide (50 mg). The reaction mixture was stirred at room temperature for 1 h. The reaction mixture was neutralized with 2N HCl till pH ~6.0. The mixture was extracted with EA/THF for 3 times. The combined organic layers were washed with brine, dried over anhydrous sodium sulfate. The dried solution was concentrated and the residue was purified by Mass Directed AutoPrep to give 1-[(2-ethyl-3-{5-[4-[(1-methylethyl)oxy]-3-(trifluoromethyl)phenyl]-1,3,4-thiadiazol-2-yl}phenyl)methyl]-3-azetidinecarboxylic acid (E2) (35 mg) as an off-white solid. δH (DMSO-d$_6$, 400 MHz): 1.10 (3H, t), 1.33 (6H, d), 2.85 (2H, m), 3.23 (3H, m), 3.42 (2H, m), 3.67 (2H, s), 4.93 (1H, m), 7.33 (1H, t), 7.50 (3H, m), 8.23 (2H, m). δF (DMSO-d$_6$, 376 MHz): −61.3. MS (ES): C$_{25}$H$_{26}$F$_3$N$_3$O$_3$S requires 505. found 506.2 (M+H$^+$).

EXAMPLE 3

1-{[3-(5-{3-chloro-4-[(1-methylethyl)oxy]phenyl}-1,3,4-thiadiazol-2-yl)-2-ethylphenyl]methyl}-4-piperidinecarboxylic acid trifluoroacetate (E3)

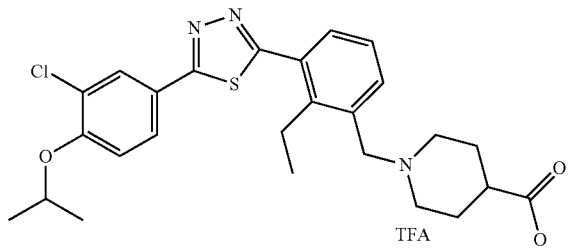 [SMILES: CCc1c(CN2CCC(C(=O)O)CC2)cccc1-c1nnc(-c2ccc(OC(C)C)c(Cl)c2)s1]

To a solution of ethyl 1-{[3-(5-{3-chloro-4-[(1-methylethyl)oxy]phenyl}-1,3,4-thiadiazol-2-yl)-2-ethylphenyl]methyl}-4-piperidinecarboxylate (D12) (60.1 mg) in isopropanol (3 mL) and water (3 mL) was added sodium hydroxide (50 mg). The reaction mixture was stirred at room temperature for 1 h. The reaction mixture was neutralized with 2N HCl till pH ~6.0. The mixture was extracted with EA/THF for 3 times. The combined organic layers were washed with brine, dried over anhydrous sodium sulfate. The dried solution was concentrated and the residue was purified by Mass Directed AutoPrep to give 1-{[3-(5-{3-chloro-4-[(1-methylethyl)oxy]phenyl}-1,3,4-thiadiazol-2-yl)-2-ethylphenyl]methyl}-4-piperidinecarboxylic acid (E3) (30 mg) as a TFA salt (off-white solid). δH (DMSO-d$_6$, 400 MHz): 1.07 (3H, t), 1.35 (6H, d), 1.78 (2H, m), 2.06 (2H, m), 2.96 (2H, m), 3.20 (2H, m), 3.37 (1H, m), 3.46 (2H, m), 4.45 (2H, m), 4.85 (1H, m), 7.39 (1H, d), 7.53 (1H, t), 7.75 (2H, m), 7.97 (1H, dd), 8.10 (1H, d), 9.20 (1H, br s), 12.58 (1H, br s). δF (DMSO-d$_6$, 376 MHz): −73.6. MS (ES): C$_{26}$H$_{30}$ClN$_3$O$_3$S requires 499. found 500.2 (M+H$^+$).

EXAMPLE 4A

1-{[3-(5-{3-chloro-4-[(1-methylethyl)oxy]phenyl}-1,3,4-thiadiazol-2-yl)-2-ethylphenyl]methyl}-3-azetidinecarboxylic acid trifluoroacetate (E4A)

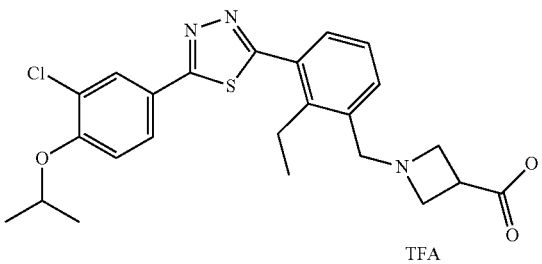 [SMILES: CCc1c(CN2CC(C(=O)O)C2)cccc1-c1nnc(-c2ccc(OC(C)C)c(Cl)c2)s1]

To a solution of crude methyl 1-{[3-(5-{3-chloro-4-[(1-methylethyl)oxy]phenyl}-1,3,4-thiadiazol-2-yl)-2-ethylphenyl]methyl}-3-azetidinecarboxylate (D13) (54 mg) in isopropanol (3 mL) and water (3 mL) was added sodium hydroxide (50 mg). The reaction mixture was stirred at room temperature for 1 h. The reaction mixture was neutralized with 2N HCl till pH ~6.0. The mixture was extracted with EA/THF for 3 times. The combined organic layers were washed with brine, dried over anhydrous sodium sulfate. The dried solution was concentrated and the residue was purified by Mass Directed AutoPrep (basic conditions) to give 1-{[3-(5-{3-chloro-4-[(1-methylethyl)oxy]phenyl}-1,3,4-thiadiazol-2-yl)-2-ethylphenyl]methyl}-3-azetidinecarboxylic acid (E4) (10 mg) as a TFA salt (off-white solid). δH (DMSO-d$_6$, 400 MHz): 1.09 (3H, t), 1.35 (6H, d), 2.89 (2H, m), 3.61 (2H, m), 4.28 (3H, br. s.), 4.53 (2H, m), 4.84 (1H, m), 7.38 (1H, d), 7.44 (1H, m), 7.58 (2H, m), 7.96 (1H, dd), 8.10 (1H, d), 13.06 (1H, br s). δF (DMSO-d$_6$, 376 MHz): −73.4. MS (ES): C$_{24}$H$_{26}$ClN$_3$O$_3$S requires 471. found 472.1 (M+H$^+$).

EXAMPLE 4B

1-{[3-(5-{3-chloro-4-[(1-methylethyl)oxy]phenyl}-1,3,4-thiadiazol-2-yl)-2-ethylphenyl]methyl}-3-azetidinecarboxylic acid (E4B)

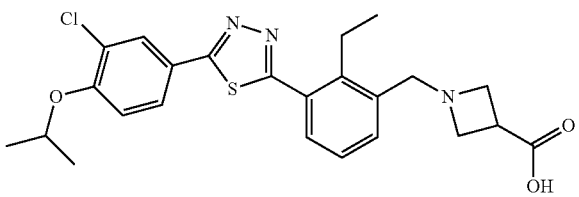 [SMILES: CCc1c(CN2CC(C(=O)O)C2)cccc1-c1nnc(-c2ccc(OC(C)C)c(Cl)c2)s1]

A solution of methyl 1-{[3-(5-{3-chloro-4-[(1-methylethyl)oxy]phenyl}-1,3,4-thiadiazol-2-yl)-2-ethylphenyl]methyl}-3-azetidinecarboxylate (D13) (30.3 g, 62.3 mmol) in Tetrahydrofuran (THF) (200 mL), Ethanol (150 mL) and Water (60 mL) was added sodium hydroxide (4.99 g, 125 mmol). The reaction mixture was stirred at room temperature overnight. Then pH of the reaction mixture was adjusted with 6 N HCl until pH ~2.0. White solid was precipitated. The organic solvent was removed in by rotary evaporator. The solid was collected through filtration. The solid was washed water (150 mL×3) and dried in vacuo to afford 1-{[3-(5-{3-chloro-4-[(1-methylethyl)oxy]phenyl}-1,3,4-thiadiazol-2-yl)-2-ethylphenyl]methyl}-3 azetidinecarboxylic acid (31 g), which was used for the following procedure without further purification.

Four reactions of: 1-{[3-(5-{3-chloro-4-[(1-methylethyl)oxy]phenyl}-1,3,4-thiadiazol-2-yl)-2-ethylphenyl]methyl}-3-azetidinecarboxylic acid (5.2 g) was dissolved in Acetonitrile (400 mL) and water (250 mL) at room temperature. Then the solution was filtered. The filtrate was basified with aqueous NH3 solution (1.593 mL, 40.9 mmol) till pH ~10. Then acetonitrile was removed in vacuo carefully. White solid was precipitated during removal of acetonitrile. The solid was collected through filtration together. Then the solid was washed with water three times (200 ml×3) and dried in vacuo to afford 1-{[3-(5-{3-chloro-4-[(1-methylethyl)oxy]phenyl}-1,3,4-thiadiazol-2-yl)-2-ethylphenyl]methyl}-3-azetidinecarboxylic acid (19 g) as a free base. δH (DMSO-d$_6$, 600 MHz): 1.11 (3H, t), 1.35 (6H, d), 2.86 (2H, m), 3.25 (3H, m), 3.43 (3H, m), 3.67 (2H, s), 4.84 (1H, dt), 7.35 (2H, m), 7.49 (2H, m), 7.95 (1H, dd), 8.09 (1H, d). MS (ES): $C_{24}H_{26}ClN_3O_3S$ requires 471. found 472.2 (M+H$^+$).

EXAMPLE 4C

1-{[3-(5-{3-chloro-4-[(1-methylethyl)oxy]phenyl}-1,3,4-thiadiazol-2-yl)-2-ethylphenyl]methyl}-3-azetidinecarboxylic acid hydrochloride (E4C)

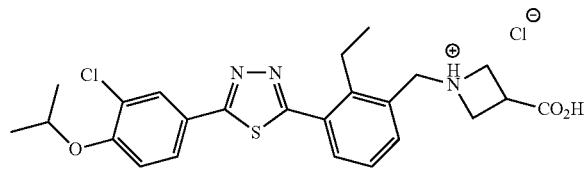

To a solution of 1-{[3-(5-{3-chloro-4-[(1-methylethyl)oxy]phenyl}-1,3,4-thiadiazol-2-yl)-2-ethylphenyl]methyl}-3-azetidinecarboxylic acid (E4B, 100 mg) in THF (2 mL) and water (1 mL) was added HCl (0.254 mL, 1M, in methanol). The mixture was stirred for 30 min at rt. Solvent was removed under the reduced pressure to give Example 4C as a white solid (107 mg). δH (DMSO-d$_6$, 600 MHz): 1.09 (3H, t), 1.34 (6H, m), 2.92 (2H, m), 3.66 (1H, m), 4.29 (4H, m), 4.58 (2H, m), 4.84 (1H, dt), 7.39 (1H, d), 7.47 (1H, t), 7.67 (2H, m), 7.97 (1H, dd), 8.10 (1H, d), 10.73 (1H, s), 13.16 (1H, br. s.).

EXAMPLE 4C

Alternative Method

Stage 1

1,3-dibromo-2-ethylbenzene

To a three litre neck round flask charged with 19.30 g of diisopropylamine and 110 mL of THF was added 76 mL of n-BuLi in hexane (2.5 M) in dropwise at −70° C. After addition was finished, the resulting mixture was stirred at the same temp. for 10 min. In another 500 mL three neck round flask, 25 g of 1,3-dibromobenzene and 49.6 g of ethyl iodide was mixed well and cooled to −70° C. The freshly prepared LDA was introduced dropwise to above mixture below −65° C. After the addition was finished, the resulting mixture was stirred for 4 h at the same temp. GCMS showed that the desired product was formed. The reaction was warmed to 0° C. in 30 mins. To the reaction mixture was added 100 mL of sat. ammonium chloride solution to quench the reaction.
The next day:

The organic layer was separated. The aqueous solution was extracted with TBME (100 mL×2). The combined organic solution was washed with brine (100 mL×2). After drying with anhydrous sodium sulfate and removal of the solvent, the residue was passed the short silica gel pad with the eluent of PE. TLC detected that all the product was flushed out, and the solvent was removed under reduced pressure. 1,3-dibromo-2-ethylbenzene (26.65 g) was obtained as pale yellow liquid.
δH (DMSO-d$_6$, 400 MHz): 1.12 (3H, m), 2.91 (2H, m), 7.04 (1H, m), 7.59 (2H, m).

Stage 2

(3-bromo-2-ethylphenyl)(hydroxy)methanesulfonic acid

To a three neck round flask charged with 2 g of 1,3-dibromo-2-ethylbenzene in 20 mL anhydrous THF was added 2.80 mL of i-PrMgBr in THF at 0° C. The resulting mixture was stirred at this temp. for 10 mins. To above colorless clear solution was added 3.93 mL of nBuLi in hexane at 0° C. The resulting grey mixture was further stirred for another 1 h. The above solution was cooled to −10° C., and 0.831 g of DMF was added dropwise. The resulting mixture was stirred to rt for 2 hours. LCMS showed that the starting material had disappeared and the desired product was formed. 30 mL of aq. citric acid solution (0.5 M) was added at rt to quench the reaction, the organic layer was separated. The aqueous phase was extracted with TBME (30 mL×2). The combined organic phase was dried with sodium sulfate and evaporated under reduced pressure. The residue was dissolved in 6.0 mL of EtOH then 0.804 g of sodium bisulfite in 6.0 mL of water was added dropwise at 0° C. After stirring for 10 mins, a sticky white suspension was formed. The solid was collected with filtering and washing with EtOH, followed with TBME. (3-bromo-2-ethylphenyl)(hydroxy)methanesulfonic acid (1.1 g) was obtained as white powder.
δH (DMSO-d$_6$, 400 MHz): 1.09 (3H, m), 2.72 (1H, m), 3.13 (1H, dq), 5.23 (1H, d), 5.94 (1H, d), 7.05 (1H, t), 7.43 (1H, d), 7.60 (1H, d).

Stage 3

3-bromo-2-ethylbenzaldehyde

To a solution of (3-bromo-2-ethylphenyl)(hydroxy)methanesulfonate (5.26 g, 16.59 mmol) in THF (25 mL) was added HCl (16.59 mL, 49.8 mmol). The mixture was stirred for an hour at rt. THF was removed under the reduced pressure. Residue was dissolved in EtOAc (50 mL) then washed with brine (10 mL). The organic phase was dried over anhydrous sodium sulfate, concentrated under the reduced pressure and dried in vacuum to give 3-bromo-2-ethylbenzaldehyde (2.89 g) as pale yellow oil.

δH (DMSO-d$_6$, 400 MHz): 1.15 (3H, m), 3.17 (2H, q), 7.38 (1H, t), 7.88 (2H, m), 10.20 (1H, s).

Stage 4 methyl 1-(3-bromo-2-ethylbenzyl)azetidine-3-carboxylate

To a solution of 3-bromo-2-ethylbenzaldehyde (2.66 g, 12.48 mmol) in Dichloromethane (DCM) (30 mL) were added methyl 3-azetidinecarboxylate (1.987 g, 13.11 mmol) and sodium acetate (1.536 g, 18.73 mmol). The mixture was stirred for 30 min at rt then sodium triacetoxyborohydride (3.97 g, 18.73 mmol) was added to above solution. The obtained mixture was stirred for an hour at rt. The solvent was removed under the reduced pressure, water (30 mL) was added to the above residue and the mixture was adjusted to pH value around 3 with HCl (1.0 N) then extracted with EtOAc (10 mL). Acidic phase was adjusted to pH value around 8 with NaOH (1.0 N) solution then extracted with EtOAc (30 mL). The organic phase was dried over anhydrous sodium sulfate, concentrated under the reduced pressure and dried in vacuum to give methyl 1-(3-bromo-2-ethylbenzyl)azetidine-3-carboxylate (3.04 g) as pale yellow oil Stage 5 methyl 1-(2-ethyl-3-(4,4,5,5-tetramethyl-1,3,2-dioxaborolan-2-yl)benzyl)azetidine-3-carboxylate To a solution of methyl 1-[(3-bromo-2-ethylphenyl)methyl]-3-azetidinecarboxylate (3.28 g, 10.51 mmol) in 1,4-Dioxane (40 mL) were added 4,4,4',4',5,5,5',5'-octamethyl-2,2'-bi-1,3,2-dioxaborolane (2.93 g, 11.56 mmol), PdCl$_2$ (dppf)-CH$_2$Cl$_2$ adduct (0.429 g, 0.525 mmol) and potassium acetate (3.09 g, 31.5 mmol). The mixture was heated to 100° C. and stirred for two hours and 20 mins. LCMS showed that the starting material was consumed completely. The solution was cooled to rt and filtered with celite, washed with EtOAc. The filtrate was concentrated under the reduced pressure. The residue was dissolved in EtOAc (50 mL) then washed with brine (50 mL). The organic phase was dried over anhydrous sodium sulfate and concentrated under the reduced pressure to give methyl 1-(2-ethyl-3-(4,4,5,5-tetramethyl-1,3,2-dioxaborolan-2-yl)benzyl)azetidine-3-carboxylate (4.97 g, crude) as black oil.

Stage 6

(2-ethyl-3-((3-(methoxycarbonyl)azetidin-1-yl)methyl)phenyl)boronic acid

To a solution of methyl 1-{[2-ethyl-3-(4,4,5,5-tetramethyl-1,3,2-dioxaborolan-2-yl)phenyl]methyl}-3-azetidinecarboxylate (5.23 g, 14.56 mmol) in Methanol (50 mL) was added potassium hydrogen fluoride (16.17 mL, 72.8 mmol). The mixture was stirred at rt for an hour. LCMS showed that the starting material was consumed completely. The solvent was removed under the reduced pressure and the residue was acidified with HCl (1.0 M) to pH value around 3 then extracted with EtOAc (50 mL). The aqueous phase was adjusted to pH value around 6 with sat. NaHCO$_3$ solution, the target product was collected by filtering and dried in vacuum to give (2-ethyl-3-((3-(methoxycarbonyl)azetidin-1-yl)methyl)phenyl)boronic acid (2.5 g) as a brown solid. δH (DMSO-d$_6$, 600 MHz): 1.02 (2H, m), 2.81 (2H, m), 3.70 (4H, m), 4.23 (4H, m), 4.33 (2H, m), 7.00 (2H, m), 7.43 (1H, m), 9.93 (1H, m).

Stage 7

1-(3-(5-(3-chloro-4-isopropoxyphenyl)-1,3,4-thiadiazol-2-yl)-2-ethylbenzyl)-3-(methoxycarbonyl)azetidin-1-ium chloride To a solution of [2-ethyl-3-({3-[(methyloxy)carbonyl]-1-azetidinyl}methyl)phenyl]boronic acid (2.2 g, 7.94 mmol)) in 1,4-dioxane (18 mL) and water (6 mL) were added 2-bromo-5-{3-chloro-4-[(1-methylethyl)oxy]phenyl}-1,3,4-thiadiazole (3.18 g, 9.53 mmol), Pd$_2$(dba)$_3$ (0.582 g, 0.635 mmol), potassium carbonate (3.29 g, 23.82 mmol) and X-Phos (0.454 g, 0.953 mmol). The mixture was heated to 90° C. and stirred for 7 hours 11 mins. LCMS showed that the boronic acid was almost consumed completely. The heating was stopped and the solution was cooled to rt. The solution was filtered with celite and washed with EtOAc. The filtrate was concentrated under the reduced pressure. The residue was dissolved in EtOAc (50 mL) then washed with NaOH (30 mL, 1.0 M), organic phase was concentrated under reduced pressure. 50 mL TBME and 50 mL HCl (1.0 M) were added to the above residue and the obtained mixture was stirred at rt for 30 min. The yellow solid was collected by filtering. The yellow solid was stirred in TBME (50 mL) for 30 min at rt. 1-(3-(5-(3-chloro-4-isopropoxyphenyl)-1,3,4-thiadiazol-2-yl)-2-ethylbenzyl)-3-(methoxycarbonyl)azetidin-1-ium chloride (1.06 g) was collected by filtering and drying in vacuum as grey solid. δH (DMSO-d$_6$, 600 MHz): 1.09 (3H, t), 1.33 (6H, m), 2.92 (2H, m), 3.72 (3H, m), 4.31 (4H, m), 4.58 (1H, m), 4.64 (1H, d), 4.84 (1H, dt), 7.39 (1H, m), 7.47 (1H, t,) 7.66 (1H, d), 7.72 (1H, d), 7.97 (1H, d), 8.10 (1H, s), 10.92 (1H, dd), 11.16 (1H, m).

Stage 8

1-(3-(5-(3-chloro-4-isopropoxyphenyl)-1,3,4-thiadiazol-2-yl)-2-ethylbenzyl)azetidine-3-carboxylic acid To a solution of methyl 1-{[3-(5-{3-chloro-4-[(1-methylethyl)oxy]phenyl}-1,3,4-thiadiazol-2-yl)-2-ethylphenyl]methyl}-3-azetidinecarboxylate (2.78 g, 5.32 mmol) in Isopropanol (20.00 mL) and Water (10 mL) was added sodium hydroxide (0.638 g, 15.96 mmol). The mixture was stirred at rt for 51 mins. Stirring was stopped and the solution was concentrated under the reduced pressure. The residue was adjusted to pH value around 6 with HCl (1.0 M) solution, 1-(3-(5-(3-chloro-4-isopropoxyphenyl)-1,3,4-thiadiazol-2-yl)-2-ethylbenzyl)azetidine-3-carboxylic acid (2.33 g) was collected by filtering and dried in vacuum as yellow solid.

δH (DMSO-d$_6$, 400 MHz): 1.10 (3H, t), 1.34 (6H, d), 2.85 (2H, q), 3.20 (3H, m) 3.42 (3H, m), 3.66 (2H, s), 4.83 (1H, dt), 7.34 (2H, m), 7.49 (2H, m), 7.94 (1H, dd), 8.08 (1H, d).

Stage 9

3-carboxy-1-(3-(5-(3-chloro-4-isopropoxyphenyl)-1,3,4-thiadiazol-2-yl)-2-ethylbenzyl)azetidin-1-ium chloride To a solution of 1-{[3-(5-{3-chloro-4-[(1-methylethyl)oxy]phenyl}-1,3,4-thiadiazol-2-yl)-2-ethylphenyl]methyl}-3-azetidinecarboxylic acid (18.95 g) in THF (700 mL), water (190 mL) and acetonitrile (50 mL) was added methanolic hydrogen chloride (44.2 mL, 1.0 M). A clear solution was obtained and stirred for 30 min at rt. The solution was concentrated under the reduced pressure then dried in vacuum at 50° C. to give 3-carboxy-1-(3-(5-(3-chloro-4-isopropoxyphenyl)-1,3,4-thiadiazol-2-yl)-2-ethylbenzyl)azetidin-1-ium chloride (Example 4C, 20.3 g) as white solid. δH (DMSO-d$_6$, 400 MHz): 1.09 (3H, t), 1.35 (6H, d), 2.92 (2H, q), 3.68 (1H, m), 4.26 (4H, m), 4.59 (2H, br. s.), 4.84 (1H, dt), 7.38 (1H, d), 7.47 (1H, m), 7.65 (1H, d), 7.73 (1H, br. s.), 7.96 (1H, dd), 8.10 (1H, d), 11.33 (1H, br. s.), 13.13 (1H, br. s.).

Stage 10

Recrystallization of Example 4C

To a 1 L round bottom flask was added 3-carboxy-1-(3-(5-(3-chloro-4-isopropoxyphenyl)-1,3,4-thiadiazol-2-yl)-2-ethylbenzyl)azetidin-1-ium chloride (20.3 g). After addition of isopropanol (200 mL) and water (60 mL), the obtained suspension was heated to reflux and stirred for 10 min. 10 ml water was added to above suspension and obtained mixture was stirred for 10 min at reflux. 10 mL water was added to above suspension and obtained mixture was stirred for 10 min at reflux. A clear solution was obtained. Heating was stopped and the solution was cooled to rt then cooled to 5° C. and stirred for 30 min. Example 4C (17.74 g) was collected by filtering and dried in vacuum at 45° C. as a white solid (Form A).

δH (DMSO-d$_6$, 600 MHz): 1.09 (3H, t), 1.35 (6H, d), 2.91 (2H, q), 3.64 (1H, m), 4.22 (3H, m), 4.54 (2H, m), 4.84 (1H, dt), 7.39 (1H, d), 7.46 (1H, t), 7.67 (2H, m), 7.97 (1H, dd), 8.10 (1H, d), 10.87 (1H, s), 13.12 (1H, s),

Crystal Forms of Example 4C

Crystallisation experiments were conducted using the following three crystallisation modes:

temperature-cycling of slurries between 5-40° C. for 48 hr cooling solutions from 25° C. to 4° C. (24 hr), then to −15° C. (6 hr)

solvent evaporation

| | XRPD Peak positions (2 theta) | | | Onset (degrees C.) | Onset (degrees C.) | Production mode and solvents |
|---|---|---|---|---|---|---|
| Form A | 3.9 | 8.1 | 16.4 | 181.2 | | see Example 4C |
| Form B | 4.0 | 8.1 | 16.4 | 163.1 | 174.2 | temperature cycling in water |
| Form C | 4.0 | 8.0 | 16.5 | 183.9 | | temperature cycling in THF/5% water or THF/10% water, or evaporation crystallisation from IPA/20% water |
| Form D | 4.0 | 8.0 | | 167.4 | | cooling crystallisation in acetonitrile/10% water, THF/10% water, dioxane/10% water, IPA/10% water, acetone/20% water or IPA/20% water |
| Form E | 4.0 | 8.0 | | 167.9 | 174.5 | cooling crystallisation in methanol/10% water |
| Other | 4.0 | 8.0 | 21.8 | 22.6 | 165.9 | 183.1 evaporation crystallisations |

EXAMPLE 4D

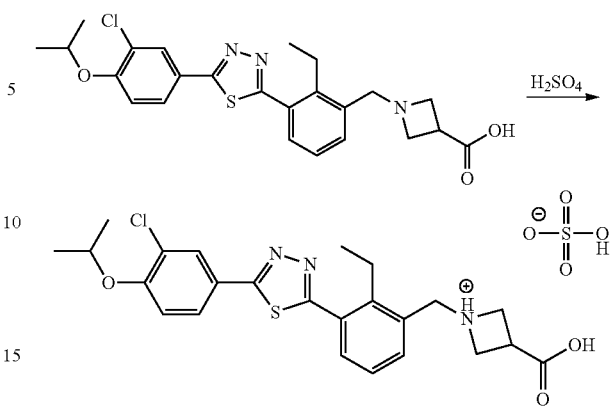

3-carboxy-1-(3-(5-(3-chloro-4-isopropoxyphenyl)-1,3,4-thiadiazol-2-yl)-2-ethylbenzyl)azetidin-1-ium hydrogensulfate To a solution of 1-(3-(5-(3-chloro-4-isopropoxyphenyl)-1,3,4-thiadiazol-2-yl)-2-ethylbenzyl)azetidine-3-carboxylic acid (100 mg, 0.212 mmol) in THF (2 mL) was added H$_2$SO$_4$ (0.286 mL, 4%, aq. solution). The mixture became clear and stirred for 30 min at rt. The solution was concentrated under the reduced pressure and dried in vacuum to give 3-carboxy-1-(3-(5-(3-chloro-4-isopropoxyphenyl)-1,3,4-thiadiazol-2-yl)-2-ethylbenzyl)azetidin-1-ium hydrogensulfate (123 mg) as pale yellow crystalline solid.

δH (DMSO-d$_6$, 600 MHz): 1.08 (2H, t), 1.35 (6H, d), 2.90 (2H, m), 3.67 (1H, m), 4.33 (5H, m), 4.61 (2H, m), 4.84 (1H, m), 7.39 (2H, d), 7.49 (2H, td), 7.67 (1H, t), 7.97 (1H, m), 8.10 (1H, d), 10.2 (1H, br. s), 13.2 (1H, br. s).

EXAMPLE 4E

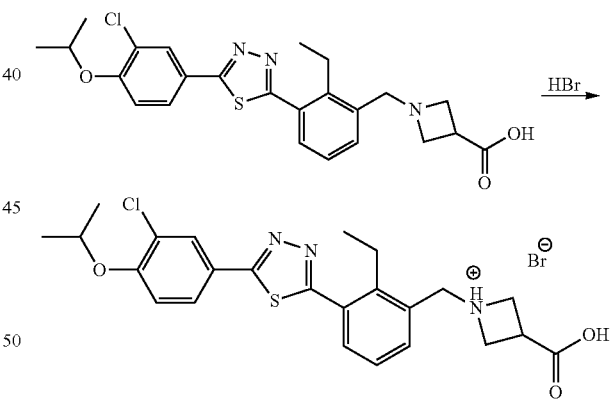

3-carboxy-1-(3-(5-(3-chloro-4-isopropoxyphenyl)-1,3,4-thiadiazol-2-yl)-2-ethylbenzyl)azetidin-1-ium bromide 1-{[3-(5-{3-chloro-4-[(1-methylethyl)oxy]phenyl}-1,3,4-thiadiazol-2-yl)-2-ethylphenyl]methyl}-3-azetidinecarboxylic acid (50 mg, 0.106 mmol) was added to a mixture of THF (2 mL), water (0.6 mL) and ACN (1 mL), a suspension was obtained to which was added HBr solution (0.016 mL, 40%, wt). A clear solution was obtained and stirred for 30 min at rt. Solvent was removed under the reduced pressure and dried in vacuum to give 3-carboxy-1-(3-(5-(3-chloro-4-isopropoxyphenyl)-1,3,4-thiadiazol-2-yl)-2-ethylbenzyl)azetidin-1-ium bromide (56 mg) as pale yellow solid. δH (DMSO-d$_6$, 600 MHz): 1.08 (3H, t), 1.35 (6H, m), 2.92 (2H, m), 3.67 (1H, m), 4.34 (4H, m), 4.61 (2H, m), 4.85 (1H, dt), 7.39 (1H, d), 7.48 (1H, m), 7.64 (2H, m), 7.97 (1H, d), 8.10 (1H, d), 10.25 (1H, s), 13.17 (1H, d).

EXAMPLE 4F

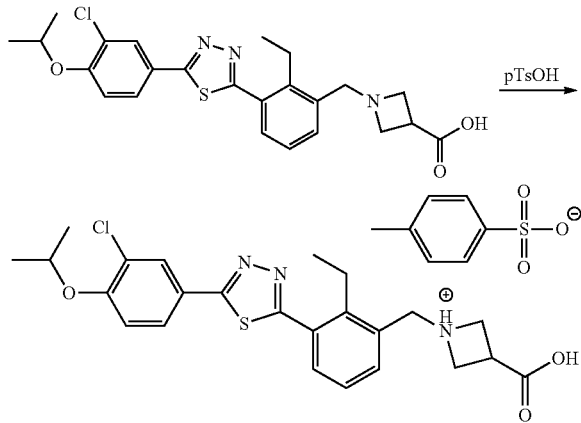

3-carboxy-1-(3-(5-(3-chloro-4-isopropoxyphenyl)-1, 3,4-thiadiazol-2-yl)-2-ethylbenzyl)azetidin-1-ium 4-methylbenzenesulfonate 1-{[3-(5-{3-chloro-4-[(1-methylethyl)oxy]phenyl}-1,3,4-thiadiazol-2-yl)-2-ethylphenyl]methyl}-3-azetidinecarboxylic acid (50 mg, 0.106 mmol) was added to a mixture of THF (1 mL), water (0.6 mL) and ACN (2 mL), a suspension was obtained to which was added p-TsOH.H$_2$O (24.26 mg, 0.117 mmol). A solution was obtained and stirred for 30 min at rt. Solvent was removed under the reduced pressure and dried in vacuum to give 3-carboxy-1-(3-(5-(3-chloro-4-isopropoxyphenyl)-1,3,4-thiadiazol-2-yl)-2-ethylbenzyl)azetidin-1-ium 4-methylbenzenesulfonate (65 mg) as pale yellow oil.

δH (DMSO-d$_6$, 600 MHz): 1.08 (4H, m), 1.34 (6H, m), 2.28 (3H, s), 2.91 (2H, m), 3.67 (1H, m), 4.34 (4H, m), 4.60 (2H, m), 4.85 (1H, m), 7.10 (2H, m), 7.39 (1H, d), 7.46 (3H, d), 7.62 (2H, m), 7.97 (1H, d), 8.10 (1H, s), 10.2 (1H, br. s.), 13.2 (1 H, br. s.).

EXAMPLE 5

1-{2-[3-(5-{3-chloro-4-[(1-methylethyl)oxy]phenyl}-1,3,4-thiadiazol-2-yl)-2-ethylphenyl]ethyl}-4-piperidinecarboxylic acid trifluoroacetate (E5)

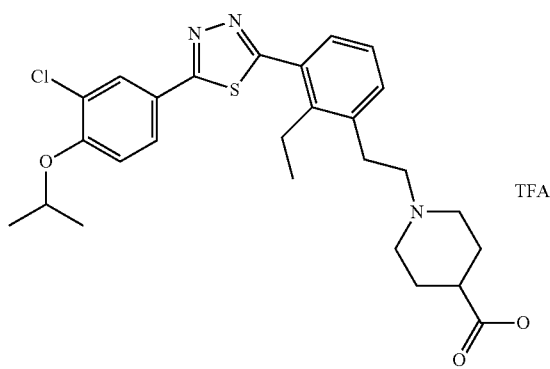 [SMILES: CCc1c(CCN2CCC(C(=O)O)CC2)cccc1-c1nnc(-c2ccc(OC(C)C)c(Cl)c2)s1]

To a solution of ethyl 1-{2-[3-(5-{3-chloro-4-[(1-methylethyl)oxy]phenyl}-1,3,4-thiadiazol-2-yl)-2-ethylphenyl]ethyl}-4-piperidinecarboxylate (D16) (95 mg)) in isopropanol (2 mL) and water (2 mL) at room temperature was added sodium hydroxide (50 mg). The reaction mixture was stirred at room temperature for 2 h. The reaction mixture was neutralized with 1 M HCl solution. The solvent was removed in vacuo. The residue was dissolved in THF, and filtered. The filtrate was purified by Mass Directed AutoPrep to give 1-{2-[3-(5-{3-chloro-4-[(1-methylethyl)oxy]phenyl}-1,3,4-thiadiazol-2-yl)-2-ethylphenyl]ethyl}-4-piperidinecarboxylic acid (E5) (23 mg) as a TFA salt (off-white solid). δH (DMSO-d$_6$, 400 MHz): 1.14 (3H, t), 1.35 (6H, d), 1.78 (2H, m), 2.13 (2H, m), 2.61 (1H, m), 2.86 (2H, m), 3.11 (4H, m), 3.28 (2H, m), 3.59 (2H, m), 4.84 (1H, m), 7.39 (2H, m), 7.51 (2H, m), 7.96 (1H, dd), 8.10 (1H, d), 9.49 (1H, br s), 12.47 (1H, br s). δF (DMSO-d$_6$, 376 MHz): −73.4. MS (ES): C$_{27}$H$_{32}$ClN$_3$O$_3$S requires 513. found 514.2 (M+H$^+$).

EXAMPLE 6

1-{2-[3-(5-{3-chloro-4-[(1-methylethyl)oxy]phenyl}-1,3,4-thiadiazol-2-yl)-2-ethylphenyl]ethyl}-3-azetidinecarboxylic acid trifluoroacetate (E6)

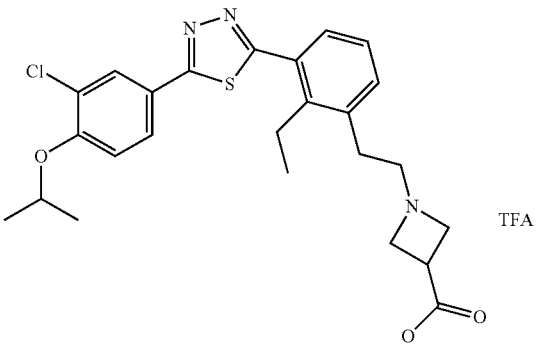 [SMILES: CCc1c(CCN2CC(C(=O)O)C2)cccc1-c1nnc(-c2ccc(OC(C)C)c(Cl)c2)s1]

To a solution of methyl 1-{2-[3-(5-{3-chloro-4-[(1-methylethyl)oxy]phenyl}-1,3,4-thiadiazol-2-yl)-2-ethylphenyl]ethyl}-3-azetidinecarboxylatein (D17) (20 mg) in isopropanol (2 mL) and water (2 mL) at room temperature was added sodium hydroxide (50 mg). The reaction mixture was stirred at room temperature for 2 h. The reaction mixture was neutralized with 1 M HCl solution. The solvent was removed in vacuo. The residue was dissolved in THF, and filtered. The filtrate was purified by Mass Directed AutoPrep to give 1-{2-[3-(5-{3-chloro-4-[(1-methylethyl)oxy]phenyl}-1,3,4-thiadiazol-2-yl)-2-ethylphenyl]ethyl}-3-azetidinecarboxylic acid (E6) (10 mg) as a TFA salt (off-white solid). δH (DMSO-d$_6$, 400 MHz): 1.11 (3H, t), 1.35 (6H, d), 2.88 (4H, m), 3.63 (3H, m), 4.29 (4H, m), 4.84 (1H, m), 7.39 (2H, m), 7.51 (2H, m), 7.96 (1H, dd), 8.09 (1H, d), 10.07 (1H, br s), 13.16 (1H, br s). δF (DMSO-d$_6$, 376 MHz): −73.7. MS (ES): C$_{25}$H$_{28}$ClN$_3$O$_3$S requires 485. found 486.2 (M+H$^+$).

EXAMPLE 7

1-[2-(2-ethyl-3-{5-[4-[(1-methylethyl)oxy]-3-(trifluoromethyl)phenyl]-1,3,4-thiadiazol-2-yl}phenyl)ethyl]-3-azetidinecarboxylic acid trifluoroacetate (E7)

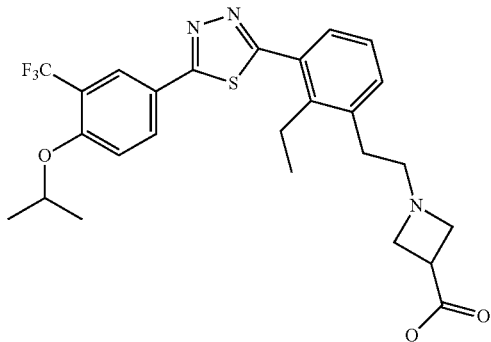

To a solution of methyl 1-[2-(2-ethyl-3-{5-[4-[(1-methylethyl)oxy]-3-(trifluoromethyl)phenyl]-1,3,4-thiadiazol-2-yl}phenyl)ethyl]-3-azetidinecarboxylate (D20) (25 mg) in isopropanol (2 mL) and water (2 mL) at room temperature was added sodium hydroxide (1.874 mg). The reaction mixture was stirred at room temperature for 2 h. The reaction mixture was neutralized with 1 M HCl solution. The solvent was removed in vacuo. The residue was dissolved in THF, and filtered. The filtrate was purified by Mass Directed AutoPrep to give 1-[2-(2-ethyl-3-{5-[4-[(1-methylethyl)oxy]-3-(trifluoromethyl)phenyl]-1,3,4-thiadiazol-2-yl}phenyl)ethyl]-3-azetidinecarboxylic acid (E7) (10 mg) as a TFA salt (off-white solid). δH (DMSO-$d_6$, 400 MHz): 1.11 (3H, t), 1.34 (6H, d), 2.88 (4H, m), 3.43 (2H, m), 3.62 (1H, m), 4.29 (4H, m), 4.94 (1H, m), 7.39 (1H, t), 7.51 (3H, m), 8.24 (2H, m), 10.08 (1H, br s), 13.13 (1H, br s). δF (DMSO-$d_6$, 376 MHz): −73.4, −61.3. MS (ES): $C_{26}H_{28}F_3N_3O_3S$ requires 519. found 520.2 (M+H$^+$).

EXAMPLE 8

1-[(3-{5-[3-cyano-4-(2-methylpropyl)phenyl]-1,3,4-thiadiazol-2-yl}-2-ethylphenyl)methyl]-4-piperidinecarboxylic acid trifluoroacetate (E8)

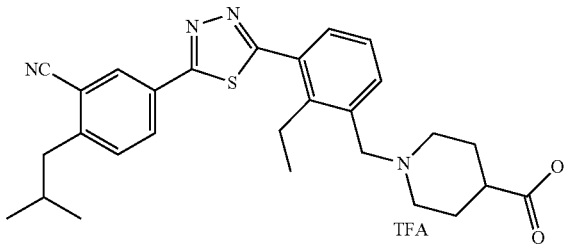 [SMILES: CCc1c(CN2CCC(C(=O)O)CC2)cccc1-c1nnc(-c2ccc(CC(C)C)c(C#N)c2)s1]

To a solution of ethyl 1-[(3-{5-[3-cyano-4-(2-methylpropyl)phenyl]-1,3,4-thiadiazol-2-yl}-2-ethylphenyl)methyl]-4-piperidinecarboxylate (D28) (38 mg) in isopropanol (3 mL) and water (3 mL) was added sodium hydroxide (50 mg). The reaction mixture was stirred at room temperature for 1 h. The reaction mixture was neutralized with 1 M HCl solution. The solvent was removed in vacuo. The residue was dissolved in THF, and filtered. The filtrate was purified by Mass Directed AutoPrep to give 1-[(3-{5-[3-cyano-4-(2-methylpropyl)phenyl]-1,3,4-thiadiazol-2-yl}-2-ethylphenyl)methyl]-4-piperidinecarboxylic acid (E8) (16 mg) as a TFA salt (off-white solid). δH (DMSO-$d_6$, 400 MHz): 0.93 (6H, d), 1.07 (3H, t), 1.78 (1H, m), 2.00 (2H, m), 2.06 (2H, m), 2.78 (2H, d), 2.95 (2H, m), 3.20 (3H, m), 3.48 (2H, m), 4.46 (2H, m), 7.54 (1H, t), 7.69 (2H, m), 7.75 (1H, m), 8.32 (1H, dd), 8.47 (1H, d), 9.17 (1H, br s), 12.57 (1H, br s). δF (DMSO-$d_6$, 376 MHz): −73.6. MS (ES): $C_{28}H_{32}N_4O_2S$ requires 488. found 489.2 (M+H$^+$).

EXAMPLE 9

1-[(3-{5-[3-cyano-4-(2-methylpropyl)phenyl]-1,3,4-thiadiazol-2-yl}-2-ethylphenyl)methyl]-3-azetidinecarboxylic acid trifluoroacetate (E9)

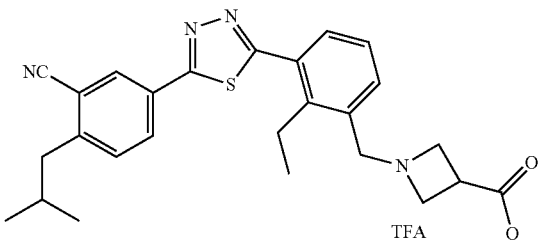 [SMILES: CCc1c(CN2CC(C(=O)O)C2)cccc1-c1nnc(-c2ccc(CC(C)C)c(C#N)c2)s1]

To a solution of methyl 1-[(3-{5-[3-cyano-4-(2-methylpropyl)phenyl]-1,3,4-thiadiazol-2-yl}-2-ethylphenyl)methyl]-3-azetidinecarboxylate (D29) (39 mg) in isopropanol (3 mL) and water (3 mL) was added sodium hydroxide (50 mg). The reaction mixture was stirred at room temperature for 2 h. The reaction mixture was neutralized with 1 M HCl solution. The solvent was removed in vacuo. The residue was dissolved in THF, and filtered. The filtrate was purified by Mass Directed AutoPrep to give 1-[(3-{5-[3-cyano-4-(2-methylpropyl)phenyl]-1,3,4-thiadiazol-2-yl}-2-ethylphenyl)methyl]-3-azetidinecarboxylic acid (E9) (12 mg) as a TFA salt (off-white solid). δH (DMSO-$d_6$, 400 MHz): 1.11 (3H, t), 1.34 (6H, d), 1.93 (1H, m), 2.71 (2H, m), 2.84 (2H, m), 3.55 (1H, m), 4.25 (4H, m), 4.50 (2H, m), 7.42 (1H, m), 7.58 (3H, m), 8.25 (1H, dd), 8.40 (1H, d), 10.12 (1H, br s), 13.10 (1H, br s). δF (DMSO-$d_6$, 376 MHz): −73.4. MS (ES): $C_{26}H_{28}N_4O_2S$ requires 460. found 461.2 (M+H$^+$).

EXAMPLE 10

1-[2-(3-{5-[3-cyano-4-(2-methylpropyl)phenyl]-1,3,4-thiadiazol-2-yl}-2-ethylphenyl)ethyl]-3-azetidinecarboxylic acid (E10)

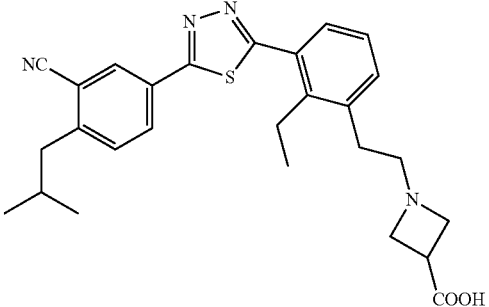 [SMILES: CCc1c(CCN2CC(C(=O)O)C2)cccc1-c1nnc(-c2ccc(CC(C)C)c(C#N)c2)s1]

To a solution of methyl 1-[2-(3-{5-[3-cyano-4-(2-methylpropyl)phenyl]-1,3,4-thiadiazol-2-yl}-2-ethylphenyl)ethyl]-3-azetidinecarboxylate (D32) (59 mg) in isopropanol (3 mL) and water (3 mL) was added sodium hydroxide (50 mg). The reaction mixture was stirred at room temperature for 1 h. The reaction mixture was neutralized with 1 M HCl solution. The solvent was removed in vacuo. The residue was dissolved in THF, and filtered. The filtrate was purified by Mass Directed AutoPrep to give 1-[2-(3-{5-[3-cyano-4-(2-methylpropyl)phenyl]-1,3,4-thiadiazol-2-yl}-2-ethylphenyl)ethyl]-3-azetidinecarboxylic acid (E10) (17 mg) as an off-white solid. δH (DMSO-$d_6$, 400 MHz): 0.93 (6H, d), 1.11 (3H, t), 1.99 (1H, m), 2.85 (6H, m), 3.38 (2H, m), 3.61 (1H, m), 4.27 (4H, m), 7.40 (1H, m), 7.51 (2H, t), 7.68 (1H, d), 8.31 (1H, dd), 8.46 (1H, d), 13.04 (1H, br s). MS (ES): $C_{27}H_{30}N_4O_2S$ requires 474. found 475.2 (M+H$^+$).

EXAMPLE 11

1-[2-(3-{5-[3-cyano-4-(2-methylpropyl)phenyl]-1,3,4-thiadiazol-2-yl}-2-ethylphenyl)ethyl]-4-piperidinecarboxylic acid (E11)

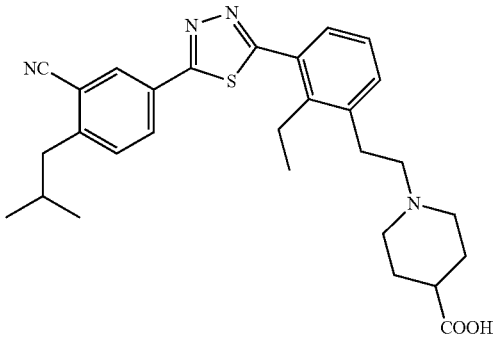 [SMILES: CCc1c(CCN2CCC(C(=O)O)CC2)cccc1-c1nnc(-c2ccc(CC(C)C)c(C#N)c2)s1]

To a solution of ethyl 1-[2-(3-{5-[3-cyano-4-(2-methylpropyl)phenyl]-1,3,4-thiadiazol-2-yl}-2-ethylphenyl)ethyl]-4-piperidinecarboxylate (D33) (64 mg) in isopropanol (3 mL) and water (3 mL) was added sodium hydroxide (50 mg). The reaction mixture was stirred at room temperature for 1 h. The reaction mixture was neutralized with 1 M HCl solution. The solvent was removed in vacuo. The residue was dissolved in THF, and filtered. The filtrate was purified by Mass Directed AutoPrep to give 1-[2-(3-{5-[3-cyano-4-(2-methylpropyl)phenyl]-1,3,4-thiadiazol-2-yl}-2-ethylphenyl)ethyl]-4-piperidinecarboxylic acid (E11) (15 mg) as an off-white solid. δH (DMSO-d$_6$, 400 MHz): 0.93 (6H, d), 1.12 (3H, t), 1.57 (2H, m), 1.79 (2H, m), 2.03 (3H, m), 2.20 (1H, m), 2.81 (8H, m), 3.25 (2H, m), 7.32 (1H, t), 7.44 (2H, d), 7.67 (1H, d), 8.31 (1H, dd), 8.45 (1H, s), 12.06 (1H, br s). MS (ES): $C_{29}H_{34}N_4O_2S$ requires 502. found 503.2 (M+H$^+$).

EXAMPLE 12

1-{2-[3-(5-{3-chloro-4-[(1-methylethyl)oxy]phenyl}-1,3,4-thiadiazol-2-yl)-2-ethylphenyl]ethyl}-3-pyrrolidinecarboxylic acid trifluoroacetate (E12)

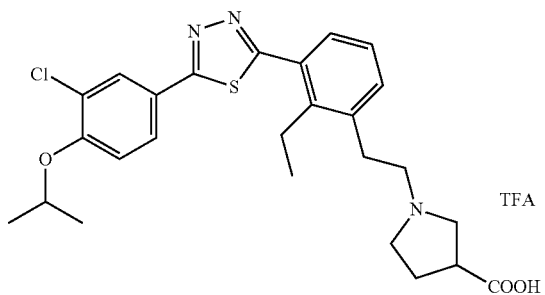 [SMILES: CCc1c(CCN2CCC(C(=O)O)C2)cccc1-c1nnc(-c2ccc(OC(C)C)c(Cl)c2)s1]

To a solution of [3-(5-{3-chloro-4-[(1-methylethyl)oxy]phenyl}-1,3,4-thiadiazol-2-yl)-2-ethylphenyl]acetaldehyde (D15) (73 mg) and 3-pyrrolidinecarboxylic acid (72.4 mg) in dichloromethane (DCM) (10 mL) stirred at room temperature was added AcOH (0.15 mL). The reaction mixture was stirred at room temperature for 10 min. Then sodium triacetoxyborohydride (66.6 mg) was added. Stirring continued for overnight. Water was added to quench the reaction, and DCM was removed by evaporation. The mixture was extracted by EA for 3 times. The combined organic solution was washed by brine, dried over anhydrous Na$_2$SO$_4$. The dried solution was filtered and concentrated, the residue was purified by Mass Directed AutoPrep to give 1-{2-[3-(5-{3-chloro-4-[(1-methylethyl)oxy]phenyl}-1,3,4-thiadiazol-2-yl)-2-ethylphenyl]ethyl}-3-pyrrolidinecarboxylic acid (E12) (27 mg) as a TFA salt (off-white solid). δH (DMSO-d$_6$, 400 MHz): 1.13 (3H, t), 1.35 (6H, d), 2.23 (1H, m), 2.86 (2H, m), 3.10 (2H, m), 3.22 (2H, m), 3.48 (4H, m), 3.72 (1H, m), 3.87 (1H, m), 4.84 (1H, m), 7.39 (2H, dd), 7.50 (2H, m), 7.96 (1H, dd), 8.10 (1H, d), 9.95 (1H, br s), 12.97 (1H, br s). δF (DMSO-d$_6$, 376 MHz): −73.5. MS (ES): $C_{26}H_{30}ClN_3O_3S$ requires 499. found 500.1 (M+H$^+$).

EXAMPLE 13

1-{2-[5-fluoro-3-{5-[4-[(1-methylethyl)oxy]-3-(trifluoromethyl)phenyl]-1,3,4-thiadiazol-2-yl}-2-(methyloxy)phenyl]ethyl}-4-piperidinecarboxylic acid (E13)

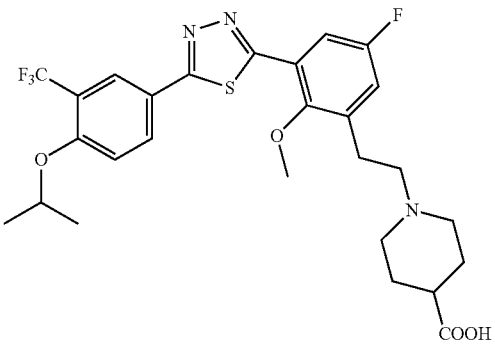 [SMILES: COc1c(CCN2CCC(C(=O)O)CC2)cc(F)cc1-c1nnc(-c2ccc(OC(C)C)c(C(F)(F)F)c2)s1]

To a solution of [5-fluoro-3-{5-[4-[(1-methylethyl)oxy]-3-(trifluoromethyl)phenyl]-1,3,4-thiadiazol-2-yl}-2-(methyloxy)phenyl]acetaldehyde (D35) (80 mg) and ethyl 4-piperidinecarboxylate (138 mg) in dichloromethane (DCM) (15 mL) stirred at room temperature was added AcOH (0.15 mL). The reaction mixture was stirred at room temperature for 10 min. Then sodium triacetoxyborohydride (74.6 mg) was added. Stirring continued for overnight. Water was added to quench the reaction, and DCM was removed by evaporation. The mixture was extracted by EA for 3 times. The combined organic solution was washed by brine, dried over anhydrous Na$_2$SO$_4$. The dried solution was filtered and concentrated. The residue was dissolved in isopropanol (10 mL) and water (10 mL), sodium hydroxide (50 mg) was added. Stirring continued for 2 h at room temperature. 1M HCl solution was added until PH=6~7. Then iPrOH was removed by evaporation. The aqueous layer was extracted by EA/THF/MeCN for 3 times. The combined organic layers were concentrated, and purified by Mass Directed AutoPrep to give 1-{2-[5-fluoro-3-{5-[4-[(1-methylethyl)oxy]-3-(trifluoromethyl)phenyl]-1,3,4-thiadiazol-2-yl}-2-(methyloxy)phenyl]ethyl}-4-piperidinecarboxylic acid (E13) (45 mg) as an off-white solid. δH (DMSO-d$_6$, 400 MHz): 1.34 (6H, d), 1.57 (2H, m), 1.79 (2H, d), 2.06 (2H, t), 2.19 (1H, m), 2.58 (2H, t), 2.87 (4H, t), 3.80 (3H, s), 4.94 (1H, m), 7.45 (1H, dd), 7.51 (1H, d), 7.88 (1H, dd), 8.23 (1H, d), 8.29 (1H, dd). δF (DMSO-d$_6$, 376 MHz): −117.4, −61.3. MS (ES): $C_{27}H_{29}F_4N_3O_4S$ requires 567. found 568.2 (M+H$^+$).

EXAMPLE 14

1-{2-[5-fluoro-3-{5-[4-[(1-methylethyl)oxy]-3-(trifluoromethyl)phenyl]-1,3,4-thiadiazol-2-yl}-2-(methyloxy)phenyl]ethyl}-3-azetidinecarboxylic acid (E14)

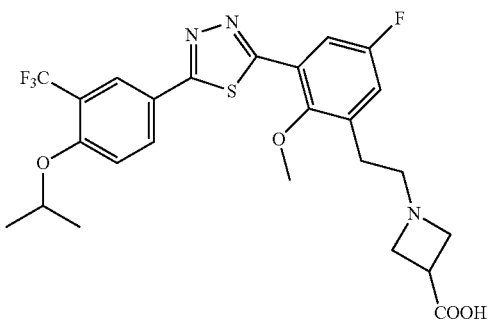 [SMILES: COc1c(CCN2CC(C(=O)O)C2)cc(F)cc1-c1nnc(-c2ccc(OC(C)C)c(C(F)(F)F)c2)s1]

To a solution of [5-fluoro-3-{5-[4-[(1-methylethyl)oxy]-3-(trifluoromethyl)phenyl]-1,3,4-thiadiazol-2-yl}-2-(methyloxy)phenyl]acetaldehyde (D35) (90 mg) and 3-azetidinecarboxylic acid (80 mg) in dichloromethane (DCM) (20 mL) stirred at room temperature was added AcOH (0.15 mL). The reaction mixture was stirred at room temperature for 10 min. Then sodium triacetoxyborohydride (84 mg) was added. Stirring continued for overnight. Water was added to quench the reaction, and DCM was removed by evaporation. The mixture was extracted by EA/THF/MeCN for 3 times. The combined organic solution was washed by brine, dried over anhydrous $Na_2SO_4$. The dried solution was filtered and concentrated. The residue was purified by Mass Directed AutoPrep to give 1-{2-[5-fluoro-3-{5-[4-[(1-methylethyl)oxy]-3-(trifluoromethyl)phenyl]-1,3,4-thiadiazol-2-yl}-2-(methyloxy)phenyl]ethyl}-3-azetidinecarboxylic acid (E14) (45 mg) as an off-white solid. δH (DMSO-$d_6$, 400 MHz): 1.34 (6H, d), 2.69 (4H, m), 3.17 (3H, m), 3.41 (2H, m), 3.79 (3H, s), 4.94 (1H, m), 7.43 (1H, dd), 7.52 (1H, d), 7.88 (1H, dd), 8.27 (2H, m). δF (DMSO-$d_6$, 376 MHz): −117.2, −61.3. MS (ES): $C_{25}H_{25}F_4N_3O_4S$ requires 539. found 540.1 (M+H$^+$).

EXAMPLE 15

1-{2-[3-{5-[3-cyano-4-(2-methylpropyl)phenyl]-1,3,4-thiadiazol-2-yl}-5-fluoro-2-(methyloxy)phenyl]ethyl}-3-azetidinecarboxylic acid (E15)

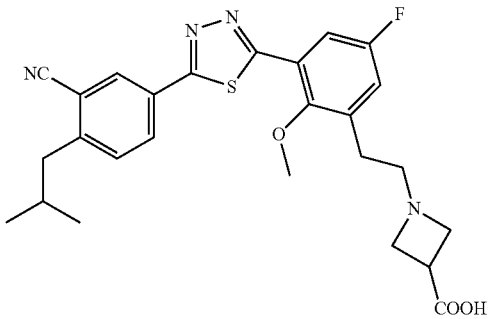 [SMILES: COc1c(CCN2CC(C(=O)O)C2)cc(F)cc1-c1nnc(-c2ccc(CC(C)C)c(C#N)c2)s1]

To a solution of 5-{5-[5-fluoro-2-(methyloxy)-3-(2-oxoethyl)phenyl]-1,3,4-thiadiazol-2-yl}-2-(2-methylpropyl)benzonitrile (D37) (75 mg) and 3-azetidinecarboxylic acid (37 mg) in dichloromethane (DCM) (15 mL) stirred at room temperature was added AcOH (0.15 mL). The reaction mixture was stirred at room temperature for 10 min. Then sodium triacetoxyborohydride (58.2 mg) was added. Stirring continued for overnight. Water was added to quench the reaction, and DCM was removed by evaporation. The mixture was extracted by EA/THF/MeCN for 3 times. The combined organic solution was washed by brine, dried over anhydrous $Na_2SO_4$. The dried solution was filtered and concentrated. The residue was purified by Mass Directed AutoPrep to give 1-{2-[3-{5-[3-cyano-4-(2-methylpropyl)phenyl]-1,3,4-thiadiazol-2-yl}-5-fluoro-2-(methyloxy)phenyl]ethyl}-3-azetidinecarboxylic acid (E15) (19 mg) as an off-white solid. δH (DMSO-$d_6$, 400 MHz): 0.94 (6H, d), 1.99 (1H, m), 2.33 (1H, m), 2.67 (4H, m), 2.77 (2H, d), 3.17 (4H, m), 3.80 (3H, s), 7.47 (1H, dd), 7.68 (1H, d), 7.90 (1H, dd), 8.34 (1H, dd), 8.50 (1H, d). δF (DMSO-$d_6$, 376 MHz): −117.2. MS (ES): $C_{26}H_{27}FN_4O_3S$ requires 494. found 495.2 (M+H$^+$).

EXAMPLE 16

1-{[3-(5-{3-cyano-4-[(1-methylethyl)oxy]phenyl}-1,2,4-thiadiazol-3-yl)-2-ethylphenyl]methyl}-4-piperidinecarboxylic acid trifluoroacetate (E16)

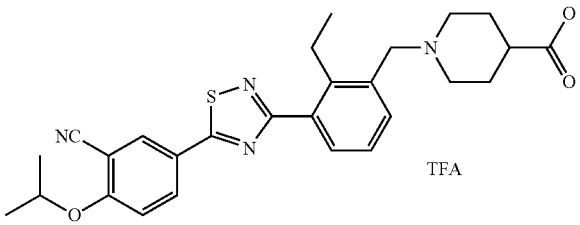 [SMILES: CCc1c(CN2CCC(C(=O)O)CC2)cccc1-c1nsc(-c2ccc(OC(C)C)c(C#N)c2)n1]

To a solution of 5-[3-(2-ethyl-3-formylphenyl)-1,2,4-thiadiazol-5-yl]-2-[(1-methylethyl)oxy]benzonitrile (D46) (100 mg) in dichloromethane (DCM) (5 mL) and methanol (5.00 mL) was added ethyl 4-piperidinecarboxylate (62.5 mg) and acetic acid (0.030 mL). The resulting solution was stirred at room temperature for overnight. Then sodium triacetoxyborohydride (112 mg) was added and the reaction solution was stirred at ambient temperature for another 2 h. The solvent was removed in vacuo and the residue was dissolved in ethyl acetate (50 mL), washed with water (10 mL), dried over sodium sulphate, concentrated to afford the ethyl ester. The ethyl ester was dissolved in isopropanol/water (1:1) 10 mL, 0.5 M NaOH (2.65 mL) was added, the resulting solution was heated to 90° C. for 2 h. Isopropanol was removed in vacuo and the residue was acidified to pH=5-6, extracted with ethyl acetate (2*20 mL). The combined organic phases were dried over sodium sulphate and concentrated, the residue was purified by Mass Directed AutoPrep to give 1-{[3-(5-{3-cyano-4-[(1-methylethyl)oxy]phenyl}-1,2,4-thiadiazol-3-yl)-2-ethylphenyl]methyl}-4-piperidinecarboxylic acid (E16) (41 mg) as a TFA salt (white solid). δH (DMSO-$d_6$, 400 MHz): 0.98 (3H, t), 1.32 (6H, d), 1.72 (2H, m), 2.02 (2H, m), 2.97 (2H, q), 3.11 (2H, m), 3.41 (3H, m), 4.42 (2H, m), 4.88 (1H, m), 7.43 (2H, m), 7.64 (1H, d), 7.86 (1H, d), 8.27 (1H, dd), 8.43 (1H, d), 9.18 (1H, s br), 12.52 (1H, br s). δF (DMSO-$d_6$, 376 MHz): −73.8. MS (ES): $C_{27}H_{30}N_4O_3S$ requires 490. found 491.2 (M+H$^+$).

EXAMPLE 17

1-{[3-(5-{3-cyano-4-[(1-methylethyl)oxy]phenyl}-1,2,4-thiadiazol-3-yl)-2-ethylphenyl]methyl}-3-azetidinecarboxylic acid trifluoroacetate (E17)

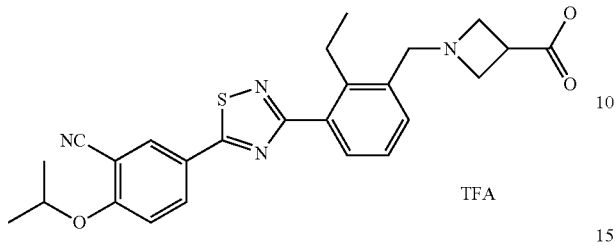

To a solution of 5-[3-(2-ethyl-3-formylphenyl)-1,2,4-thiadiazol-5-yl]-2-[(1-methylethyl)oxy]benzonitrile (D46) (110 mg) in dichloromethane (DCM) (5 mL) and methanol (5.00 mL) was added 3-azetidinecarboxylic acid (147 mg) and acetic acid (0.050 mL). The resulting solution was stirred at room temperature for overnight. Sodium triacetoxyborohydride (185 mg) was added and the reaction solution was stirred for 2 h. The solvent was removed in vacuo and the residue was purified by Mass Directed AutoPrep to give 1-{[3-(5-{3-cyano-4-[(1-methylethyl)oxy]phenyl}-1,2,4-thiadiazol-3-yl)-2-ethylphenyl]methyl}-3 azetidinecarboxylic acid (E17) (37 mg) as a TFA salt (white solid). δH (DMSO-$d_6$, 400 MHz): 1.03 (3H, t), 1.31 (6H, d), 2.93 (2H, q), 3.60 (1H, m), 4.22 (4H, m), 4.52 (2H, s), 4.89 (1H, m), 7.38 (1H, t), 7.42 (1H, d), 7.51 (1H, s br), 7.82 (1H, d), 8.27 (1H, dd), 8.42 (1H, d), 10.20 (1H, s br), 13.13 (1H, br s). δF (DMSO-$d_6$, 376 MHz): −73.7. MS (ES): $C_{26}H_{26}N_4O_3S$ requires 462. found 463.2 (M+H$^+$).

EXAMPLE 18

1-[(2-ethyl-3-{5-[4-[(1-methylethyl)oxy]-3-(trifluoromethyl)phenyl]-1,2,4-thiadiazol-3-yl}phenyl)methyl]-4-piperidinecarboxylic acid trifluoroacetate (E18)

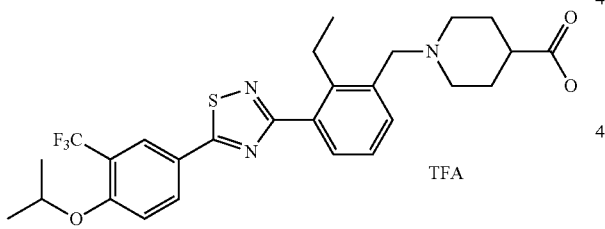

To a solution of 2-ethyl-3-{5-[4-[(1-methylethyl)oxy]-3-(trifluoromethyl)phenyl]-1,2,4-thiadiazol-3-yl}benzaldehyde (D47) (80 mg) in dichloromethane (DCM) (5 mL) and methanol (5.00 mL) was added ethyl 4-piperidinecarboxylate (90 mg) and acetic acid (0.022 mL). The reaction solution was stirred for overnight. Sodium triacetoxyborohydride (81 mg) was added and the resulting solution was stirred for another 2 h. The solvent was removed in vacuo and the residue was dissolved in ethyl acetate (50 mL), washed with water (2*10 mL), concentrated to afford the ester. The ester was added into isopropanol/water (1:1) (10 mL), followed by NaOH (1.903 mL). The reaction solution was heated to 90° C. for 2 h. Isopropanol was removed in vacuo and the residue was acidified to pH=3-4, extracted with ethyl acetate (2*20 mL). The combined organic phases were dried over sodium sulphate and concentrated, the residue was purified by Mass Directed AutoPrep to afford 1-[(2-ethyl-3-{5-[4-[(1-methylethyl)oxy]-3-(trifluoromethyl)phenyl]-1,2,4-thiadiazol-3-yl}phenyl)methyl]-4-piperidinecarboxylic acid (E18) (44 mg) as a TFA salt (white solid). δH (DMSO-$d_6$, 400 MHz): 1.02 (3H, t), 1.27 (6H, d), 2.00 (4H, m), 2.98 (2H, q), 3.12 (2H, m), 3.40 (3H, m), 4.39 (2H, m), 4.90 (1H, m), 7.45 (2H, m), 7.64 (1H, d), 7.85 (1H, d), 8.19 (1H, d), 8.27 (1H, dd), 9.17 (1H, s), 12.53 (1H, s). δF (DMSO-$d_6$, 376 MHz): −73.6, −61.5. MS (ES): $C_{27}H_{30}F_3N_3O_3S$ requires 533. found 534.3 (M+H$^+$).

EXAMPLE 19

1-[(2-ethyl-3-{5-[4-[(1-methylethyl)oxy]-3-(trifluoromethyl)phenyl]-1,2,4-thiadiazol-3-yl}phenyl)methyl]-3-azetidinecarboxylic acid (E19)

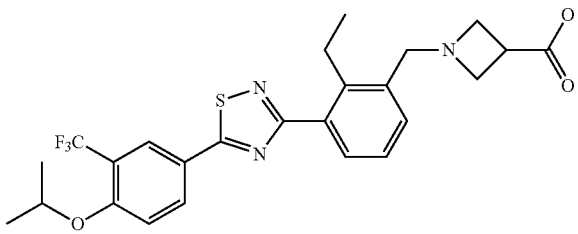 [SMILES: CCc1c(CN2CC(C(=O)O)C2)cccc1-c1nsc(-c2ccc(OC(C)C)c(C(F)(F)F)c2)n1]

To a solution of 2-ethyl-3-{5-[4-[(1-methylethyl)oxy]-3-(trifluoromethyl)phenyl]-1,2,4-thiadiazol-3-yl}benzaldehyde (D47) (100 mg) in dichloromethane (DCM) (5 mL) and methanol (5.00 mL) was added sodium acetate (39.0 mg) and hydrogen chloride-methyl 3-azetidinecarboxylate (1:1) (72.1 mg). The reaction solution was stirred at room temperature for overnight. Sodium triacetoxyborohydride (101 mg) was added and the resulting solution was stirred at ambient temperature for 2 h. The solvent was removed in vacuo and the residue was dissolved in isopropanol/water (1:1, 5 mL), sodium hydroxide (2.378 mL) was added and the resulting solution was heated to 90° C. for 2 h. Isopropanol was removed in vacuo and the residue was acidified to pH=3-4, extracted with ethyl acetate (2*20 mL), the combined organic phases were dried over sodium sulphate and concentrated, the residue was purified by Mass Directed AutoPrep to afford 1-[(2-ethyl-3-{5-[4-[(1-methylethyl)oxy]-3-(trifluoromethyl)phenyl]-1,2,4-thiadiazol-3-yl}phenyl)methyl]-3-azetidinecarboxylic acid (E19) (44 mg) as a white solid. δH (DMSO-$d_6$, 400 MHz): 1.06 (3H, t), 1.27 (6H, d), 2.87 (2H, q), 3.16 (4H, m), 3.34 (1H, m), 3.60 (2H, s), 4.89 (1H, m), 7.23 (1H, t), 7.38 (1H, dd), 7.45 (1H, d), 7.65 (1H, dd), 8.18 (1H, d), 8.25 (1H, dd). δF (DMSO-$d_6$, 376 MHz): −61.4. MS (ES): $C_{26}H_{26}F_3N_3O_3S$ requires 505. found 506.1 (M+H$^+$).

EXAMPLE 20

{1-[(2-ethyl-3-{5-[4-[(1-methylethyl)oxy]-3-(trifluoromethyl)phenyl]-1,2,4-thiadiazol-3-yl}phenyl)methyl]-4-piperidinyl}acetic acid (E20)

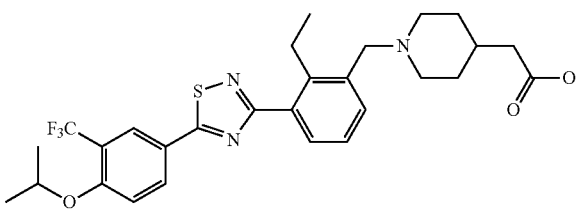 [SMILES: CCc1c(CN2CCC(CC(=O)O)CC2)cccc1-c1nsc(-c2ccc(OC(C)C)c(C(F)(F)F)c2)n1]

To a solution of 3-[3-(bromomethyl)-2-ethylphenyl]-5-[4-[(1-methylethyl)oxy]-3-(trifluoromethyl)phenyl]-1,2,4-thiadiazole (D48) (100 mg) in N,N-dimethylformamide (DMF) (5 mL) was added potassium carbonate (85 mg), hydrogen chloride-methyl 4-piperidinylacetate (1:1) (47.9 mg). The reaction solution was stirred at 60° C. for overnight. After cooling the reaction, the reaction mixture was diluted with ethyl acetate (50 mL), washed with water, dried over sodium sulphate, concentrated to afford the ester. The ester was added into isopropanol/water (1:1, 10 mL), followed by NaOH (2.060 mL), the reaction mixture was heated to 90° C. for 4 h. Isopropanol was removed in vacuo and the residue was acidified to pH=3-4, extracted with ethyl acetate (2*30 mL). The combined organic phases were dried over sodium sulphate, concentrated and the residue was purified by Mass Directed AutoPrep to afford {1-[(2-ethyl-3-{5-[4-[(1-methylethyl)oxy]-3-(trifluoromethyl)phenyl]-1,2,4-thiadiazol-3-yl}phenyl)methyl]-4-piperidinyl}acetic acid (E20) (50 mg) as a white solid. δH (DMSO-$d_6$, 400 MHz): 1.07 (5H, m), 1.27 (6H, d), 1.58 (3H, m), 1.92 (2H, m), 2.06 (2H, m), 2.73 (2H, m), 2.91 (2H, q), 3.45 (2H, s), 4.90 (1H, m), 7.23 (1H, t), 7.38 (1H, d), 7.45 (1H, d), 7.64 (1H, d), 8.18 (1H, d), 8.25 (1H, dd), 11.98 (1H, br s). δF (DMSO-$d_6$, 376 MHz): −61.5. MS (ES): $C_{28}H_{32}F_3N_3O_3S$ requires 547. found 548.2 (M+H$^+$).

EXAMPLE 21

1-[2-(2-ethyl-3-{5-[4-[(1-methylethyl)oxy]-3-(trifluoromethyl)phenyl]-1,2,4-thiadiazol-3-yl}phenyl)ethyl]-4-piperidinecarboxylic acid (E21)

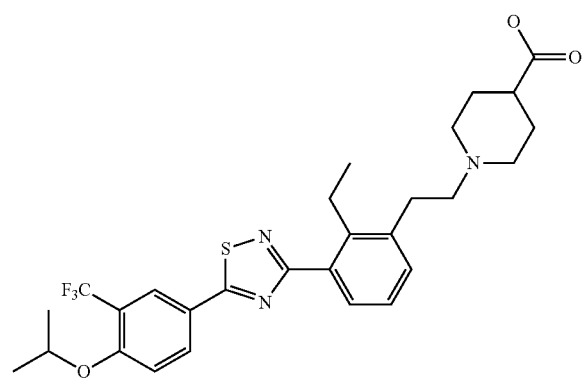 [SMILES: CCc1c(CCN2CCC(C(=O)O)CC2)cccc1-c1nsc(-c2ccc(OC(C)C)c(C(F)(F)F)c2)n1]

To a solution of {2-ethyl-3-[5-(1-methylethenyl)-1,2,4-thiadiazol-3-yl]phenyl}acetaldehyde (D50) (45 mg), ethyl 4-piperidinecarboxylate (32.6 mg) and acetic acid (0.593 μL) in dichloromethane (DCM) (8 mL) stirred under nitrogen at room temperature for 20 min was added sodium triacetoxyborohydride (43.9 mg). The reaction mixture was stirred at room temperature for 5 h. The reaction mixture was concentrated, separated between water and EA, the water phase was extracted by EA. The organic phases were concentrated in vacuo. The residue was dissolved in Isopropanol (5.00 mL) and water (0.500 mL), 20% sodium hydroxide (0.5 mL) was added, then the reaction mixture stirred at room temperature for overnight. The mixture was neutralized with acetic acid, the resulting solution was concentrated and the residue was purified by Mass Directed AutoPrep to afford 1-[2-(2-ethyl-3-{5-[4-[(1-methylethyl)oxy]-3-(trifluoromethyl)phenyl]-1,2,4-thiadiazol-3-yl}phenyl)ethyl]-4-piperidinecarboxylic acid (E21) (5 mg) as a white solid. δH (DMSO-$d_6$, 400 MHz): 1.13 (3H, t), 1.34 (6H, d), 1.56 (2H, m), 1.78 (2H, m), 2.07 (2H, m), 2.33 (1H, m), 2.88 (8H, br. s.), 4.96 (1H, m), 7.27 (1H, t), 7.36 (1H, d), 7.53 (1H, d), 7.64 (1H, dd), 8.25 (1H, d), 8.32 (1H, dd). δF (DMSO-$d_6$, 376 MHz): −61.4. MS (ES): $C_{28}H_{32}F_3N_3O_3S$ requires 547. found 548.3 (M+H$^+$).

EXAMPLE 22

1-[2-(2-ethyl-3-{5-[4-[(1-methylethyl)oxy]-3-(trifluoromethyl)phenyl]-1,2,4-thiadiazol-3-yl}phenyl)ethyl]-3-azetidinecarboxylic acid (E22)

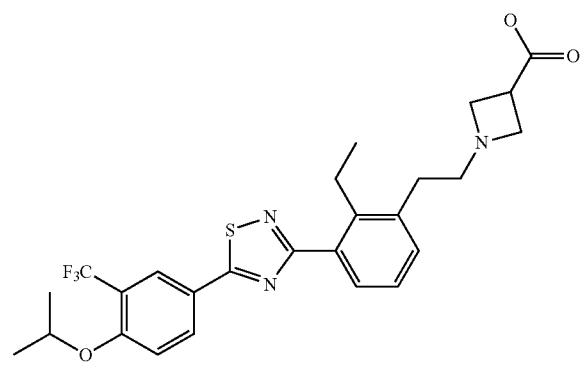 [SMILES: CCc1c(CCN2CC(C(=O)O)C2)cccc1-c1nsc(-c2ccc(OC(C)C)c(C(F)(F)F)c2)n1]

To a solution of {2-ethyl-3-[5-(1-methylethenyl)-1,2,4-thiadiazol-3-yl]phenyl}acetaldehyde (D50) (45 mg), methyl 3-azetidinecarboxylate (23.85 mg) and acetic acid (0.593 μL) in dichloromethane (DCM) (8 mL) stirred under nitrogen at room temperature for 20 min was added sodium triacetoxyborohydride (43.9 mg).

The reaction mixture was stirred at room temperature for 5 h. The reaction mixture was concentrated, separated between water and EA, the water phase was extracted by EA. The organic phases were concentrated in vacuo. The residue was dissolved in Isopropanol (5.00 mL) and water (0.500 mL), 20% sodium hydroxide (0.5 mL) was added, then the reaction mixture stirred at room temperature for overnight. The mixture was neutralized with acetic acid, the resulting solution was concentrated and the residue was purified by Mass Directed AutoPrep to afford 1-[2-(2-ethyl-3-{5-[4-[(1-methylethyl)oxy]-3-(trifluoromethyl)phenyl]-1,2,4-thiadiazol-3-yl}phenyl)ethyl]-3-azetidinecarboxylic acid (E22) (7 mg) as a white solid. δH (DMSO-$d_6$, 400 MHz): 1.12 (3H, t), 1.34 (6H, d), 2.65 (4H, m), 2.89 (2H, m), 3.17 (5H, m), 4.95 (1H, m), 7.27 (1H, t), 7.35 (1H, d), 7.53 (1H, d), 7.65 (1H, dd), 8.24 (1H, d), 8.31 (1H, dd). δF (DMSO-$d_6$, 376 MHz): −61.4. MS (ES): $C_{26}H_{28}F_3N_3O_3S$ requires 519. found 520.2 (M+H$^+$).

EXAMPLE 23

1-{2-[3-(5-{3-chloro-4-[(1-methylethyl)oxy]phenyl}-1,2,4-thiadiazol-3-yl)-2-ethylphenyl]ethyl}-3-azetidinecarboxylic acid trifluoroacetate (E23)

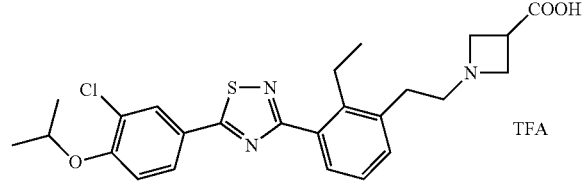 [SMILES: CCc1c(CCN2CC(C(=O)O)C2)cccc1-c1nsc(-c2ccc(OC(C)C)c(Cl)c2)n1]

To a solution of [3-(5-{3-chloro-4-[(1-methylethyl)oxy]phenyl}-1,2,4-thiadiazol-3-yl)-2-ethylphenyl]acetaldehyde (D52) (100 mg), methyl 3-azetidinecarboxylate (57.4 mg) and acetic acid (1.428 µL) in dichloromethane (DCM) (8 mL) and N,N-dimethylformamide (DMF) (0.400 mL) stirred under nitrogen at room temperature for 20 min was added sodium triacetoxyborohydride (106 mg). The reaction mixture was stirred at room temperature for 5 h. The reaction mixture was concentrated, separated between water and EA, the water phase was extracted by EA. The organic phases were concentrated in vacuo. The residue was dissolved in Isopropanol (8.00 mL) and water (0.800 mL), 20% sodium hydroxide (0.5 mL) was added, then the reaction mixture stirred at room temperature for overnight. The mixture was neutralized with acetic acid, the resulting solution was concentrated and the residue was purified by Mass Directed AutoPrep to afford 1-{2-[3-(5-{3-chloro-4-[(1-methylethyl)oxy]phenyl}-1,2,4-thiadiazol-3-yl)-2-ethylphenyl]ethyl}-3-azetidinecarboxylic acid (E23) (32 mg) as a TFA salt (white solid). δH (DMSO-d$_6$, 400 MHz): 1.12 (3H, t), 1.35 (6H, d), 2.92 (4H, m), 3.44 (2H, m), 3.63 (1H, m), 4.29 (4H, m), 4.86 (1H, m), 7.38 (3H, m), 7.74 (1H, d), 8.02 (1H, dd), 8.14 (1H, d), 10.18 (1H, br s), 13.18 (1H, br s). δF (DMSO-d$_6$, 376 MHz): −73.5. MS (ES): $C_{25}H_{28}ClN_3O_3S$ requires 485. found 486.2 (M+H$^+$).

EXAMPLE 24

1-{2-[3-(5-{3-chloro-4-[(1-methylethyl)oxy]phenyl}-1,2,4-thiadiazol-3-yl)-2-ethylphenyl]ethyl}-4-piperidinecarboxylic acid trifluoroacetate (E24)

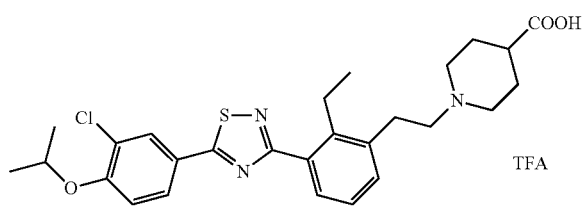 [SMILES: CCc1c(CCN2CCC(C(=O)O)CC2)cccc1-c1nsc(-c2ccc(OC(C)C)c(Cl)c2)n1]

To a solution of [3-(5-{3-chloro-4-[(1-methylethyl)oxy]phenyl}-1,2,4-thiadiazol-3-yl)-2-ethylphenyl]acetaldehyde (D52) (100 mg), ethyl 4-piperidinecarboxylate (78 mg) and acetic acid (1.428 µL) in dichloromethane (DCM) (8 mL) and N,N-dimethylformamide (DMF) (0.400 mL) stirred under nitrogen at room temperature for 20 min was added sodium triacetoxyborohydride (106 mg). The reaction mixture was stirred at room temperature for 5 h. The reaction mixture was concentrated, separated between water and EA, the water phase was extracted by EA. The organic phases were concentrated in vacuo. The residue was dissolved in Isopropanol (8.00 mL) and water (0.800 mL), 20% sodium hydroxide (0.5 mL) was added, then the reaction mixture stirred at room temperature for overnight. The mixture was neutralized with acetic acid, the resulting solution was concentrated and the residue was purified by Mass Directed AutoPrep to afford 1-{2-[3-(5-{3-chloro-4-[(1-methylethyl)oxy]phenyl}-1,2,4-thiadiazol-3-yl)-2-ethylphenyl]ethyl}-4-piperidinecarboxylic acid (E24) (40 mg) as a TFA salt (white solid). δH (DMSO-d$_6$, 400 MHz): 1.14 (3H, t), 1.35 (6H, d), 1.85 (2H, m), 2.14 (2H, m), 3.01 (6H, m), 3.27 (3H, m), 3.68 (2H, m), 4.86 (1H, m), 7.36 (3H, m), 7.73 (1H, d), 8.02 (1H, dd), 8.14 (1H, d), 9.56 (1H, br s), 12.66 (1H, br s). δF (DMSO-d$_6$, 376 MHz): −73.8. MS (ES): $C_{27}H_{32}ClN_3O_3S$ requires 513. found 514.2 (M+H$^+$).

EXAMPLE 25

1-{[3-(5-{3-chloro-4-[(1-methylethyl)oxy]phenyl}-1,2,4-thiadiazol-3-yl)-2-ethylphenyl]methyl}-3-azetidinecarboxylic acid trifluoroacetate (E25)

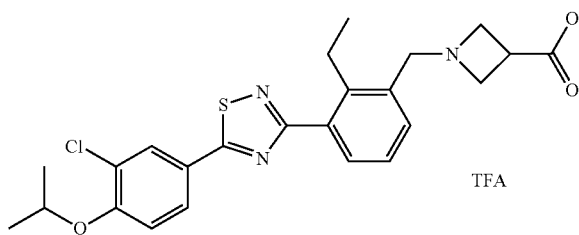 [SMILES: CCc1c(CN2CC(C(=O)O)C2)cccc1-c1nsc(-c2ccc(OC(C)C)c(Cl)c2)n1]

To a solution of 3-(5-{3-chloro-4-[(1-methylethyl)oxy]phenyl}-1,2,4-thiadiazol-3-yl)-2-ethylbenzaldehyde (D53) (100 mg) in dichloromethane (DCM) (8 mL) and methanol (8.00 mL) was added sodium acetate (31.8 mg), hydrogen chloride-methyl 3-azetidinecarboxylate (1:1) (58.8 mg) and 5 drops of acetic acid. After stirring for 30 min, sodium triacetoxyborohydride (110 mg) was added and the reaction solution was stirred at room temperature overnight. The solvent was removed in vacuo and the residue was dissolved in ethyl acetate (30 mL), the organic phase was washed with water, dried over sodium sulphate and concentrated. The residue was dissolved in isopropanol/water (10 mL, 1:1), 0.5M sodium hydroxide (2.58 mL) was added, the reaction solution was heated to 80° C. for 1 h. The solvent was removed in vacuo and the residue was acidified to pH=2-3. The resulting solution was extracted with ethyl acetate (2*15 mL), and the combined organic phases were dried over sodium sulphate, concentrated and purified by Mass Directed AutoPrep to afford 1-{[3-(5-{3-chloro-4-[(1-methylethyl)oxy]phenyl}-1,2,4-thiadiazol-3-yl)-2-ethylphenyl]methyl}-3-azetidinecarboxylic acid (E25) (40 mg) as a TFA salt (white solid). δH (DMSO-d$_6$, 400 MHz): 1.05 (3H, t), 1.28 (6H, d), 2.87 (2H, q), 3.19 (3H, m), 3.34 (2H, m), 3.60 (2H, s), 4.78 (1H, m), 7.23 (1H, t), 7.31 (1H, d), 7.38 (1H, d), 7.64 (1H, d), 7.94 (1H, dd), 8.07 (1H, d). δF (DMSO-d$_6$, 376 MHz): −73.4. MS (ES): $C_{24}H_{26}ClN_3O_3S$ requires 471. found 472.2 (M+H$^+$).

EXAMPLE 26

1-{2-[3-(5-{3-cyano-4-[(1-methylethyl)oxy]phenyl}-1,2,4-thiadiazol-3-yl)-2-ethylphenyl]ethyl}-3-azetidinecarboxylic acid trifluoroacetate (E26)

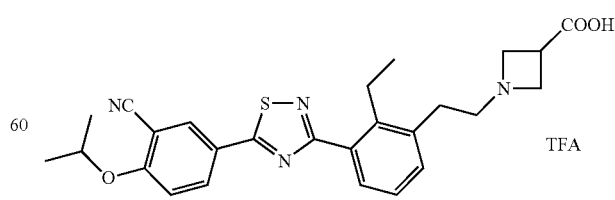

To a solution of 5-{3-[2-ethyl-3-(2-oxoethyl)phenyl]-1,2,4-thiadiazol-5-yl}-2-[(1-methylethyl)oxy]benzonitrile (D55) (150 mg) in dichloromethane (DCM) (7.5 mL) was added sodium acetate (31.4 mg), hydrogen chloride-methyl 3-azetidinecarboxylate (1:1) (58.1 mg) and 5 drops of acetic acid. After stirring for 30 min, sodium triacetoxyborohydride (122 mg) was added and the reaction solution was stirred at room temperature overnight. The solvent was removed in vacuo and the residue was dissolved in ethyl acetate (30 mL), the organic phase was washed with water, dried over sodium sulphate and concentrated. The residue was dissolved in isopropanol/water (10 mL, 1:1), 0.5M sodium hydroxide (3.83 mL) was added, the reaction solution was heated to 90° C. for 1 h. The solvent was removed in vacuo and the residue was acidified to pH=3-4. The resulting solution was extracted with ethyl acetate (2*15 mL), and the combined organic phases were dried over sodium sulphate, concentrated and purified by Mass Directed AutoPrep to afford 1-{2-[3-(5-{3-cyano-4-[(1-methylethyl)oxy]phenyl}-1,2,4-thiadiazol-3-yl)-2-ethylphenyl]ethyl}-3-azetidinecarboxylic acid (E26) (31 mg) as a TFA salt (white solid). δH (DMSO-d$_6$, 400 MHz): 1.05 (3H, t), 1.31 (6H, d), 2.84 (4H, m), 3.35 (2H, m), 3.57 (1H, m), 4.20 (4H, m), 4.90 (1H, m), 7.28 (1H, t), 7.37 (1H, d), 7.44 (1H, d), 7.68 (1H, dd), 8.26 (1H, dd), 8.41 (1H, d). δF (DMSO-d$_6$, 376 MHz): −73.5. MS (ES): $C_{26}H_{28}N_4O_3S$ requires 476. found 477.2 (M+H$^+$).

EXAMPLE 27

1-[(3-{5-[3-cyano-4-(2-methylpropyl)phenyl]-1,2,4-thiadiazol-3-yl}-2-ethylphenyl)methyl]-3-azetidinecarboxylic acid trifluoroacetate (E27)

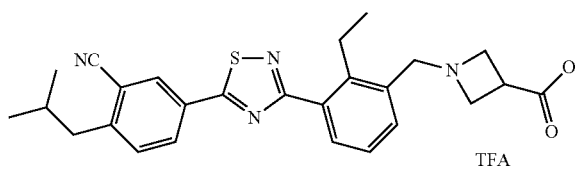 [SMILES: CCc1c(CN2CC(C(=O)O)C2)cccc1-c1nsc(-c2ccc(CC(C)C)c(C#N)c2)n1]

To a solution of 5-[3-(2-ethyl-3-formylphenyl)-1,2,4-thiadiazol-5-yl]-2-(2-methylpropyl)benzonitrile (D63) (100 mg) in dichloromethane (DCM) (15 mL) was added sodium acetate (22.9 mg), hydrogen chloride-methyl 3-azetidinecarboxylate (1:1) (42.4 mg) and 5 drops of acetic acid. After stirring for 30 min, sodium triacetoxyborohydride (85 mg) was added and the reaction solution was stirred at room temperature overnight. The solvent was removed in vacuo and the residue was dissolved in ethyl acetate (30 mL), the organic phase was washed with water, dried over sodium sulphate and concentrated. The residue was dissolved in isopropanol/water (10 mL, 1:1), 0.5M sodium hydroxide (2.66 mL) was added. The reaction solution was stirred at room temperature overnight. The isopropanol was removed in vacuo and the residue was acidified to pH=3-4. The resulting solution was extracted with ethyl acetate (2*15 mL), and the combined organic phases were dried over sodium sulphate, concentrated and purified by Mass Directed AutoPrep to afford 1-[(3-{5-[3-cyano-4-(2-methylpropyl)phenyl]-1,2,4-thiadiazol-3-yl}-2-ethylphenyl)methyl]-3-azetidinecarboxylic acid (E27) (51 mg) as a TFA salt. δH (DMSO-d$_6$, 400 MHz): 0.87 (6H, d), 1.04 (3H, t), 1.93 (1H, m), 2.71 (2H, d), 2.92 (2H, q), 3.58 (1H, m), 4.20 (4H, m), 4.51 (2H, s), 7.39 (1H, t), 7.52 (1H, d), 7.64 (1H, d), 7.84 (1H, d), 8.26 (1H, dd), 8.47 (1H, d). δF (DMSO-d$_6$, 376 MHz): −73.5. MS (ES): $C_{26}H_{28}N_4O_2S$ requires 460. found 461.1 (M+H$^+$).

EXAMPLE 28

1-[(3-{5-[3-cyano-4-(2-methylpropyl)phenyl]-1,2,4-thiadiazol-3-yl}-2-ethylphenyl)methyl]-4-piperidinecarboxylic acid (E28)

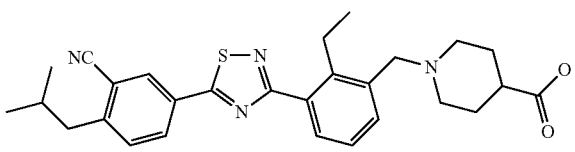 [SMILES: CCc1c(CN2CCC(C(=O)O)CC2)cccc1-c1nsc(-c2ccc(CC(C)C)c(C#N)c2)n1]

To a solution of 5-[3-(2-ethyl-3-formylphenyl)-1,2,4-thiadiazol-5-yl]-2-(2-methylpropyl)benzonitrile (D63) (100 mg) in dichloromethane (DCM) (15 mL) was added sodium acetate (22.9 mg), ethyl 4-piperidinecarboxylate (46.1 mg) and 5 drops of acetic acid. After stirring for 30 min, sodium triacetoxyborohydride (85 mg) was added and the reaction solution was stirred at room temperature overnight. The solvent was removed in vacuo and the residue was dissolved in ethyl acetate (30 mL), the organic phase was washed with water, dried over sodium sulphate and concentrated. The residue was dissolved in isopropanol/water (10 mL, 1:1), 0.5M sodium hydroxide (2.66 mL) was added. The reaction solution was stirred at room temperature overnight. The isopropanol was removed in vacuo and the residue was acidified to pH=3-4. The resulting solution was extracted with ethyl acetate (2*15 mL), and the combined organic phases were dried over sodium sulphate, concentrated and purified by Mass Directed AutoPrep to afford 1-[(3-{5-[3-cyano-4-(2-methylpropyl)phenyl]-1,2,4-thiadiazol-3-yl}-2-ethylphenyl)methyl]-4-piperidinecarboxylic acid (E28) (43 mg). δH (DMSO-d$_6$, 400 MHz): 0.87 (6H, d), 1.03 (3H, t), 1.47 (2H, m), 1.71 (2H, m), 1.92 (3H, m), 2.01 (1H, m), 2.70 (4H, m), 2.93 (2H, q), 3.47 (2H, s), 7.24 (1H, t), 7.39 (1H, dd), 7.66 (2H, m), 8.26 (1H, dd), 8.47 (1H, d).

MS (ES): $C_{28}H_{32}N_4O_2S$ requires 488. found 489.1 (M+H$^+$).

EXAMPLE 29

1-[2-(3-{5-[3-cyano-4-(2-methylpropyl)phenyl]-1,2,4-thiadiazol-3-yl}-2-ethylphenyl)ethyl]-4-piperidinecarboxylic acid trifluoroacetate (E29)

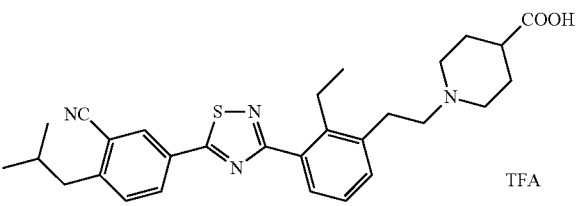 [SMILES: CCc1c(CCN2CCC(C(=O)O)CC2)cccc1-c1nsc(-c2ccc(CC(C)C)c(C#N)c2)n1]

To a solution of 5-{3-[2-ethyl-3-(2-oxoethyl)phenyl]-1,2,4-thiadiazol-5-yl}-2-(2-methylpropyl)benzonitrile (D62) (110 mg) in dichloromethane (DCM) (15 mL) was added sodium acetate (25.5 mg), ethyl 4-piperidinecarboxylate (57.7 mg) and 5 drops of acetic acid. After stirring for 30 min, sodium triacetoxyborohydride (90 mg) was added and the reaction solution was stirred at room temperature overnight.

The solvent was removed in vacuo and the residue was dissolved in ethyl acetate (30 mL), the organic phase was washed with water, dried over sodium sulphate and concentrated. The residue was dissolved in isopropanol/water (10 mL, 1:1), 0.5M sodium hydroxide (2.82 mL) was added. The reaction solution was stirred at room temperature overnight. The isopropanol was removed in vacuo and the residue was acidified to pH=3-4. The resulting solution was extracted with ethyl acetate (2*15 mL), and the combined organic phases were dried over sodium sulphate, concentrated and purified by Mass Directed AutoPrep to afford 1-[2-(3-{5-[3-cyano-4-(2-methylpropyl)phenyl]-1,2,4-thiadiazol-3-yl}-2-ethylphenyl)ethyl]-4-piperidinecarboxylic acid (E29) (86 mg) as a TFA salt. δH (DMSO-d$_6$, 400 MHz): 0.86 (6H, d), 1.09 (3H, t), 1.74 (3H, m), 2.05 (2H, m), 2.71 (2H, d), 2.87 (2H, m), 3.05 (4H, m), 3.24 (4H, m), 3.62 (1H, m), 7.32 (2H, m), 7.69 (2H, m), 8.26 (1H, dd), 8.46 (1H, d). δF (DMSO-d$_6$, 376 MHz): −73.6. MS (ES): C$_{29}$H$_{34}$N$_4$O$_2$S requires 502. found 503.2 (M+H$^+$).

EXAMPLE 30

1-[2-(3-{5-[3-cyano-4-(2-methylpropyl)phenyl]-1,2,4-thiadiazol-3-yl}-2-ethylphenyl)ethyl]-3-azetidinecarboxylic acid trifluoroacetate (E30)

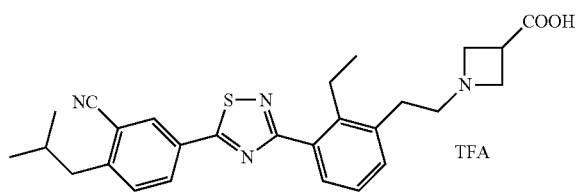 [SMILES: CCc1c(CCN2CC(C(=O)O)C2)cccc1-c1nsc(-c2ccc(CC(C)C)c(C#N)c2)n1]

To a solution of 5-{3-[2-ethyl-3-(2-oxoethyl)phenyl]-1,2,4-thiadiazol-5-yl}-2-(2-methylpropyl)benzonitrile (D62) (110 mg) in dichloromethane (DCM) (15 mL) was added sodium acetate (25.5 mg), hydrogen chloride-methyl 3-azetidinecarboxylate (1:1) (45.0 mg) and 5 drops of acetic acid. After stirring for 30 min, sodium triacetoxyborohydride (90 mg) was added and the reaction solution was stirred at room temperature overnight. The solvent was removed in vacuo and the residue was dissolved in ethyl acetate (30 mL), the organic phase was washed with water, dried over sodium sulphate and concentrated. The residue was dissolved in isopropanol/water (10 mL, 1:1), 0.5M sodium hydroxide (2.82 mL) was added. The reaction solution was stirred at room temperature overnight. The isopropanol was removed in vacuo and the residue was acidified to pH=3-4. The resulting solution was extracted with ethyl acetate (2*15 mL), and the combined organic phases were dried over sodium sulphate, concentrated and purified by Mass Directed AutoPrep to afford 1-[2-(3-{5-[3-cyano-4-(2-methylpropyl)phenyl]-1,2,4-thiadiazol-3-yl}-2-ethylphenyl)ethyl]-3-azetidinecarboxylic acid (E30) (24 mg) as a TFA salt. δH (DMSO-d$_6$, 400 MHz): 0.86 (6H, d), 1.06 (3H, t), 1.92 (1H, m), 2.70 (2H, d), 2.84 (4H, m), 3.34 (2H, m), 3.55 (1H, m), 4.21 (4H, m), 7.29 (1H, t), 7.38 (1H, d), 7.63 (1H, d), 7.69 (1H, dd), 8.26 (1H, dd), 8.46 (1H, d). δF (DMSO-d$_6$, 376 MHz): −73.6. MS (ES): C$_{27}$H$_{30}$N$_4$O$_2$S requires 474. found 475.1 (M+H$^+$).

EXAMPLE 31

1-[(2-ethyl-3-{2-[4-[(1-methylethyl)oxy]-3-(trifluoromethyl)phenyl]-1,3-thiazol-5-yl}phenyl)methyl]-3-azetidinecarboxylic acid (E31)

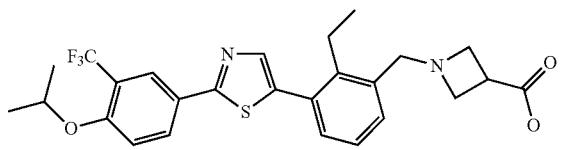 [SMILES: CCc1c(CN2CC(C(=O)O)C2)cccc1-c1cnc(-c2ccc(OC(C)C)c(C(F)(F)F)c2)s1]

To a solution of 2-ethyl-3-{2-[4-[(1-methylethyl)oxy]-3-(trifluoromethyl)phenyl]-1,3-thiazol-5-yl}benzaldehyde (D72) (60 mg), 3-azetidinecarboxylic acid (28.9 mg) and acetic acid (0.1 mL) in dichloromethane (DCM) (3 mL) stirred under nitrogen at room temperature for 1 h was added sodium triacetoxyborohydride (60.6 mg) in one charge. The reaction was stirred at room temperature overnight. The mixture was partitioned with DCM and water, washed with saturated brine and the organic phase was dried and evaporated, the residue was purified by Mass Directed AutoPrep to afford 1-[(2-ethyl-3-{2-[4-[(1-methylethyl)oxy]-3-(trifluoromethyl)phenyl]-1,3-thiazol-5-yl}phenyl)methyl]-3-azetidinecarboxylic acid (E31) (14 mg). δH (DMSO-d$_6$, 400 MHz): 1.06 (3H, t), 1.33 (6H, d), 2.73 (2H, m), 3.22 (5H, m), 3.63 (2H, s), 4.89 (1H, m), 7.26 (2H, m), 7.39 (1H, d), 7.45 (1H, d), 7.84 (1H, s), 8.15 (2H, m). δF (DMSO-d$_6$, 376 MHz): −61.3. MS (ES): C$_{26}$H$_{27}$F$_3$N$_2$O$_3$S requires 504. found 505.1 (M+H$^+$).

EXAMPLE 32

1-[(2-ethyl-3-{2-[4-[(1-methylethyl)oxy]-3-(trifluoromethyl)phenyl]-1,3-thiazol-5-yl}phenyl)methyl]-4-piperidinecarboxylic acid (E32)

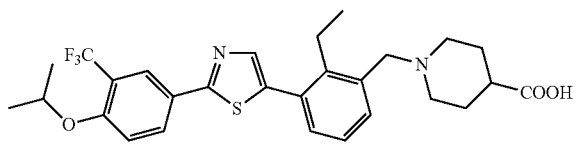 [SMILES: CCc1c(CN2CCC(C(=O)O)CC2)cccc1-c1cnc(-c2ccc(OC(C)C)c(C(F)(F)F)c2)s1]

To a solution of ethyl 1-[(2-ethyl-3-{2-[4-[(1-methylethyl)oxy]-3-(trifluoromethyl)phenyl]-1,3-thiazol-5-yl}phenyl)methyl]-4-piperidinecarboxylate (D81) (160 mg) in isopropanol (3 mL) and water (0.750 mL) stirred under nitrogen at room temperature was added a solution of NaOH (26.8 mg) in water in one charge. The reaction mixture was stirred at room temperature for 2 h. Isopropanol was removed in vacuo. The residue was dissolved in water and acidified with 1N HCl to pH=5. The solvent was removed in vacuo, the residue was dissolved in THF, and filtered. The filtrate was purified by Mass Directed AutoPrep to give 1-[(2-ethyl-3-{2-[4-[(1-methylethyl)oxy]-3-(trifluoromethyl)phenyl]-1,3-thiazol-5-yl}phenyl)methyl]-4-piperidinecarboxylic acid (E32) (28 mg). δH (DMSO-d$_6$, 400 MHz): 1.07 (3H, t), 1.33 (6H, d), 1.53 (2H, m), 1.77 (2H, m), 2.03 (2H, m), 2.22 (1H, m), 2.77 (4H, m), 3.49 (2H, s), 4.89 (1H, m), 7.24 (1H, t), 7.30 (1H, d), 7.38 (1H, d), 7.44 (1H, d), 7.86 (1H, s), 8.15 (2H, m), 12.09

(1H, br s). δF (DMSO-$d_6$, 376 MHz): −61.3. MS (ES): $C_{28}H_{31}F_3N_2O_3S$ requires 532. found 533.3 (M+H$^+$).

EXAMPLE 33

1-{2-[3-(2-{3-chloro-4-[(1-methylethyl)oxy]phenyl}-1,3-thiazol-5-yl)-5-fluoro-2-(methyloxy)phenyl]ethyl}-3-azetidinecarboxylic acid trifluoroacetate (E33)

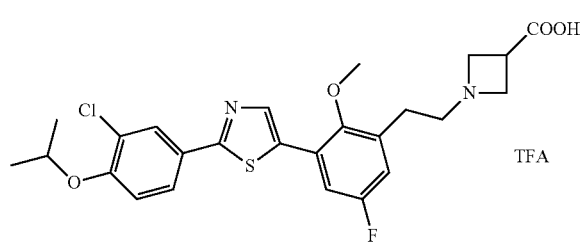 [SMILES: COc1c(CCN2CC(C(=O)O)C2)cc(F)cc1-c1cnc(-c2ccc(OC(C)C)c(Cl)c2)s1]

To a solution of methyl 1-{2-[3-(2-{3-chloro-4-[(1-methylethyl)oxy]phenyl}-1,3-thiazol-5-yl)-5-fluoro-2-(methyloxy)phenyl]ethyl}-3-azetidinecarboxylate (D82) (100 mg) in isopropanol (15 mL) and water (5 mL) stirred under nitrogen at room temperature was added 2 M NaOH (0.193 mL) in one charge. The reaction mixture was stirred at room temperature overnight. Isopropanol was removed in vacuo. The residue was dissolved in water and acidified with 1N HCl to pH=5. The solvent was removed in vacuo, the residue was dissolved in THF, and filtered. The filtrate was purified by Mass Directed AutoPrep to give 1-{2-[3-(2-{3-chloro-4-[(1-methylethyl)oxy]phenyl}-1,3-thiazol-5-yl)-5-fluoro-2-(methyloxy)phenyl]ethyl}-3-azetidinecarboxylic acid (E33) (21 mg) as a TFA salt. δH (DMSO-$d_6$, 400 MHz): 1.34 (6H, d), 2.90 (2H, t), 3.47 (2H, br. s.), 3.66 (4H, m), 4.28 (4H, m), 4.80 (1H, m), 7.26 (1H, d), 7.32 (1H, d), 7.73 (1H, dd), 7.90 (1H, dd), 8.01 (1H, d), 8.46 (1H, s), 10.12 (1H, br s), 13.13 (1H, br s). δF (DMSO-$d_6$, 376 MHz): −117.4, −73.9. MS (ES): $C_{25}H_{26}ClFN_2O_4S$ requires 504. found 505.2 (M+H$^+$).

EXAMPLE 34

1-{2-[3-(2-{3-cyano-4-[(1-methylethyl)oxy]phenyl}-1,3-thiazol-5-yl)-2-ethylphenyl]ethyl}-3-azetidinecarboxylic acid trifluoroacetate (E34)

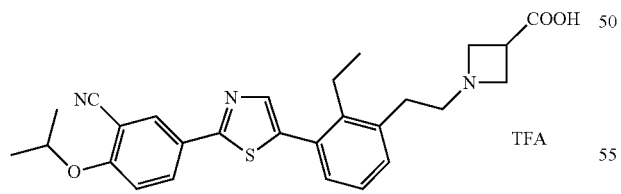

To a solution of methyl 1-{2-[3-(2-{3-cyano-4-[(1-methylethyl)oxy]phenyl}-1,3-thiazol-5-yl)-2-ethylphenyl]ethyl}-3-azetidinecarboxylate (D83) (188 mg) in isopropanol (40 mL) and water (10 mL) stirred under nitrogen at room temperature was added a solution of NaOH (30.7 mg) in water in one charge. The reaction mixture was stirred at room temperature overnight. Isopropanol was removed in vacuo. The residue was dissolved in water and acidified with 1N HCl to pH=5. The solvent was removed in vacuo, the residue was dissolved in THF, and filtered. The filtrate was purified by Mass Directed AutoPrep to give 1-{2-[3-(2-{3-cyano-4-[(1-methylethyl)oxy]phenyl}-1,3-thiazol-5-yl)-2-ethylphenyl]ethyl}-3-azetidinecarboxylic acid (E34) (14 mg) as a TFA salt (white solid). δH (DMSO-$d_6$, 400 MHz): 1.07 (3H, t), 1.36 (6H, d), 2.69 (2H, m), 2.87 (2H, m), 3.59 (3H, m), 4.28 (4H, m), 4.90 (1H, m), 7.30 (2H, m), 7.37 (1H, m), 7.44 (1H, d), 7.85 (1H, s), 8.22 (1H, dd), 8.27 (1H, d), 9.98 (1H, br s), 13.19 (1H, br s). δF (DMSO-$d_6$, 376 MHz): −73.5. MS (ES): $C_{27}H_{29}N_3O_3S$ requires 475. found 476.2 (M+H$^+$).

EXAMPLE 35

1-{[3-(2-{3-cyano-4-[(1-methylethyl)oxy]phenyl}-1,3-thiazol-5-yl)-2-ethylphenyl]methyl}-4-piperidinecarboxylic acid trifluoroacetate (E35)

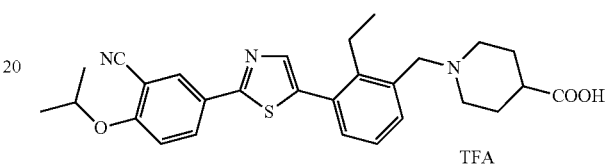

To a solution of ethyl 1-{[3-(2-{3-cyano-4-[(1-methylethyl)oxy]phenyl}-1,3-thiazol-5-yl)-2-ethylphenyl]methyl}-4-piperidinecarboxylate (D84) (160 mg) in isopropanol (40 mL) and water (10 mL) stirred under nitrogen at room temperature was added a solution of NaOH (24.7 mg) in water in one charge. The reaction mixture was stirred at room temperature overnight. Isopropanol was removed in vacuo. The residue was dissolved in water and acidified with 1N HCl to pH=5. The solvent was removed in vacuo, the residue was dissolved in THF, and filtered. The filtrate was purified by Mass Directed AutoPrep to give 1-{[3-(2-{3-cyano-4-[(1-methylethyl)oxy]phenyl}-1,3-thiazol-5-yl)-2-ethylphenyl]methyl}-4-piperidinecarboxylic acid (E35) (55 mg) as a TFA salt (white solid). δH (DMSO-$d_6$, 400 MHz): 1.02 (3H, t), 1.36 (6H, d), 1.78 (2H, m), 2.06 (2H, m), 2.52 (1H, m), 2.82 (2H, m), 3.18 (2H, m), 3.45 (2H, m), 4.41 (2H, m), 4.91 (1H, m), 7.44 (2H, m), 7.50 (1H, d), 7.64 (1H, d), 7.89 (1H, s), 8.22 (1H, dd), 8.28 (1H, d), 9.18 (1H, br s), 12.52 (1H, br s).
δF (DMSO-$d_6$, 376 MHz): −73.7. MS (ES): $C_{28}H_{31}N_3O_3S$ requires 489. found 490.2 (M+H$^+$).

EXAMPLE 36

1-{[3-(2-{3-chloro-4-[(1-methylethyl)oxy]phenyl}-1,3-thiazol-5-yl)-2-ethylphenyl]methyl}-4-piperidinecarboxylic acid trifluoroacetate (E36)

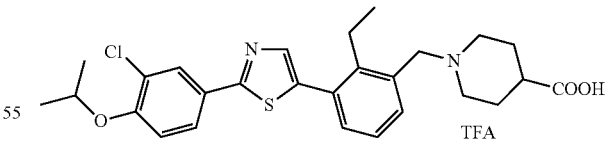

To a solution of ethyl 1-{[3-(2-{3-chloro-4-[(1-methylethyl)oxy]phenyl}-1,3-thiazol-5-yl)-2-ethylphenyl]methyl}-4-piperidinecarboxylate (D85) (160 mg) in isopropanol (40 mL) and water (10 mL) stirred under nitrogen at room temperature was added a solution of NaOH (24.3 mg) in water in one charge. The reaction mixture was stirred at room temperature overnight. Isopropanol was removed in vacuo. The residue was dissolved in water and acidified with 1N HCl to pH=5. The solvent was removed in vacuo, the residue was dissolved in THF, and filtered. The filtrate was purified by Mass Directed AutoPrep to give 1-{[3-(2-{3-chloro-4-[(1- methylethyl)oxy]phenyl}-1,3-thiazol-5-yl)-2-ethylphenyl] methyl}-4-piperidinecarboxylic acid (E36) (73 mg) as a TFA salt (white solid). δH (DMSO-d$_6$, 400 MHz): 1.02 (3H, t), 1.34 (6H, d), 1.78 (2H, m), 2.05 (2H, m), 2.54 (1H, m), 2.83 (2H, m), 3.18 (2H, m), 3.45 (2H, m), 4.42 (2H, m), 4.80 (1H, m), 7.32 (1H, d), 7.44 (2H, m), 7.63 (1H, d), 7.87 (2H, m), 7.99 (1H, d), 9.28 (1H, br s), 12.59 (1H, br s). δF (DMSO-d$_6$, 376 MHz): −74.0. MS (ES): $C_{27}H_{31}ClN_2O_3S$ requires 498. found 499.1 (M+H$^+$).

EXAMPLE 37

1-{2-[3-(2-{3-cyano-4-[(1-methylethyl)oxy]phenyl}-1,3-thiazol-5-yl)-2-ethylphenyl]ethyl}-4-piperidinecarboxylic acid trifluoroacetate (E37)

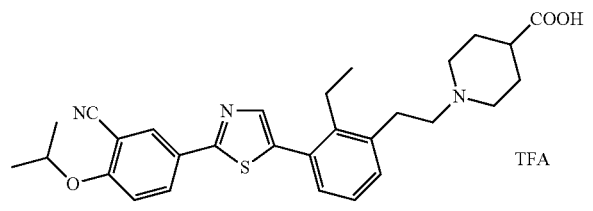 [SMILES: CCc1c(CCN2CCC(C(=O)O)CC2)cccc1-c1cnc(-c2ccc(OC(C)C)c(C#N)c2)s1]

To a solution of ethyl 1-{2-[3-(2-{3-cyano-4-[(1-methylethyl)oxy]phenyl}-1,3-thiazol-5-yl)-2-ethylphenyl]ethyl}-4-piperidinecarboxylate (D86) (204 mg) in isopropanol (40 mL) and water (10 mL) stirred under nitrogen at room temperature was added a solution of NaOH (30.7 mg) in water in one charge. The reaction mixture was stirred at room temperature overnight. Isopropanol was removed in vacuo. The residue was dissolved in water and acidified with 1N HCl to pH=5. The solvent was removed in vacuo, the residue was dissolved in THF, and filtered. The filtrate was purified by Mass Directed AutoPrep to give 1-{2-[3-(2-{3-cyano-4-[(1-methylethyl)oxy]phenyl}-1,3-thiazol-5-yl)-2-ethylphenyl]ethyl}-4-piperidinecarboxylic acid (E37) (48 mg) as a TFA salt (white solid). δH (DMSO-d$_6$, 400 MHz): 1.10 (3H, t), 1.36 (6H, d), 1.76 (2H, m), 2.13 (2H, m), 2.72 (2H, m), 3.07 (4H, m), 3.28 (3H, m), 3.67 (2H, m), 4.91 (1H, m), 7.34 (3H, m), 7.44 (1H, d), 7.85 (1H, s), 8.22 (1H, dd), 8.28 (1H, d), 9.37 (1H, br s), 12.60 (1H, br s). δF (DMSO-d$_6$, 376 MHz): −73.5. MS (ES): $C_{29}H_{33}N_3O_3S$ requires 503. found 504.1 (M+H$^+$).

EXAMPLE 38

1-{[3-(2-{3-cyano-4-[(1-methylethyl)oxy]phenyl}-1,3-thiazol-5-yl)-2-ethylphenyl]methyl}-3-azetidinecarboxylic acid trifluoroacetate (E38)

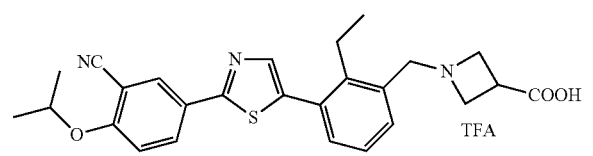 [SMILES: CCc1c(CN2CC(C(=O)O)C2)cccc1-c1cnc(-c2ccc(OC(C)C)c(C#N)c2)s1]

To a solution of methyl 1-{[3-(2-{3-cyano-4-[(1-methylethyl)oxy]phenyl}-1,3-thiazol-5-yl)-2-ethylphenyl]methyl}-3-azetidinecarboxylate (D87) (126 mg) in isopropanol (40 mL) and water (10 mL) stirred under nitrogen at room temperature was added a solution of NaOH (21.2 mg) in water in one charge. The reaction mixture was stirred at room temperature overnight. Isopropanol was removed in vacuo. The residue was dissolved in water and acidified with 1N HCl to pH=5. The solvent was removed in vacuo, the residue was dissolved in THF, and filtered. The filtrate was purified by Mass Directed AutoPrep to give 1-{[3-(2-{3-cyano-4-[(1-methylethyl)oxy]phenyl}-1,3-thiazol-5-yl)-2-ethylphenyl] methyl}-3-azetidinecarboxylic acid (E38) (60 mg) as a TFA salt (white solid). δH (DMSO-d$_6$, 400 MHz): 1.05 (3H, t), 1.36 (6H, d), 2.78 (2H, d), 3.64 (1H, m), 4.27 (4H, m), 4.54 (2H, m), 4.91 (1H, m), 7.42 (4H, m), 7.87 (1H, s), 8.22 (1H, dd), 8.28 (1H, d), 10.21 (1H, br s), 13.19 (1H, br s). δF (DMSO-d$_6$, 376 MHz): −73.6. MS (ES): $C_{26}H_{27}N_3O_3S$ requires 461. found 462.3 (M+H$^+$).

EXAMPLE 39

1-{[3-(2-{3-chloro-4-[(1-methylethyl)oxy]phenyl}-1,3-thiazol-5-yl)-2-ethylphenyl]methyl}-3-azetidinecarboxylic acid trifluoroacetate (E39)

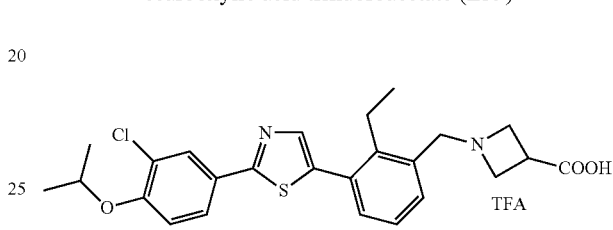

To a solution of methyl 1-{[3-(2-{3-chloro-4-[(1-methylethyl)oxy]phenyl}-1,3-thiazol-5-yl)-2-ethylphenyl]methyl}-3-azetidinecarboxylate (D88) (160 mg) in isopropanol (40 mL) and water (10 mL) stirred under nitrogen at room temperature was added a solution of NaOH (26.4 mg) in water in one charge. The reaction mixture was stirred at room temperature overnight. Isopropanol was removed in vacuo. The residue was dissolved in water and acidified with 1N HCl to pH=5. The solvent was removed in vacuo, the residue was dissolved in THF, and filtered. The filtrate was purified by Mass Directed AutoPrep to give 1-{[3-(2-{3-chloro-4-[(1-methylethyl)oxy]phenyl}-1,3-thiazol-5-yl)-2-ethylphenyl] methyl}-3-azetidinecarboxylic acid (E39) (55 mg) as a TFA salt (white solid). δH (DMSO-d$_6$, 400 MHz): 1.05 (3H, t), 1.34 (6H, d), 2.78 (2H, d), 3.65 (1H, m), 4.28 (4H, m), 4.54 (2H, s), 4.80 (1H, m), 7.36 (2H, m), 7.47 (2H, d), 7.84 (1H, s), 7.88 (1H, dd), 7.99 (1H, d), 10.09 (1H, br s), 13.19 (1H, br s). δF (DMSO-d$_6$, 376 MHz): −73.6. MS (ES): $C_{26}H_{27}ClN_2O_3S$ requires 470. found 471.2 (M+H$^+$).

EXAMPLE 40

1-{2-[3-(2-{3-chloro-4-[(1-methylethyl)oxy]phenyl}-1,3-thiazol-5-yl)-2-ethylphenyl]ethyl}-4-piperidinecarboxylic acid trifluoroacetate (E40)

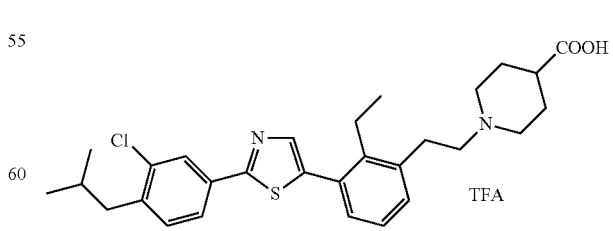

To a solution of ethyl 1-{2-[3-(2-{3-chloro-4-[(1-methylethyl)oxy]phenyl}-1,3-thiazol-5-yl)-2-ethylphenyl]ethyl}-4-piperidinecarboxylate (D89) (120 mg) in isopropanol (40 mL) and water (10 mL) stirred under nitrogen at room temperature was added a solution of NaOH (17.7 mg) in water in one charge. The reaction mixture was stirred at room temperature overnight. Isopropanol was removed in vacuo. The residue was dissolved in water and acidified with 1N HCl to pH=5. The solvent was removed in vacuo, the residue was dissolved in THF, and filtered. The filtrate was purified by Mass Directed AutoPrep to give 1-{2-[3-(2-{3-chloro-4-[(1-methylethyl)oxy]phenyl}-1,3-thiazol-5-yl)-2-ethylphenyl]ethyl}-4-piperidinecarboxylic acid (E40) (18 mg) as a TFA salt (white solid). δH (DMSO-$d_6$, 400 MHz): 1.11 (3H, t), 1.34 (6H, d), 1.76 (2H, m), 2.11 (2H, m), 2.71 (2H, m), 3.07 (4H, m), 3.27 (2H, m), 3.53 (1H, m), 3.67 (2H, m), 4.80 (1H, m), 7.33 (4H, m), 7.82 (1H, s), 7.87 (1H, dd), 7.99 (1H, d), 9.29 (1H, br s), 12.59 (1H, br s). δF (DMSO-$d_6$, 376 MHz): −73.5. MS (ES): $C_{28}H_{33}ClN_2O_3S$ requires 512. found 513.1 (M+H$^+$).

EXAMPLE 41

1-{2-[3-(2-{3-chloro-4-[(1-methylethyl)oxy]phenyl}-1,3-thiazol-5-yl)-2-ethylphenyl]ethyl}-3-azetidinecarboxylic acid trifluoroacetate (E41)

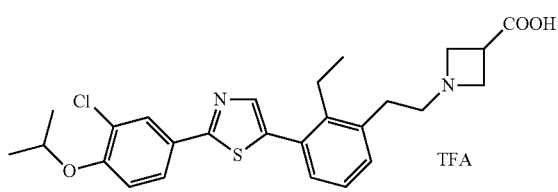 [SMILES: CCc1c(CCN2CC(C(=O)O)C2)cccc1-c1cnc(-c2ccc(OC(C)C)c(Cl)c2)s1]

To a solution of methyl 1-{2-[3-(2-{3-chloro-4-[(1-methylethyl)oxy]phenyl}-1,3-thiazol-5-yl)-2-ethylphenyl]ethyl}-3-azetidinecarboxylate (D90) (120 mg) in isopropanol (40 mL) and water (10 mL) stirred under nitrogen at room temperature was added a solution of NaOH (9.62 mg) in water in one charge. The reaction mixture was stirred at room temperature overnight. Isopropanol was removed in vacuo. The residue was dissolved in water and acidified with 1N HCl to pH=5. The solvent was removed in vacuo, the residue was dissolved in THF, and filtered. The filtrate was purified by Mass Directed AutoPrep to give 1-{2-[3-(2-{3-chloro-4-[(1-methylethyl)oxy]phenyl}-1,3-thiazol-5-yl)-2-ethylphenyl]ethyl}-3-azetidinecarboxylic acid (E41) (12 mg) as a TFA salt (white solid). δH (DMSO-$d_6$, 400 MHz): 1.07 (3H, t), 1.34 (6H, d), 2.70 (2H, m), 2.87 (2H, m), 3.59 (3H, m), 4.29 (4H, m), 4.79 (1H, m), 7.30 (4H, m), 7.82 (1H, s), 7.87 (1H, dd), 7.99 (1H, d), 10.06 (1H, br s), 13.15 (1H, br s). δF (DMSO-$d_6$, 376 MHz): −73.6. MS (ES): $C_{26}H_{29}ClN_2O_3S$ requires 484. found 485.2 (M+H$^+$).

EXAMPLE 42

1-[(3-{2-[3-cyano-4-(2-methylpropyl)phenyl]-1,3-thiazol-5-yl}-2-ethylphenyl)methyl]-4-piperidinecarboxylic acid trifluoroacetate (E42)

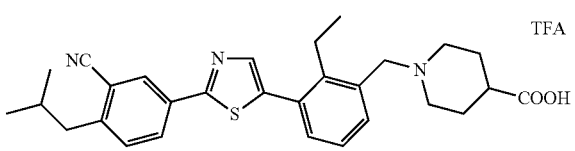 [SMILES: CCc1c(CN2CCC(C(=O)O)CC2)cccc1-c1cnc(-c2ccc(CC(C)C)c(C#N)c2)s1]

A solution of 5-[5-(2-ethyl-3-formylphenyl)-1,3-thiazol-2-yl]-2-(2-methylpropyl)benzonitrile (D92) (150 mg), ethyl 4-piperidinecarboxylate (63.0 mg) and acetic acid (0.1 mL) in dichloromethane (DCM) (10 mL) was stirred at room temperature for 15 min, then sodium triacetoxyborohydride (255 mg) was added. The mixture was stirred at room temperature for 2 h, then formaldehyde (0.11 mL) was added. The mixture was stirred at room temperature overnight. After concentration, the residue was partitioned between ethyl acetate and water, washed with saturated brine. The organic phase was collected and evaporated, the residue was dissolved in DMF (5 mL) and 2M NaOH (2 mL) solution was added. The mixture was stirred at 50° C. for 1 h, then cooled to room temperature. This reaction mixture was acidified with 2M HCl to pH 5-6, extracted with ethyl acetate for three times. The combined organic phase was concentrated and the residue purified by Mass Directed AutoPrep to afford 1-[(3-{2-[3-cyano-4-(2-methylpropyl)phenyl]-1,3-thiazol-5-yl}-2-ethylphenyl)methyl]-4-piperidinecarboxylic acid (E42) (40 mg) as a TFA salt. δH (DMSO-$d_6$, 400 MHz): 0.92 (6H, d), 1.02 (3H, t), 1.78 (2H, m), 1.98 (2H, m), 2.07 (2H, m), 2.73 (2H, d), 2.83 (2H, m), 3.19 (2H, m), 3.46 (2H, m), 4.41 (2H, m), 7.48 (2H, t), 7.63 (2H, m), 7.96 (1H, s), 8.22 (1H, dd), 8.35 (1H, d), 9.23 (1H, br s), 12.58 (1H, br s). δF (DMSO-$d_6$, 376 MHz): −74.2. MS (ES): $C_{29}H_{33}N_3O_2S$ requires 487. found 488.3 (M+H$^+$).

EXAMPLE 43

1-[(3-{2-[3-cyano-4-(2-methylpropyl)phenyl]-1,3-thiazol-5-yl}-2-ethylphenyl)methyl]-3-azetidinecarboxylic acid trifluoroacetate (E43)

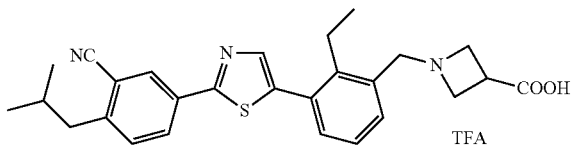 [SMILES: CCc1c(CN2CC(C(=O)O)C2)cccc1-c1cnc(-c2ccc(CC(C)C)c(C#N)c2)s1]

A solution of 5-[5-(2-ethyl-3-formylphenyl)-1,3-thiazol-2-yl]-2-(2-methylpropyl)benzonitrile (D92) (120 mg), 3-azetidinecarboxylic acid (64.8 mg) and acetic acid (0.1 mL) in ethanol (10 mL) was stirred at room temperature for 15 min, then sodium cyanoborohydride (60.4 mg) was added. The mixture was stirred at room temperature for 6 h, then formaldehyde (0.11 mL) was added. The mixture was stirred at room temperature overnight. After concentration, the residue was acidified with 2M HCl to pH 5-6, ethyl acetate was added, the organic phase was washed with saturated brine, then dried and evaporated. The residue was purified by Mass Directed AutoPrep to afford 1-[(3-{2-[3-cyano-4-(2-methylpropyl)phenyl]-1,3-thiazol-5-yl}-2-ethylphenyl)methyl]-3-azetidinecarboxylic acid (E43) (32 mg) as a TFA salt. δH (DMSO-$d_6$, 400 MHz): 0.92 (6H, d), 1.05 (3H, t), 1.98 (1H, m), 2.76 (4H, m), 3.65 (1H, m), 4.27 (4H, m), 4.54 (2H, br. s.), 7.40 (1H, m), 7.48 (2H, m), 7.62 (1H, d), 7.94 (1H, s), 8.22 (1H, dd), 8.35 (1H, d), 10.21 (1H, br s), 13.19 (1H, br s). δF (DMSO-d$_6$, 376 MHz): −73.5. MS (ES): C$_{27}$H$_{29}$N$_3$O$_2$S requires 459. found 460.2 (M+H$^+$).

EXAMPLE 44

1-{[3-(5-{3-chloro-4-[(1-methylethyl)oxy]phenyl}-1,3,4-thiadiazol-2-yl)-2-ethylphenyl]methyl}-3-pyrrolidinecarboxylic acid trifluoroacetate (E44)

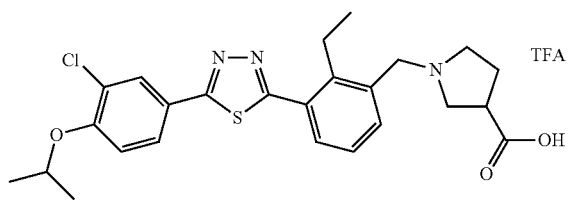 [SMILES: CCc1c(CN2CCC(C(=O)O)C2)cccc1-c1nnc(-c2ccc(OC(C)C)c(Cl)c2)s1]

To a solution of 3-(5-{3-chloro-4-[(1-methylethyl)oxy]phenyl}-1,3,4-thiadiazol-2-yl)-2-ethylbenzaldehyde (100 mg, 0.258 mmol) (D11) in Ethanol (10 mL) stirred at room temperature was added 3-pyrrolidinecarboxylic acid (119 mg, 1.034 mmol) and AcOH (0.15 mL, 2.62 mmol). The reaction mixture was stirred at room temperature for 10 min, and sodium triacetoxyborohydride (110 mg, 0.522 mmol) was added. The reaction mixture was continuously stirred overnight. The reaction was quenched with water, and EtOH was evaporated in vacuo. The mixture was extracted by EA/THF for 3 times. The combined organic solution was washed by brine, dried over anhydrous Na$_2$SO$_4$. The dried solution was filtered and concentrated, and dissolved in THF. The residue was purified by Mass Directed AutoPrep to afford 1-{[3-(5-{3-chloro-4-[(1-methylethyl)oxy]phenyl}-1,3,4-thiadiazol-2-yl)-2-ethylphenyl]methyl}-3-pyrrolidinecarboxylic acid (E44) (58 mg) as a TFA salt (off-white solid).

EXAMPLE 44-47

The following examples were prepared using similar procedures to that described for Example 44.

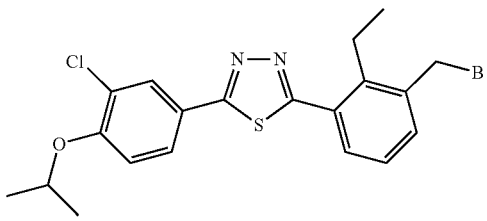

| Example | B | Salt form | characterization |
|---|---|---|---|
| 44 | ![pyrrolidine-COOH] | TFA | δH (DMSO-d$_6$, 400 MHz): 1.07 (3 H, t), 1.35 (6 H, d), 2.07 (1 H, m), 2.21 (1 H, m), 2.37 (1 H, m), 2.97 (2 H, m), 3.30 (3 H, m), 3.50 (6 H, m), 3.73 (2 H, m), 4.56 (2 H, m), 4.85 (1 H, m), 7.39 (1 H, d), 7.51 (1 H, m), 7.74 (1 H, d), 7.69 (1 H, d), 7.97 (1 H, dd), 8.11 (1 H, d), 9.90 (1 H, br. s.), 12.95 (1 H, br. s.). δF (DMSO-d$_6$, 376 MHz): −73.5. MS (ES): C$_{25}$H$_{28}$ClN$_3$O$_3$S requires 485.1; found 486.1 (M + H$^+$) |
| 45 | ![pyrrolidine-COOH] | TFA | δH (DMSO-d$_6$, 400 MHz): 1.08 (3 H, t), 1.35 (6 H, d), 2.07 (1 H, m.), 2.33 (1 H, m), 2.67 (2 H, m), 2.96 (2 H, d), 3.73 (1 H, m), 4.57 (2 H, m), 4.85 (1 H, dt), 7.39 (1 H, d), 7.68 (2 H, m), 7.97 (1 H, dd), 8.10 (1 H, d), 9.87 (1 H, m), 12.94 (1 H, br. s.). δF (DMSO-d$_6$, 376 MHz): −73.5. MS (ES): C$_{25}$H$_{28}$ClN$_3$O$_3$S requires 485.1; found 486.2 (M + H$^+$) |
| 46 | ![piperidine-COOH] | | δH (DMSO-d$_6$, 400 MHz): 1.10 (3 H, t), 1.35 (6 H, d), 1.43 (2 H, m.), 1.63 (1 H, m), 1.81 (1 H, d), 2.06 (1 H, m), 2.19 (1 H, m), 2.35 (1 H, m), 2.67 (1 H, d), 2.84 (1 H, m), 2.91 (2 H, m), 3.56 (2 H, m), 4.84 (1 H, dt), 7.35 (2 H, m), 7.50 (2 H, d), 7.96 (1 H, dd), 8.10 (1 H, d). MS (ES): C$_{26}$H$_{30}$ClN$_3$O$_3$S requires 499.1; found 500.1 (M + H$^+$) |
| 47 | ![piperidine-COOH] | | δH (DMSO-d$_6$, 400 MHz): 1.10 (3 H, t), 1.35 (7 H, d), 1.46 (1 H, m), 1.63 (1 H, m), 1.82 (1 H, m), 2.07 (1 H, m), 2.19 (1 H, m), 2.41 (1 H, m), 2.67 (1 H, m), 2.91 (3 H, dd), 3.56 (2 H, m), 4.84 (1 H, dt), 7.35 (2 H, m), 7.50 (2 H, d), 7.96 (1 H, dd), 8.09 (1 H, d), 12.22 (1 H, br. s.). MS (ES): C$_{26}$H$_{30}$ClN$_3$O$_3$S requires 499.1; found 500.1 (M + H$^+$) |

EXAMPLE 48

1-[(3-{5-[3-cyano-4-(2-methylpropyl)phenyl]-1,3,4-thiadiazol-2-yl}-2-ethylphenyl)methyl]-3-pyrrolidinecarboxylic acid (E48)

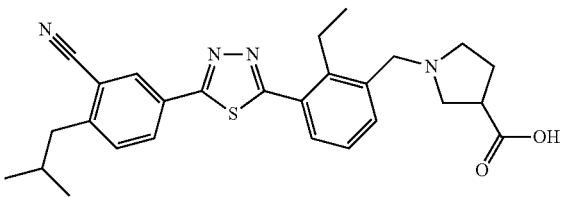 [SMILES: CCc1c(CN2CCC(C(=O)O)C2)cccc1-c1nnc(-c2ccc(CC(C)C)c(C#N)c2)s1]

To a solution of 5-[5-(2-ethyl-3-formylphenyl)-1,3,4-thiadiazol-2-yl]-2-(2-methylpropyl)benzonitrile (D27) (100 mg, 0.266 mmol) in Ethanol (10 mL) stirred at room temperature was added 3-pyrrolidinecarboxylic acid (123 mg, 1.065 mmol) and AcOH (0.15 mL, 2.62 mmol). The reaction mixture was stirred at room temperature for 10 min, and sodium triacetoxyborohydride (110 mg, 0.522 mmol) was added. The reaction mixture was continuously stirred overnight. The reaction was quenched with water, and EtOH was evaporated in vacuo. The mixture was extracted by EA for 3 times. The combined organic solution was washed by brine, dried over anhydrous $Na_2SO_4$. The dried solution was filtered and concentrated, and purified by Mass Directed AutoPrep to afford 1-[(3-{5-[3-cyano-4-(2-methylpropyl)phenyl]-1,3,4-thiadiazol-2-yl}-2-ethylphenyl)methyl]-3-pyrrolidinecarboxylic acid (E48) (55 mg) as a off-white solid.

EXAMPLE 48-51

The following examples may be prepared using similar procedures described for Example 48.

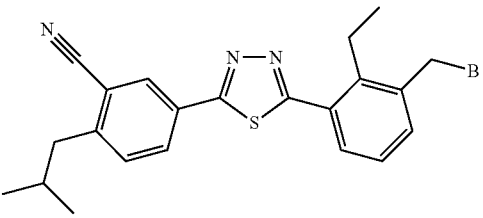

| Example | B | characterization |
|---|---|---|
| 48 | pyrrolidine-3-carboxylic acid (racemic) | δH (DMSO-$d_6$, 400 MHz): 0.94 (6 H, d), 1.10 (3 H, t), 1.98 (3 H, m), 2.54 (2 H, t), 2.71 (4 H, m), 2.93 (3 H, m), 3.34 (2 H, m), 7.35 (1 H, m), 7.54 (1 H, d), 7.52 (1 H, d), 7.67 (1 H, d), 8.31 (1 H, dd), 8.46 (1 H, d), 12.3 (1 H, br. s.). MS (ES): $C_{27}H_{30}N_4O_2S$ requires 474.2; found 475.2 (M + H$^+$) |
| 49 | pyrrolidine-3-carboxylic acid (chiral) | δH (DMSO-$d_6$, 400 MHz): 0.94 (6 H, d), 1.10 (3 H, t), 1.98 (3 H, m), 2.54 (2 H, t), 2.71 (4 H, m), 2.93 (3 H, m), 3.33 (2 H, m), 7.35 (1 H, m), 7.54 (1 H, d), 7.51 (1 H, d), 7.67 (1 H, d), 8.31 (1 H, dd), 8.46 (1 H, d). MS (ES): $C_{27}H_{30}N_4O_2S$ requires 474.2; found 475.2 (M + H$^+$) |
| 50 | piperidine-3-carboxylic acid | δH (DMSO-$d_6$, 400 MHz): 0.94 (6 H, d), 1.10 (3 H, t), 1.42 (2 H, m), 1.64 (1 H, m), 1.83 (1 H, m), 2.01 (2 H, m), 2.21 (1 H, d), 2.40 (1 H, m), 2.65 (1 H, m), 2.77 (2 H, d), 2.89 (3 H, m), 3.56 (2 H, m), 7.35 (1 H, t), 7.52 (2 H, d), 7.67 (1 H, d), 8.31 (1 H, d), 8.46 (1 H, s), 12.22 (1 H, br. s.). MS (ES): $C_{28}H_{32}N_4O_2S$ requires 488.2; found 489.2 (M + H$^+$) |
| 51 | piperidine-3-carboxylic acid (chiral) | δH (DMSO-$d_6$, 400 MHz): 0.94 (6 H, d), 1.10 (3 H, t), 1.44 (2 H, m), 1.64 (1 H, m), 1.83 (1 H, m), 1.99 (1 H, dt), 2.10 (1 H, m), 2.21 (1 H, m), 2.39 (1 H, m), 2.67 (1 H, m), 2.77 (2 H, d), 2.85 (1 H, m), 2.90 (2 H, m), 3.57 (2 H, m), 7.35 (1 H, m), 7.52 (2 H, d), 7.68 (1 H, d), 8.31 (1 H, d), 8.46 (1 H, s), 12.23 (1 H, br. s.). MS (ES): $C_{28}H_{32}N_4O_2S$ requires 488.2; found 489.2 (M + H$^+$) |

EXAMPLE 52

(3S)-1-{2-[3-(5-{3-chloro-4-[(1-methylethyl)oxy]phenyl}-1,3,4-thiadiazol-2-yl)-2-ethylphenyl]ethyl}-3-pyrrolidinecarboxylic acid (E52)

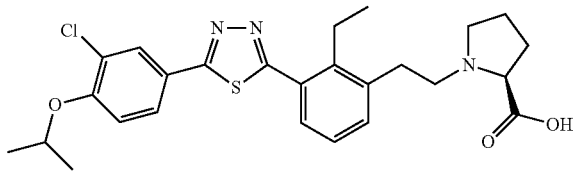 [SMILES: CCc1c(CCN2CCC[C@H]2C(=O)O)cccc1-c1nnc(-c2ccc(OC(C)C)c(Cl)c2)s1]

To a solution of [3-(5-{3-chloro-4-[(1-methylethyl)oxy]phenyl}-1,3,4-thiadiazol-2-yl)-2-ethylphenyl]acetaldehyde (90 mg, 0.224 mmol) (D15) in Dichloromethane (DCM) (20 mL) stirred at room temperature was added methyl L-prolinate (149 mg, 0.898 mmol) and AcOH (0.15 mL, 2.62 mmol). The reaction mixture was stirred at room temperature for 10 min, and sodium triacetoxyborohydride (110 mg, 0.522 mmol) was added. The reaction mixture was continuously stirred overnight. The reaction was quenched with water, and EtOH was evaporated in vacuo. i-PrOH was added, followed by sodium hydroxide (8.98 mg, 0.224 mmol). The reaction mixture was stirred for another 2 hours. i-PrOH was evaporated in vacuo. The aqeuous layer was extracted by EA/THF for 3 times. The combined organic solution was washed by brine. The organic layers were concentrated, and purified by Mass Directed AutoPrep to afford 1-{2-[3-(5-{3-chloro-4-[(1-methylethyl)oxy]phenyl}-1,3,4-thiadiazol-2-yl)-2-ethylphenyl]ethyl}-L-proline (E52) (24 mg) as a off-white solid.

EXAMPLE 52-57

The following examples may be prepared using similar procedures described for Example 52.

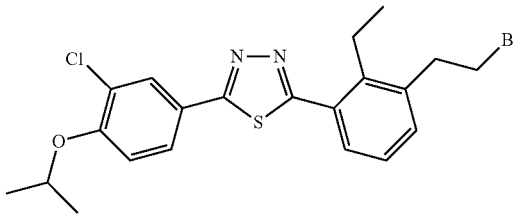

| Example | B | characterization |
|---|---|---|
| 52 | ![pyrrolidine-2-carboxylic acid] | δH (DMSO-d$_6$, 400 MHz): 1.11 (3 H, t), 1.35 (6 H, d), 1.72 (1 H, m), 1.92 (2 H, m), 2.16 (1 H, dq), 2.86 (3 H, m), 3.02 (3 H, m), 3.17 (2 H, m), 3.66 (1 H, m), 4.84 (1 H, dt), 7.35 (2 H, m), 7.47 (2 H, d), 7.95 (1 H, dd), 8.09 (1H, d) MS (ES): C$_{26}$H$_{30}$ClN$_3$O$_3$S requires 499.1; found 500.2 (M + H$^+$) |
| 53 | ![pyrrolidine-2-carboxylic acid] | δH (DMSO-d$_6$, 400 MHz): 1.12 (3 H, t), 1.35 (6 H, d), 1.72 (1 H, m), 1.92 (2 H, m), 2.15 (1 H, m), 2.86 (3 H, m), 3.02 (3 H, m), 3.18 (1 H, m), 3.45 (1H, m), 3.63 (1H, m), 4.84 (1 H, dt), 7.36 (2 H, m), 7.47 (2 H, d), 7.96 (1 H, dd), 8.09 (1 H, d). MS (ES): C$_{26}$H$_{30}$ClN$_3$O$_3$S requires 499.1; found 500.2 (M + H$^+$) |
| 54 | ![pyrrolidine-3-carboxylic acid] | δH (DMSO-d$_6$, 400 MHz): 1.12 (3 H, t), 1.35 (6 H, d), 1.95 (2 H, m), 2.62 (5 H, m), 2.88 (6 H, m), 4.84 (1 H, dt), 7.31 (1 H, m), 7.40 (3 H, m), 7.95 (1 H, dd), 8.09 (1 H, d). MS (ES): C$_{26}$H$_{30}$ClN$_3$O$_3$S requires 499.1; found 500.2 (M + H$^+$) |
| 55 | ![4-hydroxypyrrolidine-2-carboxylic acid] | δH (DMSO-d$_6$, 400 MHz): 1.11 (3 H, t), 1.34 (6 H, d), 2.01 (2 H, m), 2.70 (1H, m), 2.84 (2 H, dd), 2.96 (3 H, m), 3.13 (1 H, m), 3.22 (1 H, s), 3.51 (2 H, dd), 3.67 (1 H, t), 4.26 (1 H, m), 4.84 (1 H, dt), 5.16 (1 H, br. s.), 7.35 (2 H, m), 7.46 (2 H, d), 7.95 (1 H, dd), 8.09 (1 H, d) MS (ES): C$_{26}$H$_{30}$ClN$_3$O$_4$S requires 515.1; found 516.1 (M + H$^+$) |

-continued

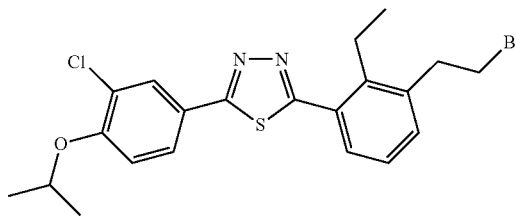

| Example | B | characterization |
|---|---|---|
| 56 | 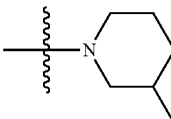 | δH (DMSO-d$_6$, 400 MHz): 1.12 (3 H, t), 1.36 (7 H, m), 1.51 (1 H, m), 1.67 (1 H, m), 1.81 (1 H, m), 2.16 (1 H, m), 2.32 (1 H, m), 2.66 (3 H, m), 2.84 (5 H, dt), 2.96 (1 H, m.), 4.83 (1 H, m), 7.36 (4 H, m), 7.95 (1 H, dd), 8.09 (1 H, d). MS (ES): C$_{27}$H$_{32}$ClN$_3$O$_3$S requires 513.2; found 514.2 (M + H$^+$) |
| 57 | 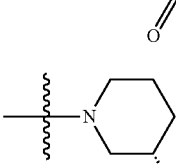 | δH (DMSO-d$_6$, 400 MHz): 1.15 (3 H, m), 1.35(6 H, m), 1.49 (2 H, m), 1.66 (1 H, m), 1.80 (1 H, m), 2.10 (1 H, m), 2.23 (1 H, m), 2.43 (1 H, m), 2.55 (2 H, m), 2.83 (5 H, m), 2.97 (1 H, m), 4.83 (1 H, dt), 7.36 (4 H, m), 7.95 (1 H, dd), 8.09 (1 H, d), 12.26 (1 H, br. s.). MS (ES): C$_{27}$H$_{32}$ClN$_3$O$_3$S requires 513.2; found 514.2 (M + H$^+$) |

EXAMPLE 58

1-{2-[3-(5-{3-chloro-4-[(1-methylethyl)oxy]phenyl}-1,3,4-thiadiazol-2-yl)-2-methylphenyl]ethyl}-4-piperidinecarboxylic acid (E58)

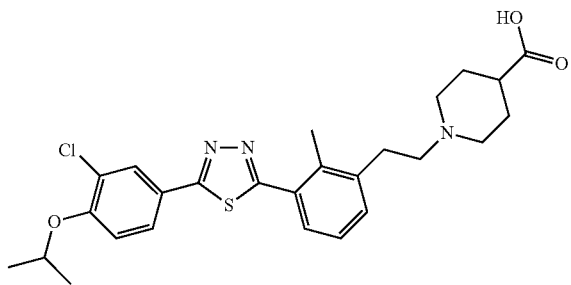 [SMILES: Cc1c(CCN2CCC(C(=O)O)CC2)cccc1-c1nnc(-c2ccc(OC(C)C)c(Cl)c2)s1]

To a solution of [3-(5-{3-chloro-4-[(1-methylethyl)oxy]phenyl}-1,3,4-thiadiazol-2-yl)-2-methylphenyl]acetaldehyde (118 mg, 0.305 mmol) (D97) in Dichloromethane (DCM) (20 mL) stirred at room temperature was added ethyl 4-piperidinecarboxylate (192 mg, 1.220 mmol) and AcOH (0.15 mL, 2.62 mmol). The reaction mixture was stirred at room temperature for 10 min, and sodium triacetoxyborohydride (129 mg, 0.610 mmol) was added. The reaction mixture was continuously stirred for 1 day. The reaction was quenched with water, and DCM was evaporated in vacuo. Sodium hydroxide (12.20 mg, 0.305 mmol) and i-PrOH was added. The reaction mixture was continuously stirred for 2 hours. 1M HCl solution was added until PH=6-7. i-PrOH was evaporated in vacuo. The aqueous layers were extracted by EA/THF for 3 times. The combined organic layers were concentrated, and purified by Mass Directed AutoPrep to afford 1-{2-[3-(5-{3-chloro-4-[(1-methylethyl)oxy]phenyl}-1,3,4-thiadiazol-2-yl)-2-methylphenyl]ethyl}-4-piperidinecarboxylic acid (E58) (80 mg) as a off-white solid. δH (DMSO-d$_6$, 400 MHz): 1.35 (6H, d), 1.55 (2H, m), 1.81 (2H, m), 2.05 (2H, t), 2.18 (1H, tt), 2.41 (3H, s), 2.45 (2H, m), 2.87 (4H, m), 4.83 (1H, dt), 7.30 (1H, m), 7.41 (3H, m), 7.94 (1H, dd), 8.08 (1H, d). MS (ES): C$_{26}$H$_{30}$ClN$_3$O$_3$S requires 499.2. found 500.2 (M+H$^+$).

EXAMPLE 59

1-[2-(3-{5-[3-cyano-4-(2-methylpropyl)phenyl]-1,3,4-thiadiazol-2-yl}-2-ethylphenyl)ethyl]-L-proline (E59)

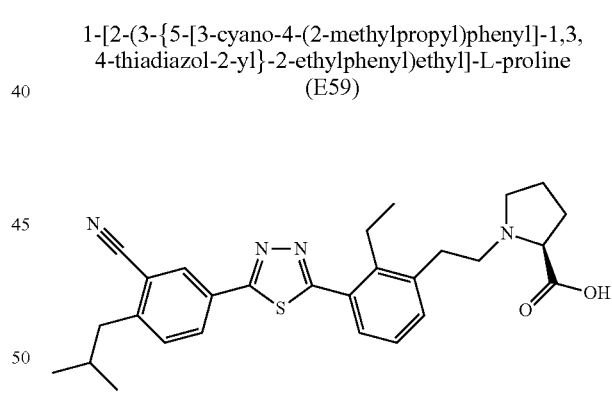

To a solution of 5-{5-[2-ethyl-3-(2-oxoethyl)phenyl]-1,3,4-thiadiazol-2-yl}-2-(2-methylpropyl)benzonitrile (D31) (99 mg, 0.254 mmol) in Ethanol (15 mL) stirred at room temperature was added L-proline (117 mg, 1.017 mmol) and AcOH (0.15 mL, 2.62 mmol). The reaction mixture was stirred at room temperature for 10 min, and sodium cyanoborohydride (31.9 mg, 0.508 mmol) was added. The reaction mixture was continuously stirred overnight. The reaction was quenched with water and DCM was evaporated in vacuo. The mixture was extracted by EA/THF for 3 times. The combined organic solution was washed with brine, concentrated and purified by Mass Directed AutoPrep to afford 1-[2-(3-{5-[3-cyano-4-(2-methylpropyl)phenyl]-1,3,4-thiadiazol-2-yl}-2-ethylphenyl)ethyl]-L-proline (E59) (52 mg) as a off-white solid.

EXAMPLE 59-64

The following examples may be prepared using similar procedures described for Example 59.

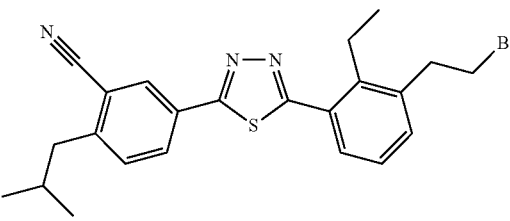

| Example | B | characterization |
|---|---|---|
| 59 | ![pyrrolidine-2-COOH] | δH (DMSO-d$_6$, 400 MHz): 0.94 (6 H, d), 1.12 (3 H, t), 1.74 (1 H, m), 1.95 (3 H, m), 2.18 (1 H, m), 2.77 (2 H, d), 2.87 (3 H, dd), 3.03 (3 H, m), 3.17 (1 H, m), 3.51 (1 H, m), 3.62 (1 H, dd), 7.36 (1 H, t), 7.49 (2 H, d), 7.67 (1 H, d), 8.31 (1 H, d), 8.46 (1 H, s). MS (ES): C$_{28}$H$_{32}$N$_4$O$_2$S requires 488.2; found 489.2 (M + H$^+$) |
| 60 | ![pyrrolidine-2-COOH] | δH (DMSO-d$_6$, 400 MHz): 0.94 (6 H, d), 1.12 (3 H, t), 1.73 (1 H, m), 1.95 (3 H, m), 2.16 (1 H, m), 2.77 (2 H, d), 2.86 (3 H, dd), 3.04 (3 H, m), 3.20 (1 H, m), 3.51 (1 H, m), 3.63 (1 H, dd), 7.36 (1 H, t), 7.49 (2 H, d), 7.68 (1 H, d), 8.31 (1 H, d), 8.46 (1 H, s). MS (ES): C$_{28}$H$_{32}$N$_4$O$_2$S requires 488.2; found 489.2 (M + H$^+$) |
| 61 | ![pyrrolidine-3-COOH] | δH (DMSO-d$_6$, 400 MHz): 0.94 (6 H, d), 1.12 (3 H, t), 1.99 (3 H, m), 2.62 (5 H, m), 2.85 (8 H, m), 7.32 (1 H, t), 7.45 (2 H, dd), 7.67 (1 H, d), 8.30 (1 H, dd), 8.45 (1 H, d). MS (ES): C$_{28}$H$_{32}$N$_4$O$_2$S requires 488.2; found 489.2 (M + H$^+$) |
| 62 | ![pyrrolidine-3-COOH] | δH (DMSO-d$_6$, 400 MHz): 0.94 (6 H, d), 1.12 (3 H, t), 1.98 (3 H, m), 2.63 (5 H, m), 2.86 (8 H, m), 7.32 (1 H, t), 7.45 (2 H, dd), 7.67 (1 H, d), 8.31 (1 H, dd), 8.45 (1 H, d). MS (ES): C$_{28}$H$_{32}$N$_4$O$_2$S requires 488.2; found 489.2 (M + H$^+$) |
| 63 | ![piperidine-3-COOH] | δH (DMSO-d$_6$, 400 MHz): 0.94 (6 H, d), 1.12 (3 H, t), 1.38 (1 H, m.), 1.48 (1 H, d), 1.66 (1 H, d), 1.80 (1 H, m), 1.99 (2 H, m), 2.23 (1 H, m), 2.41 (2 H, m), 2.57 (1 H, m), 2.82 (7 H, m), 2.95 (1 H, m), 7.32 (1 H, m), 7.44 (2 H, m), 7.67 (1 H, d), 8.31 (1 H, dd), 8.46 (1 H, d), 12.30 (1 H, br. s.). MS (ES): C$_{29}$H$_{34}$N$_4$O$_2$S requires 502.2; found 503.2 (M + H$^+$) |
| 64 | ![piperidine-3-COOH] | δH (DMSO-d$_6$, 400 MHz): 0.94 (6 H, d), 1.12 (3 H, t), 1.43 (2 H, m), 1.66 (1 H, dd), 1.81 (1 H, dd), 1.99 (1 H, dt), 2.11 (1 H, m), 2.23 (1 H, m), 2.43 (1 H, ddd), 2.55 (2 H, m), 2.83 (7 H, m), 2.98 (1 H, m), 7.32 (1 H, m), 7.44 (2 H, m), 7.67 (1 H, d), 8.30 (1 H, dd), 8.45 (1 H, d), 12.27 (1 H, br. s.). MS (ES): C$_{29}$H$_{34}$N$_4$O$_2$S requires 502.2; found 503.2 (M + H$^+$) |

EXAMPLE 65

1-{2-[3-(5-{3-chloro-4-[(1-methylethyl)oxy]phenyl}-1,2,4-thiadiazol-3-yl)-2-ethylphenyl]ethyl}-L-proline trifluoroacetate (E65)

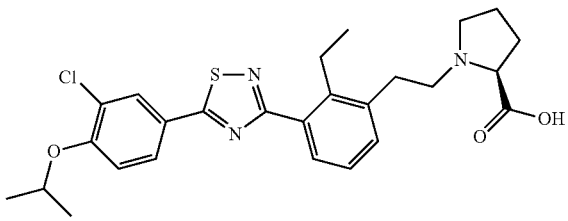 [SMILES: CCc1c(CCN2CCC[C@H]2C(=O)O)cccc1-c1nsc(-c2ccc(OC(C)C)c(Cl)c2)n1]

To a solution of [3-(5-{3-chloro-4-[(1-methylethyl)oxy]phenyl}-1,2,4-thiadiazol-3-yl)-2-ethylphenyl]acetaldehyde (D52) (110 mg, 0.274 mmol) in Dichloromethane (DCM) (10 mL) was added sodium acetate (33.8 mg, 0.412 mmol) and hydrogen chloride-methyl L-prolinate (1:1) (68.2 mg, 0.412 mmol). After 5 minutes, sodium triacetoxyborohydride (87 mg, 0.412 mmol) was added and the reaction solution was stirred at room temperature overnight. The solvent was removed in vacuo and the residue was hydrolized by NaOH (2.74 mL, 1.372 mmol) in isopropanol/water (10 mL, 1:1). The residue was purified by Mass Directed AutoPrep to afford 1-{2-[3-(5-{3-chloro-4-[(1-methylethyl)oxy]phenyl}-1,2,4-thiadiazol-3-yl)-2-ethylphenyl]ethyl}-L-proline (E65) (56 mg) as a TFA salt.

EXAMPLE 65-72

The following examples were prepared using similar procedures to that described for Example 65.

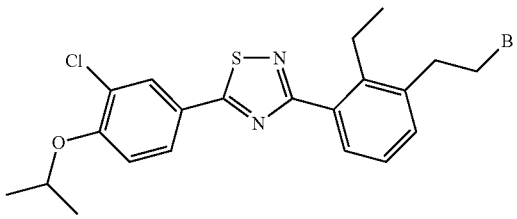

| Example | B | Salt form | characterization |
|---|---|---|---|
| 65 | pyrrolidine-2-carboxylic acid (L-proline, S) | TFA | δH (DMSO-$d_6$, 400 MHz): 1.08 (3H, t), 1.28 (6H, d), 1.88 (1H, m), 2.04 (2H, m), 2.39 (1H, m), 2.87 (2H, m), 3.06 (3H, m), 3.31 (2H, m), 3.70 (1H, m), 4.36 (1H, m), 4.80 (1H, m), 7.34 (3H, m), 7.66 (1H, dd), 7.95 (1H, dd), 8.08 (1H, d). δF (DMSO-$d_6$, 376 MHz): −73.5. MS (ES): $C_{26}H_{30}ClN_3O_3S$ requires 499.2; found 500.2 (M + H$^+$). |
| 66 | pyrrolidine-2-carboxylic acid (R) |  | δH (DMSO-$d_6$, 400 MHz): 1.06 (3H, t), 1.28 (6H, d), 1.67 (1H, m), 1.87 (2H, m), 2.09 (1H, m), 2.90 (7H, m), 3.14 (1H, m), 3.58 (1H, m), 4.80 (1H, m), 7.24 (1H, t), 7.34 (2H, m), 7.62 (1H, dd), 7.95 (1H, dd), 8.07 (1H, d). MS (ES): $C_{26}H_{30}ClN_3O_3S$ requires 499.2; found 500.2 (M + H$^+$). |
| 67 | pyrrolidine-3-carboxylic acid | TFA | δH (DMSO-$d_6$, 400 MHz): 1.07 (3H, t), 1.28 (6H, d), 2.09 (1H, m), 2.24 (1H, m), 2.86 (2H, q), 3.02 (2H, m), 3.70 (7H, m br), 4.80 (1H, m), 7.32 (3H, m), 7.65 (1H, d), 7.95 (1H, dd), 8.08 (1H, d). δF (DMSO-$d_6$, 376 MHz): −73.5. MS (ES): $C_{26}H_{30}ClN_3O_3S$ requires 499.2; found 500.2 (M + H$^+$). |
| 68 | pyrrolidine-3-carboxylic acid (R) |  | δH (DMSO-$d_6$, 400 MHz): 1.06 (3H, t), 1.28 (6H, d), 1.90 (2H, m), 2.57 (5H, m), 2.80 (6H, m), 4.79 (1H, m), 7.20 (1H, t), 7.31 (2H, m), 7.57 (1H, d), 7.94 (1H, dd), 8.07 (1H, d). δF (DMSO-$d_6$, 376 MHz): −73.4. MS (ES): $C_{26}H_{30}ClN_3O_3S$ requires 499.2; found 500.2 (M + H$^+$). |
| 69 | 4-hydroxypyrrolidine-2-carboxylic acid | TFA | δH (DMSO-$d_6$, 400 MHz): 1.07 (3H, t), 1.28 (6H, d), 2.18 (2H, m), 2.86 (2H, m), 3.03 (3H, m), 3.17 (2H, m), 3.70 (1H, m), 4.35 (1H, s), 4.45 (1H, s), 4.78 (1H, m), 5.53 (1H, s), 7.30 (3H, m), 7.65 (1H, dd), 7.95 (1H, dd), 8.08 (1H, d). δF (DMSO-$d_6$, 376 MHz): −73.5. MS (ES): $C_{26}H_{30}ClN_3O_4S$ requires 515.2; found 516.2 (M + H$^+$). |

-continued

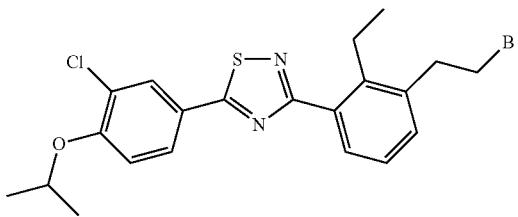

| Example | B | Salt form | characterization |
|---|---|---|---|
| 70 | | TFA | δH (DMSO-d₆, 400 MHz): 1.08 (3H, t), 1.28 (6H, d), 1.41 (1H, m), 1.87 (4H, m), 2.71 (1H, m), 2.86 (3H, m), 3.00 (4H, m), 3.60 (2H, m), 4.80 (1H, m), 7.31 (3H, m), 7.66 (1H, d), 7.95 (1H, dd), 8.07 (1H, d), 9.63 (1H, s br). δF (DMSO-d₆, 376 MHz): −73.5. MS (ES): $C_{27}H_{32}ClN_3O_3S$ requires 513.2; found 514.2 (M + H⁺) |
| 71 | | TFA | δH (DMSO-d₆, 400 MHz): 1.08 (3H, t), 1.28 (6H, d), 1.42 (1H, m), 1.91 (3H, m), 2.71 (1H, m), 2.90 (6H, m), 3.28 (2H, m), 3.60 (2H, m), 4.79 (1H, m), 7.32 (3H, m), 7.66 (1H, d), 7.95 (1H, dd), 8.08 (1H, d), 9.67 (1H, s br). δF (DMSO-d₆, 376 MHz): −73.6. MS (ES): $C_{27}H_{32}ClN_3O_3S$ requires 513.2; found 514.2 (M + H⁺) |
| 72 | | TFA | δH (DMSO-d₆, 400 MHz): 1.08 (3H, t), 1.28 (6H, d), 1.40 (2H, m), 1.86 (3H, m), 2.20 (2H, m), 2.91 (6H, m), 3.18 (2H, m), 3.58 (2H, m), 4.80 (1H, m), 7.30 (3H, m), 7.66 (1H, d), 7.95 (1H, dd), 8.08 (1H, d), 9.30 (1H, s br). δF (DMSO-d₆, 376 MHz): −73.5. MS (ES): $C_{28}H_{34}ClN_3O_3S$ requires 513.2; found 528.3 (M + H⁺) |

EXAMPLE 73

1-{2-[3-(5-{3-chloro-4-[(1-methylethyl)oxy]phenyl}-1,2,4-thiadiazol-3-yl)-2-(methyloxy)phenyl]ethyl}-4-piperidinecarboxylic acid trifluoroacetate (E73)

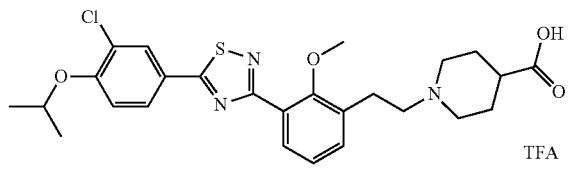 [SMILES: COc1c(CCN2CCC(C(=O)O)CC2)cccc1-c1nsc(-c2ccc(OC(C)C)c(Cl)c2)n1]

To a solution of ethyl 1-{2-[3-(5-{3-chloro-4-[(1-methylethyl)oxy]phenyl}-1,2,4-thiadiazol-3-yl)-2-(methyloxy)phenyl]ethyl}-4-piperidinecarboxylate (D104) (38.7 mg, 0.071 mmol) in Tetrahydrofuran (THF) (10 mL), Ethanol (2 mL) and Water (1 mL) was added sodium hydroxide (56.9 mg, 1.423 mmol). The reaction mixture was stirred at room temperature overnight (16 h). Sodium hydroxide (56.9 mg, 1.423 mmol) was added again. The reaction mixture was stirred at room temperature for 4 hours. The reaction mixture was acidified with 2N HCl solution till pH ~6.0. The organic solvent was removed. Then the mixture was extracted with EA/THF. The combined organic layers were concentrated. The residue was re-dissolved in THF/water and then purified by Mass Directed AutoPrep to afford 1-{2-[3-(5-{3-chloro-4-[(1-methylethyl)oxy]phenyl}-1,2,4-thiadiazol-3-yl)-2-(methyloxy)phenyl]ethyl}-4-piperidinecarboxylic acid (E73) (10 mg) as a TFA salt. δH (DMSO-d₆, 400 MHz): 1.35 (6H, d), 1.78 (2H, m), 1.94 (1H, m), 2.12 (2H, d), 2.55 (1H, m), 3.08 (4H, m), 3.29 (3H, m), 3.49 (3H, m), 3.66 (2H, d), 4.87 (1H, dt), 7.29 (1H, t), 7.40 (1H, d), 7.49 (1H, m), 7.93 (1H, m), 8.04 (1H, dd), 8.16 (1H, d), 9.51 (1H, br. s.), 12.59 (1H, br. s.). δF (DMSO-d₆, 376 MHz): −73.5. MS (ES): $C_{28}H_{34}ClN_3O_3S$ requires 515.2. found 516.2 (M+H⁺).

EXAMPLE 74

1-{2-[3-(5-{3-chloro-4-[(1-methylethyl)oxy]phenyl}-1,2,4-thiadiazol-3-yl)-2-methylphenyl]ethyl}-4-piperidinecarboxylic acid (E74)

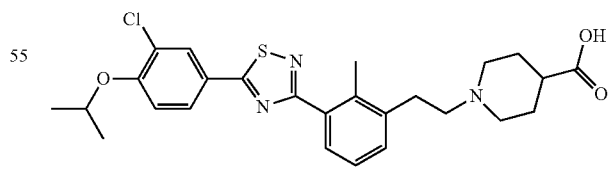

To a solution of [3-(5-{3-chloro-4-[(1-methylethyl)oxy]phenyl}-1,2,4-thiadiazol-3-yl)-2-methylphenyl]acetaldehyde (D106) (120 mg, 0.310 mmol) in Dichloromethane (DCM) (20 mL) stirred at room temperature was added ethyl 4-piperidinecarboxylate (195 mg, 1.241 mmol) and AcOH (0.15 mL, 2.62 mmol). The reaction mixture was stirred at room temperature for 10 min, and sodium triacetoxyborohydride (131 mg, 0.620 mmol) was added. The reaction mixture was continuously stirred overnight. The reaction was quenched with water and DCM was evaporated in vacuo. The residue was dissolved in Isopropanol (8 mL), and sodium hydroxide (50 mg, 1.250 mmol) was added. The reaction was stirred for 2 hours. 1M HCl solution was added until pH=6-7. Isopropanol was removed. The mixture was extracted by EA/THF/MeCN for 3 times. The combined organic solution was washed with brine. The solution was concentrated and purified by Mass Directed AutoPrep to afford 1-{2-[3-(5-{3-chloro-4-[(1-methylethyl)oxy]phenyl}-1,2,4-thiadiazol-3-yl)-2-methylphenyl]ethyl}-4-piperidinecarboxylic acid (E74) (35 mg) as a off-white solid. δH (DMSO-d$_6$, 400 MHz): 1.35 (6H, d), 1.55 (2H, m), 1.81 (2H, m), 2.05 (2H, m), 2.19 (1H, m), 2.46 (3H, s), 2.50 (2H, m), 2.87 (4H, m), 4.86 (1H, dt), 7.26 (1H, m), 7.36 (2H, m), 7.68 (1H, dd), 8.02 (1H, dd), 8.14 (1H, d), 12.18 (1H, br. s.). MS (ES): C$_{26}$H$_{30}$ClN$_3$O$_3$S requires 499.2. found 500.2 (M+H$^+$).

EXAMPLE 75

1-{2-[3-(5-{5-chloro-6-[(1-methylethyl)oxy]-3-pyridinyl}-1,2,4-thiadiazol-3-yl)-2-ethylphenyl]ethyl}-4-piperidinecarboxylic acid trifluoroacetate (E75)

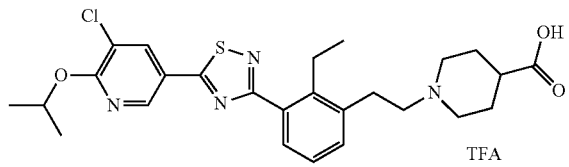 [SMILES: CCc1c(CCN2CCC(C(=O)O)CC2)cccc1-c1nsc(-c2cnc(OC(C)C)c(Cl)c2)n1]

To a solution of ethyl 1-{2-[3-(5-{5-chloro-6-[(1-methylethyl)oxy]-3-pyridinyl}-1,2,4-thiadiazol-3-yl)-2-ethylphenyl]ethyl}-4-piperidinecarboxylate (D112) (200 mg, 0.368 mmol) in Isopropanol (8 mL) and Water (8.00 mL) was added NaOH (3.68 mL, 1.841 mmol). The reaction was stirred at 90° C. for 2 hr before the isopropanol was removed in vacuo. The residue was acidified with aq HCl (2 M) until pH ~2. The aqueous layer was extracted with ethyl acetate and the organic phases were dried and concentrated, purified by Mass Directed AutoPrep to afford 1-{2-[3-(5-{5-chloro-6-[(1-methylethyl)oxy]-3-pyridinyl}-1,2,4-thiadiazol-3-yl)-2-ethylphenyl]ethyl}-4-piperidinecarboxylic acid (E75) (93 mg) as a TFA salt. δH (DMSO-d$_6$, 400 MHz): 1.06 (3H, t), 1.28 (6H, d), 1.68 (2H, m), 2.05 (2H, m), 2.51 (1H, m), 2.73 (2H, m), 3.07 (4H, m), 3.23 (2H, m), 3.48 (1H, m), 3.64 (1H, m), 5.37 (1H, m), 7.30 (2H, m), 7.68 (1H, d), 8.47 (1H, d), 8.81 (1H, d), 9.54 (1H, s br). δF (DMSO-d$_6$, 376 MHz): −73.6. MS (ES): C$_{26}$H$_{31}$ClN$_4$O$_3$S requires 514.2. found 515.0 (M+H$^+$).

EXAMPLE 76

1-[2-(3-{5-[3-cyano-4-(2-methylpropyl)phenyl]-1,2,4-thiadiazol-3-yl}-2-ethylphenyl)ethyl]-L-proline trifluoroacetate (E76)

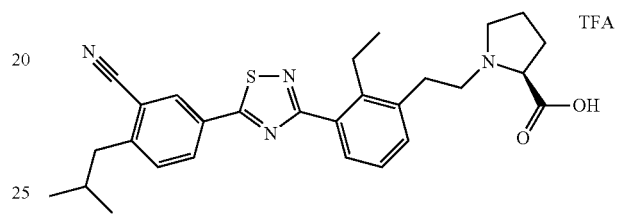

To a solution of 5-{3-[2-ethyl-3-(2-oxoethyl)phenyl]-1,2,4-thiadiazol-5-yl}-2-(2-methylpropyl)benzonitrile (D62) (100 mg, 0.257 mmol) and L-proline (59.1 mg, 0.513 mmol) stirred in Ethanol (10 mL) for 20 min was added sodium cyanoborohydride (48.4 mg, 0.770 mmol). This mixture was stirred at room temperature for 2 h. The reaction was quenched with water, then dried and dissolved in DMF. The residue was purified by for Mass Directed AutoPrep to afford 1-[2-(3-{5-[3-cyano-4-(2-methylpropyl)phenyl]-1,2,4-thiadiazol-3-yl}-2-ethylphenyl)ethyl]-L-proline (E76) (20 mg) as a TFA salt (white solid).

EXAMPLE 76-80

The following examples were prepared using similar procedures to that described for Example 76.

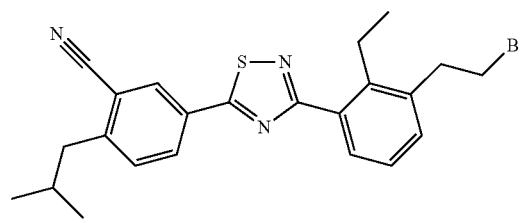

| Example | B | Salt form | characterization |
|---|---|---|---|
| 76 | ![pyrrolidine-COOH] | TFA | δH (DMSO-d$_6$, 400 MHz): 0.92 (6 H, m), 1.13 (3 H, t), 1.76 (1 H, m), 1.96 (3 H, m), 2.22 (1 H, m), 2.77 (2 H, m), 3.03 (6 H, m), 3.24 (1 H, m), 3.57 (1 H, m), 3.79 (1 H, m), 7.32 (1 H, t), 7.44 (1 H, d), 7.72 (1 H, d), 7.69 (1 H, d), 8.33 (1 H, dd), 8.53 (1 H, d). δF (DMSO-d$_6$, 376 MHz): −73.5. MS (ES): C$_{28}$H$_{32}$N$_4$O$_2$S requires 488.2; found 489.2 (M + H$^+$). |

-continued

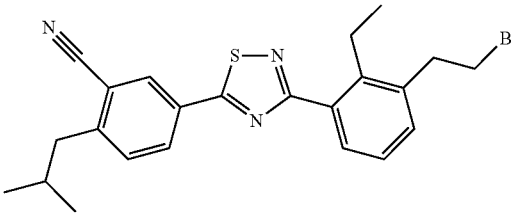

| Example | B | Salt form | characterization |
|---|---|---|---|
| 77 | (pyrrolidine-2-carboxylic acid, N-linked) | TFA | δH (DMSO-d$_6$, 400 MHz): 0.94 (6 H, d), 1.13 (3 H, t), 1.75 (1 H, m), 1.96 (3 H, m), 2.21 (1 H, m), 2.77 (2 H, m), 3.01 (6 H, m), 3.27 (1 H, m), 3.56 (1 H, m), 3.74 (1 H, m), 7.32 (1 H, m), 7.44 (1 H, m), 7.71 (2 H, m), 8.33 (1 H, dd), 8.53 (1 H, d). δF (DMSO-d$_6$, 376 MHz): −73.5. MS (ES): C$_{28}$H$_{32}$N$_4$O$_2$S requires 488.2; found 489.2 (M + H$^+$) |
| 78 | (pyrrolidine-3-carboxylic acid, N-linked) | TFA | δH (DMSO-d$_6$, 400 MHz): 0.92 (6 H, m), 1.14 (3 H, t), 2.02 (2 H, m), 2.25 (1 H, m), 2.40 (1 H, m), 2.77 (2 H, m), 2.94 (2 H, q), 3.11 (2 H, m), 3.26 (2 H, m), 3.73 (2 H, m), 3.88 (1 H, m), 7.36 (1 H, t), 7.44 (1 H, d), 7.73 (2 H, m), 8.33 (1 H, dd), 8.53 (1 H, d), 10.23 (1 H, m). δF (DMSO-d$_6$, 376 MHz): −73.8. MS (ES): C$_{28}$H$_{32}$N$_4$O$_2$S requires 488.2; found 489.2 (M + H$^+$). |
| 79 | ((3R)-pyrrolidine-3-carboxylic acid, N-linked) | TFA | δH (DMSO-d$_6$, 400 MHz): 0.94 (6 H, d), 1.15 (3 H, t), 2.01 (1 H, m), 2.07 (1H, m), 2.17 (1 H, m), 2.32 (1 H, m), 2.77 (2 H, d), 2.94 (2 H, m), 3.07 (3 H, m), 3.35(5 H, m), 7.36 (1 H, t), 7.44 (1 H, d), 7.73 (2 H, m), 8.33 (1 H, dd), 8.53 (1 H, d). δF (DMSO-d$_6$, 376 MHz): −73.5. MS (ES): C$_{28}$H$_{32}$N$_4$O$_2$S requires 488.2; found 489.2 (M + H$^+$) |
| 80 | (piperidine-3-carboxylic acid, N-linked) | | δH (DMSO-d$_6$, 400 MHz): 0.91 (6 H, m), 1.16 (3 H, t), 1.47 (1 H, m), 1.72 (1 H, m), 1.99 (2 H, m), 2.06 (1 H, m), 2.78 (3 H, m), 2.95 (3 H, m), 3.14 (3 H, m), 3.63 (2 H, m.), 3.80 (2 H, m), 7.37 (1 H, m), 7.43 (1 H, d), 7.71 (1 H, d), 7.77 (1 H, s), 8.34 (1 H, dd), 8.54 (1 H, d), 9.44 (1 H, br. s.), 12.93 (1 H, br. s.). MS (ES): C$_{29}$H$_{34}$N$_4$O$_2$S requires 502.2; found 503.3 (M + H$^+$). |

EXAMPLE 81

1-{[3-(2-{3-cyano-4-[(1-methylethyl)oxy]phenyl}-1,3-thiazol-5-yl)-2-ethylphenyl]methyl}-L-proline trifluoroacetate (E81)

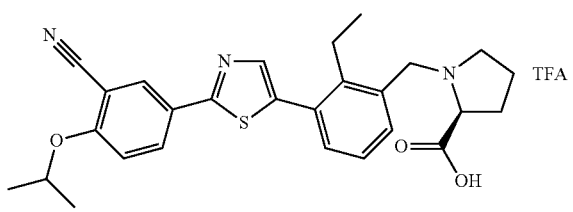 [SMILES: CCc1c(CN2CCC[C@H]2C(=O)O)cccc1-c1cnc(-c2ccc(OC(C)C)c(C#N)c2)s1]

A solution of 5-[5-(2-ethyl-3-formylphenyl)-1,3-thiazol-2-yl]-2-[(1-methylethyl)oxy]benzonitrile (D73) (80 mg, 0.212 mmol) and L-proline (48.9 mg, 0.425 mmol) in Ethanol (10 mL) was stirred at room temperature for 15 min, then sodium cyanoborohydride (40.1 mg, 0.637 mmol) was added. The mixture was stirred at room temperature for 2 h. After concentration, the residue was partitioned between ethyl acetate and aqueous diluted HCl, washed with saturated brine. The organic phase was evaporated in vacuo. The residue was purified by mass Directed AutoPrep to afford 1-{[3-(2-{3-cyano-4-[(1-methylethyl)oxy]phenyl}-1,3-thiazol-5-yl)-2-ethylphenyl]methyl}-L-proline (E81) (26 mg) as a TFA salt.

EXAMPLE 81-87

The following examples were prepared using similar procedures to that described for Example 81.

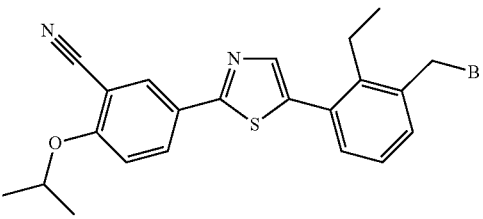

| Example | B | Salt form | characterization |
|---|---|---|---|
| 81 | (pyrrolidine-2-carboxylic acid) | TFA | δH (DMSO-d$_6$, 400 MHz): 1.04 (3 H, t), 1.36 (6 H, d), 1.89 (1 H, m), 2.04 (2 H, m), 2.46 (1 H, m), 2.83 (1 H, m), 3.00 (1 H, m), 3.34 (2 H, m), 4.37 (2 H, m), 4.67 (1 H, d), 4.91 (1 H, dt), 7.43 (3 H, m), 7.61 (1 H, d), 7.87 (1 H, s), 8.24 (2 H, m). δF (DMSO-d$_6$, 376 MHz): −73.9. MS (ES): C$_{27}$H$_{29}$N$_3$O$_3$S requires 475.2; found 476.2 (M + H$^+$). |
| 82 | (pyrrolidine-2-carboxylic acid) | TFA | δH (DMSO-d$_6$, 400 MHz): 1.04 (3 H, t), 1.36 (6 H, d), 1.88 (1 H, m), 2.02 (2 H, m), 2.44 (1 H, m), 2.82 (1 H, dq), 3.00 (1 H, m), 3.32 (2 H, m), 4.30 (2 H, m), 4.63 (1 H, d), 4.91 (1 H, dt), 7.43 (3 H, m), 7.60 (1 H, d), 7.87 (1 H, s), 8.23 (1 H, dd), 8.28 (1 H, d). δF (DMSO-d$_6$, 376 MHz): −73.7. MS (ES): C$_{27}$H$_{29}$N$_3$O$_3$S requires 475.2; found 476.2 (M + H$^+$). |
| 83 | (pyrrolidine-3-carboxylic acid) | TFA | δH (DMSO-d$_6$, 400 MHz): 1.05 (3 H, t), 1.36 (6 H, d), 2.25 (2 H, m), 2.82 (2 H, q), 3.25 (2 H, m), 3.45 (2 H, m), 3.70 (1 H, m), 4.54 (2 H, m), 4.91 (1 H, m), 7.45 (3 H, m), 7.63 (1 H, d), 7.89 (1 H, s), 8.24 (2 H, m), 9.95 (1 H, br. s.), 12.93 (1 H, br. s.). δF (DMSO-d$_6$, 376 MHz): −73.8. MS (ES): C$_{27}$H$_{29}$N$_3$O$_3$S requires 475.2; found 476.2 (M + H$^+$). |
| 84 | (pyrrolidine-3-carboxylic acid) | TFA | δH (DMSO-d$_6$, 400 MHz): 1.05 (3 H, t), 1.36 (6 H, d), 2.25 (2H, m), 2.82 (2 H, q), 3.29 (2 H, m), 3.57 (1 H, m), 3.71 (2 H, m), 4.56 (2 H, m), 4.91 (1 H, dt), 7.45 (3 H, m), 7.63 (1 H, d), 7.89 (1 H, s), 8.24 (2 H, m), 9.87 (1 H, br. s.), 12.97 (1 H, d). δF (DMSO-d$_6$, 376 MHz): −73.8. MS (ES): C$_{27}$H$_{29}$N$_3$O$_3$S requires 475.2; found 476.2 (M + H$^+$). |
| 85 | (4-hydroxypyrrolidine-2-carboxylic acid) | TFA | δH (DMSO-d$_6$, 400 MHz): 1.04 (3 H, t), 1.36 (6 H, d), 2.14 (2 H, m), 2.78 (2 H, m), 2.99 (2 H, m), 3.36 (3 H, dd), 4.08 (1 H, m.), 4.32 (1 H, m), 4.45 (1 H, m), 4.91 (1 H, dt), 7.39 (3 H, m), 7.56 (1 H, d), 7.87 (1 H, s), 8.24 (2 H, m). δF (DMSO-d$_6$, 376 MHz): −73.6. MS (ES): C$_{27}$H$_{29}$N$_3$O$_4$S requires 491.2; found 492.2 (M + H$^+$). |
| 86 | (piperidine-3-carboxylic acid) | TFA | δH (DMSO-d$_6$, 400 MHz): 1.04 (3 H, t), 1.35 (6 H, m), 1.48 (1 H, m), 1.72 (1 H, d), 1.88 (1 H, m), 2.06 (1 H, d), 2.83 (3 H, d), 3.05 (1 H, m), 3.21 (1 H, m), 3.38 (1 H, m), 3.58 (1 H, m), 4.47 (2 H, m), 4.91 (1 H, dt), 7.46 (3 H, m), 7.64 (1 H, d), 7.89 (1 H, s), 8.24 (2 H, m), 9.37 (1 H, br. s.), 12.90 (1 H, br. s.). δF (DMSO-d$_6$, 376 MHz): −73.8. MS (ES): C$_{28}$H$_{31}$N$_3$O$_3$S requires 489.2; found 490.2 (M + H$^+$). |
| 87 | (piperidin-4-yl acetic acid) | TFA | δH (DMSO-d$_6$, 400 MHz): 1.03 (3 H, t), 1.36 (6 H, d), 1.46 (2 H, m), 1.88 (3 H, m), 2.21 (2 H, d), 2.83 (2 H, m), 3.18 (2 H, m), 3.43 (2 H, m), 4.42 (2 H, m), 4.91 (1 H, dt), 7.45 (3 H, m), 7.63 (1 H, m), 7.89 (1 H, s), 8.24 (2 H, m), 9.15 (1 H, br. s.), 12.27 (1 H, br. s.). δF (DMSO-d$_6$, 376 MHz): −73.7. MS (ES): C$_{28}$H$_{31}$N$_3$O$_3$S requires 503.2; found 504.2 (M + H$^+$). |

EXAMPLE 88

1-{2-[3-(2-{3-cyano-4-[(1-methylethyl)oxy]phenyl}-1,3-thiazol-5-yl)-2-ethylphenyl]ethyl}-L-proline trifluoroacetate (E88)

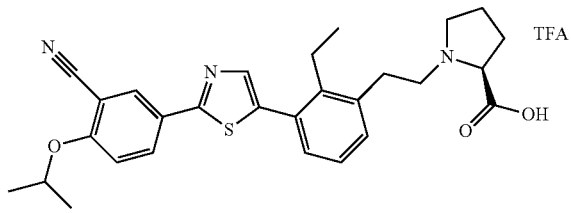 [SMILES: CCc1c(CCN2CCC[C@H]2C(=O)O)cccc1-c1cnc(-c2ccc(OC(C)C)c(C#N)c2)s1]

A solution of 5-{5-[2-ethyl-3-(2-oxoethyl)phenyl]-1,3-thiazol-2-yl}-2-[(1-methylethyl) oxy]benzonitrile (D76) (60 mg, 0.154 mmol), L-proline (35.4 mg, 0.307 mmol) and acetic acid (0.1 ml, 1.747 mmol) was stirred at room temperature for 15 min, then sodium cyanoborohydride (29.0 mg, 0.461 mmol) was added. The mixture was stirred at room temperature for 2 h. After concentration, the residue was partitioned between ethyl acetate and aqueous HCl (2M). The organic phase was washed with saturated brine, concentrated and purified by Mass Directed AutoPrep to afford 1-{2-[3-(2-{3-cyano-4-[(1-methylethyl)oxy]phenyl}-1,3-thiazol-5-yl)-2-ethylphenyl]ethyl}-L-proline (E88) (11 mg) as a TFA salt.

EXAMPLE 88-92

The following examples were prepared using similar procedures to that described described for Example 88.

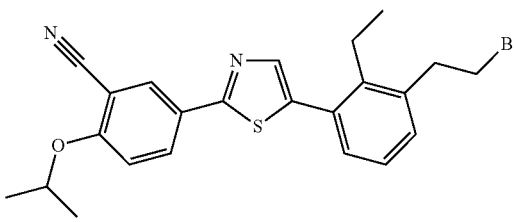

| Example | B | Salt form | characterization |
|---|---|---|---|
| 88 | ![pyrrolidine-2-COOH] | TFA | δH (DMSO-$d_6$, 400 MHz): 1.10 (3 H, t), 1.36 (6 H, d), 1.89 (1 H, m), 2.07 (2 H, m), 2.43 (1 H, m), 2.71 (2 H, m), 3.07 (2 H, m), 3.35 (3 H, m), 3.70 (1 H, m), 4.33 (1 H, m), 4.90 (1 H, dt), 7.36 (4 H, m), 7.85 (1 H, s), 8.22 (1 H, dd), 8.27 (1 H, d). δF (DMSO-$d_6$, 376 MHz): −73.5. MS (ES): $C_{28}H_{31}N_3O_3S$ requires 489.2; found 490.2 (M + H$^+$). |
| 89 | ![pyrrolidine-2-COOH] | TFA | δH (DMSO-$d_6$, 400 MHz): 1.10 (3 H, t), 1.36 (6 H, d), 1.90 (1 H, m), 2.07 (2 H, m), 2.44 (1 H, m), 2.73 (2 H, dt), 3.07 (2 H, m), 3.35 (3 H, m), 3.70 (1 H, m), 4.36 (1 H, m), 4.90 (1 H, m), 7.36 (4 H, m), 7.85 (1 H, s), 8.24 (2 H, m). δF (DMSO-$d_6$, 376 MHz): −73.5. MS (ES): $C_{28}H_{31}N_3O_3S$ requires 489.2; found 490.2 (M + H$^+$). |
| 90 | ![pyrrolidine-3-COOH] | TFA | δH (DMSO-$d_6$, 400 MHz): 1.10 (3 H, t), 1.36 (6 H, d), 2.30 (1 H, m), 2.40 (1 H, m), 2.70 (2 H, m), 3.06 (2 H, m), 3.20 (2 H, m), 3.54 (1 H, m), 3.71 (2 H, m), 3.87 (2 H, m), 4.89 (1 H, m), 7.32 (3 H, m), 7.45 (1 H, m), 7.85 (1 H, s), 8.24 (2 H, m), 9.99 (1 H, br. s.), 12.98 (1 H, br. s.). δF (DMSO-$d_6$, 376MHz): −73.7. MS (ES): $C_{28}H_{31}N_3O_3S$ requires 489.2; found 490.2 (M + H$^+$). |
| 91 | ![hydroxypyrrolidine-2-COOH] | TFA | δH (DMSO-$d_6$, 400 MHz): 1.09 (3 H, t), 1.36 (6 H, d), 2.21 (1 H, m), 2.28 (1 H, m), 2.73 (2 H, m), 3.07 (2 H, m), 3.22 (1 H, m), 3.33 (2 H, m), 3.44 (2 H, m), 3.79 (1 H, m), 4.42 (1 H, br. s.), 4.54 (1 H, br. s.), 4.90 (1 H, dt), 5.62 (1 H, br. s.), 7.29 (2 H, m), 7.41 (2 H, m), 7.85 (1 H, s), 8.23 (2 H, m). δF (DMSO-$d_6$, 376 MHz): −73.5. MS (ES): $C_{28}H_{31}N_3O_4S$ requires 505.2; found 506.2 (M + H$^+$). |

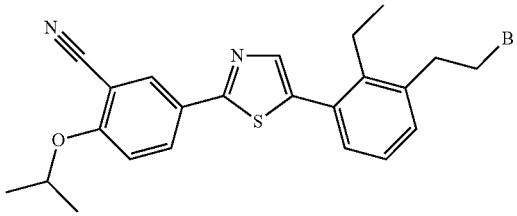

| Example | B | Salt form | characterization |
|---|---|---|---|
| 92 | 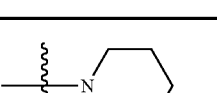 | TFA | δH (DMSO-$d_6$, 400 MHz): 1.10 (3 H, t), 1.36 (6 H, d), 1.52 (1 H, m), 1.75 (1 H, m), 1.94 (1 H, m), 2.07 (1 H, m), 2.72 (3 H, m), 2.94 (1 H, m), 3.10 (5 H, m), 3.64 (1 H, m), 3.78 (1 H, m), 4.91 (1 H, dt), 7.33 (3 H, m), 7.44 (1 H, d), 7.85 (1 H, s), 8.24 (2 H, m), 9.56 (1 H, m), 12.95 (1 H, br. s.). δF (DMSO-$d_6$, 376 MHz): −73.5. MS (ES): $C_{29}H_{33}N_3O_3S$ requires 503.2; found 504.2 (M + H⁺). |

EXAMPLE 93

1-{3-[3-(2-{3-cyano-4-[(1-methylethyl)oxy]phenyl}-1,3-thiazol-5-yl)-2-ethylphenyl]propyl}-3-azetidinecarboxylic acid trifluoroacetate (E93)

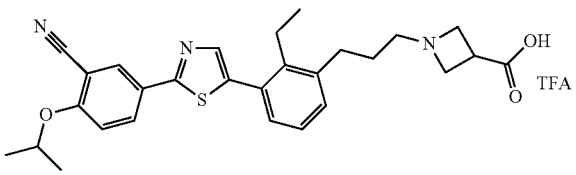 [SMILES: CCc1c(CCCN2CC(C(=O)O)C2)cccc1-c1cnc(-c2ccc(OC(C)C)c(C#N)c2)s1]

A solution of 5-{5-[2-ethyl-3-(3-oxopropyl)phenyl]-1,3-thiazol-2-yl}-2-[(1-methyl ethyl)oxy]benzonitrile (D115) (150 mg, 0.371 mmol), 3-azetidinecarboxylic acid (75.0 mg, 0.742 mmol) and acetic acid (0.1 ml, 1.747 mmol) was stirred at room temperature for 15 min, then sodium triacetoxyborohydride (236 mg, 1.112 mmol) was added. The mixture was stirred at room temperature for 2 h. After concentration, the residue was partitioned between ethyl acetate and aqueous HCl (2M). The organic phase was concentrated and purified by Mass Directed AutoPrep to afford 1-{3-[3-(2-{3-cyano-4-[(1-methylethyl)oxy]phenyl}-1,3-thiazol-5-yl)-2-ethyl phenyl]propyl}-3-azetidinecarboxylic acid (E93) (80 mg) as a TFA salt.

EXAMPLE 93-94

The following examples were prepared using similar procedures to that described for Example 93.

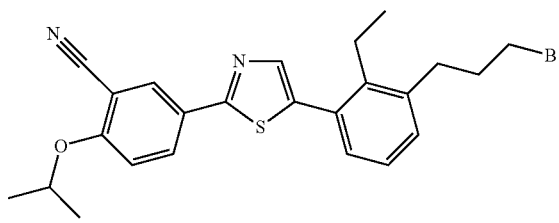

| Example | B | Salt form | characterization |
|---|---|---|---|
| 93 |  | TFA | δH (DMSO-$d_6$, 400 MHz): 1.07 (3 H, t), 1.36 (6 H, d), 1.74 (2 H, m), 2.69 (4 H, m), 3.35 (1 H, m), 3.60 (2 H, m), 4.27 (4 H, m), 4.90 (1 H, dt), 7.29 (3 H, m), 7.44 (1 H, d), 7.84 (1 H, s), 8.23 (2 H, m), 10.03 (1 H, br. s.), 13.22 (1 H, br. s.). δF (DMSO-$d_6$, 376 MHz): −73.6. MS (ES): $C_{29}H_{33}N_3O_3S$ requires 489.2; found 490.2 (M + H⁺). |

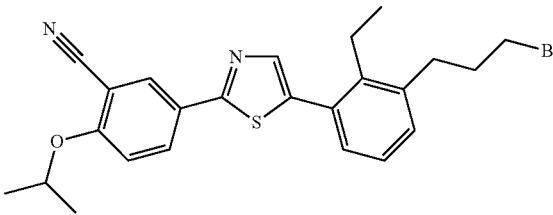

| Example | B | Salt form | characterization |
|---|---|---|---|
| 94 | ![pyrrolidine-COOH] | TFA | δH (DMSO-d₆, 400 MHz): 1.08 (3 H, t) 1.36 (6 H, d) 1.93 (2 H, m) 2.03 (1 H, m) 2.19 (1 H, m) 2.35 (1 H, m) 2.71 (4 H, m) 3.11 (1 H, m) 3.29 (4 H, m) 3.78 (1 H, m) 4.90 (1 H, dt) 7.30 (3 H, m) 7.44 (1 H, d) 7.84 (1 H, s) 8.23 (2 H, m) 9.88 (1 H, m) 9.94 (1 H, br. s.) 12.95 (1 H, br. s.). δF (DMSO-d₆, 376 MHz): −73.9. MS (ES): $C_{29}H_{33}N_3O_3S$ requires 503.2; found 504.2 (M + H⁺) |

EXAMPLE 95

3-{4-[3-(5-{3-chloro-4-[(1-methylethyl)oxy]phenyl}-1,3,4-thiadiazol-2-yl)-2-ethylphenyl]-1-piperidinyl}propanoic acid trifluoroacetate (E95)

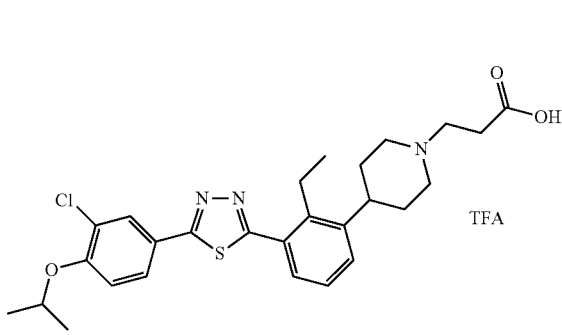 [SMILES: CCc1c(-c2nnc(-c3ccc(OC(C)C)c(Cl)c3)s2)cccc1C1CCN(CCC(=O)O)CC1]

To a solution of 4-[3-(5-{3-chloro-4-[(1-methylethyl)oxy]phenyl}-1,3,4-thiadiazol-2-yl)-2-ethylphenyl]piperidine (D120) (200 mg, 0.452 mmol) in Acetonitrile (10 mL) was added DBU (0.205 mL, 1.357 mmol) and ethyl 2-propenoate (136 mg, 1.357 mmol). The reaction solution was heated to 60° C. for 2 h. The reaction solution was concentrated and the residue was hydrolized with a solution of NaOH (4.52 mL, 2.262 mmol) in water. The reaction mixture was neutralized with 2N HCl till pH ~6.0. The mixture was extracted with EA/THF for 3 times. The combined organic layers were concentrated and purified by Mass Directed AutoPrep to afford 3-{4-[3-(5-{3-chloro-4-[(1-methylethyl)oxy]phenyl}-1,3,4-thiadiazol-2-yl)-2-ethylphenyl]-1-piperidinyl}propanoic acid (E95) (12 mg) as a TFA salt.

EXAMPLE 95-96

The following examples may be prepared using procedures described for Example 95.

| Example | | Salt form | characterization |
|---|---|---|---|
| 95 | R1 = isopropoxy  R2 = Cl | TFA | δH (DMSO-d₆, 400 MHz): 1.15 (3 H, t), 1.35 (6 H, d), 1.92 (2 H, m), 2.02 (2 H, m), 2.83 (4 H, m), 3.21 (4 H, m), 3.58(3 H, m), 4.83 (1 H, dt), 7.42 (4 H, m), 7.95 (1 H, dd), 8.09 (1 H, d). δF (DMSO-d₆, 376 MHz): −73.5. MS (ES): $C_{27}H_{32}ClN_3O_3S$ requires 513.2; found 514.2 (M + H⁺) |
| 96 | R1 = isobutyl  R2 = CN | TFA | δH (DMSO-d₆, 400 MHz): 0.94 (6 H, d), 1.15 (3 H, t), 1.99 (5 H, m), 2.82 (6 H, m), 3.24 (4 H, m), 3.59 (3 H, m), 7.46 (3 H, m), 7.68 (1 H, d), 8.31 (1 H, dd), 8.46 (1 H, d). δF (DMSO-d₆, 376 MHz): −73.5. MS (ES): $C_{27}H_{32}ClN_3O_3S$ requires 502.2; found 503.2 (M + H⁺) |

EXAMPLE 97

4-{4-[3-(5-{3-chloro-4-[(1-methylethyl)oxy]phenyl}-1,3,4-thiadiazol-2-yl)-2-ethylphenyl]-1-piperidinyl}butanoic acid trifluoroacetate (E97)

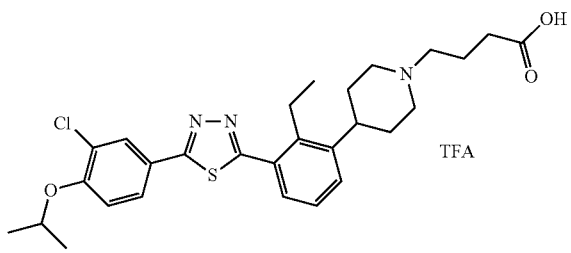 [SMILES: CCc1c(-c2nnc(-c3ccc(OC(C)C)c(Cl)c3)s2)cccc1C1CCN(CCCC(=O)O)CC1]

To a solution of 2-bromo-5-{3-chloro-4-[(1-methylethyl)oxy]phenyl}-1,3,4-thiadiazole (D10) (155 mg, 0.466 mmol) in N,N-Dimethylformamide (DMF) (6 mL) and Water (1.500 mL) was added ethyl 4-{4-[2-ethyl-3-(4,4,5,5-tetramethyl-1,3,2-dioxaborolan-2-yl)phenyl]-1-piperidinyl}butanoate (D121) (200 mg, 0.466 mmol), tripotassium phosphate (297 mg, 1.397 mmol) and Pd(Ph$_3$P)$_4$ (538 mg, 0.466 mmol). The reaction mixture was sealed and heated by Biotage Initiator to 120° C. for 30 min. Ethyl acetate was added and the resulting solution was washed with water, brine. The organic layer was dried, concentrated and purified by ISCO column chromatography to afford the ester. The ester was hydrolized by NaOH (4.66 mL, 2.329 mmol) in isopropanol/water, and purified by Mass Directed AutoPrep to afford 4-{4-[3-(5-{3-chloro-4-[(1-methylethyl)oxy]phenyl}-1,3,4-thiadiazol-2-yl)-2-ethylphenyl]-1-piperidinyl}butanoic acid (E97) (20 mg) as a TFA salt.

EXAMPLE 97-98

The following examples were prepared using similar procedures to that described for Example 97.

| Example | | Salt form | characterization |
|---|---|---|---|
| 97 | R1 = isopropoxyl R2 = Cl | TFA | δH (DMSO-d$_6$, 400 MHz): 1.08 (3H, t), 1.28 (6H, d), 1.87 (5H, m), 2.31 (2H, m), 2.77 (2H, m), 3.10 (5H, m), 3.38 (1H, m), 3.52 (2H, m), 4.77 (1H, m), 7.38 (4H, m), 7.88 (1H, dd), 8.03 (1H, d), 9.19 (1H, s br). δF (DMSO-d$_6$, 376 MHz): −73.5. MS (ES): C$_{28}$H$_{34}$ClN$_3$O$_3$S requires 527.2; found 528.1 (M + H$^+$) |
| 98 | R1 = isobutyl R2 = CN | TFA | δH (DMSO-d$_6$, 400 MHz): 0.94 (6 H, d), 1.15 (3 H, t), 1.79 (6 H, m), 2.00 (1 H, dt), 2.32 (2 H, t), 2.67 (2H, m), 2.81 (4 H, m), 2.98 (1 H, m), 3.22 (2 H, m), 7.43 (3 H, m), 7.67 (1 H, d), 8.30 (1 H, d), 8.45 (1 H, s). δF (DMSO-d$_6$, 376 MHz): −73.5. MS (ES): C$_{30}$H$_{36}$N$_4$O$_2$S requires 516.2; found 517.2 (M + H$^+$) |

EXAMPLE 99

{4-[3-(5-{3-chloro-4-[(1-methylethyl)oxy]phenyl}-1,2,4-thiadiazol-3-yl)-2-ethylphenyl]-1-piperidinyl}acetic acid trifluoroacetate (E99)

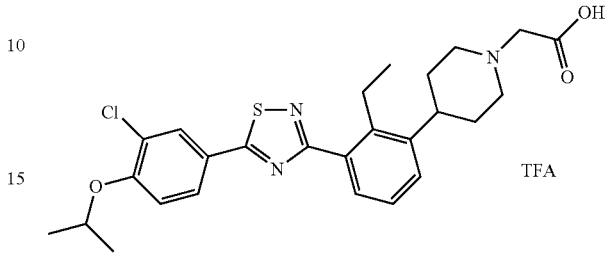

To a solution of 4-[3-(5-{3-chloro-4-[(1-methylethyl)oxy]phenyl}-1,2,4-thiadiazol-3-yl)-2-ethylphenyl]piperidine (D122) (85 mg, 0.192 mmol) and K$_2$CO$_3$ (106 mg, 0.769 mmol) in N,N-Dimethylformamide (DMF) (5 mL) was added ethyl bromoacetate (43 mg, 0.257 mmol). The tube was sealed and stirred at room temperature for 10 min.

Then sodium hydroxide (0.5 mL, 3.05 mmol), Isopropanol (5.00 mL) and Water (2 mL) was added into this solution and stirred overnight at room temperature. The reaction mixture was neutralized and purified by Mass Directed AutoPrep to afford {4-[3-(5-{3-chloro-4-[(1-methylethyl)oxy]phenyl}-1,2,4-thiadiazol-3-yl)-2-ethylphenyl]-1-piperidinyl}acetic acid (E99) (30 mg) as a TFA salt (white solid). δH (DMSO-d$_6$, 400 MHz): 1.18 (3H, t), 1.35 (6H, d), 1.93 (2H, m), 2.09 (2H, m), 2.88 (2H, m), 3.17 (1H, m), 3.29 (2H, m), 3.60 (2H, m), 4.17 (2H, m), 4.86 (1H, m), 7.39 (3H, m), 7.64 (1H, d), 8.02 (1H, dd), 8.14 (1H, m), 9.85 (1H, br. s.). δF (DMSO-d$_6$, 376 MHz): −73.5. MS (ES): C$_{26}$H$_{30}$ClN$_3$O$_3$S requires 499.2. found 500.2 (M+H$^+$)

EXAMPLE 100

3-{4-[3-(5-{3-chloro-4-[(1-methylethyl)oxy]phenyl}-1,2,4-thiadiazol-3-yl)-2-ethylphenyl]-1-piperidinyl}propanoic acid (E100)

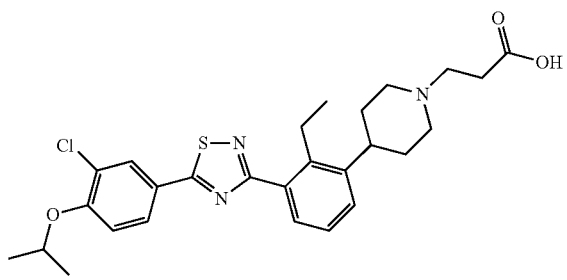 [SMILES: CCc1c(-c2nsc(-c3ccc(OC(C)C)c(Cl)c3)n2)cccc1C1CCN(CCC(=O)O)CC1]

To a solution of ethyl 3-{4-[2-ethyl-3-(4,4,5,5-tetramethyl-1,3,2-dioxaborolan-2-yl)phenyl]-1-piperidinyl}propanoate (D123) (200 mg, 0.481 mmol), 3-bromo-5-{3-chloro-4-[(1-methylethyl)oxy]phenyl}-1,2,4-thiadiazole (D43) (161 mg, 0.481 mmol) and Pd(Ph$_3$P)$_4$ (55.6 mg, 0.048 mmol) was added tripotassium phosphate (307 mg, 1.444 mmol) under nitrogen. The solution was sealed for Biotage microwave irradiation at 120° C. for 20 min. To the resulted solution, Isopropanol (10 mL) and water (2 mL) and then sodium hydroxide (0.5 mL, 3.05 mmol) was added. This solution was stirred at 50° C. for 2 hr. The solution was neutralized with AcOH, dried, dissolved in DMF and purified by Mass Directed AutoPrep to afford 3-{4-[3-(5-{3-chloro-4-[(1-methylethyl)oxy]phenyl}-1,2,4-thiadiazol-3-yl)-2-ethylphenyl]-1-piperidinyl}propanoic acid (E100) (40 mg).

EXAMPLE 100-101

The following examples were prepared using similar procedures to that described for Example 100.

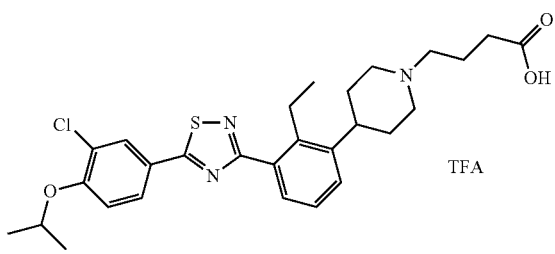 [SMILES: CCc1c(-c2nsc(-c3ccc(OC(C)C)c(Cl)c3)n2)cccc1C1CCN(CCCC(=O)O)CC1]

| Example | | Salt form | characterization |
|---|---|---|---|
| 100 | R1 = isopropoxy R2 = Cl | | δH (DMSO-d$_6$, 400 MHz): 1.16 (3 H, t), 1.35 (6 H, d), 1.73 (4 H, m), 2.22 (2 H, m), 2.42 (2 H, m), 2.67 (2 H, t), 2.87 (3 H, m), 3.06 (2 H, m), 4.86 (1 H, dt), 7.31 (1 H, m), 7.42 (2 H, m), 7.58 (1 H, d), 8.02 (1 H, dd), 8.13 (1 H, d). MS (ES): $C_{27}H_{32}ClN_3O_3S$ requires 513.2; found 514.2 (M + H$^+$) |
| 101 | R1 = isobutyl R2 = CN | TFA | δH (DMSO-d$_6$, 400 MHz): 0.92 (6 H, m), 1.17 (3 H, t), 1.96 (5 H, m), 2.77 (5 H, m), 2.89 (3 H, q), 3.20 (3 H, m), 3.56 (2 H, m), 7.38 (2 H, m), 7.67 (2 H, m), 8.32 (1 H, dd), 8.52 (1 H, d). δF (DMSO-d$_6$, 376 MHz): −73.5. MS (ES): $C_{29}H_{34}N_4O_2S$ requires 502.2; found 503.2 (M + H$^+$) |

EXAMPLE 102

4-{4-[3-(5-{3-chloro-4-[(1-methylethyl)oxy]phenyl}-1,2,4-thiadiazol-3-yl)-2-ethylphenyl]-1-piperidinyl}butanoic acid trifluoroacetate (E102)

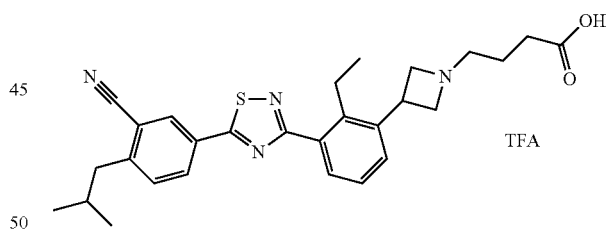

To a solution of 4-[3-(5-{3-chloro-4-[(1-methylethyl)oxy]phenyl}-1,2,4-thiadiazol-3-yl)-2-ethylphenyl]piperidine (D122) (108 mg, 0.244 mmol) and ethyl 4-bromobutanoate (95 mg, 0.489 mmol) in N,N-Dimethylformamide (DMF) (8 mL) was added K2CO3 (223 mg, 1.614 mmol). This solution was sealed and stirred for overnight at room temperature. To the above solution was added Isopropanol (10.00 mL) and Water (2 mL) and sodium hydroxide (0.5 mL, 3.05 mmol). The solution was sealed and stirred for 5 h at 40° C. The reaction was neutrolized by AcOH, dried and purified by Mass Directed AutoPrep to afford 4-{4-[3-(5-{3-chloro-4-[(1-methylethyl)oxy]phenyl}-1,2,4-thiadiazol-3-yl)-2-ethylphenyl]-1-piperidinyl}butanoic acid (E102) (62 mg) as a TFA salt.

EXAMPLE 102-103

The following examples were prepared using similar procedures to that described for Example 102.

| Example | | Salt form | characterization |
|---|---|---|---|
| 102 | R1 = isopropoxy R2 = Cl | TFA | δH (DMSO-d$_6$, 400 MHz): 1.19 (3 H, m), 1.35 (6 H, d), 1.95 (5 H, m), 2.38 (2 H, m), 2.89 (2 H, m), 3.11 (3 H, m), 3.21 (3 H, m), 3.61 (2 H, m), 4.86 (1 H, dt), 7.37 (3 H, m), 7.64 (1 H, m), 8.01 (1 H, dd), 8.13 (1 H, d), 9.24 (1 H, br. s.), 12.36 (1 H, br. s.). δF (DMSO-d$_6$, 376 MHz): −73.5. MS (ES): $C_{28}H_{34}ClN_3O_3S$ requires 527.2; found 528.2 (M + H$^+$) |
| 103 | R1 = isobutyl R2 = CN | TFA | δH (DMSO-d$_6$, 400 MHz): 0.94 (6 H, d), 1.18 (3 H, t), 1.97 (7 H, m), 2.38 (2 H, t), 2.77 (2 H, m), 2.90 (2 H, m), 3.13 (2 H, m), 3.22 (3 H, m), 3.60 (2 H, m), 7.39 (2 H, m), 7.68 (2 H, m), 8.33 (1 H, dd), 8.52 (1 H, d), 9.41 (1 H, br. s.), 12.39 (1 H, br. s.). δF (DMSO-d$_6$, 376 MHz): −73.5. MS (ES): $C_{29}H_{34}N_4O_2S$ requires 502.2; found 503.2 (M + H$^+$) |

EXAMPLE 104

4-[3-(3-{5-[3-cyano-4-(2-methylpropyl)phenyl]-1,2,4-thiadiazol-3-yl}-2-ethylphenyl)-1-azetidinyl]butanoic acid trifluoroacetate (E104)

To a solution of ethyl 4-{3-[2-ethyl-3-(4,4,5,5-tetramethyl-1,3,2-dioxaborolan-2-yl)phenyl]-1-azetidinyl}butanoate (D132) (100 mg, 0.249 mmol) in N,N-Dimethylformamide (DMF) (4 mL) and Water (1.000 mL) was added 5-(3-bromo-1,2,4-thiadiazol-5-yl)-2-(2-methylpropyl)benzonitrile (D60) (96 mg, 0.299 mmol), tripotassium phosphate (159 mg, 0.747 mmol) and Pd(Ph$_3$P)$_4$ (288 mg, 0.249 mmol). The reaction solution was heated by Biotage Initiator to 120° C. for 20 min. The solvent was removed in vacuo and the residue was purified by ISCO column chramotography to afford the ester. The ester was hydrolized by NaOH in isopropanol/water to afford 4-[3-(3-{5-[3-cyano-4-(2-methylpropyl)phenyl]-1,2,4-thiadiazol-3-yl}-2-ethylphenyl)-1-azetidinyl]butanoic acid (E104) (12 mg) as a TFA salt. δH (DMSO-d$_6$, 400 MHz): 0.87 (6H, d), 1.02 (3H, t), 1.69 (2H, m), 1.93 (1H, m), 2.29 (2H, m), 2.75 (4H, m), 3.27 (2H, m), 4.30 (5H, m), 7.40 (1H, t), 7.62 (2H, m), 7.74 (1H, d), 8.25

(1H, dd), 8.45 (1H, d). δF (DMSO-$d_6$, 376 MHz): −73.5. MS (ES): $C_{29}H_{34}N_4O_2S$ requires 488.2. found 489.0 (M+H+).

EXAMPLE 105

(4-{[3-(5-{3-chloro-4-[(1-methylethyl)oxy]phenyl}-1,2,4-thiadiazol-3-yl)-2-ethylphenyl]methyl}-1-piperidinyl)acetic acid trifluoroacetate (E105)

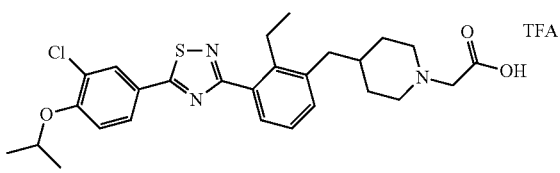 [SMILES: CCc1c(CC2CCN(CC(=O)O)CC2)cccc1-c1nsc(-c2ccc(OC(C)C)c(Cl)c2)n1]

To a solution of ethyl (4-{[3-(5-{3-chloro-4-[(1-methylethyl)oxy]phenyl}-1,2,4-thiadiazol-3-yl)-2-ethylphenyl]methyl}-1-piperidinyl)acetate (D145) (80 mg, 0.148 mmol) in Isopropanol (6 mL) and Water (6.00 mL) was added NaOH (1.476 mL, 0.738 mmol). The reaction solution was heated to 90° C. for 2 hours. The solvent was removed in vacuo and the residue was acidified to pH=3-4, extracted with ethyl acetate. The combined organic phases were dried, concentrated and purified by Mass Directed AutoPrep to afford (4-{[3-(5-{3-chloro-4-[(1-methylethyl)oxy]phenyl}-1,2,4-thiadiazol-3-yl)-2-ethylphenyl]methyl}-1-piperidinyl)acetic acid (E105) (59 mg) as a TFA salt. δH (DMSO-$d_6$, 400 MHz): 1.01 (3H, t), 1.28 (6H, d), 1.55 (2H, m), 1.72 (3H, m), 2.62 (2H, d), 2.87 (4H, m), 3.38 (2H, m), 3.98 (2H, s), 4.79 (1H, m), 7.23 (2H, m), 7.32 (1H, d), 7.59 (1H, dd), 7.95 (1H, dd), 8.07 (1H, d). δF (DMSO-$d_6$, 376 MHz): −73.5. MS (ES): $C_{27}H_{32}ClN_3O_3S$ requires 513.2. found 514.2 (M+H+).

EXAMPLE 106

3-(4-{[3-(5-{3-chloro-4-[(1-methylethyl)oxy]phenyl}-1,2,4-thiadiazol-3-yl)-2-ethylphenyl]methyl}-1-piperidinyl)propanoic acid trifluoroacetate

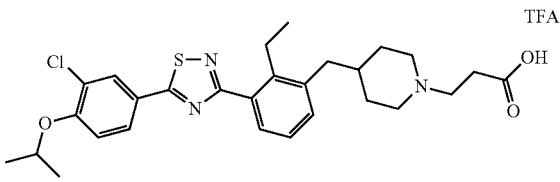 [SMILES: CCc1c(CC2CCN(CCC(=O)O)CC2)cccc1-c1nsc(-c2ccc(OC(C)C)c(Cl)c2)n1]

To a solution of ethyl 3-(4-{[3-(5-{3-chloro-4-[(1-methylethyl)oxy]phenyl}-1,2,4-thiadiazol-3-yl)-2-ethylphenyl]methyl}-1-piperidinyl)propanoate (D141) (0.63 g, 1.133 mmol) in Isopropanol (5 mL) and Water (5.00 mL) was added NaOH (2.266 mL, 1.133 mmol). The reaction solution was heated to 90° C. for 1 hour. The solvent was evaporated in vacuo and the residue was acidified to pH=2-3, extracted with ethyl acetate, washed with water, dried and purified by Mass Directed AutoPrep to afford 3-(4-{[3-(5-{3-chloro-4-[(1-methylethyl)oxy]phenyl}-1,2,4-thiadiazol-3-yl)-2-ethylphenyl]methyl}-1-piperidinyl)propanoic acid (E106) (83 mg) as a TFA salt. δH (DMSO-$d_6$, 400 MHz): 1.00 (3H, t), 1.28 (6H, d), 1.44 (2H, m), 1.72 (3H, m), 2.63 (4H, m), 2.83 (4H, m), 3.17 (4H, m), 4.79 (1H, m), 7.24 (2H, m), 7.32 (1H, d), 7.59 (1H, dd), 7.94 (1H, dd), 8.07 (1H, d). δF (DMSO-$d_6$, 376 MHz): −73.5. MS (ES): $C_{28}H_{34}ClN_3O_3S$ requires 527.2. found 528.1 (M+H+)

S1P1 Assay

Recombinant EDG1-bla/U2OS cells (contain the human Endothelial Differentiation Gene 1 (EDG1) linked to a TEV protease site and a Gal4-VP16 transcription factor stably integrated into the Tango GPCR-bla U2OS parental cell line) were harvested from growth medium and passaged into assay medium (Invitrogen Freestyle Expression Medium). The cells were starved for 24 hours at 37° C., 5% $CO_2$, harvested and resuspended in assay medium at a density of ~200,000 cells/ml. All test compounds were dissolved in DMSO at a concentration of 10 mM and were prepared in 100% DMSO to provide 10 point dose response curves. Test compounds in the free base or in a salt form were prepared by Velocity11 Bravo automation (Agilent) were added to wells in columns 2-11 and 13-22; DMSO was added to wells in columns 12 and 23 as unstimulated controls and assay medium was added to wells in columns 1 and 24 as cell-free controls. An S1P1 agonist was added to wells in row 2, columns 2-11 as stimulated controls and test compounds were added to wells in row 2, columns 13-22 and rows 3-15, columns 2-11/13-22 (row 1 and 16 were empty and not used). Compounds in solution were added to the assay plate (Greiner 781090) using an Echo (Labcyte) dose-response program (50 nl/well). The unstimulated and cell-free controls were loaded with 50 nl/well pure DMSO to ensure that the DMSO concentration was constant across the plate for all assays. 50 μl of the cell suspension was added to each well in columns 2-23 of the plate (~10,000 cells per well). 50 μl of assay medium was added to each well in the cell-free controls (columns 1 and 24). The cells were incubated overnight at 37° C./5% $CO_2$.

10 μl of 6× substrate mixture (LiveBLAzer™-FRET B/G substrate (CCF4-AM) Cat # K1096 from Invitrogen, Inc.) was added to each well using Bravo automation and the plates incubated at room temperature for 2 h in the dark. The plate was finally read on EnVision using one excitation channel (409 nm) and two emission channels (460 nm and 530 nm).

The blue/green emission ratio (460 nm/530 nm) was calculated for each well, by dividing the background-subtracted Blue emission values by the background-subtracted Green emission values. The dose response curve is based on sigmoidal dose-response model. All ratio data was normalized based upon the maximum emission ratio of positive control and minimum emission ratio of negative control (DMSO) on each plate. The intrinsic activity (IA) of each compound is defined as relative response normalised to a reference compound, whose maximum response is defined as 100% after curve fitting.

Exemplified compounds of the invention had a pEC50>6. Examples 1-4, 6-14, 15, 17-19, 21-27, 29, 31-66, 69, 70, 72-80, 83, 84, 87, 88, 90-94, 99 and 100-106 had a pEC50>7. Examples 1-4, 6-12, 14, 15, 17, 19, 21-27, 29, 31-35, 37-45, 47-51, 53-65, 69, 70, 72-76, 78-80, 83, 84, 88, 90-94, 99 and 100-104 had a pEC50≧8. Examples 1, 2, 4, 6-12, 19, 21 to 24, 26, 29, 31-34, 37-41, 43, 48, 49, 51, 54, 56, 57, 60-64, 69, 70, 74, 80, 90, 92 and 93 had a pEC50>9.

Example 4 had a pEC50 of 9.4.

S1P3 Assay

GeneBLAzer EDG3-Ga15-NFAT-bla HEK 293T cells (contain the human Endothelial Differentiation G-protein Coupled Receptor 3 (EDG3) and a beta-lactamase reporter gene under control of a NFAT response element and a promiscuous G Protein, Ga15, stably integrated into the GeneBLAzer Ga15-NFAT-bla HEK 293T cell line) were harvested from growth medium and suspended in assay medium (90% DMEM, 10% Charcoal-stripped FBS, 0.1 mM NEAA, 25 mM HEPES (pH 7.3), 100 U/ml penicillin, 100 μg/ml streptomycin) at a density of ~200,000 cells/ml. All test compounds were dissolved in DMSO at a concentration of 10 mM and were prepared in 100% DMSO to provide 10 point dose response curves. Test compounds in the free base or in a salt form were prepared by Velocity 11 Bravo automation (Agilent) were added to wells in columns 2-11 and 13-22; DMSO was added to wells in columns 12 and 23 as unstimulated controls and assay medium was added to wells in columns 1 and 24 as cell-free controls. An S1P3 agonist was added to wells in row 2, columns 2-11 as stimulated controls and test compounds were added to wells in row 2, columns 13-22 and rows 3-15, columns 2-11/13-22 (row 1 and 16 were empty and not used). Compounds in solution were added to the assay plate (Greiner 781090) using an Echo (Labcyte) dose-response program (50 nl/well). The unstimulated and cell-free controls were loaded with 50 nl/well pure DMSO to ensure that the DMSO concentration was constant across the plate for all assays.

50 µl of the cell suspension was added to each well in columns 2-23 of the plate (~10,000 cells per well). 50 µl of assay medium was added to each well in the cell-free controls (columns 1 and 24). The cells were incubated overnight at 37° C./5% $CO_2$.

10 µl of 6× substrate mixture (LiveBLAzer™-FRET B/G substrate (CCF4-AM) Cat # K1096 from Invitrogen, Inc.) was added to each well using Bravo automation and the plates incubated at room temperature for 2 h in the dark. The plate was finally read on EnVision using one excitation channel (409 nm) and two emission channels (460 nm and 530 nm).

The blue/green emission ratio (460 nm/530 nm) was calculated for each well, by dividing the background-subtracted Blue emission values by the background-subtracted Green emission values. The dose response curve is based on sigmoidal dose-response model. All ratio data was normalized based upon the maximum emission ratio of positive control and minimum emission ratio of negative control (DMSO) on each plate. The intrinsic activity (IA) of each compound is defined as relative response normalised to a reference compound, whose maximum response is defined as 100% after curve fitting.

Exemplified compounds of the invention had a pEC50<5.7 except Example 37 which had a pEC50 of 6.03. Examples 1, 3, 4, 7-17, 18, 20, 23-29, 31-34, 36, 38, 39, 41-89 and 91-106 of the invention had a pEC50<5.5. Examples 9, 13-16, 18, 20, 28, 36, 38, 39, 42, 46, 47, 50-53, 55, 59, 60, 66, 77, 81-89, 91, 96-98, 100 and 102-105 of the invention had a pEC50<5.

Example 4 had a pEC50<5.5.

The invention claimed is:

1. A compound of formula (I) or a salt thereof:

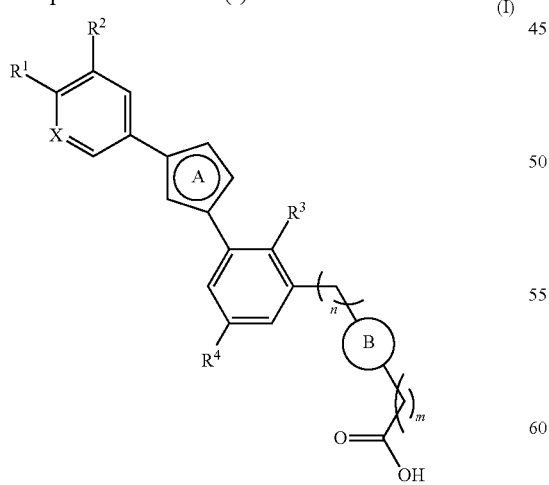

(I)

wherein
X is CH;
$R^1$ is $C_{1-6}$alkoxy or $C_{1-6}$alkyl;
$R^2$ is cyano, $CF_3$, halogen $C_{1-6}$alkoxy or $CH_2OCH_3$;
$R^3$ is halogen, $C_{1-6}$alkoxy or $C_{1-6}$alkyl;
$R^4$ is hydrogen, halogen, $C_{1-3}$alkyl, or $C_{1-3}$alkoxyl;
n=0, 1, 2 or 3;
m=0, 1, 2 or 3;
A is a 5-membered heteroaryl ring in any orientation selected from:

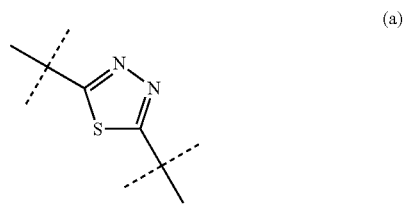

(a)

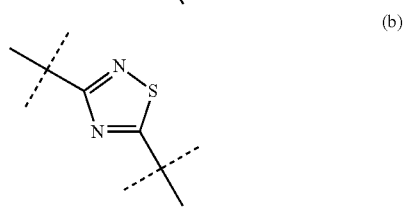

(b)

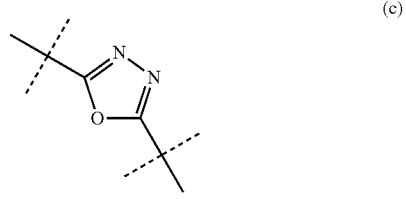

(c)

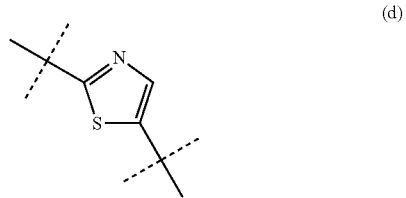

(d)

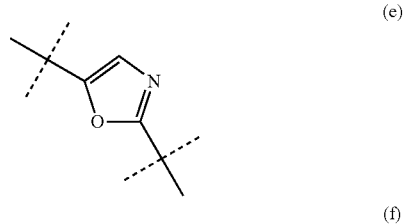

(e)

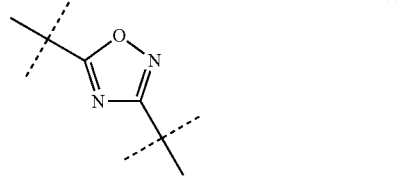

(f)

B is a 4 to 7-membered heterocyclic ring in any orientation selected from:

(g)

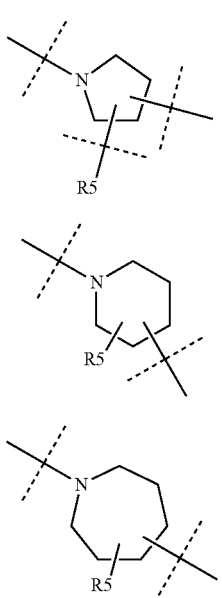

and

R⁵ is one or two substituents independently selected from hydrogen, halogen, $C_{1-3}$alkyl, $C_{1-3}$alkoxyl and hydroxyl.

2. A compound according to claim 1, wherein:
X is CH;
R¹ is $C_{1-6}$alkoxy or $C_{1-6}$alkyl;
R² is cyano, $CF_3$ or halogen;
R³ is $C_{1-6}$alkoxy or $C_{1-6}$alkyl;
R⁴ is hydrogen or halogen;
n=1 or 2;
m=0 or 1;
A is a 5-membered heteroaryl ring selected from (a), b) and (d);
B is a 4 to 7-membered heterocyclic ring selected from (g), (h) and (i); and
R⁵ is hydrogen.

3. A compound according to claim 1 or 2, wherein when A is (b) it is orientated with its sulphur atom closest to the ring containing X.

4. A compound according to claim 1 or 2, wherein B is orientated with the $(CH_2)_m$COOH group attached to a carbon atom.

5. A compound according to claim 1 selected from:
1-[(2-ethyl-3-{5-[4-[(1-methylethyl)oxy]-3-(trifluoromethyl)phenyl]-1,3,4-thiadiazol-2-yl}phenyl)methyl]-4-piperidinecarboxylic acid;
1-[(2-ethyl-3-{5-[4-[(1-methylethyl)oxy]-3-(trifluoromethyl)phenyl]-1,3,4-thiadiazol-2-yl}phenyl)methyl]-3-azetidinecarboxylic acid;
1-{[3-(5-{3-chloro-4-[(1-methylethyl)oxy]phenyl}-1,3,4-thiadiazol-2-yl)-2-ethylphenyl]methyl}-4-piperidinecarboxylic acid;
1-{[3-(5-{3-chloro-4-[(1-methylethyl)oxy]phenyl}-1,3,4-thiadiazol-2-yl)-2-ethylphenyl]methyl}-3-azetidinecarboxylic acid;
1-{2-[3-(5-{3-chloro-4-[(1-methylethyl)oxy]phenyl}-1,3,4-thiadiazol-2-yl)-2-ethylphenyl]ethyl}-4-piperidinecarboxylic acid;
1-{2-[3-(5-{3-chloro-4-[(1-methylethyl)oxy]phenyl}-1,3,4-thiadiazol-2-yl)-2-ethylphenyl]ethyl}-3-azetidinecarboxylic acid;
1-[2-(2-ethyl-3-{5-[4-[(1-methylethyl)oxy]-3-(trifluoromethyl)phenyl]-1,3,4-thiadiazol-2-yl}phenyl)ethyl]-3-azetidinecarboxylic acid;
1-[(3-{5-[3-cyano-4-(2-methylpropyl)phenyl]-1,3,4-thiadiazol-2-yl]-2-ethylphenyl)methyl]-4-piperidinecarboxylic acid;
1-[(3-{5-[3-cyano-4-(2-methylpropyl)phenyl]-1,3,4-thiadiazol-2-yl]-2-ethylphenyl)methyl]-3-azetidinecarboxylic acid;
1-[2-(3-{5-[3-cyano-4-(2-methylpropyl)phenyl]-1,3,4-thiadiazol-2-yl}-2-ethylphenyl)ethyl]-3-azetidinecarboxylic acid;
1-[2-(3-{5-[3-cyano-4-(2-methylpropyl)phenyl]-1,3,4-thiadiazol-2-yl}-2-ethylphenyl)ethyl]-4-piperidinecarboxylic acid;
1-{2-[3-(5-{3-chloro-4-[(1-methylethyl)oxy]phenyl}-1,3,4-thiadiazol-2-yl)-2-ethylphenyl]ethyl}-3-pyrrolidinecarboxylic acid;
1-{2-[5-fluoro-3-{5-[4-[(1-methylethyl)oxy]-3-(trifluoromethyl)phenyl]-1,3,4-thiadiazol-2-yl}-2-(methyloxy)phenyl]ethyl}-4-piperidinecarboxylic acid;
1-{2-[5-fluoro-3-{5-[4-[(1-methylethyl)oxy]-3-(trifluoromethyl)phenyl]-1,3,4-thiadiazol-2-yl}-2-(methyloxy)phenyl]ethyl}-3-azetidinecarboxylic acid;
1-{2-[3-{5-[3-cyano-4-(2-methylpropyl)phenyl]-1,3,4-thiadiazol-2-yl}-5-fluoro-2-(methyloxy)phenyl]ethyl}-3-azetidinecarboxylic acid;
1-{[3-(5-{3-cyano-4-[(1-methylethyl)oxy]phenyl}-1,2,4-thiadiazol-3-yl)-2-ethylphenyl]methyl}-4-piperidinecarboxylic acid;
1-{[3-(5-{3-cyano-4-[(1-methylethyl)oxy]phenyl}-1,2,4-thiadiazol-3-yl)-2-ethylphenyl]methyl}-3-azetidinecarboxylic acid;
1-[(2-ethyl-3-{5-[4-[(1-methylethyl)oxy]-3-(trifluoromethyl)phenyl]-1,2,4-thiadiazol-3-yl}phenyl)methyl]-4-piperidinecarboxylic acid;
1-[(2-ethyl-3-{5-[4-[(1-methylethyl)oxy]-3-(trifluoromethyl)phenyl]-1,2,4-thiadiazol-3-yl}phenyl)methyl]-3-azetidinecarboxylic acid;
{1-[(2-ethyl-3-{5-[4-[(1-methylethyl)oxy]-3-(trifluoromethyl)phenyl]-1,2,4-thiadiazol-3-yl}phenyl)methyl]-4-piperidinyl}acetic acid;
1-[2-(2-ethyl-3-{5-[4-[(1-methylethyl)oxy]-3-(trifluoromethyl)phenyl]-1,2,4-thiadiazol-3-yl}phenyl)ethyl]-4-piperidinecarboxylic acid;
1-[2-(2-ethyl-3-{5-[4-[(1-methylethyl)oxy]-3-(trifluoromethyl)phenyl]-1,2,4-thiadiazol-3-yl}phenyl)ethyl]-3-azetidinecarboxylic acid;
1-{2-[3-(5-{3-chloro-4-[(1-methylethyl)oxy]phenyl}-1,2,4-thiadiazol-3-yl)-2-ethylphenyl]ethyl}-3-azetidinecarboxylic acid;
1-{2-[3-(5-{3-chloro-4-[(1-methylethyl)oxy]phenyl}-1,2,4-thiadiazol-3-yl)-2-ethylphenyl]ethyl}-4-piperidinecarboxylic acid;
1-{[3-(5-{3-chloro-4-[(1-methylethyl)oxy]phenyl}-1,2,4-thiadiazol-3-yl)-2-ethylphenyl]methyl}-3-azetidinecarboxylic acid;
1-{2-[3-(5-{3-cyano-4-[(1-methylethyl)oxy]phenyl}-1,2,4-thiadiazol-3-yl)-2-ethylphenyl]ethyl}-3-azetidinecarboxylic acid;
1-[(3-{5-[3-cyano-4-(2-methylpropyl)phenyl]-1,2,4-thiadiazol-3-yl}-2-ethylphenyl)methyl]-3-azetidinecarboxylic acid;
1-[(3-{5-[3-cyano-4-(2-methylpropyl)phenyl]-1,2,4-thiadiazol-3-yl}-2-ethylphenyl)methyl]-4-piperidinecarboxylic acid;
1-[2-(3-{5-[3-cyano-4-(2-methylpropyl)phenyl]-1,2,4-thiadiazol-3-yl}-2-ethylphenyl)ethyl]-4-piperidinecarboxylic acid;

1-[2-(3-{5-[3-cyano-4-(2-methylpropyl)phenyl]-1,2,4-thiadiazol-3-yl}-2-ethylphenyl)ethyl]-3-azetidinecarboxylic acid;

1-[(2-ethyl-3-{2-[4-[(1-methylethyl)oxy]-3-(trifluoromethyl)phenyl]-1,3-thiazol-5-yl}phenyl)methyl]-3-azetidinecarboxylic acid;

1-[(2-ethyl-3-{2-[4-[(1-methylethyl)oxy]-3-(trifluoromethyl)phenyl]-1,3-thiazol-5-yl}phenyl)methyl]-4-piperidinecarboxylic acid;

1-{2-[3-(2-{3-chloro-4-[(1-methylethyl)oxy]phenyl}-1,3-thiazol-5-yl)-5-fluoro-2-(methyloxy)phenyl]ethyl}-3-azetidinecarboxylic acid;

1-{2-[3-(2-{3-cyano-4-[(1-methylethyl)oxy]phenyl}-1,3-thiazol-5-yl)-2-ethylphenyl]ethyl}-3-azetidinecarboxylic acid;

1-{[3-(2-{3-cyano-4-[(1-methylethyl)oxy]phenyl}-1,3-thiazol-5-yl)-2-ethylphenyl]methyl}-4-piperidinecarboxylic acid;

1-{[3-(2-{3-chloro-4-[(1-methylethyl)oxy]phenyl}-1,3-thiazol-5-yl)-2-ethylphenyl]methyl}-4-piperidinecarboxylic acid;

1-{2-[3-(2-{3-cyano-4-[(1-methylethyl)oxy]phenyl}-1,3-thiazol-5-yl)-2-ethylphenyl]ethyl}-4-piperidinecarboxylic acid;

1-{[3-(2-{3-cyano-4-[(1-methylethyl)oxy]phenyl}-1,3-thiazol-5-yl)-2-ethylphenyl]methyl}-3-azetidinecarboxylic acid;

1-{[3-(2-{3-chloro-4-[(1-methylethyl)oxy]phenyl}-1,3-thiazol-5-yl)-2-ethylphenyl]methyl}-3-azetidinecarboxylic acid;

1-{2-[3-(2-{3-chloro-4-[(1-methylethyl)oxy]phenyl}-1,3-thiazol-5-yl)-2-ethylphenyl]ethyl}-4-piperidinecarboxylic acid;

1-{2-[3-(2-{3-chloro-4-[(1-methylethyl)oxy]phenyl}-1,3-thiazol-5-yl)-2-ethylphenyl]ethyl}-3-azetidinecarboxylic acid;

1-[(3-{2-[3-cyano-4-(2-methylpropyl)phenyl]-1,3-thiazol-5-yl}-2-ethylphenyl)methyl]-4-piperidinecarboxylic acid;

1-[(3-{2-[3-cyano-4-(2-methylpropyl)phenyl]-1,3-thiazol-5-yl}-2-ethylphenyl)methyl]-3-azetidinecarboxylic acid;

1-{[3-(5-{3-chloro-4-[(1-methylethyl)oxy]phenyl}-1,3,4-thiadiazol-2-yl)-2-ethylphenyl]methyl}-3-pyrrolidinecarboxylic acid;

(3S)-1-{[3-(5-{3-chloro-4-[(1-methylethyl)oxy]phenyl}-1,3,4-thiadiazol-2-yl)-2-ethylphenyl]methyl}-3-pyrrolidinecarboxylic acid;

1-{[3-(5-{3-chloro-4-[(1-methylethyl)oxy]phenyl}-1,3,4-thiadiazol-2-yl)-2-ethylphenyl]methyl}-3-piperidinecarboxylic acid;

(3S)-1-{[3-(5-{3-chloro-4-[(1-methylethyl)oxy]phenyl}-1,3,4-thiadiazol-2-yl)-2-ethylphenyl]methyl}-3-piperidinecarboxylic acid;

1-[(3-{5-[3-cyano-4-(2-methylpropyl)phenyl]-1,3,4-thiadiazol-2-yl}-2-ethylphenyl)methyl]-3-pyrrolidinecarboxylic acid;

(3S)-1-[(3-{5-[3-cyano-4-(2-methylpropyl)phenyl]-1,3,4-thiadiazol-2-yl}-2-ethylphenyl)methyl]-3-pyrrolidinecarboxylic acid;

1-[(3-{5-[3-cyano-4-(2-methylpropyl)phenyl]-1,3,4-thiadiazol-2-yl}-2-ethylphenyl)methyl]-3-piperidinecarboxylic acid;

(3S)-1-[(3-{5-[3-cyano-4-(2-methylpropyl)phenyl]-1,3,4-thiadiazol-2-yl}-2-ethylphenyl)methyl]-3-piperidinecarboxylic acid;

1-{2-[3-(5-{3-chloro-4-[(1-methylethyl)oxy]phenyl}-1,3,4-thiadiazol-2-yl)-2-ethylphenyl]ethyl}-L-proline;

1-{2-[3-(5-{3-chloro-4-[(1-methylethyl)oxy]phenyl}-1,3,4-thiadiazol-2-yl)-2-ethylphenyl]ethyl}-D-proline;

(3S)-1-{2-[3-(5-{3-chloro-4-[(1-methylethyl)oxy]phenyl}-1,3,4-thiadiazol-2-yl)-2-ethylphenyl]ethyl}-3-pyrrolidinecarboxylic acid;

(4R)-1-{2-[3-(5-{3-chloro-4-[(1-methylethyl)oxy]phenyl}-1,3,4-thiadiazol-2-yl)-2-ethylphenyl]ethyl}-4-hydroxy-L-proline;

1-{2-[3-(5-{3-chloro-4-[(1-methylethyl)oxy]phenyl}-1,3,4-thiadiazol-2-yl)-2-ethylphenyl]ethyl}-3-piperidinecarboxylic acid;

(3S)-1-{2-[3-(5-{3-chloro-4-[(1-methylethyl)oxy]phenyl}-1,3,4-thiadiazol-2-yl)-2-ethylphenyl]ethyl}-3-piperidinecarboxylic acid;

1-{2-[3-(5-{3-chloro-4-[(1-methylethyl)oxy]phenyl}-1,3,4-thiadiazol-2-yl)-2-methylphenyl]ethyl}-4-piperidinecarboxylic acid;

1-[2-(3-{5-[3-cyano-4-(2-methylpropyl)phenyl]-1,3,4-thiadiazol-2-yl}-2-ethylphenyl)ethyl]-L-proline;

1-[2-(3-{5-[3-cyano-4-(2-methylpropyl)phenyl]-1,3,4-thiadiazol-2-yl}-2-ethylphenyl)ethyl]-D-proline;

1-[2-(3-{5-[3-cyano-4-(2-methylpropyl)phenyl]-1,3,4-thiadiazol-2-yl}-2-ethylphenyl)ethyl]-3-pyrrolidinecarboxylic acid;

(3S)-1-[2-(3-{5-[3-cyano-4-(2-methylpropyl)phenyl]-1,3,4-thiadiazol-2-yl}-2-ethylphenyl)ethyl]-3-pyrrolidinecarboxylic acid;

1-[2-(3-{5-[3-cyano-4-(2-methylpropyl)phenyl]-1,3,4-thiadiazol-2-yl}-2-ethylphenyl)ethyl]-3-piperidinecarboxylic acid;

(3S)-1-[2-(3-{5-[3-cyano-4-(2-methylpropyl)phenyl]-1,3,4-thiadiazol-2-yl}-2-ethylphenyl)ethyl]-3-piperidinecarboxylic acid;

1-{2-[3-(5-{3-chloro-4-[(1-methylethyl)oxy]phenyl}-1,2,4-thiadiazol-3-yl)-2-ethylphenyl]ethyl}-L-proline;

1-{2-[3-(5-{3-chloro-4-[(1-methylethyl)oxy]phenyl}-1,2,4-thiadiazol-3-yl)-2-ethylphenyl]ethyl}-D-proline;

1-{2-[3-(5-{3-chloro-4-[(1-methylethyl)oxy]phenyl}-1,2,4-thiadiazol-3-yl)-2-ethylphenyl]ethyl}-3-pyrrolidinecarboxylic acid;

(3S)-1-{2-[3-(5-{3-chloro-4-[(1-methylethyl)oxy]phenyl}-1,2,4-thiadiazol-3-yl)-2-ethylphenyl]ethyl}-3-pyrrolidinecarboxylic acid;

(4R)-1-{2-[3-(5-{3-chloro-4-[(1-methylethyl)oxy]phenyl}-1,2,4-thiadiazol-3-yl)-2-ethylphenyl]ethyl}-4-hydroxy-L-proline;

1-{2-[3-(5-{3-chloro-4-[(1-methylethyl)oxy]phenyl}-1,2,4-thiadiazol-3-yl)-2-ethylphenyl]ethyl}-3-piperidinecarboxylic acid;

(3S)-1-{2-[3-(5-{3-chloro-4-[(1-methylethyl)oxy]phenyl}-1,2,4-thiadiazol-3-yl)-2-ethylphenyl]ethyl}-3-piperidinecarboxylic acid;

(1-{2-[3-(5-{3-chloro-4-[(1-methylethyl)oxy]phenyl}-1,2,4-thiadiazol-3-yl)-2-ethylphenyl]ethyl}-4-piperidinyl)acetic acid;

1-{2-[3-(5-{3-chloro-4-[(1-methylethyl)oxy]phenyl}-1,2,4-thiadiazol-3-yl)-2-(methyloxy)phenyl]ethyl}-4-piperidinecarboxylic acid trifluoroacetate;

1-{2-[3-(5-{3-chloro-4-[(1-methylethyl)oxy]phenyl}-1,2,4-thiadiazol-3-yl)-2-methylphenyl]ethyl}-4-piperidinecarboxylic acid;

1-[2-(3-{5-[3-cyano-4-(2-methylpropyl)phenyl]-1,2,4-thiadiazol-3-yl}-2-ethylphenyl)ethyl]-L-proline;

1-[2-(3-{5-[3-cyano-4-(2-methylpropyl)phenyl]-1,2,4-thiadiazol-3-yl}-2-ethylphenyl)ethyl]-D-proline;

1-[2-(3-{5-[3-cyano-4-(2-methylpropyl)phenyl]-1,2,4-thiadiazol-3-yl}-2-ethylphenyl)ethyl]-3-pyrrolidinecarboxylic acid;

(3S)-1-[2-(3-{5-[3-cyano-4-(2-methylpropyl)phenyl]-1,2,4-thiadiazol-3-yl}-2-ethylphenyl)ethyl]-3-pyrrolidinecarboxylic acid;

(3S)-1-[2-(3-{5-[3-cyano-4-(2-methylpropyl)phenyl]-1,2,4-thiadiazol-3-yl}-2-ethylphenyl)ethyl]-3-piperidinecarboxylic acid;

1-{[3-(2-{3-cyano-4-[(1-methylethyl)oxy]phenyl}-1,3-thiazol-5-yl)-2-ethylphenyl]methyl}-L-proline;

1-{[3-(2-{3-cyano-4-[(1-methylethyl)oxy]phenyl}-1,3-thiazol-5-yl)-2-ethylphenyl]methyl}-D-proline;

1-{[3-(2-{3-cyano-4-[(1-methylethyl)oxy]phenyl}-1,3-thiazol-5-yl)-2-ethylphenyl]methyl}-3-pyrrolidinecarboxylic acid;

(3S)-1-{[3-(2-{3-cyano-4-[(1-methylethyl)oxy]phenyl}-1,3-thiazol-5-yl)-2-ethylphenyl]methyl}-3-pyrrolidinecarboxylic acid;

(4R)-1-{[3-(2-{3-cyano-4-[(1-methylethyl)oxy]phenyl}-1,3-thiazol-5-yl)-2-ethylphenyl]methyl}-4-hydroxy-L-proline;

1-{[3-(2-{3-cyano-4-[(1-methylethyl)oxy]phenyl}-1,3-thiazol-5-yl)-2-ethylphenyl]methyl}-3-piperidinecarboxylic acid;

(1-{[3-(2-{3-cyano-4-[(1-methylethyl)oxy]phenyl}-1,3-thiazol-5-yl)-2-ethylphenyl]methyl}-4-piperidinyl)acetic acid;

1-{2-[3-(2-{3-cyano-4-[(1-methylethyl)oxy]phenyl}-1,3-thiazol-5-yl)-2-ethylphenyl]ethyl}-L-proline;

1-{2-[3-(2-{3-cyano-4-[(1-methylethyl)oxy]phenyl}-1,3-thiazol-5-yl)-2-ethylphenyl]ethyl}-D-proline;

1-{2-[3-(2-{3-cyano-4-[(1-methylethyl)oxy]phenyl}-1,3-thiazol-5-yl)-2-ethylphenyl]ethyl}-3-pyrrolidinecarboxylic acid;

(4R)-1-{2-[3-(2-{3-cyano-4-[(1-methylethyl)oxy]phenyl}-1,3-thiazol-5-yl)-2-ethylphenyl]ethyl}-4-hydroxy-L-proline;

1-{2-[3-(2-{3-cyano-4-[(1-methylethyl)oxy]phenyl}-1,3-thiazol-5-yl)-2-ethylphenyl]ethyl}-3-piperidinecarboxylic acid;

1-{3-[3-(2-{3-cyano-4-[(1-methylethyl)oxy]phenyl}-1,3-thiazol-5-yl)-2-ethylphenyl]propyl}-3-azetidinecarboxylic acid;

1-{3-[3-(2-{3-cyano-4-[(1-methylethyl)oxy]phenyl}-1,3-thiazol-5-yl)-2-ethylphenyl]propyl}-3-pyrrolidinecarboxylic acid;

3-{4-[3-(5-{3-chloro-4-[(1-methylethyl)oxy]phenyl}-1,3,4-thiadiazol-2-yl)-2-ethylphenyl]-1-piperidinyl}propanoic acid;

3-[4-(3-{5-[3-cyano-4-(2-methylpropyl)phenyl]-1,3,4-thiadiazol-2-yl}-2-ethylphenyl)-1-piperidinyl]propanoic acid;

4-{4-[3-(5-{3-chloro-4-[(1-methylethyl)oxy]phenyl}-1,3,4-thiadiazol-2-yl)-2-ethylphenyl]-1-piperidinyl}butanoic acid;

4-[4-(3-{5-[3-cyano-4-(2-methylpropyl)phenyl]-1,3,4-thiadiazol-2-yl}-2-ethylphenyl)-1-piperidinyl]butanoic acid;

{4-[3-(5-{3-chloro-4-[(1-methylethyl)oxy]phenyl}-1,2,4-thiadiazol-3-yl)-2-ethylphenyl]-1-piperidinyl}acetic acid;

3-{4-[3-(5-{3-chloro-4-[(1-methylethyl)oxy]phenyl}-1,2,4-thiadiazol-3-yl)-2-ethylphenyl]-1-piperidinyl}propanoic acid;

3-[4-(3-{5-[3-cyano-4-(2-methylpropyl)phenyl]-1,2,4-thiadiazol-3-yl}-2-ethylphenyl)-1-piperidinyl]propanoic acid;

4-{4-[3-(5-{3-chloro-4-[(1-methylethyl)oxy]phenyl}-1,2,4-thiadiazol-3-yl)-2-ethylphenyl]-1-piperidinyl}butanoic acid;

4-[4-(3-{5-[3-cyano-4-(2-methylpropyl)phenyl]-1,2,4-thiadiazol-3-yl}-2-ethylphenyl)-1-piperidinyl]butanoic acid;

4-[3-(3-{5-[3-cyano-4-(2-methylpropyl)phenyl]-1,2,4-thiadiazol-3-yl}-2-ethylphenyl)-1-azetidinyl]butanoic acid;

(4-{[3-(5-{3-chloro-4-[(1-methylethyl)oxy]phenyl}-1,2,4-thiadiazol-3-yl)-2-ethylphenyl]methyl}-1-piperidinyl)acetic acid;

3-(4-{[3-(5-{3-chloro-4-[(1-methylethyl)oxy]phenyl}-1,2,4-thiadiazol-3-yl)-2-ethylphenyl]methyl}-1-piperidinyl)propanoic acid;

and salts thereof.

6. A compound according to claim 1, in the form of the free base or a pharmaceutically acceptable salt.

7. A compound according to claim 5, which is 1-{[3-(5-{3-chloro-4-[(1-methylethyl)oxy]phenyl}-1,3,4-thiadiazol-2-yl)-2-ethylphenyl]methyl}-3-azetidinecarboxylic acid hydrochloride.

8. A process for preparing a pharmaceutical composition comprising mixing a compound according to claim 1 or a pharmaceutically acceptable salt thereof and a pharmaceutically acceptable carrier or excipient for use in the treatment of conditions or disorders mediated by S1P1 receptors.

9. A pharmaceutical composition comprising a compound of formula (I) or a pharmaceutically acceptable salt thereof according to any one of claims 6 to 7 and a pharmaceutically acceptable carrier.

* * * * *